(12) United States Patent
Bendels et al.

(10) Patent No.: US 9,303,012 B2
(45) Date of Patent: Apr. 5, 2016

(54) PYRIDINE-2-AMIDES USEFUL AS CB2 AGONISTS

(71) Applicant: Hoffmann-La Roche Inc., Little Falls, NJ (US)

(72) Inventors: Stefanie Bendels, Riehen (CH); Uwe Grether, Efringen-Kirchen (DE); Atsushi Kimbara, Tokyo (JP); Matthias Nettekoven, Grenzach-Wyhlen (DE); Stephan Roever, Inzlingen (DE); Mark Rogers-Evans, Bottmingen (CH); Ernst Schaffter, Aesch (CH); Tanja Schulz-Gasch, Ziefen (CH)

(73) Assignee: HOFFMAN-LA ROCHE INC., Little Falls, NJ (US)

( * ) Notice: Subject to any disclaimer, the term of this patent is extended or adjusted under 35 U.S.C. 154(b) by 0 days.

(21) Appl. No.: 14/648,418

(22) PCT Filed: Dec. 4, 2013

(86) PCT No.: PCT/EP2013/075443
§ 371 (c)(1),
(2) Date: May 29, 2015

(87) PCT Pub. No.: WO2014/086806
PCT Pub. Date: Jun. 12, 2014

(65) Prior Publication Data
US 2015/0299165 A1    Oct. 22, 2015

(30) Foreign Application Priority Data

Dec. 7, 2012 (EP) .................................... 12196032

(51) Int. Cl.
| | |
|---|---|
| *C07D 401/04* | (2006.01) |
| *C07D 401/14* | (2006.01) |
| *C07D 405/14* | (2006.01) |
| *C07D 413/14* | (2006.01) |
| *C07D 491/08* | (2006.01) |
| *C07D 213/81* | (2006.01) |
| *C07D 405/12* | (2006.01) |
| *C07D 413/06* | (2006.01) |
| *C07D 417/06* | (2006.01) |
| *C07D 417/14* | (2006.01) |
| *C07D 471/10* | (2006.01) |
| *C07D 487/08* | (2006.01) |
| *C07D 491/04* | (2006.01) |
| *C07D 491/10* | (2006.01) |
| *C07D 495/10* | (2006.01) |
| *C07D 491/107* | (2006.01) |
| *C07D 495/08* | (2006.01) |
| *C07D 401/06* | (2006.01) |

(52) U.S. Cl.
CPC ............ *C07D 401/04* (2013.01); *C07D 213/81* (2013.01); *C07D 401/06* (2013.01); *C07D 401/14* (2013.01); *C07D 405/12* (2013.01); *C07D 405/14* (2013.01); *C07D 413/06* (2013.01); *C07D 413/14* (2013.01); *C07D 417/06* (2013.01); *C07D 417/14* (2013.01); *C07D 471/10* (2013.01); *C07D 487/08* (2013.01); *C07D 491/04* (2013.01); *C07D 491/08* (2013.01); *C07D 491/10* (2013.01); *C07D 491/107* (2013.01); *C07D 495/08* (2013.01); *C07D 495/10* (2013.01)

(58) Field of Classification Search
None
See application file for complete search history.

(56) References Cited

U.S. PATENT DOCUMENTS

| | | | |
|---|---|---|---|
| 7,691,863 B2 * | 4/2010 | Dietz | ................... C07D 241/26 514/255.05 |
| 2008/0085905 A1 | 4/2008 | Dietz et al. | |
| 2012/0065212 A1 | 3/2012 | Hebeisen et al. | |

FOREIGN PATENT DOCUMENTS

| | | |
|---|---|---|
| WO | 2008/040649 A2 | 4/2008 |
| WO | 2012/032018 A1 | 3/2012 |
| WO | 2012/168350 A1 | 12/2012 |

OTHER PUBLICATIONS

Dubois et al., "A new pathway to substituted 6-chloro-2-pyridinecarboxylic acid derivatives from the reaction of 4,6-dichloro-2-oxa-5-aza-bicyclo[2.2.2]oct-5-en-3-ones with nucleophiles" Tetrahedron 52(20):6997-7002 (1996).
International Search Report issued in International Application No. PCT/EP2013/075225, dated Jan. 17, 2014 (in 2 pages).
International Search Report issued in International Application No. PCT/EP2013/075442, dated Feb. 17, 2014 (in 2 pages).
International Search Report issued in International Application No. PCT/EP2013/075443, dated Feb. 18, 2014 (in 3 pages).
International Search Report issued in International Application No. PCT/EP2013/075444, dated Jan. 22, 2014 (in 4 pages).
Sammakia et al., "Total Synthesis of Caerulomycin C via the Halogen Dance Reaction" Organic Letters 4(14):2385-2388 (2002).

* cited by examiner

*Primary Examiner* — Timothy R Rozof
(74) *Attorney, Agent, or Firm* — Alex Andrus

(57) ABSTRACT

The invention relates to CB2 agonists of formula (I) wherein $R^1$ to $R^4$ are defined as in the description and in the claims. The compound of formula (I) can be used as a medicament.

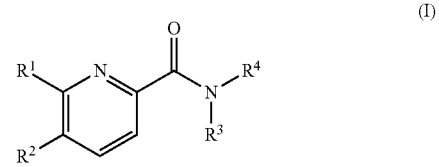

(I)

16 Claims, No Drawings

PYRIDINE-2-AMIDES USEFUL AS CB2 AGONISTS

CROSS-REFERENCE TO RELATED APPLICATIONS

This application is a 371 application of International Application No. PCT/EP2013/075443, filed on Dec. 4, 2013, which claims priority to European Patent Application No. 12196032.2, filed on Dec. 7, 2012, the entire contents of which are incorporated herein by reference.

The present invention relates to organic compounds useful for therapy and/or prophylaxis in a mammal, and in particular to compounds that are preferential agonists of the Cannabinoid Receptor 2.

The invention relates in particular to a compound of formula (I)

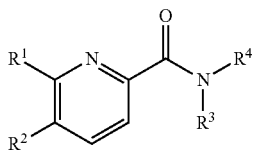

wherein
$R^1$ is cycloalkylalkoxy, halophenyl, tetrahydrofuranylalkoxy, halophenylalkyl, haloalkyloxy, alkylsulfonyl, tetrahydropyranylalkoxy or halogen;
$R^2$ is alkyl, pyrrolidinyl, cycloalkyl, haloazetidinyl, haloalkyl, cycloalkylalkoxy, haloalkyloxy, halocycloalkyl, hydroxycycloalkyl or halooxetanyl;
one of $R^3$ and $R^4$ is alkyl, cycloalkyl, haloalkyl or hydroxyalkyl and the other one is alkyl, alkyloxyalkyl, (haloazetidinyl)(cycloalkyloxy)pyridinylcarbonyloxyalkyl, haloalkylcycloalkyl, hydroxyalkyl, phenylalkyl, alkoxycarbonylalkyl, carboxyalkyl, alkylaminocarbonylalkyl, (alkyloxadiazolyl)(cycloalkylalkyl)alkyl, (alkyloxadiazolyl)(cycloalkyl)alkyl, pyridazinylalkyl, aminocarbonylalkyl, alkyloxadiazolylalkyl, alkyltetrazolylalkyl, formyl, phenyl, dialkylpyrazolyl, alkylcarbonylpiperidinyl or cycloalkylalkyl;
or $R^3$ and $R^4$ together with the nitrogen atom to which they are attached form heterocyclyl or substituted heterocyclyl;
wherein heterocyclyl is 6-oxa-1-aza-spiro[3.3]heptyl, oxazolidinyl, morpholinyl, pyrrolidinyl, piperazinyl, 2-oxa-5-aza-spiro[3.4]octyl, piperidinyl, 6-aza-bicyclo[3.2.1.]octyl, imidazolidinyl, 4-aza-spiro[2.4]heptyl, 2-aza-bicyclo[2.2.1]heptyl, 2-thia-5-aza-bicyclo[2.2.1]heptyl, 2,5-diazabicyclo[2.2.1]heptyl, 2-oxa-5-aza-bicyclo[2.2.1]heptyl, hexahydrofuro[2,3-c]pyrrolyl, 2-thia-6-aza-spiro[3.3]heptyl, 1,8-diaza-spiro[4.5]decyl, 1-oxa-7-aza-spiro[4.4]nonyl, 5-oxa-2-aza-spiro[3.4]octyl, 8-oxa-3-aza-bicyclo[3.2.1]octyl, 3-oxa-8-aza-bicyclo[3.2.1]octyl, thiomorpholinyl, thiazolidinyl, 5-aza-spiro[3.4]octyl, azetidinyl, 5-aza-spiro[2.4]heptyl, 3-aza-bicyclo[3.1.0]hexyl or 5-aza-spiro[2.4]heptyl, 1,3,3a,4,6,6a-hexahydrofuro[3,4-c]pyrrolyl; and
wherein substituted heterocyclyl is heterocyclyl substituted with one to four substituents independently selected from alkyl, oxo, hydroxyl, carboxyl, alkylcarbonylamino, alkyloxyalkyl, hydroxyalkyl, aminocarbonyl, halogen, phenylalkyl, phenyl, alkoxycarbonyl, cycloalkylalkyl, phenylalkoxycarbonyl, cycloalkyl, halohydroxyalkyl and haloalkyl;
provided that $R^3$ and $R^4$ together with the nitrogen atom to which they are attached don't form unsubstituted piperidinyl, unsubstituted thiomorpholinyl or hydroxyalkylpyrrolidinyl;
or a pharmaceutically acceptable salt or ester thereof.

The compound of formula (I) is particularly useful in the treatment or prophylaxis of e.g. pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, amyotrophic lateral sclerosis, stroke, transient ischemic attack or uveitis.

The compound of formula (I) is in particular useful in the treatment or prophylaxis of diabetic retinopathy, retinal vein occlusion or uveitis.

The cannabinoid receptors are a class of cell membrane receptors belonging to the G protein-coupled receptor superfamily. There are currently two known subtypes, termed Cannabinoid Receptor 1 (CB1) and Cannabinoid Receptor 2 (CB2). The CB1 receptor is mainly expressed in the central nervous (i.e. amygdala cerebellum, hippocampus) system and to a lesser amount in the periphery. CB2, which is encoded by the CNR2 gene, is mostly expressed peripherally, on cells of the immune system, such as macrophages and T-cells (Ashton, J. C. et al. Curr Neuropharmacol 2007, 5(2), 73-80; Miller, A. M. et al. Br J Pharmacol 2008, 153(2), 299-308; Centonze, D., et al. Curr Pharm Des 2008, 14(23), 2370-42), and in the gastrointestinal system (Wright, K. L. et al. Br J Pharmacol 2008, 153(2), 263-70). The CB2 receptor is also widely distributed in the brain where it is found primarily on microglia and not neurons (Cabral, G. A. et al. Br J Pharmacol 2008, 153(2): 240-51).

The interest in CB2 receptor agonists has been steadily on the rise during the last decade (currently 30-40 patent applications/year) due to the fact that several of the early compounds have been shown to have beneficial effects in preclinical models for a number of human diseases including chronic pain (Beltramo, M. Mini Rev Med Chem 2009, 9(1), 11-25), atherosclerosis (Mach, F. et al. J Neuroendocrinol 2008, 20 Suppl 1, 53-7), regulation of bone mass (Bab, I. et al. Br J Pharmacol 2008, 153(2), 182-8), neuroinflammation (Cabral, G. A. et al. J Leukoc Biol 2005, 78(6), 1192-7), ischemia/reperfusion injury (Pacher, P. et al. Br J Pharmacol 2008, 153(2), 252-62), systemic fibrosis (Akhmetshina, A. et al. Arthritis Rheum 2009, 60(4), 1129-36; Garcia-Gonzalez, E. et al. Rheumatology (Oxford) 2009, 48(9), 1050-6), liver fibrosis (Julien, B. et al. Gastroenterology 2005, 128(3), 742-55; Munoz-Luque, J. et al. J Pharmacol Exp Ther 2008, 324(2), 475-83).

Ischemia/reperfusion (I/R) injury is the principal cause of tissue damage occurring in conditions such as stroke, myocardial infarction, cardiopulmonary bypass and other vascular surgeries, and organ transplantation, as well as a major mechanism of end-organ damage complicating the course of circulatory shock of various etiologies. All these conditions are characterized by a disruption of normal blood supply resulting in an insufficient tissue oxygenation. Re-oxygenation e.g., reperfusion is the ultimate treatment to restore normal tissue oxygenation. However the absence of oxygen and nutrients from blood creates a condition in which the restoration of circulation results in further tissue damage. The damage of reperfusion injury is due in part to the inflammatory response of damaged tissues. White blood cells, carried to the area by the newly returning blood, release a host of inflammatory factors such as interleukins as well as free radicals in response to tissue damage. The restored blood flow reintroduces oxygen within cells that damages cellular proteins, DNA, and the plasma membrane.

Remote ischemic preconditioning (RIPC) represents a strategy for harnessing the body's endogenous protective capabilities against the injury incurred by ischemia and reperfusion. It describes the intriguing phenomenon in which transient non-lethal ischemia and reperfusion of one organ or tissue confers resistance to a subsequent episode of "lethal" ischemia reperfusion injury in a remote organ or tissue. The actual mechanism through which transient ischemia and reperfusion of an organ or tissue confers protection is currently unknown although several hypotheses have been proposed.

The humoral hypothesis proposes that the endogenous substance (such as adenosine, bradykinin, opioids, CGRP, endocannabinoids, Angiotensin I or some other as yet unidentified humoral factor) generated in the remote organ or tissue enters the blood stream and activates its respective receptor in the target tissue and thereby recruiting the various intracellular pathways of cardioprotection implicated in ischemic preconditioning.

Recent data indicates that endocannabinnoids and their receptors, in particular CB2 might be involved in pre-conditioning and contribute to prevent reperfusion injury by down-regulation of the inflammatory response (Pacher, P. et al. Br J Pharmacol 2008, 153(2), 252-62). Specifically, recent studies using CB2 tool agonists demonstrated the efficacy of this concept for reducing the I/R injury in the heart (Defer, N. et al. Faseb J 2009, 23(7), 2120-30), the brain (Zhang, M. et al. J Cereb Blood Flow Metab 2007, 27(7), 1387-96), the liver (Batkai, S. et al. Faseb J 2007, 21(8), 1788-800) and the kidney (Feizi, A. et al. Exp Toxicol Pathol 2008, 60(4-5), 405-10).

Moreover, over the last few years, a growing body of literature indicates that CB2 can also be of interest in sub-chronic and chronic setting. Specific upregulation of CB1 and CB2 has been shown to be associated in animal models of chronic diseases associated with fibrosis (Garcia-Gonzalez, E. et al. Rheumatology (Oxford) 2009, 48(9), 1050-6; Yang, Y. Y. et al. Liver Int 2009, 29(5), 678-85) with a relevant expression of CB2 in myofibroblasts, the cells responsible for fibrosis progression.

Activation of CB2 receptor by selective CB2 agonist has in fact been shown to exert anti-fibrotic effect in diffuse systemic sclerosis (Garcia-Gonzalez, E. et al. Rheumatology (Oxford) 2009, 48(9), 1050-6) and CB2 receptor has emerged as a critical target in experimental dermal fibrosis (Akhmetshina, A. et al. Arthritis Rheum 2009, 60(4), 1129-36) and in liver pathophysiology, including fibrogenesis associated with chronic liver diseases (Lotersztajn, S. et al. Gastroenterol Clin Biol 2007, 31(3), 255-8; Mallat, A. et al. Expert Opin Ther Targets 2007, 11(3), 403-9; Lotersztajn, S. et al. Br J Pharmacol 2008, 153(2), 286-9).

The compounds of the invention bind to and modulate the CB2 receptor and have lower CB1 receptor activity.

In the present description the term "alkyl", alone or in combination, signifies a straight-chain or branched-chain alkyl group with 1 to 8 carbon atoms, particularly a straight or branched-chain alkyl group with 1 to 6 carbon atoms and more particularly a straight or branched-chain alkyl group with 1 to 4 carbon atoms. Examples of straight-chain and branched-chain $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, particularly methyl, ethyl, propyl, butyl and pentyl more particularly methyl, ethyl, propyl, isopropyl, isobutyl, tert.-butyl and isopentyl. Particular examples of alkyl are methyl, ethyl, isopropyl and tert.-butyl, in particular methyl and tert.-butyl.

The term "cycloalkyl", alone or in combination, signifies a cycloalkyl ring with 3 to 8 carbon atoms and particularly a cycloalkyl ring with 3 to 6 carbon atoms. Examples of cycloalkyl are cyclopropyl, cyclobutyl, cyclopentyl and cyclohexyl, cycloheptyl and cyclooctyl. Particular examples of "cycloalkyl" are cyclopropyl and cyclobutyl. A particular example of "cycloalkyl" is cyclopropyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec-butoxy and tert.-butoxy. Particular "alkoxy" are methoxy and tert.-butoxy, and in particular methoxy.

The term "oxy", alone or in combination, signifies the —O— group.

The term "oxa", alone or in combination, denotes an intracyclic —O— group.

The term "oxo", alone or in combination, signifies the =O group.

The terms "halogen" or "halo", alone or in combination, signifies fluorine, chlorine, bromine or iodine and particularly fluorine, chlorine or bromine, more particularly fluorine and chlorine. The term "halo", in combination with another group, denotes the substitution of said group with at least one halogen, particularly substituted with one to five halogens, particularly one to four halogens, i.e. one, two, three or four halogens. A particular "halogen" is fluorine.

The term "haloalkyl", alone or in combination, denotes an alkyl group substituted with at least one halogen, particularly substituted with one to five halogens, particularly one to three halogens. A particular "haloalkyl" is trifluoromethyl.

The term "haloalkoxy" or "haloalkyloxy", alone or in combination, denotes an alkoxy group substituted with at least one halogen, particularly substituted with one to five halogens, particularly one to three halogens. Particular "haloalkoxy" are pentafluoropropyloxy and trifluoropropyloxy, fluoroethoxy, fluoropropyloxy, difluoroethyloxy and difluoropropyloxy. Particular "haloalkoxy" are pentafluoropropyloxy and trifluoropropyloxy.

The terms "hydroxyl" and "hydroxy", alone or in combination, signify the —OH group.

The term "carbonyl", alone or in combination, signifies the —C(O)— group.

The term "amino", alone or in combination, signifies the primary amino group (—$NH_2$), the secondary amino group (—NH—), or the tertiary amino group (—N—).

The term "aminocarbonyl", alone or in combination, signifies the —C(O)—$NH_2$ group.

The term "sulfonyl", alone or in combination, signifies the —$S(O)_2$— group.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein. In addition these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins. The compound of formula (I) can also be present in the form of zwitterions. Particularly preferred pharmaceutically acceptable salts of compounds of formula (I) are the salts of hydrochloric acid, hydrobromic acid, sulfuric acid, phosphoric acid and methanesulfonic acid.

"Pharmaceutically acceptable esters" means that the compound of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compound of general formula (I), similar to the metabolically labile esters, which are capable of producing the parent compound of general formula (I) in vivo, are within the scope of this invention.

If one of the starting materials or compounds of formula (I) contain one or more functional groups which are not stable or are reactive under the reaction conditions of one or more reaction steps, appropriate protecting groups (as described e.g. in "Protective Groups in Organic Chemistry" by T. W. Greene and P. G. M. Wuts, 3$^{rd}$ Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

The compound of formula (I) can contain several asymmetric centers and can be present in the form of optically pure enantiomers, mixtures of enantiomers such as, for example, racemates, mixtures of diastereoisomers, diastereoisomeric racemates or mixtures of diastereoisomeric racemates.

The term "asymmetric carbon atom" means a carbon atom with four different substituents. According to the Cahn-Ingold-Prelog Convention an asymmetric carbon atom can be of the "R" or "S" configuration.

The invention relates in particular to a compound of formula (I) wherein
  $R^2$ is alkyl, pyrrolidinyl, cycloalkyl, haloazetidinyl, haloalkyl, cycloalkylalkoxy or haloalkyloxy;
  one of $R^3$ and $R^4$ is alkyl, cycloalkyl, haloalkyl or hydroxyalkyl and the other one is alkyl, alkyloxyalkyl, (haloazetidinyl)(cycloalkyloxy)pyridinylcarbonyloxyalkyl, haloalkylcycloalkyl, hydroxyalkyl, phenylalkyl, alkoxycarbonylalkyl, carboxyalkyl, alkylaminocarbonylalkyl, (alkyloxadiazolyl)(cycloalkylalkyl)alkyl, (alkyloxadiazolyl)(cycloalkyl)alkyl, pyridazinylalkyl, aminocarbonylalkyl, alkyloxadiazolylalkyl, alkyltetrazolylalkyl, formyl, phenyl, dialkylpyrazolyl, alkylcarbonylpiperidinyl or cycloalkylalkyl;
  or $R^3$ and $R^4$ together with the nitrogen atom to which they are attached form heterocyclyl or substituted heterocyclyl;
  wherein heterocyclyl is 6-oxa-1-aza-spiro[3.3]heptyl, oxazolidinyl, morpholinyl, pyrrolidinyl, piperazinyl, 2-oxa-5-aza-spiro[3.4]octyl, piperidinyl, 6-aza-bicyclo[3.2.1.]octyl, imidazolidinyl, 4-aza-spiro[2.4]heptyl, 2-aza-bicyclo[2.2.1]heptyl, 2-thia-5-aza-bicyclo[2.2.1]heptyl, 2,5-diazabicyclo[2.2.1]heptyl, 2-oxa-5-aza-bicyclo[2.2.1]heptyl, hexahydrofuro[2,3-c]pyrrolyl, 2-thia-6-aza-spiro[3.3]heptyl, 1,8-diaza-spiro[4.5]decyl, 1-oxa-7-aza-spiro[4.4]nonyl, 5-oxa-2-aza-spiro[3.4]octyl, 8-oxa-3-aza-bicyclo[3.2.1]octyl, 3-oxa-8-aza-bicyclo[3.2.1]octyl, thiomorpholinyl, thiazolidinyl, 5-aza-spiro[3.4]octyl, azetidinyl, 5-aza-spiro[2.4]heptyl or 3-aza-bicyclo[3.1.0]hexyl; and
  wherein substituted heterocyclyl is heterocyclyl substituted with one to four substituents independently selected from alkyl, oxo, hydroxyl, carboxyl, alkylcarbonylamino, alkyloxyalkyl, hydroxyalkyl, aminocarbonyl, halogen, phenylalkyl, phenyl, alkoxycarbonyl, cycloalkylalkyl and phenylalkoxycarbonyl.

The invention further relates in particular to:
A compound of formula (I) wherein $R^1$ is cycloalkylalkoxy, tetrahydrofuranylalkoxy, alkylsulfonyl or halophenylalkyl;

A compound of formula (I) wherein $R^1$ is cyclopropylmethoxy, tetrahydrofuranylmethoxy, isobutylsulfonyl or fluorophenylmethyl;

A compound of formula (I) wherein $R^2$ is haloazetidinyl, cycloalkyl or halocycloalkyl;

A compound of formula (I) wherein $R^2$ is difluoroazetidinyl, cyclopropyl or fluorocyclobutyl;

A compound of formula (I) wherein $R^2$ is haloazetidinyl or cycloalkyl;

A compound of formula (I) wherein $R^2$ is difluoroazetidinyl or cyclopropyl;

A compound of formula (I) wherein one of $R^3$ and $R^4$ is alkyl and the other one is alkyl or haloalkylcycloalkyl;

A compound of formula (I) wherein one of $R^3$ and $R^4$ is methyl and the other one is tert.-butyl or trifluoromethylcyclopropyl;

A compound of formula (I) wherein $R^3$ and $R^4$ together with the nitrogen atom to which they are attached form heterocyclyl or substituted heterocyclyl, wherein heterocyclyl is oxazolidinyl, morpholinyl, pyrrolidinyl, 6-aza-bicyclo[3.2.1.]octyl, 4-aza-spiro[2.4]heptyl, 2-thia-5-aza-bicyclo[2.2.1]heptyl, 5-aza-spiro[3.4]octyl, 5-aza-spiro[2.4]heptyl, 1,8-diaza-spiro[4.5]decyl, thiazolidinyl or 5-aza-spiro[2.4]heptyl, and wherein substituted heterocyclyl is heterocyclyl substituted with one to three substituents independently selected from alkyl, hydroxyalkyl, halogen, aminocarbonyl, alkoxycarbonyl, oxo or hydroxyl;

A compound of formula (I) wherein $R^3$ and $R^4$ together with the nitrogen atom to which they are attached form heterocyclyl or substituted heterocyclyl, wherein heterocyclyl is oxazolidinyl, morpholinyl, pyrrolidinyl, 6-aza-bicyclo[3.2.1.]octyl, 4-aza-spiro[2.4]heptyl, 2-thia-5-aza-bicyclo[2.2.1]heptyl, 5-aza-spiro[3.4]octyl, 5-aza-spiro[2.4]heptyl, 1,8-diaza-spiro[4.5]decyl, thiazolidinyl or 5-aza-spiro[2.4]heptyl, and wherein substituted heterocyclyl is heterocyclyl substituted with one to three substituents independently selected from methyl, hydroxymethyl, fluoro, aminocarbonyl, tert.-butoxycarbonyl, oxo or hydroxyl;

A compound of formula (I) wherein $R^3$ and $R^4$ together with the nitrogen atom to which they are attached form dimethyloxazolidinyl, dimethylmorpholinyl, dimethylpyrrolidinyl, trimethyl-6-aza-bicyclo[3.2.1.]octyl, (hydroxymethyl)(difluoro)pyrrolidinyl, 4-aza-spiro[2.4]heptyl, (aminocarbonyl)(difluoro)pyrrolidinyl, 2-thia-5-aza-bicyclo[2.2.1]heptyl, (aminocarbonyl)(dimethyl)pyrrolidinyl, 5-aza-spiro[3.4]octyl, difluoro-5-aza-spiro[2.4]heptyl, 5-aza-spiro[2.4]heptyl, tert.-butoxycarbonyl-1,8-diaza-spiro[4.5]decyl, aminocarbonyl-1,1-dioxo-1$\lambda$6-thiazolidinyl, aminocarbonyl-1,1-dioxo-1,3-thiazolidinyl, (aminocarbonyl)(methyl)(hydroxyl)pyrrolidinyl or (aminocarbonyl)-5-aza-spiro[2.4]heptyl;

A compound of formula (I) wherein $R^3$ and $R^4$ together with the nitrogen atom to which they are attached form heterocyclyl or substituted heterocyclyl, wherein heterocyclyl is oxazolidinyl, morpholinyl, pyrrolidinyl, 6-aza-bicyclo[3.2.1.]octyl, 4-aza-spiro[2.4]heptyl, 2-thia-5-aza-bicyclo[2.2.1]heptyl, 5-aza-spiro[3.4]octyl, 5-aza-spiro[2.4]heptyl, 1,8-diaza-spiro[4.5]decyl or thiazolidinyl, and wherein substituted heterocyclyl is heterocyclyl substituted with one to three substituents independently selected from alkyl, hydroxyalkyl, halogen, aminocarbonyl, alkoxycarbonyl and oxo;

A compound of formula (I) wherein $R^3$ and $R^4$ together with the nitrogen atom to which they are attached form heterocyclyl or substituted heterocyclyl, wherein heterocyclyl is oxazolidinyl, morpholinyl, pyrrolidinyl, 6-aza-bicyclo[3.2.1.]octyl, 4-aza-spiro[2.4]heptyl, 2-thia-5-aza-bicyclo[2.2.1]heptyl, 5-aza-spiro[3.4]octyl, 5-aza-spiro[2.4]heptyl, 1,8-diaza-spiro[4.5]decyl or thiazolidinyl, and wherein substituted heterocyclyl is heterocyclyl substituted with one to three substituents independently selected from methyl, hydroxymethyl, fluoro, aminocarbonyl, tert.-butoxycarbonyl and oxo;

A compound of formula (I) wherein $R^3$ and $R^4$ together with the nitrogen atom to which they are attached form dimethyloxazolidinyl, dimethylmorpholinyl, dimethylpyrrolidinyl, trimethyl-6-aza-bicyclo[3.2.1.]octyl, (hydroxymethyl)(difluoro)pyrrolidinyl, 4-aza-spiro[2.4]heptyl, (aminocarbonyl)(difluoro)pyrrolidinyl, 2-thia-5-aza-bicyclo[2.2.1]heptyl, (aminocarbonyl)(dimethyl)pyrrolidinyl, 5-aza-spiro[3.4]octyl, difluoro-5-aza-spiro[2.4]heptyl, 5-aza-spiro[2.4]heptyl, tert.-butoxycarbonyl-1,8-diaza-spiro[4.5]decyl or aminocarbonyl-1,1-dioxo-1$\lambda$6-thiazolidinyl;

A compound of formula (I) wherein $R^3$ and $R^4$ together with the nitrogen atom to which they are attached form 6-oxa-1-aza-spiro[3.3]heptyl, dialkyloxazolidinyl, dialkylmorpholinyl, dialkylpyrrolidinyl, (dialkyl)(oxo)piperazinyl, (hydroxyl)(alkyl)pyrrolidinyl, 2-oxa-5-aza-spiro[3.4]octyl, alkylcarbonylaminopyrrolidinyl, dialkylpiperidinyl, trialkyl-6-aza-bicyclo[3.2.1.]octyl, alkyloxyalkylpyrrolidinyl, (halo)(hydroxyalkyl)pyrrolidinyl, (dialkyl)(oxo)imidazolyl, 4-aza-spiro[2.4]heptyl, (dialkyl)(oxo)pyrrolidinyl-piperidinyl, 2-aza-bicyclo[2.2.1]heptyl, (aminocarbonyl)(halo)pyrrolidinyl, (hydroxyl)(alkyl)piperidinyl, 2-thia-5-aza-bicyclo[2.2.1]heptyl, phenylalkyl-2,5-diazabicyclo[2.2.1]heptyl, (phenyl)(alkyl)piperidinyl, 2-oxa-5-aza-bicyclo[2.2.1]heptyl, (hydroxyl)(dialkyl)piperidinyl, (alkoxycarbonyl)(phenyl)piperidinyl, hexahydrofuro[2,3-c]pyrrolyl, 2,2-dioxo-2$\lambda$6-thia-6-aza-spiro[3.3]heptyl, (alkoxycarbonyl)-1,8-diaza-spiro[4.5]decyl, (aminocarbonyl)(dialkyl)pyrrolidinyl, (aminocarbonyl)(hydroxyl)pyrrolidinyl, hydroxy-1-oxa-7-aza-spiro[4.4]nonyl, hydroxy-5-oxa-2-aza-spiro[3.4]octyl, 8-oxa-3-aza-bicyclo[3.2.1]octyl, 3-oxa-8-aza-bicyclo[3.2.1]octyl, aminocarbonylpiperidinyl, aminocarbonylthiomorpholinyl, aminocarbonylthiazolidinyl, 5-oxa-2-aza-spiro[3.4]octyl, 1-oxa-7-aza-spiro[4.4]nonyl, 5-aza-spiro[3.4]octyl, haloazetidinyl, halo-5-aza-spiro[2.4]heptyl, 5-aza-spiro[2.4]heptyl, cycloalkylalkylpiperazinyl, alkoxycarbonyl-3-aza-bicyclo[3.1.0]hexyl, phenylalkoxycarbonylpiperazinyl, carboxy-3-aza-bicyclo[3.1.0]hexyl, 1,8-diaza-spiro[4.5]decyl, aminocarbonylpyrrolidinyl, aminocarbonyl-1,1-dioxo-1$\lambda$6-thiazolidinyl, aminocarbonyl-1-oxo-1$\lambda$4-thiazolidinyl, tetrafluoropyrrolidinyl, (dialkyl)(aminocarbonyl)thiazolidinyl, (aminocarbonyl)(halo)pyrrolidinyl, (aminocarbonyl)-1-oxo-1,3-thiazolidinyl, (aminocarbonyl)-1,1-dioxo-1,3-thiazolidinyl, (aminocarbonyl)(hydroxyl)(alkyl)pyrrolidinyl, (aminocarbonyl)-5-aza-spiro[2.4]heptyl, (hydroxyhaloalkyl)pyrrolidinyl, (haloalkyl)(hydroxyalkyl)pyrrolidinyl, (haloalkyl)(hydroxyl)pyrrolidinyl, (haloalkyl)(hydroxyl)azetidinyl, 1,3,3a,4,6,6a-hexahydrofuro[3,4-c]pyrrolyl, (halo)(hydroxyalkyl)azetidinyl or (halo)(alkyl)azetidinyl; and A compound of formula (I) wherein $R^3$ and $R^4$ together with the nitrogen atom to which they are attached form 6-oxa-1-aza-spiro[3.3]heptyl, dialkyloxazolidinyl, dialkylmorpholinyl, dialkylpyrrolidinyl, (dialkyl)(oxo)piperazinyl, (hydroxyl)(alkyl)pyrrolidinyl, 2-oxa-5-aza-spiro[3.4]octyl, alkylcarbonylaminopyrrolidinyl, dialkylpiperidinyl, trialkyl-6-aza-bicyclo[3.2.1.]octyl, alkyloxyalkylpyrrolidinyl, (halo)(hydroxyalkyl)pyrrolidinyl, (dialkyl)(oxo)imidazolyl, 4-aza-spiro[2.4]heptyl, (dialkyl)(oxo)pyrrolidinyl-piperidinyl, 2-aza-bicyclo[2.2.1]heptyl, (aminocarbonyl)(halo)pyrrolidinyl, (hydroxyl)(alkyl)piperidinyl, 2-thia-5-aza-bicyclo[2.2.1]heptyl, phenylalkyl-2,5-diazabicyclo[2.2.1]heptyl, (phenyl)(alkyl)piperidinyl, 2-oxa-5-aza-bicyclo[2.2.1]heptyl, (hydroxyl)(dialkyl)piperidinyl, (alkoxycarbonyl)(phenyl)piperidinyl, hexahydrofuro[2,3-c]pyrrolyl, 2,2-dioxo-2$\lambda$6-thia-6-aza-spiro[3.3]heptyl, (alkoxycarbonyl)-1,8-diaza-spiro[4.5]decyl, (aminocarbonyl)(dialkyl)pyrrolidinyl, (aminocarbonyl)(hydroxyl)pyrrolidinyl, hydroxy-1-oxa-7-aza-spiro[4.4]nonyl, hydroxy-5-oxa-2-aza-spiro[3.4]octyl, 8-oxa-3-aza-bicyclo[3.2.1]octyl, 3-oxa-8-aza-bicyclo[3.2.1]octyl, aminocarbonylpiperidinyl, aminocarbonylthiomorpholinyl, aminocarbonylthiazolidinyl, 5-oxa-2-aza-spiro[3.4]octyl, 1-oxa-7-aza-spiro[4.4]nonyl, 5-aza-spiro[3.4]octyl, haloazetidinyl, halo-5-aza-spiro[2.4]heptyl, 5-aza-spiro[2.4]heptyl, cycloalkylalkylpiperazinyl, alkoxycarbonyl-3-aza-bicyclo[3.1.0]hexyl, phenylalkoxycarbonylpiperazinyl, carboxy-3-aza-bicyclo[3.1.0]hexyl, 1,8-diaza-spiro[4.5]decyl, aminocarbonylpyrrolidinyl, aminocarbonyl-1,1-dioxo-1$\lambda$6-thiazolidinyl, aminocarbonyl-1-oxo-1$\lambda$4-thiazolidinyl, tetrafluoropyrrolidinyl or (dialkyl)(aminocarbonyl)thiazolidinyl.

The invention further relates to a compound selected from:
6-Cyclopropylmethoxy-5-(3,3-difluoro-azetidin-1-yl)-pyridine-2-carboxylic acid tert-butyl-methyl-amide;
6-Cyclopropylmethoxy-5-(3,3-difluoro-azetidin-1-yl)-pyridine-2-carboxylic acid dimethylamide;
5-Cyclopropyl-6-cyclopropylmethoxy-pyridine-2-carboxylic acid tert-butyl-methyl-amide;
5-Cyclopropyl-6-(tetrahydro-furan-2-ylmethoxy)-pyridine-2-carboxylic acid tert-butyl-methyl-amide;
5-Cyclopropyl-6-(4-fluoro-benzyl)-pyridine-2-carboxylic acid tert-butyl-methyl-amide;
5-Cyclopropyl-6-(2-methyl-propane-1-sulfonyl)-pyridine-2-carboxylic acid tert-butyl-methyl-amide;
6-Cyclopropylmethoxy-5-(3,3-difluoro-azetidin-1-yl)-pyridine-2-carboxylic acid tert-butyl-ethyl-amide;
6-Cyclopropylmethoxy-5-(3,3-difluoro-azetidin-1-yl)-pyridine-2-carboxylic acid diisopropylamide;

6-Cyclopropylmethoxy-5-(3,3-difluoro-azetidin-1-yl)-pyridine-2-carboxylic acid (2-methoxy-1,1-dimethyl-ethyl)-methyl-amide;
[6-Cyclopropylmethoxy-5-(3,3-difluoro-azetidin-1-yl)-pyridin-2-yl]-(6-oxa-1-aza-spiro[3.3]hept-1-yl)-methanone;
[6-Cyclopropylmethoxy-5-(3,3-difluoro-azetidin-1-yl)-pyridin-2-yl]-(2-oxa-6-aza-spiro[3.3]hept-6-yl)-methanone;
6-Cyclopropylmethoxy-5-(3,3-difluoro-azetidin-1-yl)-pyridine-2-carboxylic acid 2-{[6-cyclopropylmethoxy-5-(3,3-difluoro-azetidin-1-yl)-pyridine-2-carbonyl]-methyl-amino}-2-methyl-propyl ester;
5-Cyclopropyl-6-(2,2,2-trifluoro-1-methyl-ethoxy)-pyridine-2-carboxylic acid tert-butyl-methyl-amide;
[6-Cyclopropylmethoxy-5-(3,3-difluoro-azetidin-1-yl)-pyridin-2-yl]-(4,4-dimethyl-oxazolidin-3-yl)-methanone;
6-(Tetrahydro-furan-2-ylmethoxy)-5-trifluoromethyl-pyridine-2-carboxylic acid tert-butyl-methyl-amide;
6-Cyclopropylmethoxy-5-(3,3-difluoro-azetidin-1-yl)-pyridine-2-carboxylic acid methyl-(1-trifluoromethyl-cyclopropyl)-amide;
[6-Cyclopropylmethoxy-5-(3,3-difluoro-azetidin-1-yl)-pyridin-2-yl]-(3,3-dimethyl-morpholin-4-yl)-methanone;
[6-Cyclopropylmethoxy-5-(3,3-difluoro-azetidin-1-yl)-pyridin-2-yl]-(2,2-dimethyl-pyrrolidin-1-yl)-methanone;
6-Cyclopropylmethoxy-5-(3,3-difluoro-azetidin-1-yl)-pyridine-2-carboxylic acid (2-hydroxy-1,1-dimethyl-ethyl)-(2-methoxy-ethyl)-amide;
6-Cyclopropylmethoxy-5-(3,3-difluoro-azetidin-1-yl)-pyridine-2-carboxylic acid tert-butyl-(2-methoxy-ethyl)-amide;
6-Cyclopropylmethoxy-5-(3,3-difluoro-azetidin-1-yl)-pyridine-2-carboxylic acid ethyl-(1-trifluoromethyl-cyclopropyl)-amide;
6-Cyclopropylmethoxy-5-(3,3-difluoro-azetidin-1-yl)-pyridine-2-carboxylic acid benzyl-(1-trifluoromethyl-cyclopropyl)-amide;
{tert-Butyl-[6-cyclopropylmethoxy-5-(3,3-difluoro-azetidin-1-yl)-pyridine-2-carbonyl]-amino}-acetic acid ethyl ester;
{tert-Butyl-[6-cyclopropylmethoxy-5-(3,3-difluoro-azetidin-1-yl)-pyridine-2-carbonyl]-amino}-acetic acid;
6-Cyclopropylmethoxy-5-(3,3-difluoro-azetidin-1-yl)-pyridine-2-carboxylic acid benzyl-tert-butyl-amide;
6-Cyclopropylmethoxy-5-(3,3-difluoro-azetidin-1-yl)-pyridine-2-carboxylic acid tert-butyl-methylcarbamoylmethyl-amide;
6-Cyclopropylmethoxy-5-(3,3-difluoro-azetidin-1-yl)-pyridine-2-carboxylic acid tert-butyl-dimethylcarbamoylmethyl-amide;
4-[6-Cyclopropylmethoxy-5-(3,3-difluoro-azetidin-1-yl)-pyridine-2-carbonyl]-3,3-dimethyl-piperazin-2-one;
4-[6-Cyclopropylmethoxy-5-(3,3-difluoro-azetidin-1-yl)-pyridine-2-carbonyl]-3,3-diethyl-piperazin-2-one;
[5-Cyclopropyl-6-(2-methyl-propane-1-sulfonyl)-pyridin-2-yl]-(2,2-dimethyl-pyrrolidin-1-yl)-methanone;
[5-Cyclopropyl-6-(2-methyl-propane-1-sulfonyl)-pyridin-2-yl]-(4,4-dimethyl-oxazolidin-3-yl)-methanone;
6-Cyclopropylmethoxy-5-(3,3-difluoro-azetidin-1-yl)-pyridine-2-carboxylic acid [(S)-2-cyclopropyl-1-(5-methyl-[1,2,4]oxadiazol-3-yl)-ethyl]-methyl-amide;
5-Cyclopropyl-6-(tetrahydro-pyran-4-ylmethoxy)-pyridine-2-carboxylic acid [cyclopropyl-(5-methyl-[1,2,4]oxadiazol-3-yl)-methyl]-methyl-amide;
(+)-6-Cyclopropylmethoxy-5-(3,3-difluoro-azetidin-1-yl)-pyridine-2-carboxylic acid methyl-(3-methyl-1-pyridazin-3-yl-butyl)-amide;
6-Cyclopropylmethoxy-5-(3,3-difluoro-azetidin-1-yl)-pyridine-2-carboxylic acid tert-butyl-carbamoylmethyl-amide;
6-Cyclopropylmethoxy-5-(3,3-difluoro-azetidin-1-yl)-pyridine-2-carboxylic acid tert-butyl-(5-methyl-[1,3,4]oxadiazol-2-ylmethyl)-amide;
[6-Cyclopropylmethoxy-5-(3,3-difluoro-azetidin-1-yl)-pyridin-2-yl]-(3-hydroxy-3-methyl-pyrrolidin-1-yl)-methanone;
[6-Cyclopropylmethoxy-5-(3,3-difluoro-azetidin-1-yl)-pyridin-2-yl]-(2-oxa-5-aza-spiro[3.4]oct-5-yl)-methanone;
6-Cyclopropylmethoxy-5-(3,3-difluoro-azetidin-1-yl)-pyridine-2-carboxylic acid ethyl-(2-methoxy-ethyl)-amide;
6-Cyclopropylmethoxy-5-(3,3-difluoro-azetidin-1-yl)-pyridine-2-carboxylic acid tert-butyl-(1-methyl-1H-tetrazol-5-ylmethyl)-amide;
N-{1-[6-Cyclopropylmethoxy-5-(3,3-difluoro-azetidin-1-yl)-pyridine-2-carbonyl]-pyrrolidin-3-yl}-acetamide;
[5-Cyclopropyl-6-(4-fluoro-benzyl)-pyridin-2-yl]-(4,4-dimethyl-piperidin-1-yl)-methanone;
[5-Cyclopropyl-6-(tetrahydro-furan-2-ylmethoxy)-pyridin-2-yl]-(4,4-dimethyl-piperidin-1-yl)-methanone;
[5-Cyclopropyl-6-(4-fluoro-benzyl)-pyridin-2-yl]-(4,4-dimethyl-oxazolidin-3-yl)-methanone;
[6-Cyclopropylmethoxy-5-(3,3-difluoro-azetidin-1-yl)-pyridin-2-yl]-((1S,5R)-1,3,3-trimethyl-6-aza-bicyclo[3.2.1]oct-6-yl)-methanone;
[6-Cyclopropylmethoxy-5-(3,3-difluoro-azetidin-1-yl)-pyridin-2-yl]-((R)-2-methoxymethyl-pyrrolidin-1-yl)-methanone;
(6-Chloro-5-cyclopropylmethoxy-pyridin-2-yl)-(2,2-dimethyl-pyrrolidin-1-yl)-methanone;
(6-Cyclopropylmethoxy-5-trifluoromethoxy-pyridin-2-yl)-(4,4-dimethyl-oxazolidin-3-yl)-methanone;
(6-Chloro-5-cyclopropylmethoxy-pyridin-2-yl)-(4,4-dimethyl-oxazolidin-3-yl)-methanone;
6-Cyclopropylmethoxy-5-(3,3-difluoro-azetidin-1-yl)-pyridine-2-carboxylic acid (1-acetyl-piperidin-4-yl)-cyclopropyl-amide;
6-(Cyclopropylmethoxy)-5-(3,3-difluoroazetidin-1-yl)-N-formyl-N-methylpyridine-2-carboxamide;
6-Cyclopropylmethoxy-5-(3,3-difluoro-azetidin-1-yl)-pyridine-2-carboxylic acid methyl-phenyl-amide;
[6-Cyclopropylmethoxy-5-(3,3-difluoro-azetidin-1-yl)-pyridin-2-yl]-((S)-4,4-difluoro-2-hydroxymethyl-pyrrolidin-1-yl)-methanone;
6-Cyclopropylmethoxy-5-(3,3-difluoro-azetidin-1-yl)-pyridine-2-carboxylic acid (1,4-dimethyl-1H-pyrazol-3-yl)-methyl-amide;
[6-Cyclopropylmethoxy-5-(3,3-difluoro-azetidin-1-yl)-pyridin-2-yl]-(2,2-dimethyl-morpholin-4-yl)-methanone;
(R)-2-tert-Butyl-1-[6-cyclopropylmethoxy-5-(3,3-difluoro-azetidin-1-yl)-pyridine-2-carbonyl]-3-methyl-imidazolidin-4-one;
(4-Aza-spiro[2.4]hept-4-yl)-[6-cyclopropylmethoxy-5-(3,3-difluoro-azetidin-1-yl)-pyridin-2-yl]-methanone;
3-{1-[6-Cyclopropylmethoxy-5-(3,3-difluoro-azetidin-1-yl)-pyridine-2-carbonyl]-piperidin-4-yl}-5,5-dimethyl-pyrrolidin-2-one;
(1S,4R)-2-Aza-bicyclo[2.2.1]hept-2-yl-[6-cyclopropylmethoxy-5-(3,3-difluoro-azetidin-1-yl)-pyridin-2-yl]-methanone;
(S)-1-[6-Cyclopropylmethoxy-5-(3,3-difluoro-azetidin-1-yl)-pyridine-2-carbonyl]-4,4-difluoro-pyrrolidine-2-carboxylic acid amide;

[6-Cyclopropylmethoxy-5-(3,3-difluoro-azetidin-1-yl)-pyridin-2-yl]-(4-hydroxy-4-methyl-piperidin-1-yl)-methanone;
[6-Cyclopropylmethoxy-5-(3,3-difluoro-azetidin-1-yl)-pyridin-2-yl]-(1S,4S)-2-thia-5-aza-bicyclo[2.2.1]hept-5-yl-methanone;
((1S,4S)-5-Benzyl-2,5-diaza-bicyclo[2.2.1]hept-2-yl)-[6-cyclopropylmethoxy-5-(3,3-difluoro-azetidin-1-yl)-pyridin-2-yl]-methanone;
[6-Cyclopropylmethoxy-5-(3,3-difluoro-azetidin-1-yl)-pyridin-2-yl]-(2-methyl-3-phenyl-piperidin-1-yl)-methanone;
[6-Cyclopropylmethoxy-5-(3,3-difluoro-azetidin-1-yl)-pyridin-2-yl]-(1S,4S)-2-oxa-5-aza-bicyclo[2.2.1]hept-5-yl-methanone;
[6-Cyclopropylmethoxy-5-(3,3-difluoro-azetidin-1-yl)-pyridin-2-yl]-(4-hydroxy-2,2-dimethyl-piperidin-1-yl)-methanone;
1-[6-Cyclopropylmethoxy-5-(3,3-difluoro-azetidin-1-yl)-pyridine-2-carbonyl]-2-phenylpiperidine-3-carboxylic acid ethyl ester;
(S)-1-(5-Cyclopropyl-6-cyclopropylmethoxy-pyridine-2-carbonyl)-4,4-difluoro-pyrrolidine-2-carboxylic acid amide;
(2S,4S)-1-(5-Cyclopropyl-6-cyclopropylmethoxy-pyridine-2-carbonyl)-4-fluoro-pyrrolidine-2-carboxylic acid amide;
[6-Cyclopropylmethoxy-5-(3,3-difluoro-azetidin-1-yl)-pyridin-2-yl]-(hexahydrofuro[2,3-c]pyrrol-5-yl)-methanone;
[6-Cyclopropylmethoxy-5-(3,3-difluoro-azetidin-1-yl)-pyridin-2-yl]-(2,2-dioxo-2λ6-thia-6-aza-spiro[3.3]hept-6-yl)-methanone;
6-Cyclopropylmethoxy-5-(3,3-difluoro-azetidin-1-yl)-pyridine-2-carboxylic acid tert-butyl-(2-carbamoyl-ethyl)-amide;
(S)-1-(5-Cyclopropyl-6-cyclopropylmethoxy-pyridine-2-carbonyl)-pyrrolidine-2-carboxylic acid amide;
1-[6-Cyclopropylmethoxy-5-(3,3-difluoro-azetidin-1-yl)-pyridine-2-carbonyl]-1,8-diaza-spiro[4.5]decane-8-carboxylic acid tert-butyl ester;
(S)-1-{5-Cyclopropyl-6-[(R,S)-1-(tetrahydro-furan-2-yl)methoxy]-pyridine-2-carbonyl}-4,4-difluoro-pyrrolidine-2-carboxylic acid amide;
(S)-1-[5-Cyclopropyl-6-(4-fluoro-benzyl)-pyridine-2-carbonyl]-4,4-difluoro-pyrrolidine-2-carboxylic acid amide;
(+)-1-[6-Cyclopropylmethoxy-5-(3,3-difluoro-azetidin-1-yl)-pyridine-2-carbonyl]-4,4-dimethyl-pyrrolidine-2-carboxylic acid amide;
(−)-1-[6-Cyclopropylmethoxy-5-(3,3-difluoro-azetidin-1-yl)-pyridine-2-carbonyl]-4,4-dimethyl-pyrrolidine-2-carboxylic acid amide;
(2S,4S)-1-[6-Cyclopropylmethoxy-5-(3,3-difluoro-azetidin-1-yl)-pyridine-2-carbonyl]-4-hydroxy-pyrrolidine-2-carboxylic acid amide;
(2S,4S)-1-[6-Cyclopropylmethoxy-5-(3,3-difluoro-azetidin-1-yl)-pyridine-2-carbonyl]-4-fluoro-pyrrolidine-2-carboxylic acid amide;
6-Cyclopropylmethoxy-5-(3,3-difluoro-azetidin-1-yl)-pyridine-2-carboxylic acid cyclopropyl-(5-methyl-[1,3,4]oxadiazol-2-ylmethyl)-amide;
[6-Cyclopropylmethoxy-5-(3,3-difluoro-azetidin-1-yl)-pyridin-2-yl]-(3-hydroxy-1-oxa-7-aza-spiro[4.4]non-7-yl)-methanone;
[6-Cyclopropylmethoxy-5-(3,3-difluoro-azetidin-1-yl)-pyridin-2-yl]-(7-hydroxy-5-oxa-2-aza-spiro[3.4]oct-2-yl)-methanone;
[5-Cyclopropyl-6-(2,2,3,3,3-pentafluoro-propoxy)-pyridin-2-yl]-(2,2-dimethyl-pyrrolidin-1-yl)-methanone;
[6-Cyclopropylmethoxy-5-(3,3-difluoro-azetidin-1-yl)-pyridin-2-yl]-(1S,5R)-8-oxa-3-aza-bicyclo[3.2.1]oct-3-yl-methanone;
[6-Cyclopropylmethoxy-5-(3,3-difluoro-azetidin-1-yl)-pyridin-2-yl]-(1R,5S)-3-oxa-8-aza-bicyclo[3.2.1]oct-8-yl-methanone;
(R)-1-[5-Cyclopropyl-6-(2,2,3,3,3-pentafluoro-propoxy)-pyridine-2-carbonyl]-4,4-difluoro-pyrrolidine-2-carboxylic acid amide;
1-(5-Cyclopropyl-6-cyclopropylmethoxy-pyridine-2-carbonyl)-piperidine-2-carboxylic acid amide;
4-(5-Cyclopropyl-6-cyclopropylmethoxy-pyridine-2-carbonyl)-thiomorpholine-3-carboxylic acid amide;
1-(5-Cyclopropyl-6-cyclopropylmethoxy-pyridine-2-carbonyl)-4,4-dimethyl-pyrrolidine-2-carboxylic acid amide;
(+)-1-(5-Cyclopropyl-6-cyclopropylmethoxy-pyridine-2-carbonyl)-piperidine-2-carboxylic acid amide;
(−)-1-(5-Cyclopropyl-6-cyclopropylmethoxy-pyridine-2-carbonyl)-piperidine-2-carboxylic acid amide;
(−)-4-(5-Cyclopropyl-6-cyclopropylmethoxy-pyridine-2-carbonyl)-thiomorpholine-3-carboxylic acid amide;
(+)-1-(5-Cyclopropyl-6-cyclopropylmethoxy-pyridine-2-carbonyl)-4,4-dimethyl-pyrrolidine-2-carboxylic acid amide;
(−)-1-(5-Cyclopropyl-6-cyclopropylmethoxy-pyridine-2-carbonyl)-4,4-dimethyl-pyrrolidine-2-carboxylic acid amide;
3-(5-Cyclopropyl-6-cyclopropylmethoxy-pyridine-2-carbonyl)-thiazolidine-4-carboxylic acid amide;
(−)-3-(5-Cyclopropyl-6-cyclopropylmethoxy-pyridine-2-carbonyl)-thiazolidine-4-carboxylic acid amide;
1-[6-Cyclopropylmethoxy-5-(3,3-difluoro-azetidin-1-yl)-pyridine-2-carbonyl]-4,4-dimethyl-pyrrolidine-2-carboxylic acid amide;
[6-Cyclopropylmethoxy-5-(3,3-difluoro-azetidin-1-yl)-pyridin-2-yl]-(5-oxa-2-aza-spiro[3.4]oct-2-yl)-methanone;
[6-Cyclopropylmethoxy-5-(3,3-difluoro-azetidin-1-yl)-pyridin-2-yl]-(1-oxa-7-aza-spiro[4.4]non-7-yl)-methanone;
(5-Aza-spiro[3.4]oct-5-yl)-[6-cyclopropylmethoxy-5-(3,3-difluoro-azetidin-1-yl)-pyridin-2-yl]-methanone;
[6-Cyclopropylmethoxy-5-(3,3-difluoro-azetidin-1-yl)-pyridin-2-yl]-(3,3-difluoro-azetidin-1-yl)-methanone;
[6-Cyclopropylmethoxy-5-(3,3-difluoro-azetidin-1-yl)-pyridin-2-yl]-(1,1-difluoro-5-aza-spiro[2.4]hept-5-yl)-methanone;
(5-Aza-spiro[2.4]hept-5-yl)-[6-cyclopropylmethoxy-5-(3,3-difluoro-azetidin-1-yl)-pyridin-2-yl]-methanone;
6-Cyclopropylmethoxy-5-(3,3-difluoro-azetidin-1-yl)-pyridine-2-carboxylic acid cyclopropylmethyl-methyl-amide;
[6-Cyclopropylmethoxy-5-(3,3-difluoro-azetidin-1-yl)-pyridin-2-yl]-(4-cyclopropylmethyl-piperazin-1-yl)-methanone;
3-[6-Cyclopropylmethoxy-5-(3,3-difluoro-azetidin-1-yl)-pyridine-2-carbonyl]-3-aza-bicyclo[3.1.0]hexane-6-carboxylic acid ethyl ester;
1-[6-Cyclopropylmethoxy-5-(3,3-difluoro-azetidin-1-yl)-pyridine-2-carbonyl]-pyrrolidine-2-carboxylic acid methyl ester;
4-[6-Cyclopropylmethoxy-5-(3,3-difluoro-azetidin-1-yl)-pyridine-2-carbonyl]-piperazine-1-carboxylic acid benzyl ester;
3-[6-Cyclopropylmethoxy-5-(3,3-difluoro-azetidin-1-yl)-pyridine-2-carbonyl]-3-aza-bicyclo[3.1.0]hexane-6-carboxylic acid;
1-[5-Cyclopropyl-6-(4-fluoro-benzyl)-pyridine-2-carbonyl]-1,8-diaza-spiro[4.5]decane-8-carboxylic acid tert-butyl ester;

(−)-3-[6-Cyclopropylmethoxy-5-(3,3-difluoro-azetidin-1-yl)-pyridine-2-carbonyl]-thiazolidine-4-carboxylic acid amide;
[5-Cyclopropyl-6-(4-fluoro-benzyl)-pyridin-2-yl]-(1,8-diaza-spiro[4.5]dec-1-yl)-methanone;
1-[6-Cyclopropylmethoxy-5-(3,3-difluoro-azetidin-1-yl)-pyridine-2-carbonyl]-pyrrolidine-2-carboxylic acid amide;
(−)-3-(5-Cyclopropyl-6-cyclopropylmethoxy-pyridine-2-carbonyl)-1,1-dioxo-1λ6-thiazolidine-4-carboxylic acid amide;
(1S,4R)-3-(5-Cyclopropyl-6-cyclopropylmethoxy-pyridine-2-carbonyl)-1-oxo-1λ4-thiazolidine-4-carboxylic acid amide;
(1R,4S)-3-(5-Cyclopropyl-6-cyclopropylmethoxy-pyridine-2-carbonyl)-1-oxo-1λ4-thiazolidine-4-carboxylic acid amide;
(+)-3-(5-Cyclopropyl-6-cyclopropylmethoxy-pyridine-2-carbonyl)-1,1-dioxo-1λ6-thiazolidine-4-carboxylic acid amide;
[6-Cyclopropylmethoxy-5-(3,3-difluoro-azetidin-1-yl)-pyridin-2-yl]-(3,3,4,4-tetrafluoro-pyrrolidin-1-yl)-methanone;
[6-Cyclopropylmethoxy-5-(3,3-difluoro-azetidin-1-yl)-pyridin-2-yl]-(2,6-dimethyl-morpholin-4-yl)-methanone;
(R)-3-[6-Cyclopropylmethoxy-5-(3,3-difluoro-azetidin-1-yl)-pyridine-2-carbonyl]-5,5-dimethyl-thiazolidine-4-carboxylic acid amide;
(S)-1-[6-Cyclopropylmethoxy-5-(3,3-difluoro-azetidin-1-yl)-pyridine-2-carbonyl]-5,5-dimethyl-pyrrolidine-2-carboxylic acid amide; and
3-[6-Cyclopropylmethoxy-5-(3,3-difluoro-azetidin-1-yl)-pyridine-2-carbonyl]-thiazolidine-4-carboxylic acid amide.

The invention further relates in particular to a compound selected from:
(2S,4R)-1-[5-Cyclopropyl-6-(cyclopropylmethoxy)pyridine-2-carbonyl]-4-fluoropyrrolidine-2-carboxamide;
3-[6-(Cyclopropylmethoxy)-5-(3,3-difluoroazetidin-1-yl)pyridine-2-carbonyl]-1-oxo-1,3-thiazolidine-4-carboxamide;
3-[6-(Cyclopropylmethoxy)-5-(3,3-difluoroazetidin-1-yl)pyridine-2-carbonyl]-1,1-dioxo-1,3-thiazolidine-4-carboxamide;
(2S,4R)-1-[6-(Cyclopropylmethoxy)-5-(3,3-difluoroazetidin-1-yl)pyridine-2-carbonyl]-4-fluoropyrrolidine-2-carboxamide;
(−)-3-[6-(Cyclopropylmethoxy)-5-(3,3-difluoroazetidin-1-yl)pyridine-2-carbonyl]-1,1-dioxo-1,3-thiazolidine-4-carboxamide;
3-[6-(Cyclopropylmethoxy)-5-(3-methoxyazetidin-1-yl)pyridine-2-carbonyl]-1,1-dioxo-1,3-thiazolidine-4-carboxamide;
(2S)-1-[6-(Cyclopropylmethoxy)-5-(1-hydroxycyclobutyl)pyridine-2-carbonyl]-4,4-difluoropyrrolidine-2-carboxamide;
(2S)-1-[6-(Cyclopropylmethoxy)-5-(1-fluorocyclobutyl)pyridine-2-carbonyl]-4,4-difluoropyrrolidine-2-carboxamide;
3-[6-(Cyclopropylmethoxy)-5-(1-hydroxycyclobutyl)pyridine-2-carbonyl]-1,1-dioxo-1,3-thiazolidine-4-carboxamide;
(2S)-1-[6-(Cyclopropylmethoxy)-5-(3,3-difluoroazetidin-1-yl)pyridine-2-carbonyl]-4-hydroxy-4-methylpyrrolidine-2-carboxamide;
3-[6-(Cyclopropylmethoxy)-5-(1-fluorocyclobutyl)pyridine-2-carbonyl]-1,1-dioxo-1,3-thiazolidine-4-carboxamide;
(2S)-1-[6-(Cyclopropylmethoxy)-5-(3-fluorooxetan-3-yl)pyridine-2-carbonyl]-4,4-difluoropyrrolidine-2-carboxamide;
5-[6-(Cyclopropylmethoxy)-5-(3,3-difluoroazetidin-1-yl)pyridine-2-carbonyl]-5-azaspiro[2.4]heptane-6-carboxamide;
[6-(Cyclopropylmethoxy)-5-(3,3-difluoroazetidin-1-yl)pyridin-2-yl]-[3-(2,2,2-trifluoro-1-hydroxyethyl)pyrrolidin-1-yl]methanone;
[6-(Cyclopropylmethoxy)-5-(3,3-difluoroazetidin-1-yl)pyridin-2-yl]-[3-(hydroxymethyl)-3-(trifluoromethyl)pyrrolidin-1-yl]methanone;
[6-(Cyclopropylmethoxy)-5-(3,3-difluoroazetidin-1-yl)pyridin-2-yl]-[3-hydroxy-3-(trifluoromethyl)pyrrolidin-1-yl]methanone;
[6-(Cyclopropylmethoxy)-5-(3,3-difluoroazetidin-1-yl)pyridin-2-yl]-[3-hydroxy-3-(trifluoromethyl)azetidin-1-yl]methanone;
(+)-(2S)-1-[6-(Cyclopropylmethoxy)-5-(3,3-difluoroazetidin-1-yl)pyridine-2-carbonyl]-4-hydroxy-4-methylpyrrolidine-2-carboxamide;
[5-Cyclopropyl-6-(cyclopropylmethoxy)pyridin-2-yl]-[3-(2,2,2-trifluoro-1-hydroxyethyl)pyrrolidin-1-yl]methanone;
[5-Cyclopropyl-6-(cyclopropylmethoxy)pyridin-2-yl]-[3-(hydroxymethyl)-3-(trifluoromethyl)pyrrolidin-1-yl]methanone;
[5-Cyclopropyl-6-(cyclopropylmethoxy)pyridin-2-yl]-[3-hydroxy-3-(trifluoromethyl)pyrrolidin-1-yl]methanone;
[5-Cyclopropyl-6-(cyclopropylmethoxy)pyridin-2-yl]-[3-hydroxy-3-(trifluoromethyl)azetidin-1-yl]methanone;
(6S)-5-[6-(Cyclopropylmethoxy)-5-(3,3-difluoroazetidin-1-yl)pyridine-2-carbonyl]-5-azaspiro[2.4]heptane-6-carboxamide;
[(3aR,6aS)-1,3,3a,4,6,6a-Hexahydrofuro[3,4-c]pyrrol-5-yl]-[6-(cyclopropylmethoxy)-5-(3,3-difluoroazetidin-1-yl)pyridin-2-yl]methanone;
(2S)-1-[5-(3,3-Difluoroazetidin-1-yl)-6-(2-fluoroethoxy)pyridine-2-carbonyl]-4,4-difluoro-pyrrolidine-2-carboxamide;
[6-(Cyclopropylmethoxy)-5-(3,3-difluoroazetidin-1-yl)-2-pyridyl]-[3-fluoro-3-(hydroxymethyl)azetidin-1-yl]methanone;
[6-(Cyclopropylmethoxy)-5-(3,3-difluoroazetidin-1-yl)-2-pyridyl]-(3-fluoro-3-methyl-azetidin-1-yl)methanone;
(3-Cyclopropyl-3-fluoroazetidin-1-yl)-[6-(cyclopropylmethoxy)-5-(3,3-difluoroazetidin-1-yl)pyridin-2-yl]methanone;
(−)-5-[6-(Cyclopropylmethoxy)-5-(3,3-difluoroazetidin-1-yl)pyridine-2-carbonyl]-5-azaspiro[2.4]heptane-4-carboxamide; and
(+)-5-[6-(Cyclopropylmethoxy)-5-(3,3-difluoroazetidin-1-yl)pyridine-2-carbonyl]-5-azaspiro[2.4]heptane-4-carboxamide.

The invention also relates in particular to a compound selected from:
6-Cyclopropylmethoxy-5-(3,3-difluoro-azetidin-1-yl)-pyridine-2-carboxylic acid tert-butyl-methyl-amide;
5-Cyclopropyl-6-(tetrahydro-furan-2-ylmethoxy)-pyridine-2-carboxylic acid tert-butyl-methyl-amide;
[6-Cyclopropylmethoxy-5-(3,3-difluoro-azetidin-1-yl)-pyridin-2-yl]-(4,4-dimethyl-oxazolidin-3-yl)-methanone;
6-Cyclopropylmethoxy-5-(3,3-difluoro-azetidin-1-yl)-pyridine-2-carboxylic acid methyl-(1-trifluoromethyl-cyclopropyl)-amide;
[6-Cyclopropylmethoxy-5-(3,3-difluoro-azetidin-1-yl)-pyridin-2-yl]-(3,3-dimethyl-morpholin-4-yl)-methanone;
[5-Cyclopropyl-6-(2-methyl-propane-1-sulfonyl)-pyridin-2-yl]-(2,2-dimethyl-pyrrolidin-1-yl)-methanone;

[5-Cyclopropyl-6-(4-fluoro-benzyl)-pyridin-2-yl]-(4,4-dimethyl-oxazolidin-3-yl)-methanone;
[6-Cyclopropylmethoxy-5-(3,3-difluoro-azetidin-1-yl)-pyridin-2-yl]-((1S,5R)-1,3,3-trimethyl-6-aza-bicyclo[3.2.1]oct-6-yl)-methanone;
[6-Cyclopropylmethoxy-5-(3,3-difluoro-azetidin-1-yl)-pyridin-2-yl]-((S)-4,4-difluoro-2-hydroxymethyl-pyrrolidin-1-yl)-methanone;
(4-Aza-spiro[2.4]hept-4-yl)-[6-cyclopropylmethoxy-5-(3,3-difluoro-azetidin-1-yl)-pyridin-2-yl]-methanone;
[6-Cyclopropylmethoxy-5-(3,3-difluoro-azetidin-1-yl)-pyridin-2-yl]-(1S,4S)-2-thia-5-aza-bicyclo[2.2.1]hept-5-yl-methanone;
(S)-1-(5-Cyclopropyl-6-cyclopropylmethoxy-pyridine-2-carbonyl)-4,4-difluoro-pyrrolidine-2-carboxylic acid amide;
(−)-1-[6-Cyclopropylmethoxy-5-(3,3-difluoro-azetidin-1-yl)-pyridine-2-carbonyl]-4,4-dimethyl-pyrrolidine-2-carboxylic acid amide;
(5-Aza-spiro[3.4]oct-5-yl)-[6-cyclopropylmethoxy-5-(3,3-difluoro-azetidin-1-yl)-pyridin-2-yl]-methanone;
[6-Cyclopropylmethoxy-5-(3,3-difluoro-azetidin-1-yl)-pyridin-2-yl]-(1,1-difluoro-5-aza-spiro[2.4]hept-5-yl)-methanone;
(5-Aza-spiro[2.4]hept-5-yl)-[6-cyclopropylmethoxy-5-(3,3-difluoro-azetidin-1-yl)-pyridin-2-yl]-methanone;
1-[5-Cyclopropyl-6-(4-fluoro-benzyl)-pyridine-2-carbonyl]-1,8-diaza-spiro[4.5]decane-8-carboxylic acid tert-butyl ester; and
(−)-3-(5-Cyclopropyl-6-cyclopropylmethoxy-pyridine-2-carbonyl)-1,1-dioxo-1λ6-thiazolidine-4-carboxylic acid amide.

The invention also relates in particular to a compound selected from:
3-[6-(Cyclopropylmethoxy)-5-(3,3-difluoroazetidin-1-yl)pyridine-2-carbonyl]-1,1-dioxo-1,3-thiazolidine-4-carboxamide;
(−)-3-[6-(Cyclopropylmethoxy)-5-(3,3-difluoroazetidin-1-yl)pyridine-2-carbonyl]-1,1-dioxo-1,3-thiazolidine-4-carboxamide;
(2S)-1-[6-(Cyclopropylmethoxy)-5-(1-hydroxycyclobutyl)pyridine-2-carbonyl]-4,4-difluoropyrrolidine-2-carboxamide;
(2S)-1-[6-(Cyclopropylmethoxy)-5-(1-fluorocyclobutyl)pyridine-2-carbonyl]-4,4-difluoropyrrolidine-2-carboxamide;
(2S)-1-[6-(Cyclopropylmethoxy)-5-(3,3-difluoroazetidin-1-yl)pyridine-2-carbonyl]-4-hydroxy-4-methylpyrrolidine-2-carboxamide;
3-[6-(Cyclopropylmethoxy)-5-(1-fluorocyclobutyl)pyridine-2-carbonyl]-1,1-dioxo-1,3-thiazolidine-4-carboxamide; and
5-[6-(Cyclopropylmethoxy)-5-(3,3-difluoroazetidin-1-yl)pyridine-2-carbonyl]-5-azaspiro[2.4]heptane-6-carboxamide.

(S)-1-[6-Cyclopropylmethoxy-5-(3,3-difluoro-azetidin-1-yl)-pyridine-2-carbonyl]-4,4-difluoro-pyrrolidine-2-carboxylic acid amide is a particular compound of formula (I).

The compounds of the present invention can be prepared, for example, by the general synthetic procedures described below.

In the following schemes and description, $R^1$ to $R^4$ have, unless otherwise indicated, the meaning of $R^1$ to $R^4$ as defined above.

Following the procedure according to scheme 1, compound AA (X=Cl, Br, I, trifluoromethanesulfonate; R'=H, methyl, ethyl, isopropyl, tert. butyl or another suitable protecting group described for example in T. W. Greene et al., Protective Groups in Organic Chemistry, John Wiley and Sons Inc. New York 1999, 3$^{rd}$ edition) can be used as starting material. AA is either commercially available, described in the literature, can be synthesized by a person skilled in the art, can be synthesized as described in schemes 3 and 5 or as described in the experimental part.

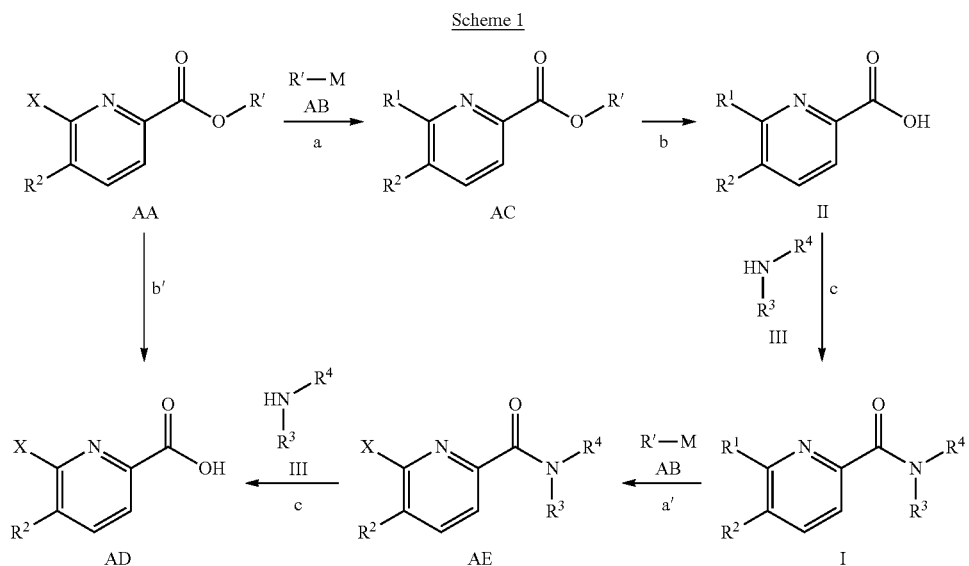

Scheme 1

Compound AC can be prepared from AA by coupling a suitably substituted aryl, heteroaryl or alkenyl metal species of formula AB (M is e.g. a boronic acid $B(OH)_2$ or a boronic acid pinacol ester) (step a), particularly an arylboronic acid or arylboronic acid ester in the presence of a suitable catalyst, in particular a palladium catalyst and more particularly palladium(II)acetate/triphenylphosphine mixtures or palladium (II)chloride-dppf (1,1'-bis(diphenylphosphino)ferrocene) complexes and a base such as triethylamine, sodium carbonate or potassium phosphate in an inert solvent such as dimethylformamide, toluene, tetrahydrofuran, acetonitrile and dimethoxyethane. Optionally, alkenyl containing $R^1$ residues can be transformed to the corresponding alkyl congeners AC using conditions described in the literature such as e.g. via a hydrogenation reaction using hydrogen gas in the presence of a catalyst such as palladium on carbon in a solvent such as ethanol or ethyl acetate particularly at ambient temperature.

The saponification of the ester of general formula AC(R'≠H) by methods well known to the ones skilled in the art—using e.g. aqueous LiOH, NaOH or KOH in tetrahydrofuran/ethanol or another suitable solvent at temperatures between 0° C. and the reflux temperature of the solvent employed—leads to an acid of general formula II (step b).

Compound I can be prepared from II and the corresponding amine of formula III by suitable amide bond forming reactions (step c). These reactions are known in the art. For example coupling reagents like N,N'-carbonyl-diimidazole (CDI), N,N'-dicyclohexylcarbodiimide (DCC), 1-(3-dimethylaminopropyl)-3-ethylcarbodiimide hydrochloride (EDCI), 1-[bis(dimethylamino)-methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU), and O-benzotriazole-N,N,N',N'-tetramethyl-uronium-hexafluoro-phosphate (HBTU) can be employed to affect such transformation. A convenient method is to use for example HBTU and a base, for example N-methylmorpholine in an inert solvent such as for example dimethylformamide at room temperature.

Alternatively esters of general formula AA (R'≠H) can be saponified by methods well known to the ones skilled in the art—using e.g. aqueous LiOH, NaOH or KOH in tetrahydrofuran/ethanol or another suitable solvent at temperatures between 0° C. and the reflux temperature of the solvent employed—to give acids of general formula AD (step b').

Compounds AE can be prepared from AD and the corresponding amine of formula III by suitable amide bond forming reactions (step c'). These reactions are known in the art. For example coupling reagents like N,N'-carbonyl-diimidazole (CDI), N,N'-dicyclohexylcarbodiimide (DCC), 1-(3-dimethylaminopropyl)-3-ethylcarbodiimide hydrochloride (EDCI), 1-[bis(dimethylamino)-methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU), and O-benzotriazole-N,N,N',N'-tetramethyl-uronium-hexafluoro-phosphate (HBTU) can be employed to affect such transformation. A convenient method is to use for example HBTU and a base, for example N-methylmorpholine in an inert solvent such as for example dimethylformamide at room temperature.

Compound I can be prepared from AE by coupling a suitably substituted aryl, heteroaryl or alkenyl metal species of formula AB (M is e.g. a boronic acid $B(OH)_2$ or a boronic acid pinacol ester) (step a'), particularly an arylboronic acid or arylboronic acid ester in the presence of a suitable catalyst, in particular a palladium catalyst and more particularly palladium(II)acetate/triphenylphosphine mixtures or palladium (II)chloride-dppf (1,1'-bis(diphenylphosphino)ferrocene) complexes and a base such as triethylamine, sodium carbonate or potassium phosphate in an inert solvent such as dimethylformamide, toluene, tetrahydrofuran, acetonitrile and dimethoxyethane. Optionally, alkenyl containing $R^1$ residues can be transformed to the corresponding alkyl congeners AE using conditions described in the literature such as e.g. via a hydrogenation reaction using hydrogen gas in the presence of a catalyst such as palladium on carbon in a solvent such as ethanol or ethyl acetate particularly at ambient temperature.

If one of $R^3$ and $R^4$ in amides AE or I is equal to hydrogen, alkylation towards the corresponding tertiary amides AE or I can be accomplished e.g. by conversion of secondary amide AE or I to its conjugated base by treatment with e.g. sodium hydride in a solvent such as DMF and subsequent alkylation e.g. with an alkyl halide preferentially at ambient temperature, or by applying any other suitable method known to a person skilled in the art.

Amines III are either commercially available, described in the literature, can be synthesized by a person skilled in the art or as described in the experimental part.

If one of the starting materials, compounds of formulae AA, AB, AE (with one of $R^3$ and $R^4$ being equal to hydrogen) III or I (with one of $R^3$ and $R^4$ being equal to hydrogen) contains one or more functional groups which are not stable or are reactive under the reaction conditions of one or more reaction steps, appropriate protecting groups (P) (as described e.g. in T. W. Greene et al., Protective Groups in Organic Chemistry, John Wiley and Sons Inc. New York 1999, 3$^{rd}$ edition) can be introduced before the critical step applying methods well known in the art. Such protecting groups can be removed at a later stage of the synthesis using standard methods known in the art.

If one or more compounds of formulae AA to AE, II or III contain chiral centers, picolines of formula I can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

Following the procedure according to scheme 2, compound BA (R'=H, methyl, ethyl, isopropyl, tert. butyl or another suitable protecting group described for example in T. W. Greene et al., Protective Groups in Organic Chemistry, John Wiley and Sons Inc. New York 1999, 3$^{rd}$ edition) can be used as starting material. BA is either commercially available, described in the literature or can be synthesized by a person skilled in the art.

Scheme 2

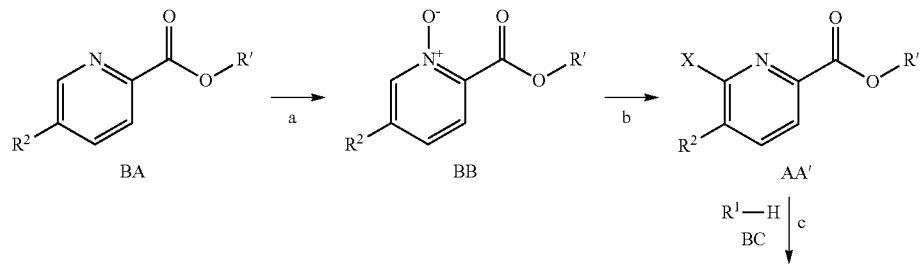

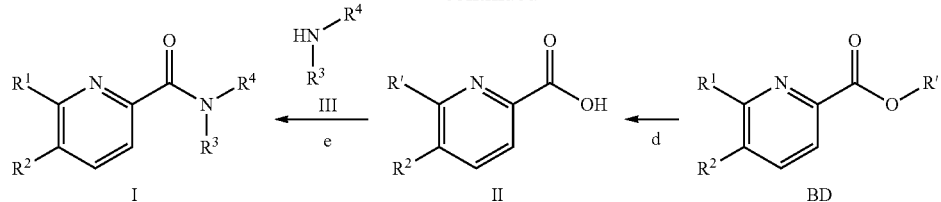

Compound BB can be prepared from BA by oxidation with a suitable oxidizing reagent under conditions known to a person skilled in the art (step a), e.g. by treatment with 3-chloro perbenzoic acid in dichloromethane at ambient temperature.

Conversion of compound BB to 6-chloro or 6-bromo-picoline AA' (X=Cl, Br) can be achieved e.g. by treatment with phosphoryl trichloride or tribromide either without an additional solvent or in a suitable solvent such as chloroform at temperatures between 20° C. and the boiling point of the solvent, or by using other conditions known in the literature (step b).

6-Chloro- or bromo-picoline AA' (X=Cl, Br) can be transformed to compound BD by reaction with a suitably substituted primary or secondary alcohol BC in the presence of a base, for example sodium hydride, with or without an inert solvent, for example dimethylformamide, at temperatures ranging from room temperature to the reflux temperature of the solvent, particularly at room temperature (step c).

Compound BD can be further elaborated to compound I by: i) saponification (for compounds BD with R'≠H) as described in step b of scheme 1 (step d); ii) amide bond formation as described in step c of scheme 1 (step e).

Alternatively, compound AA' (R'=methyl, ethyl, isopropyl, tert. butyl or another suitable protecting group described for example in T. W. Greene et al., Protective Groups in Organic Chemistry, John Wiley and Sons Inc. New York 1999, 3$^{rd}$ edition) can be: i) converted into its acid congener AA' (R'=H) as described in step b of scheme 1; ii) transformed into the corresponding amide by treatment with amine III as described in step c of scheme 1; and iii) reacted with alcohol BC as described in step c to arrive at compound I.

If one of $R^3$ and $R^4$ in amide I is equal to hydrogen, alkylation towards the corresponding tertiary amide I can be accomplished e.g. by conversion of secondary amide I to its conjugated base by treatment with e.g. sodium hydride in a solvent such as DMF and subsequent alkylation e.g. with an alkyl halide preferentially at ambient temperature, or by applying any other suitable method known to a person skilled in the art.

If one of the starting materials, compounds of formulae BA, BC, III or I (with one of $R^3$ and $R^4$ being equal to hydrogen), contains one or more functional groups which are not stable or are reactive under the reaction conditions of one or more reaction steps, appropriate protecting groups (P) (as described e.g. in T. W. Greene et al., Protective Groups in Organic Chemistry, John Wiley and Sons Inc. New York 1999, 3$^{rd}$ edition) can be introduced before the critical step applying methods well known in the art. Such protecting groups can be removed at a later stage of the synthesis using standard methods known in the art.

If one or more compounds of formulae BA to BD, AA', II or III contain chiral centers, picolines of formula I can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

Following the procedure according to scheme 3, compound CA (R'=H, methyl, ethyl, isopropyl, tert. butyl or another suitable protecting group described for example in T. W. Greene et al., Protective Groups in Organic Chemistry, John Wiley and Sons Inc. New York 1999, 3$^{rd}$ edition) can be used as starting material. CA is either commercially available (e.g. for R'=methyl: 5-bromo-6-chloro-pyridine-2-carboxylic acid methyl ester CAN 1214353-79-3), described in the literature or can be synthesized by a person skilled in the art.

Scheme 3

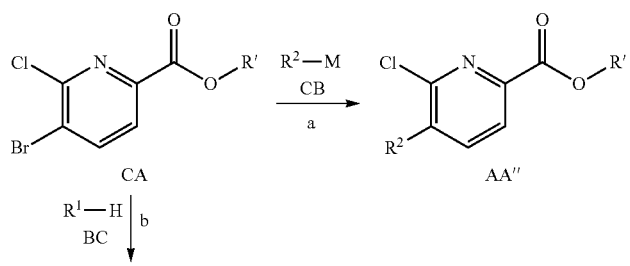

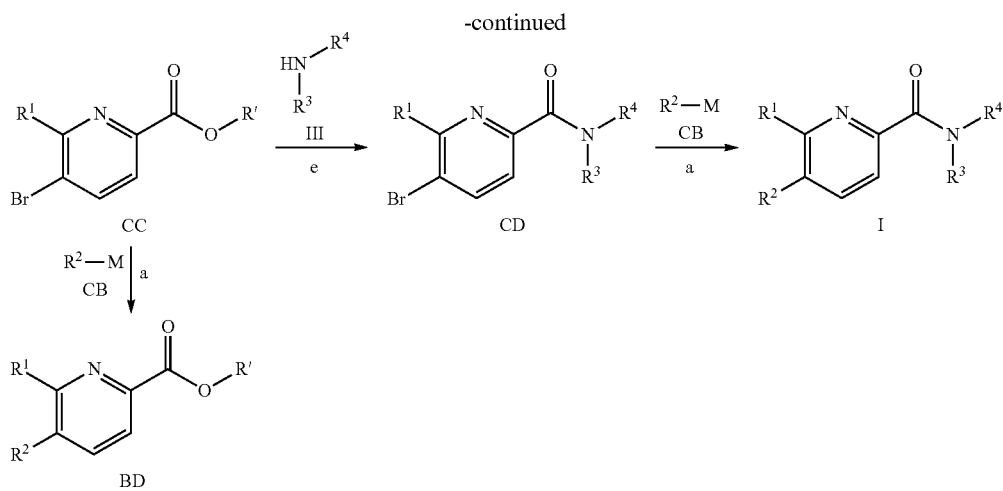

Compound AA" can be prepared from CA by coupling a suitably substituted aryl, heteroaryl or alkenyl metal species of formula CB (M is e.g. a trifluoroborate $[BF_3]^-K^+$, a boronic acid $B(OH)_2$ or a boronic acid pinacol ester) (step a), e.g. an organotrifluoroborate potassium salt in the presence of a palladium catalyst such as palladium(II)acetate/butyl-1-adamantylphosphine and a base such as cesium carbonate in an inert solvent such as toluene at temperatures between 50° C. and the boiling temperature of the solvent, or an arylboronic acid or arylboronic acid ester in the presence of a suitable catalyst, in particular a palladium catalyst and more particularly palladium(II)acetate/triphenylphosphine mixtures or palladium(II)chloride-dppf (1,1'-bis(diphenylphosphino)ferrocene) complexes and a base such as triethylamine, sodium carbonate or potassium phosphate in an inert solvent such as dimethylformamide, toluene, tetrahydrofuran, acetonitrile or dimethoxyethane. Optionally, compound CB can also be an amine or amide which is coupled to CA by methods well known to a person skilled in the art, e.g. using a palladium catalyst such as tris(dibenzylideneacetone)dipalladium/dimethylbisdiphenyl-phosphinoxanthene and a base such as cesium carbonate in a solvent such as 1,4-dioxane, preferentially at the boiling point of the solvent. Alternatively, compound CB can also be a sulfonamide which undergoes a copper(I) mediated reaction with CA to form AA" following procedures described in the literature, e.g. using copper(I) iodide and 1,3-di(pyridin-2-yl)propane-1,3-dione in the presence of a base such as potassium carbonate in a solvent such as dimethylformamide at elevated temperatures preferentially at the boiling point of the solvent. Optionally, alkenyl containing $R^2$ residues can be transformed to the corresponding alkyl congeners AA" using conditions described in the literature such as e.g. a hydrogenation reaction using hydrogen gas in the presence of a catalyst such as palladium on carbon in a solvent such as ethanol or ethyl acetate particularly at ambient temperature.

Compound AA" can be further elaborated to compound I by: i) reaction with compound BC to form compound BD as described in step c of scheme 2; ii) saponification as described in step b of scheme 1; and iii) amide bond formation as described in step c of scheme 1.

Furthermore, compound CA can be converted into compound CC by treatment with compound BC as described in step c of scheme 2 (step b).

Subsequent transformation of compound CC into compound BD can be achieved as discussed for the conversion of CA into AA" (step a).

Compound BD can be further elaborated to compound I by: i) saponification as described in step b of scheme 1; ii) amide bond formation as described in step c of scheme 1.

Alternatively, compound CC(R'=methyl, ethyl, isopropyl, tert. butyl or another suitable protecting group described for example in T. W. Greene et al., Protective Groups in Organic Chemistry, John Wiley and Sons Inc. New York 1999, $3^{rd}$ edition) can be: i) converted into its acid congener CC(R'=H) as described in step b of scheme 1; ii) transformed into the corresponding amide CD by treatment with amine III as described in step c of scheme 1; and iii) reacted with CB as described in step a to arrive at compound I.

In addition, compounds of formula I with $R^1$ being an alkylsulfonyl residue can be synthesized using the following reaction sequence: i) Reaction of compound CA (e.g. for R'=H: 5-bromo-6-chloro-pyridine-2-carboxylic acid; CAN 959958-25-9) with a thiol BC to yield thioether CC, e.g. in the presence of a base such as cesium carbonate in a solvent such as DMSO, preferentially at temperatures between 100 and 150° C.; ii) conversion of thioethers CC($R^1$=S-Alkyl) to its corresponding sulfonyl congeners CC($R^1$=S(O)$_2$—Alkyl), e.g. by using an oxidizing reagent such as 3-chlorobenzoperoxoic acid in a solvent such as dichloromethane, preferentially at ambient temperature; iii) transformation of sulfonyl derivatives CC into compound BD as discussed for the conversion of CA into AA" (step a); and iv) further elaboration to sulfonyl derivative I via saponification as described in step b of scheme 1 followed by an amide bond formation as described in step c of scheme 1. Optionally, the row order of the reaction sequence can be interchanged.

Furthermore, compound I can also be synthesized applying the following reaction sequence: i) saponification of compound CA (R'=methyl, ethyl, isopropyl, tert. butyl or another suitable protecting group described for example in T. W. Greene et al., Protective Groups in Organic Chemistry, John Wiley and Sons Inc. New York 1999, $3^{rd}$ edition) to its acid congener CC(R'=H) as described in step b of scheme 1; ii) conversion to the corresponding amide by treatment with amine III as described in step c of scheme 1; iii) reaction with compound CB as described in step a; and iv) reaction with compound BC as described in step c. Optionally step iii) and step iv) can be interchanged.

If one of $R^3$ and $R^4$ in amides CD or I is equal to hydrogen, alkylation towards the corresponding tertiary amides CD or I can be accomplished e.g. by conversion of secondary amide CD or I to its conjugated base by treatment with e.g. sodium hydride in a solvent such as DMF and subsequent alkylation e.g. with an alkyl halide preferentially at ambient temperature, or by applying any other suitable method known to a person skilled in the art.

If one of the starting materials, compounds of formulae CA, CB, CD (with one of $R^3$ and $R^4$ being equal to hydrogen), BC, III or I (with one of $R^3$ and $R^4$ being equal to hydrogen) contains one or more functional groups which are not stable or are reactive under the reaction conditions of one or more reaction steps, appropriate protecting groups (P) (as described e.g. in T. W. Greene et al., Protective Groups in Organic Chemistry, John Wiley and Sons Inc. New York 1999, $3^{rd}$ edition) can be introduced before the critical step applying methods well known in the art. Such protecting groups can be removed at a later stage of the synthesis using standard methods known in the art.

If one or more compounds of formulae CA, CB, BC or III contain chiral centers, picolines of formula AA', BD and I can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

Following the procedure according to scheme 4, compound CC(R'=H, methyl, ethyl, isopropyl, tert. butyl or another suitable protecting group described for example in T. W. Greene et al., Protective Groups in Organic Chemistry, John Wiley and Sons Inc. New York 1999, $3^{rd}$ edition) can be used as starting material. CC is either commercially available, described in the literature, can be synthesized by methods described in scheme 3 or by other methods known to a person skilled in the art.

Scheme 4

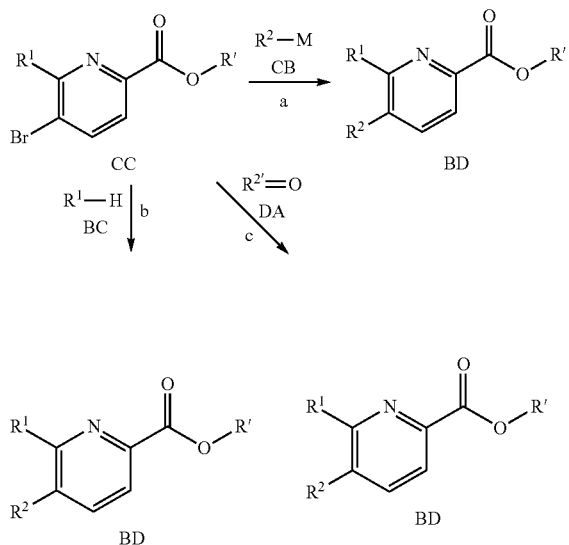

Compound BD can be prepared from CC by coupling a suitably substituted aryl, heteroaryl or alkenyl metal species of formula CB (M is e.g. a trifluoroborate $[BF_3]^-K^+$, a boronic acid $B(OH)_2$ or a boronic acid pinacol ester) (step a), e.g. an organotrifluoroborate potassium salt in the presence of a palladium catalyst such as palladium(II)acetate/butyl-1-adamantylphosphine and a base such as cesium carbonate in an inert solvent such as toluene at temperatures between 50° C. and the boiling temperature of the solvent, or an arylboronic acid or arylboronic acid ester in the presence of a suitable catalyst, in particular a palladium catalyst and more particularly palladium(II)acetate/triphenylphosphine mixtures or palladium(II)chloride-dppf (1,1'-bis(diphenylphosphino)ferrocene) complexes and a base such as triethylamine, sodium carbonate or potassium phosphate in an inert solvent such as dimethylformamide, toluene, tetrahydrofuran, acetonitrile and dimethoxyethane. Optionally, alkenyl containing $R^2$ residues can be transformed to the corresponding alkyl congeners BD using conditions described in the literature such as e.g. a hydrogenation reaction using hydrogen gas in the presence of a catalyst such as palladium on carbon in a solvent such as ethanol or ethyl acetate particularly at ambient temperature.

Alternatively, compound CC can be converted to amino derivatives BD by treatment with an amine BC applying methods well known in the art (step b), for example using a palladium promoted amination with palladium(II)acetate/2-(dicyclohexylphosphino) biphenyl in the presence of a base such as potassium carbonate in dioxane under reflux conditions or by using tris(dibenzylideneacetone)dipalladium/rac-BINAP (2,2'-bis(diphenylphosphino)-1,1'-binaphthyl) in the presence of a base such as cesium carbonate in toluene at 100° C.

Compound CC can furthermore be reacted with ketone DA ($R^{2'}$=alkyl, cycloalkyl, or oxyoxetanyl) to obtain compound BD following procedures known to a person skilled in the art, e.g.: i) treatment with n-butyl lithium in a solvent such as tetrahydrofuran at a temperature of –78° C.; ii) addition of a ketone DA or optionally another suitable electrophile at temperatures between –78° C. and ambient temperature (step c).

Compound BD can be further elaborated to compound I by: i) saponification as described in step b of scheme 1; ii) amide bond formation as described in step c of scheme 1.

If one of the starting materials, compounds of formulae CC, CB, BC or DA, contains one or more functional groups which are not stable or are reactive under the reaction conditions of one or more reaction steps, appropriate protecting groups (P) (as described e.g. in T. W. Greene et al., Protective Groups in Organic Chemistry, John Wiley and Sons Inc. New York 1999, $3^{rd}$ edition) can be introduced before the critical step applying methods well known in the art. Such protecting groups can be removed at a later stage of the synthesis using standard methods known in the art.

If one or more compounds of formulae CC, CB, BC or DA, contain chiral centers, picolines of formula BD can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbens or a chiral eluent.

Following the procedure according to scheme 5, compound GA (X=Cl, Br, I, trifluoromethanesulfonate; R'=H, methyl, ethyl, isopropyl, tert. butyl or another suitable protecting group described for example in T. W. Greene et al., Protective Groups in Organic Chemistry, John Wiley and Sons Inc. New York 1999, $3^{rd}$ edition) can be used as starting material. GA is either commercially available, described in the literature or can be synthesized by a person skilled in the art.

Scheme 5

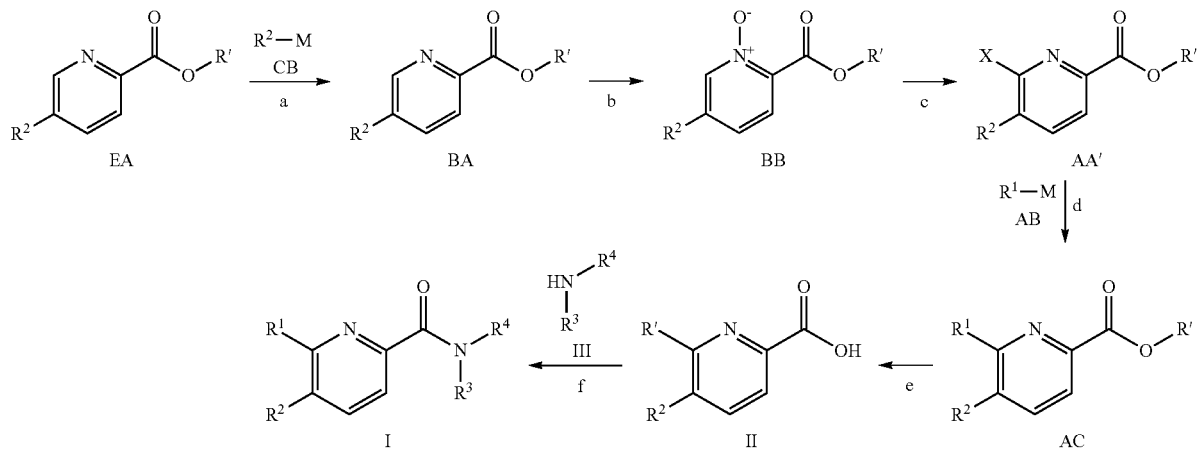

Compound BA can be prepared from EA by coupling a suitably substituted aryl, heteroaryl or alkenyl metal species of formula CB (M is e.g. a trifluoroborate $[BF_3]^-K^+$, a boronic acid $B(OH)_2$ or a boronic acid pinacol ester) (step a), e.g. an organotrifluoroborate potassium salt in the presence of a palladium catalyst such as palladium(II)acetate/butyl-1-adamantylphosphine and a base such as cesium carbonate in an inert solvent such as toluene at temperatures between 50° C. and the boiling temperature of the solvent, or an arylboronic acid or arylboronic acid ester in the presence of a suitable catalyst, in particular a palladium catalyst and more particularly palladium(II)acetate/triphenylphosphine mixtures or palladium(II)chloride-dppf (1,1'-bis(diphenylphosphino)ferrocene) complexes and a base such as triethylamine, sodium carbonate or potassium phosphate in an inert solvent such as dimethylformamide, toluene, tetrahydrofuran, acetonitrile and dimethoxyethane. Optionally, compound CB can also be an amine or amide which is coupled to EA by methods well known to a person skilled in the art, e.g. using a palladium catalyst such as tris(dibenzylideneacetone)dipalladium/dimethylbisdiphenyl-phosphinoxanthene and a base such as cesium carbonate in a solvent such as 1,4-dioxane preferentially at the boiling point of the solvent. Optionally, alkenyl containing $R^2$ residues can be transformed to the corresponding alkyl congeners BA using conditions described in the literature such as e.g. a hydrogenation reaction using hydrogen gas in the presence of a catalyst such as palladium on carbon in a solvent such as ethanol or ethyl acetate particularly at ambient temperature.

Compound BB can be prepared from BA by oxidation with a suitable oxidizing reagent as described in step a of scheme 2 (step b).

Conversion of compound BB to 6-chloro- or 6-bromopicoline AA' (X=Cl, Br) can be achieved as described in step b of scheme 2 (step c).

Compound AC can be prepared from AA' by coupling a suitably substituted aryl, heteroaryl or alkenyl metal species of formula AB (M is e.g. a boronic acid $B(OH)_2$ or a boronic acid pinacol ester) (step d), particularly an arylboronic acid or arylboronic acid ester in the presence of a suitable catalyst, in particular a palladium catalyst and more particularly palladium(II)acetate/triphenylphosphine mixtures or palladium (II)chloride-dppf (1,1'-bis(diphenylphosphino)ferrocene) complexes and a base such as triethylamine, sodium carbonate or potassium phosphate in an inert solvent such as dimethylformamide, toluene, tetrahydrofuran, acetonitrile and dimethoxyethane. Optionally, alkenyl containing $R^1$ residues can be transformed to the corresponding alkyl congeners AC using conditions described in the literature such as e.g. a hydrogenation reaction using hydrogen gas in the presence of a catalyst such as palladium on carbon in a solvent such as ethanol or ethyl acetate particularly at ambient temperature.

Compound AC can be further elaborated to compound I by: i) saponification as described in step b of scheme 1 (step e); ii) amide bond formation as described in step c of scheme 1 (step f).

If one of $R^3$ and $R^4$ in amide I is equal to hydrogen, alkylation towards the corresponding tertiary amide I can be accomplished e.g. by conversion of secondary amide I to its conjugated base by treatment with e.g. sodium hydride in a solvent such as DMF and subsequent alkylation e.g. with an alkyl halide preferentially at ambient temperature, or by applying any other suitable method known to a person skilled in the art.

If one of the starting materials, compounds of formulae EA, CB, AB, III or I (with one of $R^3$ and $R^4$ being equal to hydrogen) contains one or more functional groups which are not stable or are reactive under the reaction conditions of one or more reaction steps, appropriate protecting groups (P) (as described e.g. in T. W. Greene et al., Protective Groups in Organic Chemistry, John Wiley and Sons Inc. New York 1999, $3^{rd}$ edition) can be introduced before the critical step applying methods well known in the art. Such protecting groups can be removed at a later stage of the synthesis using standard methods known in the art.

If one or more compounds of formulae EA, CB, BA, BB, AA', AB, AC, II or III contain chiral centers, picolines of formula I can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

Following the procedure according to scheme 6, compound FA can be used as starting material. FA is either commercially available, described in the literature or can be synthesized by a person skilled in the art.

Scheme 6

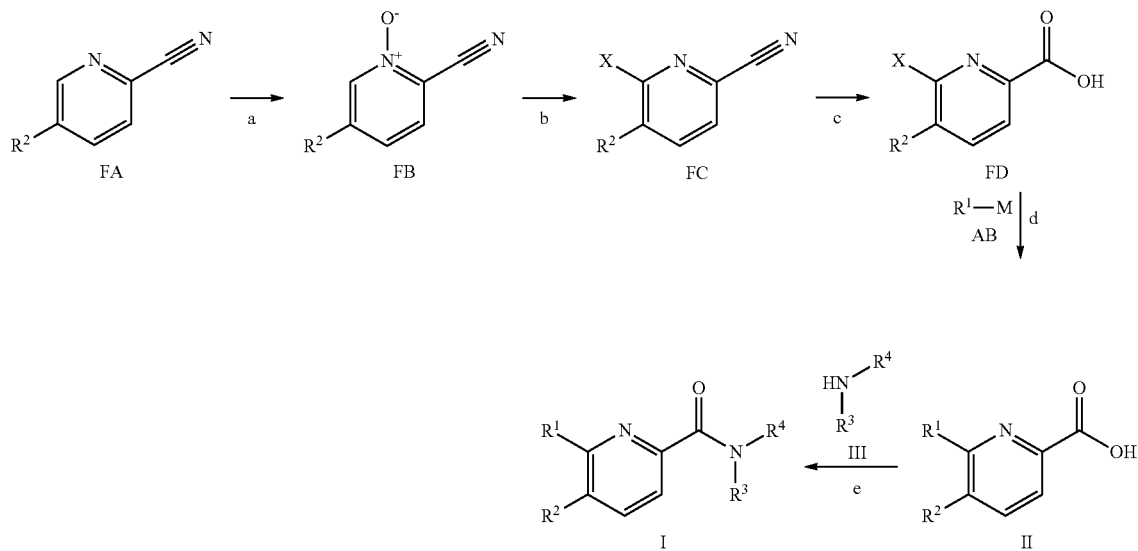

Compound FB can be prepared from FA by oxidation with a suitable oxidizing reagent under conditions known to a person skilled in the art (step a), e.g. by treatment with 3-chloro perbenzoic acid in dichloromethane at ambient temperature.

Conversion of compound FB to 6-chloro or 6-bromo compound FC (X=Cl, Br) can be achieved e.g. by treatment with phosphoryl trichloride or tribromide either without an additional solvent or in a suitable solvent such as chloroform at temperatures between 20° C. and the boiling point of the solvent or by using other conditions known in the literature (step b).

Hydrolysis of compound FC leads to picoline FD and can be performed under acidic or basic conditions known to a person skilled in the art, e.g. by treatment with an aqueous solution of sodium hydroxide at 100° C. (step c).

Compound II can be prepared from FD by coupling a suitably substituted aryl, heteroaryl or alkenyl metal species of formula AB (M is e.g. a boronic acid $B(OH)_2$ or a boronic acid pinacol ester) (step d) as described in step d of scheme 6. Optionally, alkenyl containing $R^1$ residues can be transformed to the corresponding alkyl congeners II using conditions described in the literature such as e.g. a hydrogenation reaction using hydrogen gas in the presence of a catalyst such as palladium on carbon in a solvent such as ethanol or ethyl acetate particularly at ambient temperature. In cases where the acid group of compound FD is not compatible with the conditions applied to introduce the $R^1$ residue, suitable protecting groups such as ester protecting groups e.g. a methyl ester can be introduced prior to step d and removed at a later point of the synthesis. Protecting group introduction and removal can be carried out by suitable methods known in the art (for more details see T. W. Greene et al., Protective Groups in Organic Chemistry, John Wiley and Sons Inc. New York 1999, $3^{rd}$ edition).

Further conversion of compound II to compound I can be done by applying amide bond formation conditions as depicted in step c of scheme 1 (step e).

If one of $R^3$ and $R^4$ in amide I is equal to hydrogen, alkylation towards the corresponding tertiary amide I can be accomplished e.g. by conversion of secondary amide I to its conjugated base by treatment with e.g. sodium hydride in a solvent such as DMF and subsequent alkylation e.g. with an alkyl halide preferentially at ambient temperature, or by applying any other suitable method known to a person skilled in the art.

If one of the starting materials, compounds of formulae FA, AB, III or I (with one of $R^3$ and $R^4$ being equal to hydrogen) contains one or more functional groups which are not stable or are reactive under the reaction conditions of one or more reaction steps, appropriate protecting groups (P) (as described e.g. in T. W. Greene et al., Protective Groups in Organic Chemistry, John Wiley and Sons Inc. New York 1999, $3^{rd}$ edition) can be introduced before the critical step applying methods well known in the art. Such protecting groups can be removed at a later stage of the synthesis using standard methods known in the art.

If one or more compounds of formulae FA, to FD, AB, II or III contain chiral centers, picolines of formula I can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

Following the procedure according to scheme 7, commercially available 5-bromo-6-methyl-pyridine-2-carbonitrile GA (CAN 1173897-86-3) can be used as starting material. In scheme 7, $R^1$ is benzyl or halobenzyl; $R^{1'}$ is phenyl or halophenyl.

Scheme 7

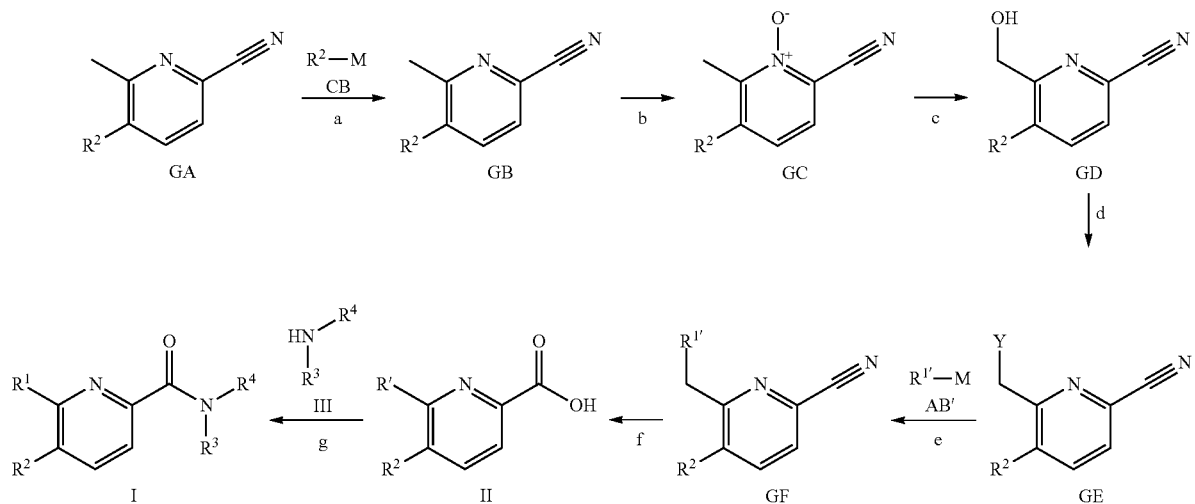

Compound GB can be prepared from GA by treatment with compound CB (M is e.g. a trifluoroborate $[BF_3]^-K^+$, a boronic acid $B(OH)_2$ or a boronic acid pinacol ester) as described in step a of scheme 5 (step a).

Further transformation of GB to GC can be achieved by oxidation with a suitable oxidizing reagent as described in step a of scheme 6 (step b).

Conversion of N-oxide GC to alcohol GD can be performed under conditions well known to a person skilled in the art, e.g. by reaction with trifluoroacetic acid anhydride in a solvent such as dichloromethane preferentially at ambient temperature and subsequent treatment with a base such as sodium hydroxide (step c).

Reactions how to convert alcohol GD into compound GE containing a leaving group (Y=Cl, Br or another suitable leaving group) are well described in the literature and known to those skilled in the art (step d). For example alcohol GD can be transformed to compound GE with Y=Br by reaction with carbon tetrabromide and triphenylphosphine in a solvent such as tetrahydrofuran at temperatures between 0° C. and the boiling point of the solvent, preferentially at 40° C.

Conversion of compound GE to compound GF can e.g. be accomplished by coupling a suitably substituted aryl metal species of formula AB' (M is e.g. a boronic acid $B(OH)_2$ or a boronic acid pinacol ester), particularly an arylboronic acid or arylboronic acid ester in the presence of a suitable catalyst, in particular a palladium catalyst and more particularly palladium(II)acetate/triphenylphosphine mixtures or palladium (II)chloride-dppf (1,1'-bis(diphenylphosphino)ferrocene) complexes and a base such as triethylamine, cesium carbonate or potassium phosphate in an inert solvent such as dimethylformamide, toluene, tetrahydrofuran and 1,4-dioxane (step e).

Nitrile GF can be hydrolyzed to acid II applying the method described in step c of scheme 6 (step f).

Further conversion of compound II to compound I can be done by applying amide bond formation conditions as depicted in step c of scheme 1 (step e).

If one of $R^3$ and $R^4$ in amide I is equal to hydrogen, alkylation towards the corresponding tertiary amide I can be accomplished e.g. by conversion of secondary amide I to its conjugated base by treatment with e.g. sodium hydride in a solvent such as DMF and subsequent alkylation e.g. with an alkyl halide preferentially at ambient temperature, or by applying any other suitable method known to a person skilled in the art.

If one of the starting materials, compounds of formulae GA, CB, AB', III or I (with one of $R^3$ and $R^4$ being equal to hydrogen) contains one or more functional groups which are not stable or are reactive under the reaction conditions of one or more reaction steps, appropriate protecting groups (P) (as described e.g. in T. W. Greene et al., Protective Groups in Organic Chemistry, John Wiley and Sons Inc. New York 1999, $3^{rd}$ edition) can be introduced before the critical step applying methods well known in the art. Such protecting groups can be removed at a later stage of the synthesis using standard methods known in the art.

If one or more compounds of formulae GA to GF, CB, AB', II or III contain chiral centers, picolines of formula I can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

The invention also relates to a process for the preparation of a compound of formula (I) comprising one of the following steps:

(a) the reaction of a compound of formula (A)

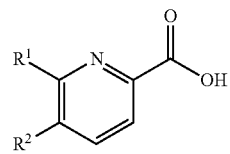

(A)

in the presence of $NHR^3R^4$, an amide bond forming coupling agent and a base; or (b) the reaction of a compound of formula (B)

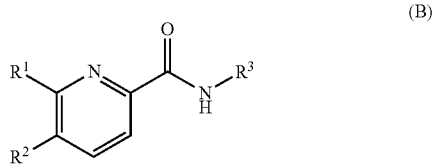

with a compound of formula $R^4$—X;
wherein $R^1$ to $R^4$ are as defined above and X is a leaving group.

X is for example Cl, Br or I. X can be any other suitable leaving group known to a person skilled in the art.

Compounds of formula (A) or $NHR^3R^4$ may contain functional groups that would interfere with the coupling procedures described for the amide coupling step. In this case it is understood that (A) or $NHR^3R^4$ need to be suitably protected by methods known in the art before conducting the amide coupling procedure and compounds need to be deprotected after the coupling step by methods known in the art to deliver compounds of formula (I).

Suitable coupling agents are for example N,N'-carbonyl-diimidazole (CDI), N,N'-dicyclohexylcarbodiimide (DCC), 1-(3-dimethylaminopropyl)-3-ethylcarbodiimide hydrochloride (EDCI), 1-[bis(dimethylamino)-methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU) or O-benzotriazole-N,N,N',N'-tetramethyl-uronium-hexafluoro-phosphate (HBTU). A particular coupling agent is HBTU.

Examples of suitable bases include triethylamine, diisopropylethylamine and particularly N-methylmorpholine.

The reaction temperature is for example room temperature.

A convenient method is to use for example HBTU and a base, for example N-methylmorpholine, in an inert solvent such as for example dimethylformamide, in particular at room temperature.

The invention also relates in particular to:

The use of a compound of formula (I) for the treatment or prophylaxis of pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, amyotrophic lateral sclerosis, stroke, transient ischemic attack or uveitis;

The use of a compound according of formula (I) for the preparation of a medicament for the treatment or prophylaxis of pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, amyotrophic lateral sclerosis, stroke, transient ischemic attack or uveitis;

A compound of formula (I) for the treatment or prophylaxis of pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, amyotrophic lateral sclerosis, stroke, transient ischemic attack or uveitis; and A method for the treatment or prophylaxis of pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, amyotrophic lateral sclerosis, stroke, transient ischemic attack or uveitis, which method comprises administering an effective amount of a compound of formula (I) to a patient in need thereof.

The invention particularly relates to a compound of formula (I) for the treatment or prophylaxis of ischemia, reperfusion injury, liver fibrosis or kidney fibrosis, in particular ischemia or reperfusion injury.

The invention further particularly relates to a compound of formula (I) for the treatment or prophylaxis of diabetic retinopathy, retinal vein occlusion or uveitis.

The invention is further directed to a compound of formula (I), when manufactured according to a process according to the invention.

Another embodiment of the invention provides a pharmaceutical composition or medicament containing a compound of the invention and a therapeutically inert carrier, diluent or excipient, as well as a method of using the compounds of the invention to prepare such composition and medicament. In one example, the compound of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compound of formula (I) is sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration. The compounds of the invention may be administered in particular by intravitreal administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The invention will now be illustrated by the following examples which have no limiting character.

EXAMPLES

Abbreviations

BINAP=2,2'-Bis(diphenylphosphino)-1,1'-binaphthyl; CAN=CAS Registry Number; DCM=dichloromethane; DIEA=N-ethyl-N-isopropylpropan-2-amine; DMF=dimethylformamide; DMSO=dimethyl-sulfoxide; dppf=1,1'-bis(diphenylphosphino)ferrocene; EI=electron ionization; ESI=electrospray; EtOAc=ethyl acetate; HPLC=LC=high performance liquid chromatography; m-CPBA=meta-chloroperoxybenzoic acid; MS=mass spectrometry; NMR=nuclear magnetic resonance; TBTU=O-(benzotriazol-1-yl)-N,N,N',N'-tetramethyl-uronium-tetrafluoroborate; TBME=methyl tert-butylether, TEMPO=(2,2,6,6-tetramethylpiperidin-1-yl)oxidanyl; THF=tetrahydrofuran; tlc=thin layer chromatography.

Example 1

6-Cyclopropylmethoxy-5-(3,3-difluoro-azetidin-1-yl)-pyridine-2-carboxylic acid tert-butyl-methyl-amide a) 6-Chloro-5-(3,3-difluoro-azetidin-1-yl)-pyridine-2-carboxylic acid methyl ester

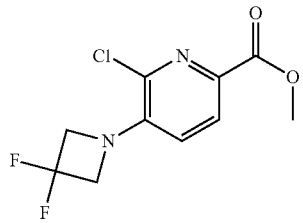 [SMILES: COC(=O)c1ccc(N2CC(F)(F)C2)c(Cl)n1]

Under a nitrogen atmosphere a mixture of methyl 5-bromo-6-chloro-pyridine-2-carboxylic acid methyl ester (Example 3 a, 2 g, 8 mmol), 3,3-difluoroazetidine hydrochloride (CAN 288315-03-7, 1 g, 8 mmol), tris(dibenzylideneacetone)dipalladium (CAN 51364-51-3, 0.16 g, 0.16 mmol), (R)-(+)-2,2'-bis(diphenylphosphino)-1,1'-binaphthyl (CAN 76189-55-4, 0.19 g, 0.32 mmol) and cesium carbonate (3.9 g, 12 mmol) in toluene (50 mL) was stirred at 110° C. overnight. After concentration, the residue was partitioned between water (50 mL) and ethyl acetate (40 mL), the aqueous phase was extracted with ethyl acetate (2×40 mL). The combined organic phase was washed with brine (40 mL), dried over anhydrous sodium sulfate, filtered and concentrated to give a residue. The residue was purified by column chromatography (silica gel, 20 g, 10% ethyl acetate in petroleum ether) to give the target compound (0.44 g, 21%) as light-yellow solid; MS (EI): m/e=263.0 [MH$^+$].

b) 6-Cyclopropylmethoxy-5-(3,3-difluoro-azetidin-1-yl)-pyridine-2-carboxylic acid

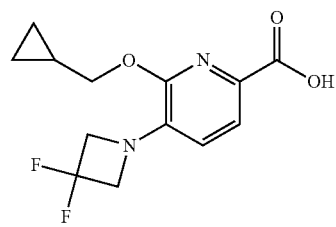 [SMILES: O=C(O)c1ccc(N2CC(F)(F)C2)c(OCC2CC2)n1]

Sodium hydride (0.29 g, 8.4 mmol) was added in portion to a solution of cyclopropylmethanol (CAN 2516-33-8, 0.36 g, 5 mmol) in DMF (3 mL) and the mixture was stirred at room temperature for 2 h. 6-Chloro-5-(3,3-difluoro-azetidin-1-yl)-pyridine-2-carboxylic acid methyl ester (0.44 g, 1.68 mmol) was added to the mixture and the resulting solution was stirred at 110° C. overnight. After concentration, water (20 mL) was added to the residue and the solution was acidified with an aqueous solution of hydrochloride (6 N), then extracted with ethyl acetate (2×20 mL). The combined organic phase was washed with brine (20 mL), dried over anhydrous sodium sulfate, filtered and concentrated to give a residue. The residue was purified by prep-TLC (eluting with 50% ethyl acetate in petroleum ether) to give the target compound (0.07 g, 14%); MS (EI): m/e=285.1 [MH⁺].

c) 6-Cyclopropylmethoxy-5-(3,3-difluoro-azetidin-1-yl)-pyridine-2-carboxylic acid tert-butyl-methyl-amide

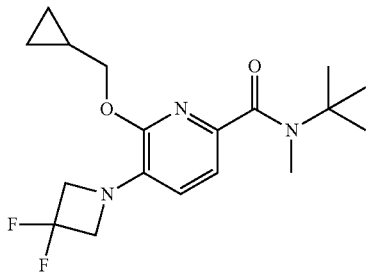 [SMILES: CN(C(=O)c1ccc(N2CC(F)(F)C2)c(OCC2CC2)n1)C(C)(C)C]

A solution of 6-(cyclopropylmethoxy)-5-(3,3-difluoroazetidin-1-yl)picolinic acid (10 mg, 35 µmol), N,2-dimethylpropan-2-amine (CAN 94896-77-2, 3.68 mg, 42.2 µmol), 1-hydroxybenzotriazole hydrate (11 mg, 70 µmol), 1-(3-dimethylaminopropyl)-3-ethylcarbodiimide hydrochloride (12 mg, 70 µmol) and DIEA (18.2 mg, 24 µl, 141 µmol) in DMF (157 µL) was stirred for 2 d at ambient temperature. The reaction mixture was poured onto ice-water/1N HCl (20 mL), extracted with EtOAc (2×30 mL) and washed with ice-water/brine (20 mL). The organic layers were combined, dried over Na₂SO₄ and concentrated in vacuo to give 24 mg of a yellow oil which was purified by TLC (silica gel, Heptane/EtOAc 1:1, elution with DCM/EtOAc 1:1) to give the title compound (11 mg, 89%) as light yellow oil; MS (EI): m/e=354.5 [MH⁺].

Example 2

6-Cyclopropylmethoxy-5-(3,3-difluoro-azetidin-1-yl)-pyridine-2-carboxylic acid dimethylamide

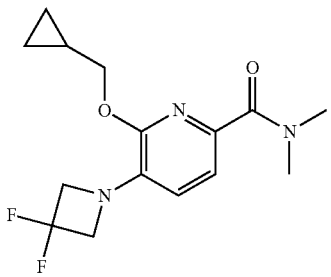 [SMILES: CN(C)C(=O)c1ccc(N2CC(F)(F)C2)c(OCC2CC2)n1]

In analogy to the procedure described in Example 47 b), 6-cyclopropylmethoxy-5-(3,3-difluoro-azetidin-1-yl)-pyridine-2-carboxylic acid (Example 1 b)) was reacted with dimethylamine hydrochloride (CAN 506-59-2) in the presence of TBTU and DIEA to give the title compound as light yellow oil; MS (EI): m/e=312.4 [MH⁺].

Example 3

5-Cyclopropyl-6-cyclopropylmethoxy-pyridine-2-carboxylic acid tert-butyl-methyl-amide a) 5-Bromo-6-chloro-pyridine-2-carboxylic acid methyl ester

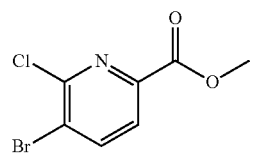

A mixture of 5-bromo-pyridine-2-carboxylic acid methyl ester (CAN 29682-15-3, 50 g, 0.23 mol) and m-CPBA (CAN 937-14-4, 80 g, 0.46 mol) in 400 mL dry methylene chloride was heated to 60° C. for 20 h. After that, the mixture was quenched with saturated sodium sulfite solution and extracted with ethyl acetate (2×200 mL). The organic layer was washed with brine (2×200 mL) and evaporated to dryness. The residue was purified with by column chromatography (silica gel, 300 g, eluting with 15% ethyl acetate in petroleum ether) to obtain a brown oil. The brown oil, 5-bromo-2-(methoxycarbonyl)pyridine 1-oxide (30 g, 0.13 mol) was added into phosphoryl trichloride (CAN 10025-87-3, 80 mL) at 0° C. over 1 h, then the mixture was heated to 95° C. for 1 h. After that the mixture was evaporated to dryness, the residue was dissolved in water (50 mL), extracted with ethyl acetate (3×50 mL) and the organic layer was evaporated to dryness to obtain the product as a white solid (19 g, 59%); MS (EI): m/e=249.9 [MH⁺].

b) 5-Bromo-6-cyclopropylmethoxy-pyridine-2-carboxylic acid

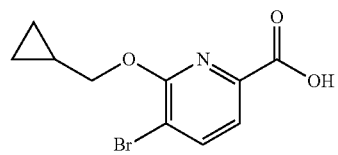 [SMILES: O=C(O)c1ccc(Br)c(OCC2CC2)n1]

Sodium hydride (4.83 g, 0.12 mol) was added into cyclopropanemethanol (CAN 2516-33-8, 30 g) at 0° C. and the mixture was stirred at 0° C. for 1 h. Then to the mixture was added methyl 5-bromo-6-chloro-pyridine-2-carboxylic acid methyl ester (3 g, 12.75 mmol). The obtained solution was heated to 90° C. for 2 h. Then the mixture was evaporated to dryness, the residue was dissolved in 40 mL of water, and adjusted to pH=4 with hydrochloric acid (3 N), and extracted with ethyl acetate (3×30 mL). The combined organic layer was washed with water (2×30 mL) and brine (2×50 mL) then evaporated to dryness to obtain the product as a white solid (2.5 g, 76.7%); MS (EI): m/e=272.0 [MH⁺].

c) 5-Cyclopropyl-6-cyclopropylmethoxy-pyridine-2-carboxylic acid

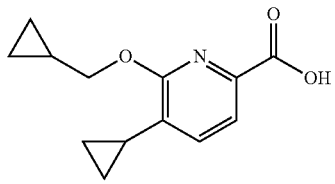 [SMILES: O=C(O)c1ccc(C2CC2)c(OCC2CC2)n1]

A mixture of 5-bromo-6-(cyclopropylmethoxy)-pyridine-2-carboxylic acid (1.5 g, 5.5 mmol), cyclopropylboronic acid (CAN 411235-57-9, 0.57 g, 7 mmol), palladium diacetate (CAN 3375-31-3, 62 mg, 0.28 mmol), tricyclohexylphosphine (CAN 2622-14-2, 154 mg, 0.1 mmol) and potassium phosphate (4.1 g, 19 mmol) in toluene/water (20/1 v/v, 30 mL) was heated to 100° C. overnight. After that the mixture was evaporated to dryness, dissolved in 30 mL of water, extracted with ethyl acetate (30 mL) and the organic layer was dropped. The water layer was adjusted to pH=3 and extracted with ethyl acetate (2×30 mL), this organic layer was washed with water (30 mL) and brine (30 mL), dried over anhydrous sodium sulfate then evaporated to dryness. The residue was purified by column chromatography (silica gel, 10 g, eluting with 15% ethyl acetate in petroleum ether) to obtain the title compound (0.96 g, 75%) as white solid; MS (LC/MS): 234.1 [MH+].

d) 5-Cyclopropyl-6-cyclopropylmethoxy-pyridine-2-carboxylic acid tert-butyl-methyl-amide

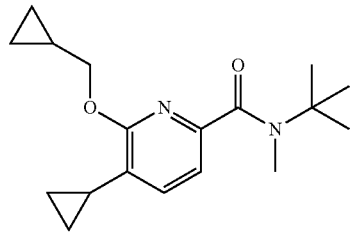 [SMILES: CN(C(=O)c1ccc(C2CC2)c(OCC2CC2)n1)C(C)(C)C]

In analogy to the procedure described in Example 47 b), 5-cyclopropyl-6-cyclopropylmethoxy-pyridine-2-carboxylic acid was reacted with N,2-dimethylpropan-2-amine (CAN 94896-77-2) in the presence of TBTU and DIEA to give the title compound as colorless oil; MS (EI): m/e=303.4 [MH+].

Example 4

5-Cyclopropyl-6-(tetrahydro-furan-2-ylmethoxy)-pyridine-2-carboxylic acid tert-butyl-methyl-amide a) 5-Bromo-6-(tetrahydro-furan-2-ylmethoxy)-pyridine-2-carboxylic acid

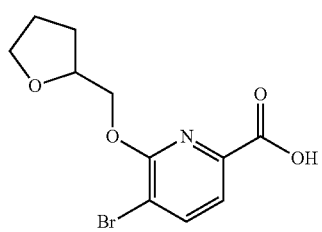 [SMILES: O=C(O)c1ccc(Br)c(OCC2CCCO2)n1]

5-Bromo-6-chloropicolinic acid (200 mg, 846 µmol; CAN 959958-25-9) and powdered potassium hydroxide (190 mg, 3.38 mmol) were combined with DMSO (1.93 mL) to give a colorless solution which was stirred for 15 min at ambient temperature before tetrahydro-2-furanmethanol (130 mg, 123 µl, 1.27 mmol, CAN 97-99-4) was added, and stirring continued for 1 day at ambient temperature. The reaction mixture was poured into a mixture of ice-water and 1 M NaOH, and extracted with t-butylmethyl ether (2×25 mL) and washed with ice-water/brine. The water phases were combined acidified with ice/1 N HCl and extracted with isopropyl acetate (2×30 mL). The organic layers were washed with ice-water/brine (2×30 mL), dried with $Na_2SO_4$ and concentrated in vacuo to give the title compound (254 mg, 99%) as light brown oil; MS (ESI): 301.8 [M−H]−.

b) 5-Cyclopropyl-6-(tetrahydro-furan-2-ylmethoxy)-pyridine-2-carboxylic acid

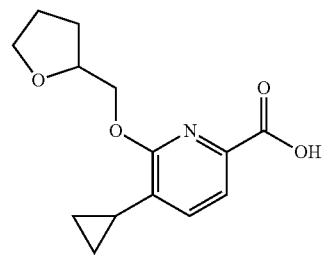 [SMILES: O=C(O)c1ccc(C2CC2)c(OCC2CCCO2)n1]

Palladium(II)acetate (1.19 mg, 5.3 µmol), butylbis(tricyclo [3.3.1.13,7]dec-1-yl)-phosphine (2.85 mg, 7.94 µmol, CAN 321921-71-5), potassium cyclopropyltrifluoroborate (39.6 mg, 267 µmol) and cesium carbonate (259 mg, 794 µmol) were combined to give a white solid. To this solid a degassed solution of 5-bromo-6-(tetrahydro-furan-2-ylmethoxy)-pyridine-2-carboxylic acid (80 mg, 265 µmol) in toluene (2.02 mL)/water (224 µL) was added through a septum cap. The reaction mixture was heated to 120° C. and stirred for 20 h. After cooling to ambient temperature the reaction mixture was diluted with water (2 mL), poured onto 20 mL ice water/brine/1 N HCl, extracted with isopropyl acetate (2×40 mL), and washed with 20 mL ice water/brine. The organic layers were dried with $Na_2SO_4$ and concentrated in vacuo to give a light brown oily residue which was purified by preparative TLC (silica gel, 2.0 mm, DCM/MeOH, 49:1). The title compound (25 mg, 36%) was isolated as light yellow liquid; MS (ESI): 262.0 [M−H]−.

c) 5-Cyclopropyl-6-(tetrahydro-furan-2-ylmethoxy)-pyridine-2-carboxylic acid tert-butyl-methyl-amide

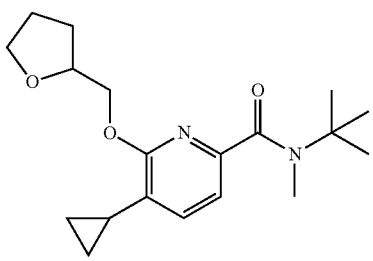 [SMILES: CN(C(=O)c1ccc(C2CC2)c(OCC2CCCO2)n1)C(C)(C)C]

In analogy to the procedure described in Example 47 b), 5-cyclopropyl-6-(tetrahydro-furan-2-ylmethoxy)-pyridine-2-carboxylic acid was reacted with N,2-dimethylpropan-2-amine (CAN 94896-77-2) in the presence of TBTU and DIEA to give the title compound as colorless oil; MS (EI): m/e=333.5 [MH]+.

Example 5

5-Cyclopropyl-6-(4-fluoro-benzyl)-pyridine-2-carboxylic acid tert-butyl-methyl-amide a) 5-Bromo-6-methyl-pyridine-2-carbonitrile

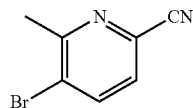

NaCN (4 g, 82 mmol) was added to a solution of 3-bromo-6-fluoro-2-methyl-pyridine (4 g, 21 mmol) in DMSO (100 mL) The mixture was stirred for 2 h at 100° C., poured into H₂O (100 mL) and extracted with ethyl acetate (2×100 mL). The organic layers were dried over Na₂SO₄, concentrated and purified by flash column chromatography (silica gel, 10 g, eluting with 10% ethyl acetate in petroleum ether) to give the title compound (0.6 g, 15%) as white solid; MS (EI): m/e=197.0 [1\4+H]+.

b) 5-Cyclopropyl-6-methyl-pyridine-2-carbonitrile

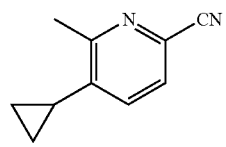

5-Bromo-6-methyl-pyridine-2-carbonitrile (0.5 g, 2.5 mmol), cyclopropylboronic acid (CAN 411235-57-9, 0.36 g, 4 mmol), Pd₂(dba)₃ (CAN 411235-57-9, 0.1 g, 0.2 mmol), xantphos (CAN 161265-03-8, 0.15 g, 0.26 mmol) and Cs₂CO₃ (1.1 g, 3 mmol) were suspended in 1,4-dioxane (30 mL) under a nitrogen atmosphere. The mixture was stirred for 12 h at 110° C., filtered, concentrated under reduced pressure and purified by column chromatography (silica gel, 5 g, eluting with 10% ethyl acetate in petroleum ether) to give the title compound (0.3 g, 75%) as yellow solid; MS (EI): m/e=159.2 [M+H]+.

c) 5-Cyclopropyl-6-methyl-1-oxy-pyridine-2-carbonitrile

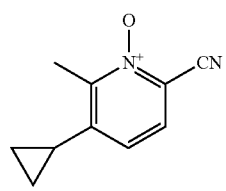

A mixture of 5-cyclopropyl-6-methyl-pyridine-2-carbonitrile (0.2 g, 1.3 mmol) and m-CPBA (0.5 g, 3 mmol) in CH₂Cl₂ (10 mL) was stirred for 12 hours at 60° C. After cooling to ambient temperature, the mixture was filtered, concentrated under reduced pressure and purified by column chromatography (silica gel, 3 g, eluting with 50% ethyl acetate in petroleum ether) to give the title compound (0.2 g, 91%) as yellow solid; MS (EI): m/e=175.0 [M+H]+.

d) 5-Cyclopropyl-6-hydroxymethyl-pyridine-2-carbonitrile

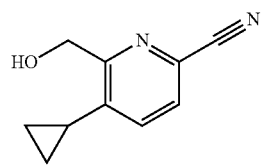 [SMILES: N#Cc1ccc(C2CC2)c(CO)n1]

Trifluoroacetic acid anhydride (CAN 457-25-0, 1 mL) was added to a solution of 5-cyclopropyl-6-methyl-1-oxy-pyridine-2-carbonitrile (0.2 g, 1.1 mmol) in CH₂Cl₂ (10 mL). The reaction mixture was stirred for 12 h at ambient temperature and then partitioned between 6 N NaOH aq. (10 mL) and CH₂Cl₂ (10 mL). The aqueous phase was washed several times with CH₂Cl₂ and the combined organic fractions were dried over Na₂SO₄ and concentrated under reduced pressure. The residue was purified by column chromatography (silica gel, 3 g, eluting with 1% methanol in methylene chloride) to give the title compound (0.1 g, 50%) as yellow oil; MS (EI): m/e=175.2 [M+H]+.

e) 6-Bromomethyl-5-cyclopropyl-pyridine-2-carbonitrile

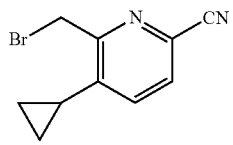 [SMILES: N#Cc1ccc(C2CC2)c(CBr)n1]

A solution of 5-cyclopropyl-6-hydroxymethyl-pyridine-2-carbonitrile (0.1 g, 0.6 mmol), CBr₄ (0.8 g, 1.2 mmol), PPh₃ (0.3 g, 1.2 mmol) in THF (10 mL) was stirred for 12 h at 40° C. The solvent was removed under reduced pressure and the crude product purified by flash column chromatography (silica gel, 3 g, eluting with 25% ethyl acetate in petroleum ether) to give the title compound (0.1 g, 74%) as yellow solid; MS (EI): m/e=236.9 [M+H]+.

f) 5-Cyclopropyl-6-(4-fluoro-benzyl)-pyridine-2-carbonitrile

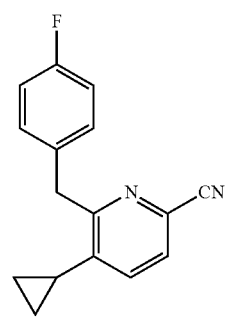 [SMILES: N#Cc1ccc(C2CC2)c(Cc2ccc(F)cc2)n1]

A mixture of 6-bromomethyl-5-cyclopropyl-pyridine-2-carbonitrile (0.1 g, 0.4 mmol), 4-fluoro-benzylboronic acid (CAN 1765-93-1, 0.1 g, 0.7 mmol), Pd(dppf)Cl$_2$ (CAN 95464-05-4, 50 mg, 0.068 mmol), Cs$_2$CO$_3$ (0.2 g, 0.6 mmol) in 1.4-dioxane (10 mL) was stirred for 12 h at 110° C. under a nitrogen atmosphere. The mixture was filtered, concentrated and purified by flash column chromatography (silica gel, 3 g, eluting with 25% ethyl acetate in petroleum ether) to give the title compound (80 mg, 75%) as yellow solid; MS (EI): m/e=253.2 [M+H]$^+$.

g) 5-Cyclopropyl-6-(4-fluoro-benzyl)-pyridine-2-carboxylic acid

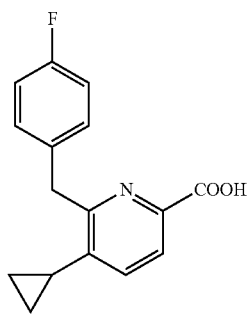 [SMILES: O=C(O)c1ccc(C2CC2)c(Cc2ccc(F)cc2)n1]

A solution of 5-cyclopropyl-6-(4-fluoro-benzyl)-pyridine-2-carbonitrile (0.08 g, 0.3 mmol) and NaOH (0.05 g, 1.2 mmol) in H$_2$O (10 mL) was stirred for 2 hours at 90° C. The pH was adjusted to 3 with 1 M HCl. The mixture was extracted with ethyl acetate (3×10 mL), dried over Na$_2$SO$_4$, concentrated under reduced pressure and purified by column chromatography to give the title compound (0.06 g, 70%) as yellow solid; MS (EI): m/e=272.1 [M+H]$^+$.

h) 5-Cyclopropyl-6-(4-fluoro-benzyl)-pyridine-2-carboxylic acid tert-butyl-methyl-amide

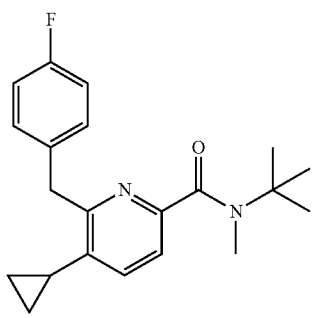 [SMILES: CN(C(=O)c1ccc(C2CC2)c(Cc2ccc(F)cc2)n1)C(C)(C)C]

In analogy to the procedure described in Example 47 b), 5-cyclopropyl-6-(4-fluoro-benzyl)-pyridine-2-carboxylic acid was reacted with N,2-dimethylpropan-2-amine (CAN 94896-77-2) in the presence of TBTU and DIEA to give the title compound as colorless oil; MS (EI): m/e=341.1 [MH$^+$].

Example 6

5-Cyclopropyl-6-(2-methyl-propane-1-sulfonyl)-pyridine-2-carboxylic acid tert-butyl-methyl-amide a) 5-Bromo-6-(isobutylthio)picolinic acid

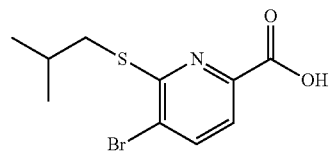

5-Bromo-6-chloropicolinic acid (2 g, 8.46 mmol; CAN 959958-25-9), 2-methylpropane-1-thiol (915 mg, 1.1 mL, 10.2 mmol) and cesium carbonate (6.89 g, 21.1 mmol) were suspended in DMSO (100 mL). The reaction mixture was heated to 150° C. and stirred for 1 d and was poured onto ice-water/1N HCl (100 mL). The aqueous layer was extracted with EtOAc (2×250 mL). The combined extracts were washed with ice-water/brine (100 mL), dried over Na$_2$SO$_4$ and concentrated in vacuo to give the title compound (2.49 g, 51%) as an orange solid which was used in the next step without further purification. MS (EI): m/e=288.4 [M−H]$^−$.

b) Methyl 5-bromo-6-(isobutylthio)picolinate

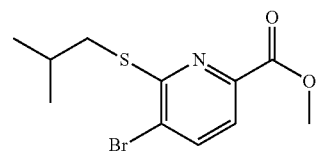 [SMILES: COC(=O)c1ccc(Br)c(SCC(C)C)n1]

5-Bromo-6-(isobutylthio)picolinic acid (500 mg, 1.72 mmol) was dissolved in methanol (5 mL) to give a yellow solution. Sulfuric acid (169 mg, 92.3 µL, 1.72 mmol) was added. The reaction mixture was heated to 80° C. and stirred for 1 d. The reaction mixture was cooled to 0° C. and poured onto ice-water/brine (25 mL). The aqueous layer was extracted with EtOAc (2×40 mL) and washed with ice-water/brine (20 mL). The organic layers were combined, dried over Na$_2$SO$_4$ and concentrated in vacuo to give crude title compound as a yellow oil. The oil was purified by flash chromatography (silica gel, 5 g, 0% to 15% EtOAc in heptane) to give the title product (205 mg, 39%) as a colorless oil. MS (EI): m/e=306.3 [M+H]$^+$.

c) Methyl 5-bromo-6-(isobutylsulfonyl)picolinate

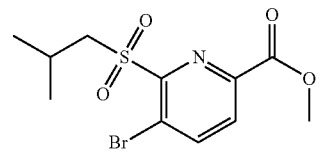 [SMILES: COC(=O)c1ccc(Br)c(S(=O)(=O)CC(C)C)n1]

Methyl 5-bromo-6-(isobutylthio)picolinate (30 mg, 98.6 µmol) was dissolved in dichloromethane (1 mL). The solution was cooled to 0° C. 3-Chlorobenzoperoxoic acid (34.0 mg, 197 µmol) was added. The reaction mixture was stirred for 1 d at ambient temp., poured onto ice-water (20 mL) and extracted with dichloromethane (2×30 mL). The extract was washed with a 10% aqueous $Na_2S_2O_3$-solution (15 mL). The aqueous layer was back-extracted with dichloromethane (30 mL). The combined organic layers were washed with an aqueous 10% sodium hydrogen carbonate solution, dried over $Na_2SO_4$ and concentrated in vacuo to give the crude product as a white solid. Filtration through silica gel (3 g, heptane/EtOAc 1:1) provided the title compound (19 mg, 70%) as a white oil. MS (EI): m/e=338.3 $[M+H]^+$.

d) 5-Cyclopropyl-6-(isobutylsulfonyl)picolinic acid

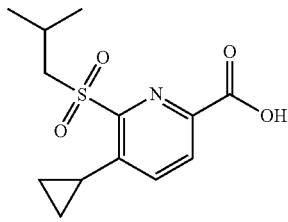 [SMILES: CC(C)CS(=O)(=O)c1nc(C(=O)O)ccc1C1CC1]

The title compound was prepared in analogy to the procedure described in Example 3 c), using methyl 5-bromo-6-(isobutylsulfonyl)picolinate as starting material. MS (EI): m/e=284.3 $[M+H]^+$.

e) 5-Cyclopropyl-6-(2-methyl-propane-1-sulfonyl)-pyridine-2-carboxylic acid tert-butyl-methyl-amide

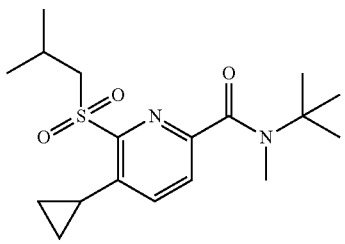 [SMILES: CC(C)CS(=O)(=O)c1nc(C(=O)N(C)C(C)(C)C)ccc1C1CC1]

In analogy to the procedure described in Example 47 b), 5-cyclopropyl-6-(isobutylsulfonyl)picolinic acid was reacted with N,2-dimethylpropan-2-amine (CAN 94896-77-2) in the presence of TBTU and DIEA to give the title compound as white solid; MS (EI): m/e=353.5 $[MH^+]$.

Example 7

6-Cyclopropylmethoxy-5-(3,3-difluoro-azetidin-1-yl)-pyridine-2-carboxylic acid tert-butyl-ethyl-amide

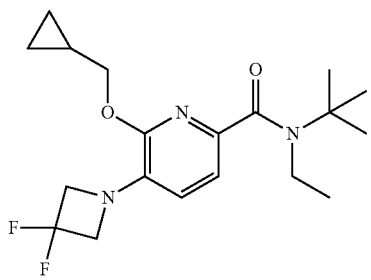 [SMILES: CCN(C(=O)c1ccc(N2CC(F)(F)C2)c(OCC2CC2)n1)C(C)(C)C]

In analogy to the procedure described in Example 47 b), 6-cyclopropylmethoxy-5-(3,3-difluoro-azetidin-1-yl)-pyridine-2-carboxylic acid (Example 1 b)) was reacted with N-ethyl-2-methylpropan-2-amine (CAN 4432-77-3) in the presence of TBTU and DIEA to give the title compound as colorless oil; MS (EI): m/e=368.5 $[MH^+]$.

Example 8

Cyclopropylmethoxy-5-(3,3-difluoro-azetidin-1-yl)-pyridine-2-carboxylic acid diisopropylamide

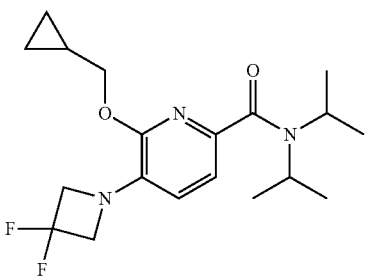 [SMILES: CC(C)N(C(=O)c1ccc(N2CC(F)(F)C2)c(OCC2CC2)n1)C(C)C]

In analogy to the procedure described in Example 47 b), 6-cyclopropylmethoxy-5-(3,3-difluoro-azetidin-1-yl)-pyridine-2-carboxylic acid (Example 1 b)) was reacted with (3-methyloxetan-3-yl)methanamine (CAN 153209-97-3) in the presence of TBTU and DIEA to give the title compound as a byproduct as colorless oil; MS (EI): m/e=368.5 $[MH^+]$.

Example 9

6-Cyclopropylmethoxy-5-(3,3-difluoro-azetidin-1-yl)-pyridine-2-carboxylic acid (2-methoxy-1,1-dimethyl-ethyl)-methyl-amide

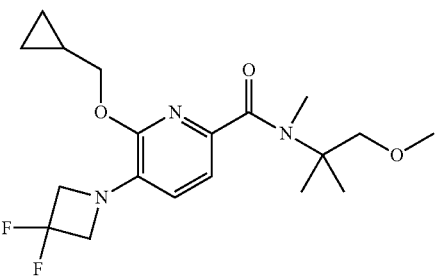 [SMILES: COCC(C)(C)N(C)C(=O)c1ccc(N2CC(F)(F)C2)c(OCC2CC2)n1]

In analogy to the procedure described in Example 47 b), 6-cyclopropylmethoxy-5-(3,3-difluoro-azetidin-1-yl)-pyridine-2-carboxylic acid (Example 1 b)) was reacted with 3-methoxy-2,2-dimethylpropan-1-amine (CAN 1177316-

77-6) in the presence of TBTU and DIEA to give the title compound as colorless oil; MS (EI): m/e=384.5 [MH⁺].

Example 10

[6-Cyclopropylmethoxy-5-(3,3-difluoro-azetidin-1-yl)-pyridin-2-yl]-(6-oxa-1-aza-spiro[3.3]hept-1-yl)-methanone

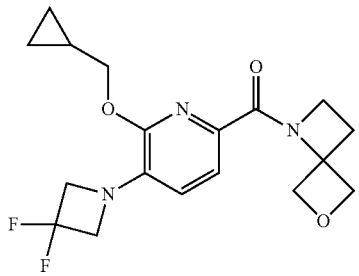 [SMILES: O=C(c1ccc(N2CC(F)(F)C2)c(OCC2CC2)n1)N1CCC12COC2]

In analogy to the procedure described in Example 47 b), 6-cyclopropylmethoxy-5-(3,3-difluoro-azetidin-1-yl)-pyridine-2-carboxylic acid (Example 1 b)) was reacted with 6-oxa-1-azaspiro[3.3]heptane oxalate (CAN 1359655-43-8) in the presence of TBTU and DIEA to give the title compound as colorless oil; MS (EI): m/e=366.4 [MH⁺].

Example 11

[6-Cyclopropylmethoxy-5-(3,3-difluoro-azetidin-1-yl)-pyridin-2-yl]-(2-oxa-6-aza-spiro[3.3]hept-6-yl)-methanone

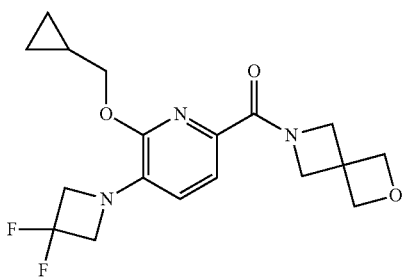 [SMILES: O=C(c1ccc(N2CC(F)(F)C2)c(OCC2CC2)n1)N1CC2(COC2)C1]

In analogy to the procedure described in Example 47 b), 6-cyclopropylmethoxy-5-(3,3-difluoro-azetidin-1-yl)-pyridine-2-carboxylic acid (Example 1 b)) was reacted with 2-oxa-6-azaspiro[3.3]heptane oxalate (CAN 1159599-99-1) in the presence of TBTU and DIEA to give the title compound as colorless oil; MS (EI): m/e=366.4 [MH⁺].

Example 12

6-Cyclopropylmethoxy-5-(3,3-difluoro-azetidin-1-yl)-pyridine-2-carboxylic acid 2-{[6-cyclopropyl-methoxy-5-(3,3-difluoro-azetidin-1-yl)-pyridine-2-carbonyl]-methyl-amino}-2-methyl-propyl ester

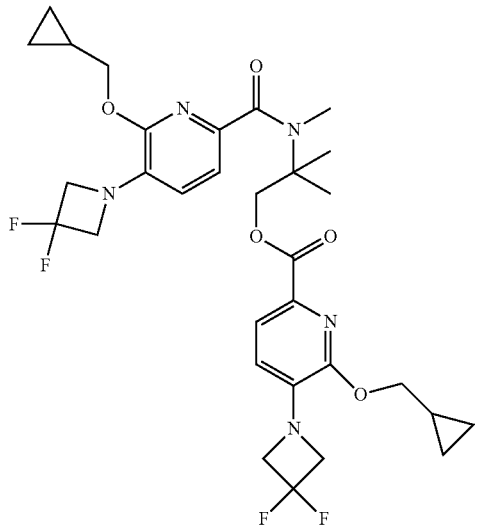 [SMILES: CN(C(=O)c1ccc(N2CC(F)(F)C2)c(OCC2CC2)n1)C(C)(C)COC(=O)c1ccc(N2CC(F)(F)C2)c(OCC2CC2)n1]

In analogy to the procedure described in Example 47 b), 6-cyclopropylmethoxy-5-(3,3-difluoro-azetidin-1-yl)-pyridine-2-carboxylic acid (Example 1 b)) was reacted with 2-methyl-2-(methylamino)propan-1-ol (CAN 27646-80-6) in the presence of TBTU and DIEA to obtain the title compound as colorless oil; MS (EI): m/e=636.3 [MH⁺].

Example 13

5-Cyclopropyl-6-(2,2,2-trifluoro-1-methyl-ethoxy)-pyridine-2-carboxylic acid tert-butyl-methyl-amide a) 5-Bromo-6-(1,1,1-trifluoropropan-2-yloxy)picolinic acid

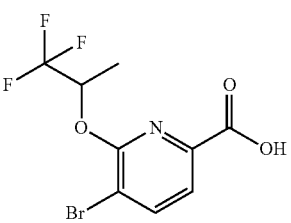 [SMILES: CC(Oc1nc(C(=O)O)ccc1Br)C(F)(F)F]

5-Bromo-6-chloropicolinic acid (5 g, 21.1 mmol; CAN 959958-25-9) was dissolved in DMSO (100 mL) to give a colorless solution. To this solution potassium hydroxide (4.75 g, 84.6 mmol) was added. The reaction mixture turned into a white suspension which was stirred for 15 min. Then 1,1,1-trifluoropropan-2-ol (2.41 g, 1.92 mL, 21.1 mmol) was added. The mixture was stirred for 1 d at ambient temp., poured onto ice-water/1N HCl (200 mL) and extracted with EtOAc (2×400 mL). The organic layers were washed with ice-water/brine (200 mL), combined and dried over $Na_2SO_4$ and concentrated in vacuo to give the title compound (6.9 g, quant.) as orange solid. MS (EI): m/e=312.3 [M−H]⁻.

b) 5-Cyclopropyl-6-(1,1,1-trifluoropropan-2-yloxy) picolinic acid

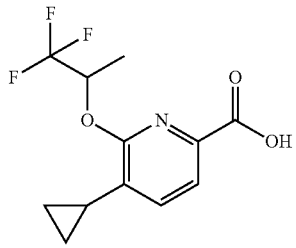 [SMILES: CC(Oc1nc(C(=O)O)ccc1C1CC1)C(F)(F)F]

5-Bromo-6-(1,1,1-trifluoropropan-2-yloxy)picolinic acid (2 g, 6.37 mmol), potassium cyclopropyltrifluoroborate (952 mg, 6.43 mmol), cesium carbonate (6.22 g, 19.1 mmol) and palladium(II)acetate (28.6 mg, 127 µmol) were suspended in toluene (55 mL) and water (6.11 mL) under an argon atmosphere. Butyl-1-adamantylphosphin (68.5 mg, 191 µmol) was added, the reaction mixture was heated to 120° C. for 1 d, poured onto ice-water/1N HCl (150 mL) and extracted with EtOAc (2×300 mL). The combined organic layers were washed with ice-water/brine (150 mL), dried over $Na_2SO_4$ and concentrated in vacuo to give the title compound (1.38 g, 79%) as a yellow solid. MS (EI): m/e=276.2 [M+H]⁺.

c) 5-Cyclopropyl-6-(2,2,2-trifluoro-1-methyl-ethoxy)-pyridine-2-carboxylic acid tert-butyl-methyl-amide

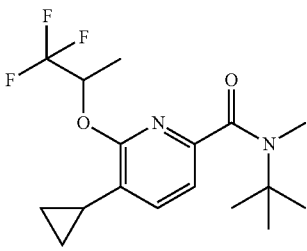 [SMILES: CC(Oc1nc(C(=O)N(C)C(C)(C)C)ccc1C1CC1)C(F)(F)F]

In analogy to the procedure described in Example 47 b), 5-cyclopropyl-6-(1,1,1-trifluoropropan-2-yloxy)picolinic acid was reacted with 2-methyl-2-(methylamino)propan-1-ol (CAN 27646-80-6) in the presence of TBTU and DIEA to obtain the title compound as white solid; MS (EI): m/e=345.4 [MH⁺].

Example 14

[6-Cyclopropylmethoxy-5-(3,3-difluoro-azetidin-1-yl)-pyridin-2-yl]-(4,4-dimethyl-oxazolidin-3-yl)-methanone

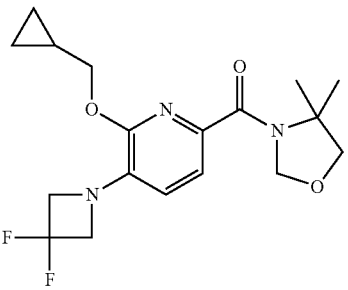 [SMILES: CC1(C)COCN1C(=O)c1ccc(N2CC(F)(F)C2)c(OCC2CC2)n1]

In analogy to the procedure described in Example 47 b), 6-cyclopropylmethoxy-5-(3,3-difluoro-azetidin-1-yl)-pyridine-2-carboxylic acid (Example 1 b)) was reacted with 4,4-dimethyloxazolidine (CAN 51200-87-4) in the presence of TBTU and DIEA to obtain the title compound as white solid; MS (EI): m/e=368.5 [MH⁺].

Example 15

6-(Tetrahydro-furan-2-ylmethoxy)-5-trifluoromethyl-pyridine-2-carboxylic acid tert-butyl-methyl-amide a) 6-(Tetrahydro-furan-2-ylmethoxy)-5-trifluoromethyl-pyridine-2-carboxylic acid

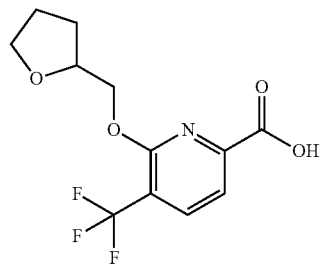 [SMILES: O=C(O)c1ccc(C(F)(F)F)c(OCC2CCCO2)n1]

In analogy to the procedure described in Example 4 a), 6-chloro-5-(trifluoromethyl)picolinic acid (CAN 855915-21-8) was reacted with (tetrahydrofuran-2-yl)methanol (CAN 97-99-4) in the presence of potassium hydroxide to yield the title compound as yellow solid; MS (EI): m/e=290.0 [MH⁺].

b) 6-(Tetrahydro-furan-2-ylmethoxy)-5-trifluoromethyl-pyridine-2-carboxylic acid tert-butyl-methyl-amide

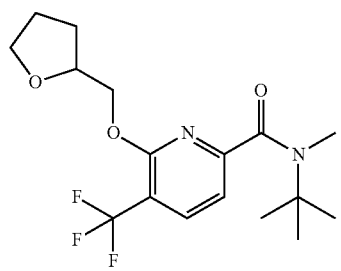 [SMILES: CN(C(=O)c1ccc(C(F)(F)F)c(OCC2CCCO2)n1)C(C)(C)C]

In analogy to the procedure described in Example 47 b), 6-((tetrahydrofuran-2-yl)methoxy)-5-(trifluoromethyl)picolinic acid was reacted with N,2-dimethylpropan-2-amine (CAN 94896-77-2) in the presence of TBTU and DIEA to give the title compound as colorless oil; MS (EI): m/e=361.5 [MH⁺].

Example 16

6-Cyclopropylmethoxy-5-(3,3-difluoro-azetidin-1-yl)-pyridine-2-carboxylic acid methyl-(1-trifluoromethyl-cyclopropyl)-amide a) 6-Cyclopropylmethoxy-5-(3,3-difluoro-azetidin-1-yl)-pyridine-2-carboxylic acid (1-trifluoromethyl-cyclopropyl)-amide

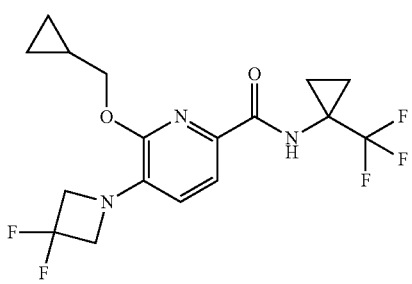

The title compound was synthesized in analogy to the procedure described in Example 47 b), using 6-cyclopropylmethoxy-5-(3,3-difluoro-azetidin-1-yl)-pyridine-2-carboxylic acid (Example 1 b)) and 1-(trifluoromethyl)cyclopropanamine (CAN 112738-68-8) as starting materials. MS (EI): m/e=392.4 [M+H]⁺.

b) 6-Cyclopropylmethoxy-5-(3,3-difluoro-azetidin-1-yl)-pyridine-2-carboxylic acid methyl-(1-trifluoromethyl-cyclopropyl)-amide

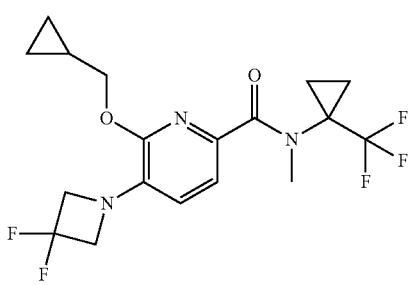 [SMILES: O=C(NC1(C(F)(F)F)CC1)c1ccc(N2CC(F)(F)C2)c(OCC2CC2)n1]

A solution of 6-cyclopropylmethoxy-5-(3,3-difluoro-azetidin-1-yl)-pyridine-2-carboxylic acid (1-trifluoromethyl-cyclopropyl)-amide (20 mg, 51.1 µmol) and sodium hydride (3.3 mg, 76.7 µmol) in DMF (0.2 mL) was stirred for 15 min. at ambient temperature. Iodomethane (14.5 mg, 6.38 µL, 102 µmol) was added and stirring was continued for 1 h. The reaction mixture was poured onto ice/sat. aqueous NaHCO₃ solution (15 mL) and extracted with EtOAc (2×25 mL). The combined extracts were washed with ice water/brine (2×20 mL), dried over Na₂SO₄ and brought to dryness. The crude brown oil was purified by preparative TLC (silica gel, 1 mm, heptan/EtOAc 4:1, elution with EtOAc) to give the title compound (13 mg, 63%) as colorless oil; MS (EI): m/e=406.4 [MH⁺].

Example 17

[6-Cyclopropylmethoxy-5-(3,3-difluoro-azetidin-1-yl)-pyridin-2-yl]-(3,3-dimethyl-morpholin-4-yl)-methanone

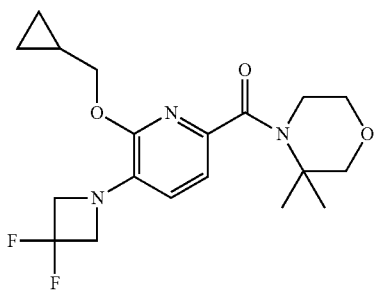 [SMILES: CC1(C)COCCN1C(=O)c1ccc(N2CC(F)(F)C2)c(OCC2CC2)n1]

In analogy to the procedure described in Example 47 b), 6-cyclopropylmethoxy-5-(3,3-difluoro-azetidin-1-yl)-pyridine-2-carboxylic acid (Example 1 b)) was reacted with 3,3-dimethylmorpholine (CAN 59229-63-9) in the presence of TBTU and DIEA to obtain the title compound as colorless oil; MS (EI): m/e=382.4 [MH⁺].

Example 18

[6-Cyclopropylmethoxy-5-(3,3-difluoro-azetidin-1-yl)-pyridin-2-yl]-(2,2-dimethyl-pyrrolidin-1-yl)-methanone

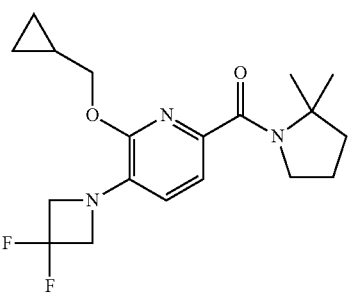 [SMILES: CC1(C)CCCN1C(=O)c1ccc(N2CC(F)(F)C2)c(OCC2CC2)n1]

In analogy to the procedure described in Example 47 b), 6-cyclopropylmethoxy-5-(3,3-difluoro-azetidin-1-yl)-pyridine-2-carboxylic acid (Example 1 b)) was reacted with 2,2- dimethylpyrrolidine (CAN 35018-15-6) in the presence of TBTU and DIEA to obtain the title compound as colorless oil; MS (EI): m/e=366.4 [MH+].

Example 19

6-Cyclopropylmethoxy-5-(3,3-difluoro-azetidin-1-yl)-pyridine-2-carboxylic acid (2-hydroxy-1,1-dimethyl-ethyl)-(2-methoxy-ethyl)-amide

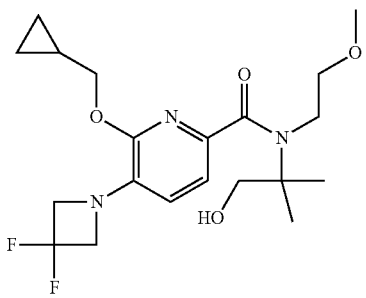 [SMILES: COCCN(C(=O)c1ccc(N2CC(F)(F)C2)c(OCC2CC2)n1)C(C)(C)CO]

In analogy to the procedure described in Example 47 b), 6-cyclopropylmethoxy-5-(3,3-difluoro-azetidin-1-yl)-pyridine-2-carboxylic acid (Example 1 b)) was reacted with 2-(2-methoxyethylamino)-2-methylpropan-1-ol (CAN 1156380-97-0) in the presence of TBTU and DIEA to obtain the title compound as colorless oil; MS (EI): m/e=414.4 [MH+].

Example 20

6-Cyclopropylmethoxy-5-(3,3-difluoro-azetidin-1-yl)-pyridine-2-carboxylic acid tert-butyl-(2-methoxy-ethyl)-amide

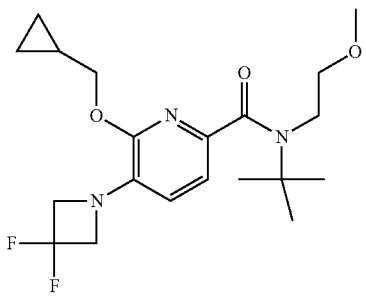 [SMILES: COCCN(C(=O)c1ccc(N2CC(F)(F)C2)c(OCC2CC2)n1)C(C)(C)C]

In analogy to the procedure described in Example 47 b), 6-cyclopropylmethoxy-5-(3,3-difluoro-azetidin-1-yl)-pyridine-2-carboxylic acid (Example 1 b)) was reacted with N-(2-methoxyethyl)-2-methylpropan-2-amine (CAN 22687-22-5) in the presence of TBTU and DIEA to obtain the title compound as colorless oil; MS (EI): m/e=398.4 [MH+].

Example 21

6-Cyclopropylmethoxy-5-(3,3-difluoro-azetidin-1-yl)-pyridine-2-carboxylic acid ethyl-(1-trifluoromethyl-cyclopropyl)-amide

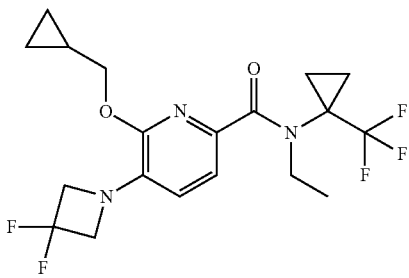 [SMILES: CCN(C(=O)c1ccc(N2CC(F)(F)C2)c(OCC2CC2)n1)C1(C(F)(F)F)CC1]

A solution of 6-(cyclopropylmethoxy)-5-(3,3-difluoroazetidin-1-yl)-N-(1-(trifluoromethyl)cyclopropyl)picolinamide (Example 16 a), 15 mg, 38 μmol) and sodium 2-methylbutan-2-olate (5 mg, 46 μmol) in DMF (150 μL) was stirred for 15 minutes at ambient temperature. Iodoethane (9 mg, 7 μL, 58 μmol) was added and stirring was continued for 1 h. The reaction mixture was poured onto ice/sat. aqueous NaHCO$_3$ solution (15 mL) and extracted with EtOAc (2×25 mL). The combined extracts were washed with ice/brine (2×20 mL), dried over Na$_2$SO$_4$ and brought to dryness. The crude product was purified by preparative TLC (silica gel, 1 mm, heptan/EtOAc 2:1, elution with EtOAc) to give the title compound (12 mg, 75%) as colorless oil; MS (EI): m/e=420.2 [MH]+.

Example 22

6-Cyclopropylmethoxy-5-(3,3-difluoro-azetidin-1-yl)-pyridine-2-carboxylic acid benzyl-(1-trifluoromethyl-cyclopropyl)-amide

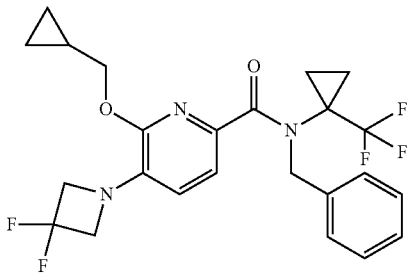 [SMILES: O=C(c1ccc(N2CC(F)(F)C2)c(OCC2CC2)n1)N(Cc1ccccc1)C1(C(F)(F)F)CC1]

In analogy to the procedure described in Example 16 b), 6-(cyclopropylmethoxy)-5-(3,3-difluoroazetidin-1-yl)-N-(1-(trifluoromethyl)cyclopropyl)picolinamide (Example 16 a) was reacted with (chloromethyl)benzene (CAN 27987-13-

9) in the presence of sodium hydride to give the title compound as colorless oil; MS (EI): m/e=482.4 [MH]⁺.

Example 23

{tert-Butyl-[6-cyclopropylmethoxy-5-(3,3-difluoro-azetidin-1-yl)-pyridine-2-carbonyl]-amino}-acetic acid ethyl ester

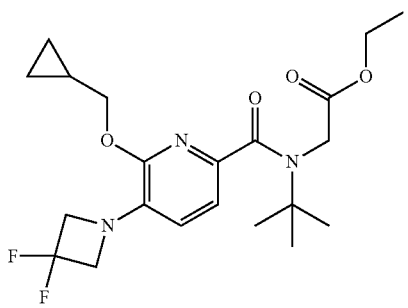 [SMILES: CCOC(=O)CN(C(=O)c1ccc(N2CC(F)(F)C2)c(OCC2CC2)n1)C(C)(C)C]

In analogy to the procedure described in Example 47 b), 6-cyclopropylmethoxy-5-(3,3-difluoro-azetidin-1-yl)-pyridine-2-carboxylic acid (Example 1 b)) was reacted with ethyl 2-(tert-butylamino)acetate (CAN 37885-76-0) in the presence of TBTU and DIEA to obtain the title compound as colorless oil; MS (EI): m/e=426.5 [MH⁺].

Example 24

{tert-Butyl-[6-cyclopropylmethoxy-5-(3,3-difluoro-azetidin-1-yl)-pyridine-2-carbonyl]-amino}-acetic acid

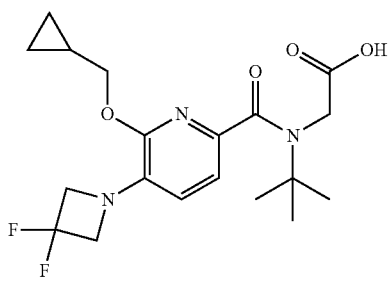 [SMILES: CC(C)(C)N(CC(=O)O)C(=O)c1ccc(N2CC(F)(F)C2)c(OCC2CC2)n1]

A solution of 2-(N-tert-butyl-6-(cyclopropylmethoxy)-5-(3,3-difluoroazetidin-1-yl)picolinamido)acetate (Example 23, 58 mg, 136 μmol) in a mixture of 1N aqueous NaOH solution (164 μL, 164 μmol), THF (0.5 mL), MeOH (0.2 mL) and water (0.05 mL) was stirred at ambient temperature for 24 h and evaporated to dryness. The residue was partitioned between ice water/0.1N aqueous HCl solution (25 mL) and EtOAc (25 mL). The aqueous layer was extracted one more time with EtOAc (25 mL). The combined extracts were washed with ice/brine (25 mL), dried over Na₂SO₄ and brought to dryness to give the title compound (51 mg, 128 μmol, 94%) as light yellow solid; MS (EI): m/e=398.4 [MH⁺].

Example 25

6-Cyclopropylmethoxy-5-(3,3-difluoro-azetidin-1-yl)-pyridine-2-carboxylic acid benzyl-tert-butyl-amide

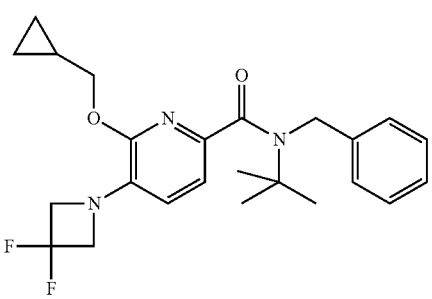 [SMILES: CC(C)(C)N(Cc1ccccc1)C(=O)c1ccc(N2CC(F)(F)C2)c(OCC2CC2)n1]

In analogy to the procedure described in Example 47 b), 6-cyclopropylmethoxy-5-(3,3-difluoro-azetidin-1-yl)-pyridine-2-carboxylic acid (Example 1 b)) was reacted with N-benzyl-2-methylpropan-2-amine (CAN 3378-72-1) in the presence of TBTU and DIEA to obtain the title compound as colorless solid; MS (EI): m/e=430.5 [MH⁺].

Example 26

6-Cyclopropylmethoxy-5-(3,3-difluoro-azetidin-1-yl)-pyridine-2-carboxylic acid tert-butyl-methylcarbamoylmethyl-amide

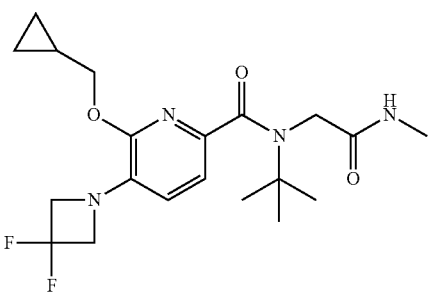 [SMILES: CNC(=O)CN(C(=O)c1ccc(N2CC(F)(F)C2)c(OCC2CC2)n1)C(C)(C)C]

In analogy to the procedure described in Example 47 b), {tert-butyl-[6-cyclopropylmethoxy-5-(3,3-difluoro-azetidin-1-yl)-pyridine-2-carbonyl]-amino}-acetic acid (Example 24) was reacted with a 2 M solution of methanamine (CAN 74-89-5) in MeOH in the presence of TBTU and DIEA to obtain the title compound as colorless oil; MS (EI): m/e=411.5 [MH⁺].

Example 27

6-Cyclopropylmethoxy-5-(3,3-difluoro-azetidin-1-yl)-pyridine-2-carboxylic acid tert-butyl-dimethyl-carbamoylmethyl-amide

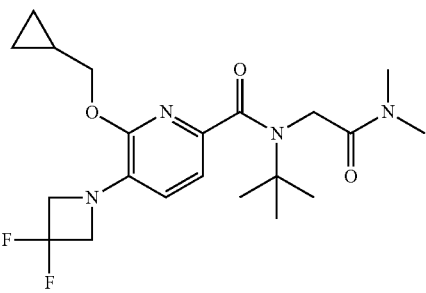 [SMILES: CN(C)C(=O)CN(C(=O)c1ccc(N2CC(F)(F)C2)c(OCC2CC2)n1)C(C)(C)C]

In analogy to the procedure described in Example 47 b), {tert-butyl-[6-cyclopropylmethoxy-5-(3,3-difluoro-azetidin-1-yl)-pyridine-2-carbonyl]-amino}-acetic acid (Example 24) was reacted with dimethylamine hydrochloride (CAN 506-59-2) in the presence of TBTU and DIEA to obtain the title compound as colorless oil; MS (EI): m/e=425.5 [MH$^+$].

Example 28

4-[6-Cyclopropylmethoxy-5-(3,3-difluoro-azetidin-1-yl)-pyridine-2-carbonyl]-3,3-dimethyl-piperazin-2-one

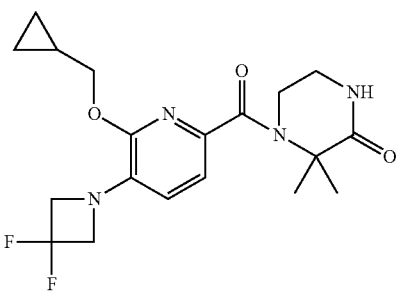 [SMILES: CC1(C)C(=O)NCCN1C(=O)c1ccc(N2CC(F)(F)C2)c(OCC2CC2)n1]

In analogy to the procedure described in Example 47 b), 6-cyclopropylmethoxy-5-(3,3-difluoro-azetidin-1-yl)-pyridine-2-carboxylic acid (Example 1 b)) was reacted with 3,3-dimethylpiperazin-2-one hydrochloride (CAN 1104383-07-4) in the presence of TBTU and DIEA to obtain the title compound as white solid; MS (EI): m/e=395.4 [MH$^+$].

Example 29

4-[6-Cyclopropylmethoxy-5-(3,3-difluoro-azetidin-1-yl)-pyridine-2-carbonyl]-3,3-diethyl-piperazin-2-one

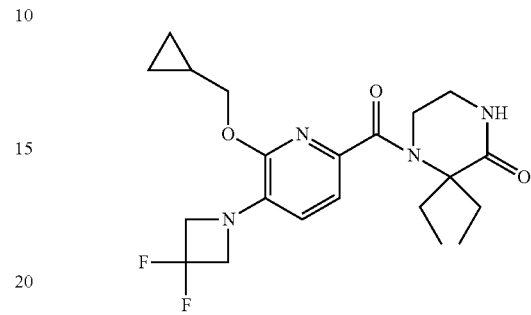

In analogy to the procedure described in Example 47 b), 6-cyclopropylmethoxy-5-(3,3-difluoro-azetidin-1-yl)-pyridine-2-carboxylic acid (Example 1 b)) was reacted with 3,3-dimethylpiperazin-2-one hydrochloride (CAN 907973-05-1) in the presence of TBTU and DIEA to obtain the title compound as colorless solid; MS (EI): m/e=423.4 [MH$^+$].

Example 30

[5-Cyclopropyl-6-(2-methyl-propane-1-sulfonyl)-pyridin-2-yl]-(2,2-dimethyl-pyrrolidin-1-yl)-methanone

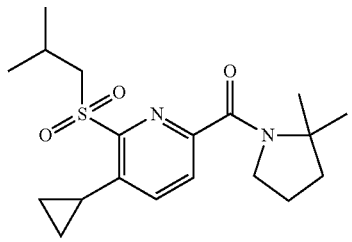 [SMILES: CC(C)CS(=O)(=O)c1nc(C(=O)N2CCCC2(C)C)ccc1C1CC1]

In analogy to the procedure described in Example 47 b), 5-cyclopropyl-6-(isobutylsulfonyl)picolinic acid (Example 6 d)) was reacted with 2,2-dimethylpyrrolidine (CAN 35018-15-6) in the presence of TBTU and DIEA to obtain the title compound as colorless solid; MS (EI): m/e=365.5 [MH$^+$].

Example 31

[5-Cyclopropyl-6-(2-methyl-propane-1-sulfonyl)-pyridin-2-yl]-(4,4-dimethyl-oxazolidin-3-yl)-methanone

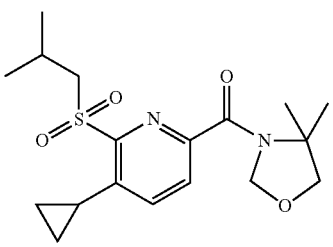 [SMILES: CC(C)CS(=O)(=O)c1nc(C(=O)N2COCC2(C)C)ccc1C1CC1]

In analogy to the procedure described in Example 47 b), 5-cyclopropyl-6-(isobutylsulfonyl)picolinic acid (Example 6 d)) was reacted with 4,4-dimethyloxazolidine (CAN 51200-87-4) in the presence of TBTU and DIEA to obtain the title compound as colorless solid; MS (EI): m/e=367.4 [MH⁺].

Example 32

6-Cyclopropylmethoxy-5-(3,3-difluoro-azetidin-1-yl)-pyridine-2-carboxylic acid [(S)-2-cyclopropyl-1-(5-methyl-[1,2,4]oxadiazol-3-yl)-ethyl]-methyl-amide a) (S)-tert-Butyl 1-amino-3-cyclopropyl-1-oxopropan-2-ylcarbamate

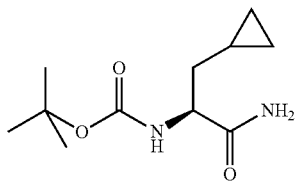 [SMILES: CC(C)(C)OC(=O)N[C@@H](CC1CC1)C(N)=O]

A mixture of (S)-2-(tert-butoxycarbonylamino)-3-cyclopropylpropanoic acid (CAN 89483-06-7, 10 g, 44 mmol), di-tert-butyl dicarbonate (CAN:24424-99-5, 14.28 g, 66 mmol) and pyridine (2.4 mL) in acetonitrile (200 mL) was stirred at room temperature for 20 min. Ammonia (10 mL) was added dropwise for 20 min. The resulting reaction mixture was stirred for 4 h. During removal of most of the solvent under reduced pressure the product precipitated and the solid was filtered off and washed with acetonitrile (20 mL). The solid was dried under reduced pressure to give the title compound (7.73 g, 78%) as white solid; MS (EI): m/e 251.2 [M+Na]⁺.

b) (S)-tert-Butyl 1-cyano-2-cyclopropylethylcarbamate

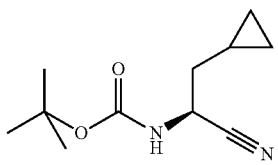

To a solution of (S)-tert-butyl 1-amino-3-cyclopropyl-1-oxopropan-2-ylcarbamate (3.7 g, 16 mmol) and triethylamine (6.55 g, 65 mmol) in methylene chloride (50 mL) was added trifluoroacetic acid anhydride (6.81 g, 32 mmol) dropwise at 0° C. The resulting mixture was allowed to warm to room temperature and stirred for 4 h. The mixture was washed with water (150 mL), citric acid (150 mL, 5 M) and brine (150 mL). The organic phase was dried over anhydrous sodium sulfate and concentrated to give product (3.31 g, 97%) as a yellow solid; MS (EI): m/e 233.1 [M+Na]⁺.

c) (S,Z)-tert-Butyl 1-amino-3-cyclopropyl-1-(hydroxyimino)propan-2-ylcarbamate

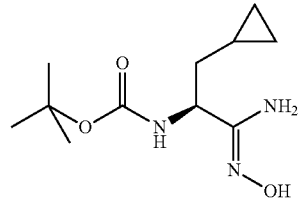 [SMILES: CC(C)(C)OC(=O)N[C@@H](CC1CC1)/C(N)=N/O]

Potassium carbonate (2.18 g, 16 mmol) was dissolved in water (8 mL) and hydroxylamine hydrochloride (1.1 g, 16 mmol) was added. A solution of (S)-tert-butyl 1-cyano-2-cyclopropylethylcarbamate (3.31 g, 16 mmol) in ethanol (24 mL) was added thereto and the resulting reaction mixture was stirred for 72 h. After evaporation of solvents, the residue was dissolved with ethyl acetate (20 mL) and then filtered. The filtrate was concentrated to yield crude product as yellow solid (3.61 g, 94%); MS (EI): m/e 244.2 [M+H]⁺.

d) (S)-tert-Butyl 2-cyclopropyl-1-(5-methyl-1,2,4-oxadiazol-3-yl)ethylcarbamate

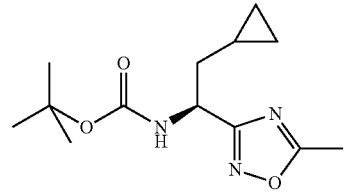 [SMILES: Cc1nc([C@H](CC2CC2)NC(=O)OC(C)(C)C)no1]

To a solution of acetic acid (0.224 g, 4 mmol) in DMF (5 mL) was added N,N'-carbonyldiimidazole (0.6 g, 4 mmol) and the mixture was stirred for 0.5 h at room temperature. (S,Z)-tert-butyl 1-amino-3-cyclopropyl-1-(hydroxyimino)propan-2-ylcarbamate (0.84 g, 3 mmol) was added and the mixture was heated to 120° C. and stirred for 4 h. After evaporation of solvents, the residue was purified by column chromatography (silica gel, 20 g, eluting with 10% ethyl acetate in petroleum ether) to give the title compound (0.5 g; 54%) as yellow solid; MS (EI): m/e 290.1 [M+Na]⁺.

e) (S)-2-Cyclopropyl-1-(5-methyl-[1,2,4]oxadiazol-3-yl)-ethylamine

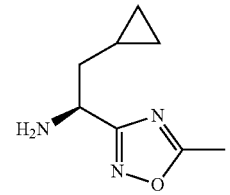

A solution of (S)-tert-butyl 2-cyclopropyl-1-(5-methyl-1,2,4-oxadiazol-3-yl)ethylcarbamate (0.5 g, 2 mmol) in sat.

hydrochloric acid (10 mL) was stirred at room temperature for 1 h. Then water (20 mL) was added. The water phase was washed with ethyl acetate (2×20 mL) and adjusted with 2 M sodium hydroxide solution to pH=9-10. It was then extracted with ethyl acetate (2×20 mL). The organic layer was washed with brine (20 mL), dried over anhydrous sodium sulfate and concentrated to give crude product as a white solid (0.25 g, 80%); MS (EI): m/e 168.2 [M+H]$^+$.

f) 6-Cyclopropylmethoxy-5-(3,3-difluoro-azetidin-1-yl)-pyridine-2-carboxylic acid [(S)-2-cyclopropyl-1-(5-methyl-[1,2,4]oxadiazol-3-yl)-ethyl]-amide

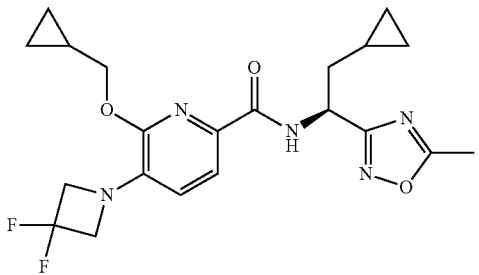 [SMILES: Cc1nc([C@H](CC2CC2)NC(=O)c2ccc(N3CC(F)(F)C3)c(OCC3CC3)n2)no1]

In analogy to the procedure described in Example 47 b), 6-cyclopropylmethoxy-5-(3,3-difluoro-azetidin-1-yl)-pyridine-2-carboxylic acid (Example 1 b)) was reacted with (S)-2-cyclopropyl-1-(5-methyl-[1,2,4]oxadiazol-3-yl)-ethylamine in the presence of TBTU and DIEA to obtain the title compound; MS (EI): m/e=434.2 [MH$^+$].

g) 6-Cyclopropylmethoxy-5-(3,3-difluoro-azetidin-1-yl)-pyridine-2-carboxylic acid [(S)-2-cyclopropyl-1-(5-methyl-[1,2,4]oxadiazol-3-yl)-ethyl]-methyl-amide

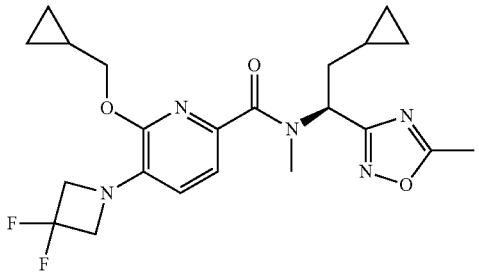 [SMILES: Cc1nc([C@H](CC2CC2)N(C)C(=O)c2ccc(N3CC(F)(F)C3)c(OCC3CC3)n2)no1]

In analogy to the procure described in Example 16 b), 6-cyclopropylmethoxy-5-(3,3-difluoro-azetidin-1-yl)-pyridine-2-carboxylic acid [(S)-2-cyclopropyl-1-(5-methyl-[1,2,4]oxadiazol-3-yl)-ethyl]-amide was reacted with methyl iodide (CAN 74-88-4) in the presence of sodium hydride to give the title compound as colorless oil; MS (EI): m/e=448.2 [MH]$^+$.

Example 33

5-Cyclopropyl-6-(tetrahydro-pyran-4-ylmethoxy)-pyridine-2-carboxylic acid [cyclopropyl-(5-methyl-[1,2,4]oxadiazol-3-yl)-methyl]-methyl-amide a) 5-Cyclopropyl-6-(tetrahydro-pyran-4-ylmethoxy)-pyridine-2-carboxylic acid [cyclopropyl-(5-methyl-[1,2,4]oxadiazol-3-yl)-methyl]-amide

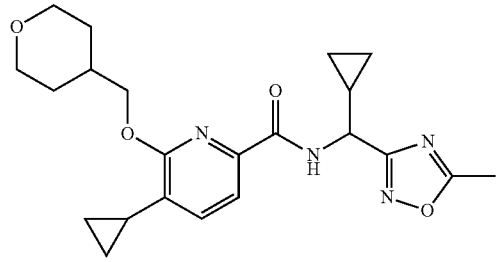 [SMILES: Cc1nc(C(NC(=O)c2ccc(C3CC3)c(OCC3CCOCC3)n2)C2CC2)no1]

In analogy to the procedure described in Example 47 b), 5-cyclopropyl-6-(tetrahydro-pyran-4-ylmethoxy)-pyridine-2-carboxylic acid (which can e.g. be prepared in a similar manner than 5-cyclopropyl-6-(tetrahydro-furan-2-yl-methoxy)-pyridine-2-carboxylic acid (Example 4 b)) was reacted with cyclopropyl-(5-methyl-[1,2,4]oxadiazol-3-yl)-methylamine (which can e.g. be prepared in a similar manner than (S)-2-cyclopropyl-1-(5-methyl-[1,2,4]oxadiazol-3-yl)-ethylamine (Example 32 e)) in the presence of TBTU and DIEA to obtain the title compound as colorless oil; MS (EI): m/e=413.1 [MH$^+$].

b) 5-Cyclopropyl-6-(tetrahydro-pyran-4-ylmethoxy)-pyridine-2-carboxylic acid [cyclopropyl-(5-methyl-[1,2,4]oxadiazol-3-yl)-methyl]-methyl-amide

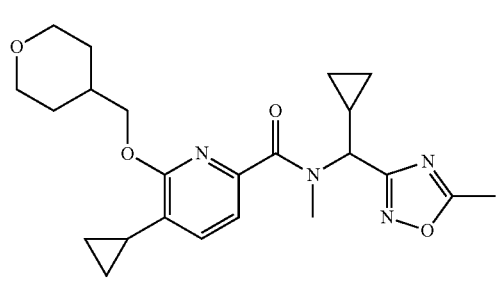 [SMILES: Cc1nc(C(C2CC2)N(C)C(=O)c2ccc(C3CC3)c(OCC3CCOCC3)n2)no1]

In analogy to the procure described in Example 16 b), 5-cyclopropyl-6-(tetrahydro-pyran-4-ylmethoxy)-pyridine-2-carboxylic acid [cyclopropyl-(5-methyl-[1,2,4]oxadiazol-3-yl)-methyl]-amide was reacted with methyl iodide (CAN 74-88-4) in the presence of sodium hydride to give the title compound as colorless oil; MS (EI): m/e=427.2 [MH]+.

Example 34

(+)-6-Cyclopropylmethoxy-5-(3,3-difluoro-azetidin-1-yl)-pyridine-2-carboxylic acid methyl-(3-methyl-1-pyridazin-3-yl-butyl)-amide a) 3-Methyl-1-(pyridazin-3-yl)butan-1-amine

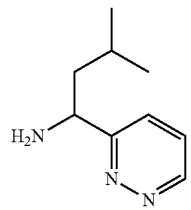

A suspension of 3-methyl-1-(pyridazin-3-yl)butan-1-one (0.85 g, 5.2 mmol; CAN 138835-88-8), sodium cyanoborohydride (1.2 g, 19.2 mmol) and ammonium acetate (1.28 g, 16.6 mmol) in methanol (11.1 mL) was heated at 70° C. for 12 h. The solvent was removed under reduced pressure and the residual oil was partitioned between EtOAc and 1 M aqueous HCl solution. The aqueous layer was basified with 10% aqueous NaOH solution and extracted with EtOAc. The combined extracts were washed with brine and dried over $Na_2SO_4$. Filtration and evaporation provided the title compound (233 mg, 27%) as brown oil which was sufficiently pure to be used in the next reaction step. MS (EI): m/e=166.2 [M+H]+.

b) (+)-6-Cyclopropylmethoxy-5-(3,3-difluoro-azetidin-1-yl)-pyridine-2-carboxylic acid (3-methyl-1-pyridazin-3-yl-butyl)-amide

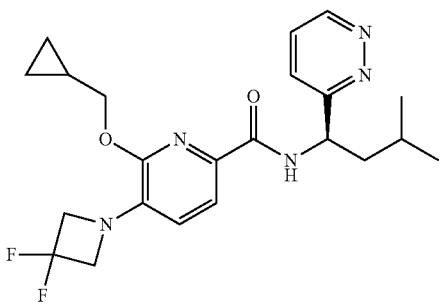 [SMILES: CC(C)C[C@@H](NC(=O)c1ccc(N2CC(F)(F)C2)c(OCC2CC2)n1)c1cccnn1]

The title compound was synthesized in analogy to Example 47 b), using 6-cyclopropylmethoxy-5-(3,3-difluoro-azetidin-1-yl)-pyridine-2-carboxylic acid (Example 1 b)) and 3-methyl-1-(pyridazin-3-yl)butan-1-amine as starting materials. The product was isolated by chiral chromatography on Reprosil Chiral NR using a mixture of heptane, ethanol and 2-propanol as eluent. The (+)-enantiomer was isolated. MS (EI): m/e=432.5 [MH+].

c) (+)-6-Cyclopropylmethoxy-5-(3,3-difluoro-azetidin-1-yl)-pyridine-2-carboxylic acid methyl-(3-methyl-1-pyridazin-3-yl-butyl)-amide

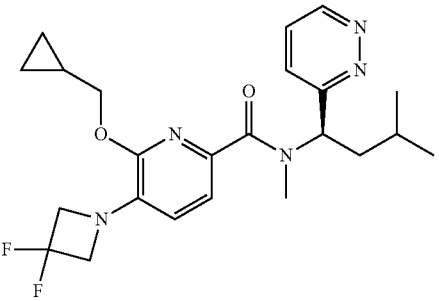 [SMILES: CC(C)C[C@H](c1cccnn1)N(C)C(=O)c1ccc(N2CC(F)(F)C2)c(OCC2CC2)n1]

In analogy to the procure described in Example 16 b), (+)-6-cyclopropylmethoxy-5-(3,3-difluoro-azetidin-1-yl)-pyridine-2-carboxylic acid (3-methyl-1-pyridazin-3-yl-butyl)-amide was reacted with methyl iodide (CAN 74-88-4) in the presence of sodium hydride to give the title compound as colorless oil; MS (EI): m/e=446.2 [MH]+.

Example 35

6-Cyclopropylmethoxy-5-(3,3-difluoro-azetidin-1-yl)-pyridine-2-carboxylic acid tert-butyl-carbamoylmethyl-amide

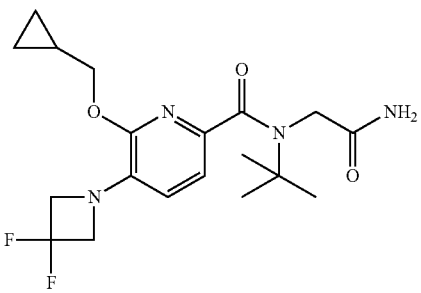 [SMILES: CC(C)(C)N(CC(N)=O)C(=O)c1ccc(N2CC(F)(F)C2)c(OCC2CC2)n1]

In analogy to the procedure described in Example 47 b), 6-cyclopropylmethoxy-5-(3,3-difluoro-azetidin-1-yl)-pyridine-2-carboxylic acid (Example 1 b)) was reacted with 2-(tert-butylamino)acetamide (207925-15-3) in the presence of TBTU and DIEA to obtain the title compound as white solid; MS (EI): m/e=397.5 [MH+].

Example 36

6-Cyclopropylmethoxy-5-(3,3-difluoro-azetidin-1-yl)-pyridine-2-carboxylic acid tert-butyl-(5-methyl-[1,3,4]oxadiazol-2-ylmethyl)-amide a) 2-Methyl-N-((5-methyl-1,3,4-oxadiazol-2-yl)methyl)propan-2-amine

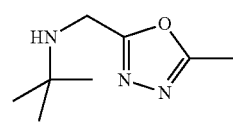

A suspension of 2-methylpropan-2-amine (75-64-9, 141 mg, 202 μL, 1.92 mmol) and 2-(chloromethyl)-5-methyl-1,3,4-oxadiazole (3914-42-9, 50 mg, 377 μmol) in DMF (200 μL) was stirred at ambient temperature for 16 h. The mixture was poured onto ice-water (20 mL) and extracted with CH$_2$Cl$_2$ (2×30 mL). The combined extracts were washed with ice-water (20 mL), dried over Na$_2$SO$_4$ and concentrated in vacuo to give a yellow oil. The crude product was purified by preparative TLC (silica gel 1 mm, EtOAc/diethyl amine 95:5, elution with DCM/EtOAc 1:1) to give the title compound (45 mg, 71%) as yellow oil; MS (EI): m/e=170.2 [MH$^+$].

b) 6-Cyclopropylmethoxy-5-(3,3-difluoro-azetidin-1-yl)-pyridine-2-carboxylic acid tert-butyl-(5-methyl-[1,3,4]oxadiazol-2-ylmethyl)-amide

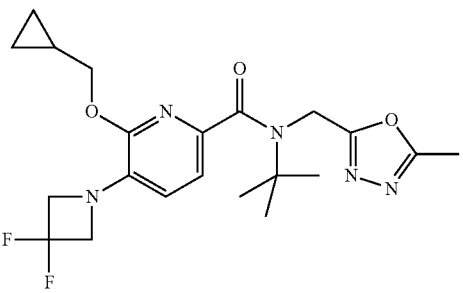 [SMILES: Cc1nnc(CN(C(=O)c2ccc(N3CC(F)(F)C3)c(OCC3CC3)n2)C(C)(C)C)o1]

In analogy to the procedure described in Example 47 b), 6-cyclopropylmethoxy-5-(3,3-difluoro-azetidin-1-yl)-pyridine-2-carboxylic acid (Example 1 b)) was reacted with 2-methyl-N-((5-methyl-1,3,4-oxadiazol-2-yl)methyl)propan-2-amine in the presence of TBTU and DIEA to obtain the title compound as yellow solid; MS (EI): m/e=436.4 [MH$^+$].

Example 37

[6-Cyclopropylmethoxy-5-(3,3-difluoro-azetidin-1-yl)-pyridin-2-yl]-(3-hydroxy-3-methyl-pyrrolidin-1-yl)-methanone

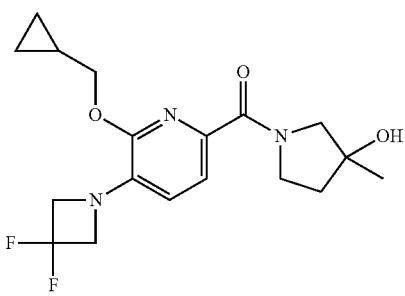 [SMILES: CC1(O)CCN(C(=O)c2ccc(N3CC(F)(F)C3)c(OCC3CC3)n2)C1]

In analogy to the procedure described in Example 47 b), 6-cyclopropylmethoxy-5-(3,3-difluoro-azetidin-1-yl)-pyridine-2-carboxylic acid (Example 1 b)) was reacted with 3-methylpyrrolidin-3-ol (125032-87-3) in the presence of TBTU and DIEA to obtain the title compound as yellow solid; MS (EI): m/e=368.5 [MH$^+$].

Example 38

5-Chloro-4-(2,2,2-trifluoro-ethoxy)-pyridine-2-carboxylic acid (2,2-dimethyl-1-thiazol-2-yl-propyl)-amide

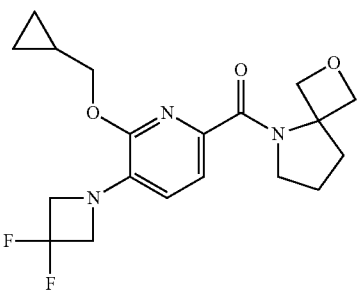 [SMILES: O=C(c1ccc(N2CC(F)(F)C2)c(OCC2CC2)n1)N1CCCC12COC2]

In analogy to the procedure described in Example 47 b), 6-cyclopropylmethoxy-5-(3,3-difluoro-azetidin-1-yl)-pyridine-2-carboxylic acid (Example 1 b)) was reacted with 2-oxa-5-azaspiro[3.4]octane oxalate (90207-55-9) in the presence of TBTU and DIEA to obtain the title compound as yellow solid; MS (EI): m/e=380.3 [MH$^+$].

Example 39

6-Cyclopropylmethoxy-5-(3,3-difluoro-azetidin-1-yl)-pyridine-2-carboxylic acid ethyl-(2-methoxy-ethyl)-amide

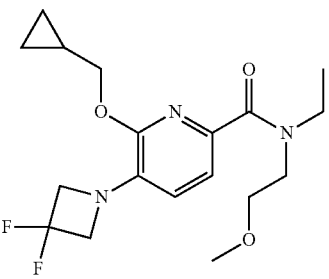 [SMILES: CCN(CCOC)C(=O)c1ccc(N2CC(F)(F)C2)c(OCC2CC2)n1]

In analogy to the procedure described in Example 47 b), 6-cyclopropylmethoxy-5-(3,3-difluoro-azetidin-1-yl)-pyridine-2-carboxylic acid (Example 1 b)) was reacted with N-ethyl-2-methoxyethanamine (34322-82-2) in the presence of TBTU and DIEA to obtain the title compound as colorless oil; MS (EI): m/e=370.6 [MH$^+$].

Example 40

6-Cyclopropylmethoxy-5-(3,3-difluoro-azetidin-1-yl)-pyridine-2-carboxylic acid tert-butyl-(1-methyl-1H-tetrazol-5-ylmethyl)-amide a) 2-Methyl-N-((1-methyl-1H-tetrazol-5-yl)methyl)propan-2-amine hydrochloride

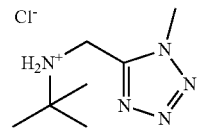

A mixture of 2-methylpropan-2-amine (75-64-9, 281 mg, 404 μL, 3.85 mmol) and 5-(chloromethyl)-1-methyl-1H-tetrazole (57235-84-4, 100 mg, 754 μmol) was stirred at ambient temperature for 16 h and concentrated in vacuo to give the title compound (112 mg, 72%) as yellow solid; MS (EI): m/e=169 [M+].

b) 6-Cyclopropylmethoxy-5-(3,3-difluoro-azetidin-1-yl)-pyridine-2-carboxylic acid tert-butyl-(1-methyl-1H-tetrazol-5-ylmethyl)-amide

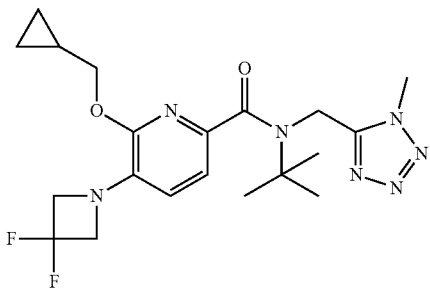 [SMILES: Cn1nnnc1CN(C(=O)c1ccc(N2CC(F)(F)C2)c(OCC2CC2)n1)C(C)(C)C]

In analogy to the procedure described in Example 47 b), 6-cyclopropylmethoxy-5-(3,3-difluoro-azetidin-1-yl)-pyridine-2-carboxylic acid (Example 1 b)) was reacted with 2-methyl-N-((1-methyl-1H-tetrazol-5-yl)methyl)propan-2-amine hydrochloride in the presence of TBTU and DIEA to obtain the title compound as yellow solid; MS (EI): m/e=436.5 [MH+].

Example 41

N-{1-[6-Cyclopropylmethoxy-5-(3,3-difluoro-azetidin-1-yl)-pyridine-2-carbonyl]-pyrrolidin-3-yl}-acetamide

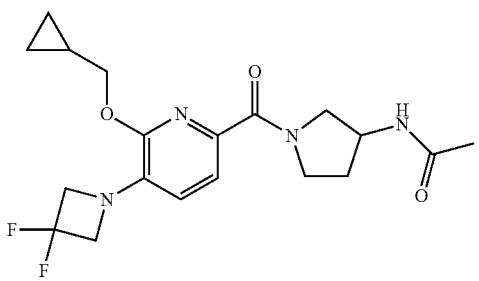 [SMILES: CC(=O)NC1CCN(C(=O)c2ccc(N3CC(F)(F)C3)c(OCC3CC3)n2)C1]

In analogy to the procedure described in Example 47 b), 6-cyclopropylmethoxy-5-(3,3-difluoro-azetidin-1-yl)-pyridine-2-carboxylic acid (Example 1 b)) was reacted with N-(pyrrolidin-3-yl)acetamide (79286-74-1) in the presence of TBTU and DIEA to obtain the title compound as colorless oil; MS (EI): m/e=395.5 [MH+].

Example 42

[5-Cyclopropyl-6-(4-fluoro-benzyl)-pyridin-2-yl]-(4,4-dimethyl-piperidin-1-yl)-methanone

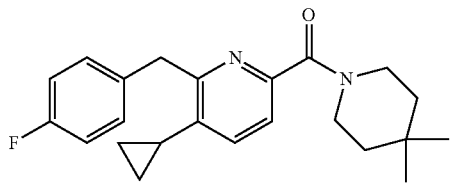 [SMILES: CC1(C)CCN(C(=O)c2ccc(C3CC3)c(Cc3ccc(F)cc3)n2)CC1]

In analogy to the procedure described in Example 47 b), 5-cyclopropyl-6-(4-fluoro-benzyl)-pyridine-2-carboxylic acid (Example 5 g)) was reacted with 4,4-dimethyl-piperidine (4045-30-1) in the presence of TBTU and DIEA to obtain the title compound as colorless oil; MS (EI): m/e=367.5 [MH+].

Example 43

[5-Cyclopropyl-6-(tetrahydro-furan-2-ylmethoxy)-pyridin-2-yl]-(4,4-dimethyl-piperidin-1-yl)-methanone

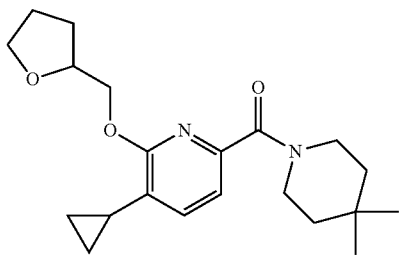 [SMILES: CC1(C)CCN(C(=O)c2ccc(C3CC3)c(OCC3CCCO3)n2)CC1]

In analogy to the procedure described in Example 47 b), 5-cyclopropyl-6-(tetrahydro-furan-2-ylmethoxy)-pyridine-2-carboxylic acid (Example 4 b)) was reacted with 4,4-dimethyl-piperidine (4045-30-1) in the presence of TBTU and DIEA to obtain the title compound as colorless oil; MS (EI): m/e=359.6 [MH+].

Example 44

[5-Cyclopropyl-6-(4-fluoro-benzyl)-pyridin-2-yl]-(4,4-dimethyl-oxazolidin-3-yl)-methanone

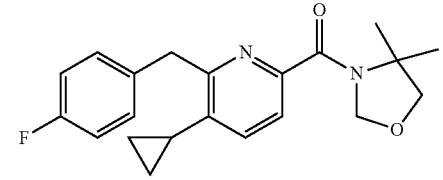 [SMILES: CC1(C)COCN1C(=O)c1ccc(C2CC2)c(Cc2ccc(F)cc2)n1]

In analogy to the procedure described in Example 47 b), 5-cyclopropyl-6-(4-fluoro-benzyl)-pyridine-2-carboxylic acid (Example 5 g)) was reacted with 4,4-dimethyloxazolidine (CAN 51200-87-4) in the presence of TBTU and DIEA to obtain the title compound as colorless oil; MS (EI): m/e=355.5 [MH⁺].

Example 45

[6-Cyclopropylmethoxy-5-(3,3-difluoro-azetidin-1-yl)-pyridin-2-yl]-((1S,5R)-1,3,3-trimethyl-6-azabicyclo[3.2.1]oct-6-yl)-methanone

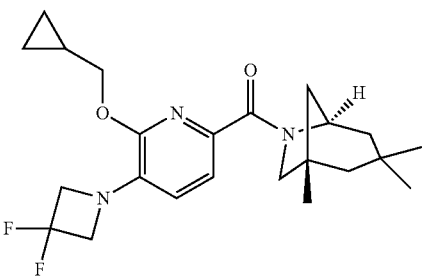 [SMILES: CC1(C)C[C@@H]2C[C@@](C)(CN2C(=O)c2ccc(N3CC(F)(F)C3)c(OCC3CC3)n2)C1]

In analogy to the procedure described in Example 47 b), 6-cyclopropylmethoxy-5-(3,3-difluoro-azetidin-1-yl)-pyridine-2-carboxylic acid (Example 1 b)) was reacted with (1S,5R)-1,3,3-trimethyl-6-azabicyclo[3.2.1]octane hydrochloride (380228-03-5) in the presence of TBTU and DIEA to obtain the title compound as colorless oil; MS (EI): m/e=420.2 [MH⁺].

Example 46

[6-Cyclopropylmethoxy-5-(3,3-difluoro-azetidin-1-yl)-pyridin-2-yl]-((R)-2-methoxymethyl-pyrrolidin-1-yl)-methanone

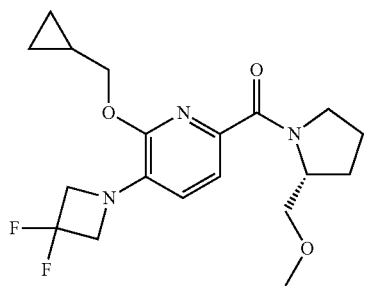 [SMILES: COC[C@H]1CCCN1C(=O)c1ccc(N2CC(F)(F)C2)c(OCC2CC2)n1]

In analogy to the procedure described in Example 47 b), 6-cyclopropylmethoxy-5-(3,3-difluoro-azetidin-1-yl)-pyridine-2-carboxylic acid (Example 1 b)) was reacted with (R)-2-(methoxymethyl)pyrrolidine (84025-81-0) in the presence of TBTU and DIEA to obtain the title compound as colorless oil; MS (EI): m/e=382.5 [MH⁺].

Example 47

(6-Chloro-5-cyclopropylmethoxy-pyridin-2-yl)-(2,2-dimethyl-pyrrolidin-1-yl)-methanone a) Mixture of 6-cyclopropylmethoxy-5-trifluoromethoxy-pyridine-2-carboxylic acid and 6-chloro-5-cyclopropylmethoxy-pyridine-2-carboxylic acid

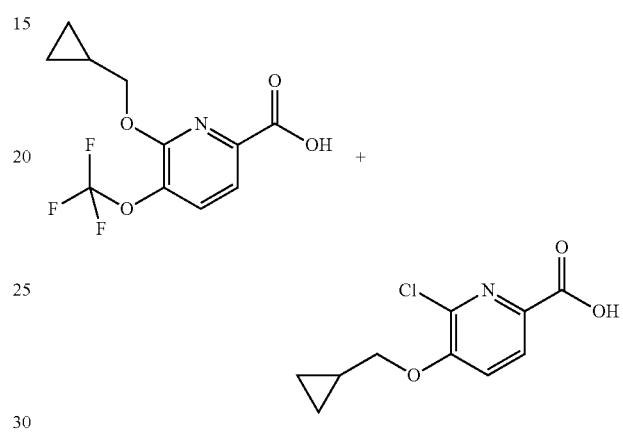

To a solution of 6-chloro-5-trifluoromethoxy-pyridine-2-carboxylic acid (CAN 1221171-90-9, 1.0 g, 4.14 mmol) in DMSO (16 mL) was added potassium hydroxide (0.93 g, 16.6 mmol) and the reaction mixture was stirred at room temperature for 15 minutes. To this suspension was added cyclopropylmethanol (335 µL, 4.14 mmol) and the mixture was stirred at ambient temperature for 16 hours. More cyclopropylmethanol (335 µL, 4.14 mmol) was added and stirring continued for 4 hours at 50° C. The mixture was cooled, added to 2 N sodium hydroxide solution (50 mL) with cooling and partitioned between TBME and 1 N sodium hydroxide solution. The organic phase was discarded; the water phases were pooled, acidified with 2 N hydrochloric acid and extracted with TBME. Organic phases were pooled, dried with Na₂SO₄, filtered and concentrated in vacuo. The crude material (1.05 g) of a light brown solid was used without and contained a mixture of 6-cyclopropylmethoxy-5-trifluoromethoxy-pyridine-2-carboxylic acid and 6-chloro-5-cyclopropylmethoxy-pyridine-2-carboxylic acid (~7/3 by NMR); LC-MS (UV peak area, ESI) 48.8%, 228.0425 [MH⁺], 51.2%, 278.0628 [MH⁺].

b) (6-Chloro-5-cyclopropylmethoxy-pyridin-2-yl)-(2,2-dimethyl-pyrrolidin-1-yl)-methanone

The mixture of 6-cyclopropylmethoxy-5-trifluoromethoxy-pyridine-2-carboxylic acid and 6-chloro-5-cyclopropylmethoxy-pyridine-2-carboxylic acid (Example 47 a, 50 mg, 180 μmol) was dissolved in DMF (2 mL). TBTU (63.7 mg, 198 μmol), DIEA (154 μl, 902 μmol) and 2,2-dimethylpyrrolidine (CAN 35018-15-6, 24 μl, 198 μmol) were added and the reaction mixture was stirred at room temperature for 16 hours. Ethyl acetate (3 mL) and 1 N sodium hydroxide solution (2 mL) were added; the mixture was dried by passage through ChemElut® and concentrated in vacuo. The crude material was purified by flash chromatography (silica gel, ethyl acetate/n-heptane gradient) to give the title compound (17 mg, 31%) as off-white wax; LC-MS (UV peak area, ESI) 97%, 309.1367 [MH+].

Example 48

(6-Cyclopropylmethoxy-5-trifluoromethoxy-pyridin-2-yl)-(4,4-dimethyl-oxazolidin-3-yl)-methanone

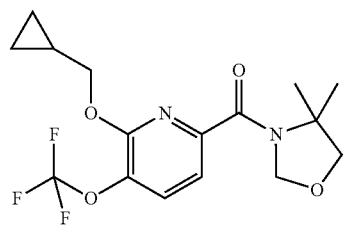 [SMILES: CC1(C)COCN1C(=O)c1ccc(OC(F)(F)F)c(OCC2CC2)n1]

The title compound was synthesized in analogy to Example 47 b, using the mixture of 6-cyclopropylmethoxy-5-trifluoromethoxy-pyridine-2-carboxylic acid and 6-chloro-5-cyclopropylmethoxy-pyridine-2-carboxylic acid (Example 47 a, 50 mg, 180 μmol) and 4,4-dimethyl-oxazolidine (CAN 51200-87-4; 28.4 μl (75%), 198 μmol) as starting materials and isolated (24 mg, 37%) as colorless oil; LC-MS (UV peak area, ESI) 100%, 361.1370 [MH+].

Example 49

(6-Chloro-5-cyclopropylmethoxy-pyridin-2-yl)-(4,4-dimethyl-oxazolidin-3-yl)-methanone

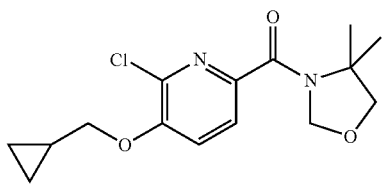 [SMILES: CC1(C)COCN1C(=O)c1ccc(OCC2CC2)c(Cl)n1]

The title compound was synthesized in analogy to Example 47 b, using the mixture of 6-cyclopropylmethoxy-5-trifluoromethoxy-pyridine-2-carboxylic acid and 6-chloro-5-cyclopropylmethoxy-pyridine-2-carboxylic acid (Example 47 a, 50 mg, 180 μmol) and 4,4-dimethyl-oxazolidine (CAN 51200-87-4; 28.4 μl (75%), 198 μmol) as starting materials and isolated (13 mg, 23%) as colorless oil; LC-MS (UV peak area, ESI) 100%, 311.1158 [MH+].

Example 50

6-Cyclopropylmethoxy-5-(3,3-difluoro-azetidin-1-yl)-pyridine-2-carboxylic acid (1-acetyl-piperidin-4-yl)-cyclopropyl-amide

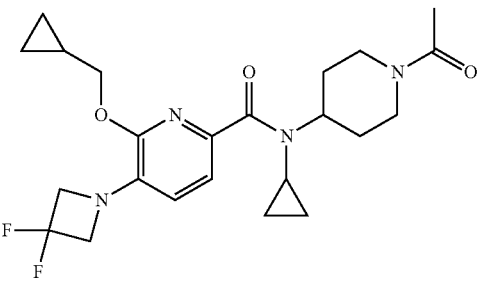 [SMILES: CC(=O)N1CCC(N(C(=O)c2ccc(N3CC(F)(F)C3)c(OCC3CC3)n2)C2CC2)CC1]

The title compound was synthesized in analogy to Example 47 b), using 6-(cyclopropylmethoxy)-5-(3,3-difluoroazetidin-1-yl)picolinic acid and 1-(4-(cyclopropylamino)piperidin-1-yl)ethanone (CAS 387358-46-5) as starting materials and isolated as colorless oil. MS (EI): m/e=449.6 [MH+].

Example 51

6-(Cyclopropylmethoxy)-5-(3,3-difluoroazetidin-1-yl)-N-formyl-N-methylpyridine-2-carboxamide a) 6-(Cyclopropylmethoxy)-5-(3,3-difluoroazetidin-1-yl)-N-((3-(trifluoromethyl)-1,2,4-oxadiazol-5-yl)methyl)picolinamide

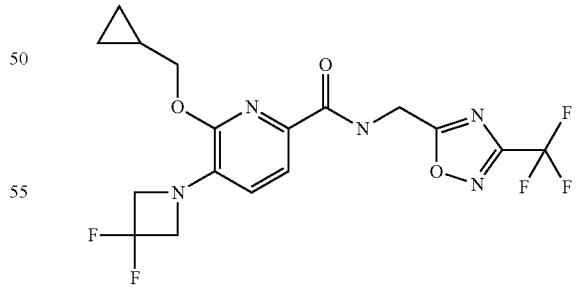

In analogy to the procedure described in Example 47 b), 6-cyclopropylmethoxy-5-(3,3-difluoro-azetidin-1-yl)-pyridine-2-carboxylic acid (Example 1 b) was reacted with C-(3-trifluoromethyl-[1,2,4]oxadiazol-5-yl)-methyl amine hydrochloride (CAS 944905-93-5) in the presence of TBTU and DIEA to give the title compound as white solid; MS (EI): m/e=434.5 [MH+].

b) 6-(Cyclopropylmethoxy)-5-(3,3-difluoroazetidin-1-yl)-N-formyl-N-methylpyridine-2-carboxamide

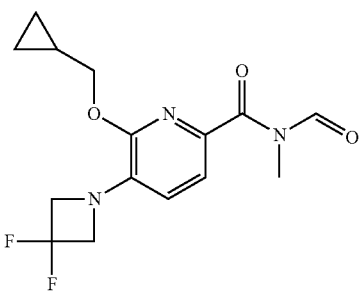 [SMILES: CN(C=O)C(=O)c1ccc(N2CC(F)(F)C2)c(OCC2CC2)n1]

The title compound was synthesized in analogy to the procedure described in Example 47 b), using 6-(cyclopropylmethoxy)-5-(3,3-difluoroazetidin-1-yl)-N-((3-(trifluoromethyl)-1,2,4-oxadiazol-5-yl)methyl)picolinamide as starting material. MS (EI): m/e=326.1 [M+H]$^+$.

Example 52

6-Cyclopropylmethoxy-5-(3,3-difluoro-azetidin-1-yl)-pyridine-2-carboxylic acid methyl-phenyl-amide

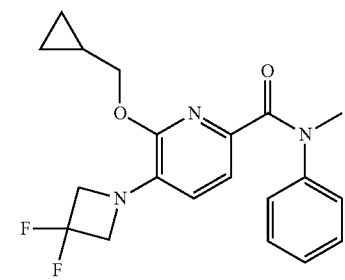 [SMILES: CN(C(=O)c1ccc(N2CC(F)(F)C2)c(OCC2CC2)n1)c1ccccc1]

The title compound was synthesized in analogy to Example 47b), using 6-(cyclopropylmethoxy)-5-(3,3-difluoroazetidin-1-yl)picolinic acid (Example 1 b) and N-methylaniline 2,2,2-trifluoroacetate (CAS 29885-95-8) as starting materials and isolated as colorless oil. MS (EI): m/e=374.5 [MH$^+$].

Example 53

[6-Cyclopropylmethoxy-5-(3,3-difluoro-azetidin-1-yl)-pyridin-2-yl]-((S)-4,4-difluoro-2-hydroxymethyl-pyrrolidin-1-yl)-methanone

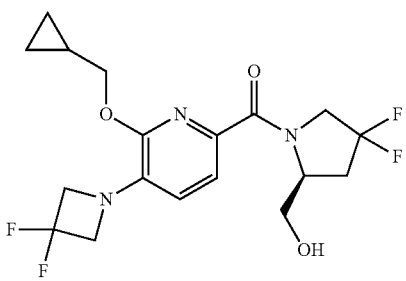 [SMILES: O=C(c1ccc(N2CC(F)(F)C2)c(OCC2CC2)n1)N1CC(F)(F)C[C@H]1CO]

The title compound was synthesized in analogy to Example 47b), using 6-(cyclopropylmethoxy)-5-(3,3-difluo-
roazetidin-1-yl)picolinic acid (Example 1 b) and (S)-(4,4-difluoropyrrolidin-2-yl)methanol hydrochloride (CAS 623583-10-8) as starting materials and isolated as colorless oil. MS (EI): m/e=404.5 [MH$^+$].

Example 54

6-Cyclopropylmethoxy-5-(3,3-difluoro-azetidin-1-yl)-pyridine-2-carboxylic acid (1,4-dimethyl-1H-pyrazol-3-yl)-methyl-amide

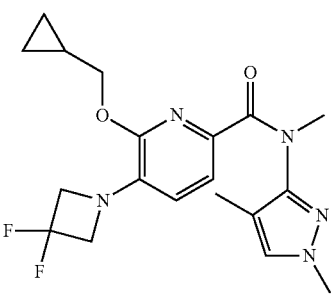 [SMILES: Cc1cn(C)nc1N(C)C(=O)c1ccc(N2CC(F)(F)C2)c(OCC2CC2)n1]

The title compound was synthesized in analogy to Example 47b), using 6-(cyclopropylmethoxy)-5-(3,3-difluoroazetidin-1-yl)picolinic acid (Example 1 b) and N,1,4-trimethyl-1H-pyrazol-3-amine (which can be prepared from 3-formylamino-1-methyl-1H-pyrazole-4-carboxylic acid ethyl ester CAN 114936-04-8 via reduction with lithium aluminum hydride in diethyl ether at ambient temperature) as starting materials and isolated as colorless oil. MS (EI): m/e=392.5 [MH$^+$].

Example 55

[6-Cyclopropylmethoxy-5-(3,3-difluoro-azetidin-1-yl)-pyridin-2-yl]-(2,2-dimethyl-morpholin-4-yl)-methanone

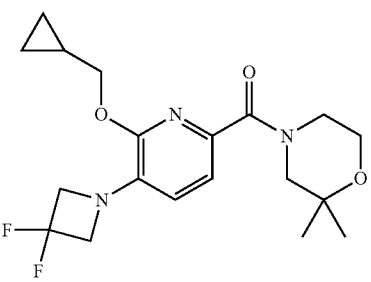 [SMILES: CC1(C)CN(C(=O)c2ccc(N3CC(F)(F)C3)c(OCC3CC3)n2)CCO1]

The title compound was synthesized in analogy to Example 47b), using 6-(cyclopropylmethoxy)-5-(3,3-difluoroazetidin-1-yl)picolinic acid (Example 1 b) and 2,2-dimethylmorpholine (CAS 147688-58-2) as starting materials and isolated as colorless oil. MS (EI): m/e=382.5 [MH$^+$].

Example 56

(R)-2-tert-Butyl-1-[6-cyclopropylmethoxy-5-(3,3-difluoro-azetidin-1-yl)-pyridine-2-carbonyl]-3-methyl-imidazolidin-4-one

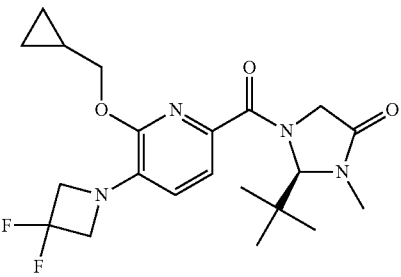 [SMILES: CN1C(=O)CN(C(=O)c2ccc(N3CC(F)(F)C3)c(OCC3CC3)n2)[C@@H]1C(C)(C)C]

The title compound was synthesized in analogy to Example 47b), using 6-(cyclopropylmethoxy)-5-(3,3-difluoroazetidin-1-yl)picolinic acid (Example 1 b) and N-methylaniline 2,2,2-trifluoroacetate (CAS 101143-57-1) as starting materials and isolated as colorless oil. MS (EI): m/e=423.5 [MH$^+$].

Example 57

(4-Aza-spiro[2.4]hept-4-yl)-[6-cyclopropylmethoxy-5-(3,3-difluoro-azetidin-1-yl)-pyridin-2-yl]-methanone

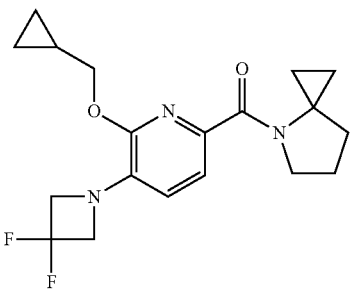 [SMILES: O=C(c1ccc(N2CC(F)(F)C2)c(OCC2CC2)n1)N1CCCC12CC2]

In analogy to the procedure described in Example 47 b), 6-cyclopropylmethoxy-5-(3,3-difluoro-azetidin-1-yl)-pyridine-2-carboxylic acid (Example 1 b)) was reacted with 4-azaspiro[2.4]heptane (95442-76-5) in the presence of TBTU and DIEA to obtain the title compound as colorless oil; MS (EI): m/e=364.5 [MH$^+$].

Example 58

3-{1-[6-Cyclopropylmethoxy-5-(3,3-difluoro-azetidin-1-yl)-pyridine-2-carbonyl]-piperidin-4-yl}-5,5-dimethyl-pyrrolidin-2-one

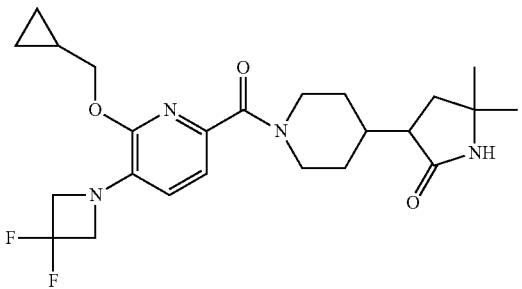 [SMILES: CC1(C)CC(C2CCN(C(=O)c3ccc(N4CC(F)(F)C4)c(OCC4CC4)n3)CC2)C(=O)N1]

In analogy to the procedure described in Example 47 b), 6-cyclopropylmethoxy-5-(3,3-difluoro-azetidin-1-yl)-pyridine-2-carboxylic acid (Example 1 b)) was reacted with 5,5-dimethyl-3-(piperidin-4-yl)pyrrolidin-2-one hydrochloride in the presence of TBTU and DIEA to obtain the title compound as colorless oil; MS (EI): m/e=463.6 [MH$^+$].

Example 59

(1S,4R)-2-Aza-bicyclo[2.2.1]hept-2-yl-[6-cyclopropylmethoxy-5-(3,3-difluoro-azetidin-1-yl)-pyridin-2-yl]-methanone

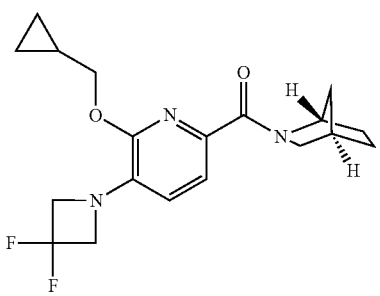 [SMILES: O=C(c1ccc(N2CC(F)(F)C2)c(OCC2CC2)n1)N1C[C@@H]2CC[C@H]1C2]

In analogy to the procedure described in Example 47 b), 6-cyclopropylmethoxy-5-(3,3-difluoro-azetidin-1-yl)-pyridine-2-carboxylic acid (Example 1 b)) was reacted with (1S,4R)-2-azabicyclo[2.2.1]heptane hydrochloride (175275-72-6) in the presence of TBTU and DIEA to obtain the title compound as colorless oil; MS (EI): m/e=364.5 [MH$^+$].

Example 60

(S)-1-[6-Cyclopropylmethoxy-5-(3,3-difluoro-azetidin-1-yl)-pyridine-2-carbonyl]-4,4-difluoro-pyrrolidine-2-carboxylic acid amide

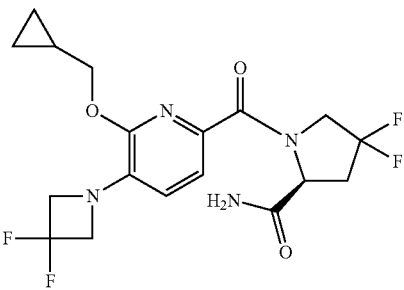 [SMILES: NC(=O)[C@@H]1CC(F)(F)CN1C(=O)c1ccc(N2CC(F)(F)C2)c(OCC2CC2)n1]

In analogy to the procedure described in Example 47 b), 6-cyclopropylmethoxy-5-(3,3-difluoro-azetidin-1-yl)-pyridine-2-carboxylic acid (Example 1 b)) was reacted with (S)-4,4-difluoropyrrolidine-2-carboxamide hydrochloride (426844-51-1) in the presence of TBTU and DIEA to obtain the title compound as colorless oil; MS (EI): m/e=417.5 [MH⁺].

Example 61

[6-Cyclopropylmethoxy-5-(3,3-difluoro-azetidin-1-yl)-pyridin-2-yl]-(4-hydroxy-4-methyl-piperidin-1-yl)-methanone

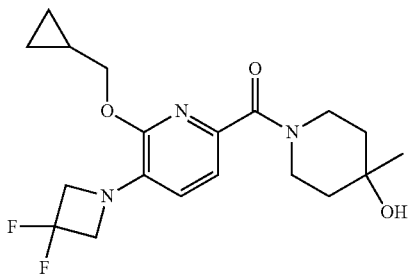 [SMILES: CC1(O)CCN(C(=O)c2ccc(N3CC(F)(F)C3)c(OCC3CC3)n2)CC1]

In analogy to the procedure described in Example 47 b), 6-cyclopropylmethoxy-5-(3,3-difluoro-azetidin-1-yl)-pyridine-2-carboxylic acid (Example 1 b)) was reacted with 4-methylpiperidin-4-ol hydrochloride (586375-35-1) in the presence of TBTU and DIEA to obtain the title compound as colorless oil; MS (EI): m/e=382.6 [MH⁺].

Example 62

[6-Cyclopropylmethoxy-5-(3,3-difluoro-azetidin-1-yl)-pyridin-2-yl]-(1S,4S)-2-thia-5-aza-bicyclo[2.2.1]hept-5-yl-methanone

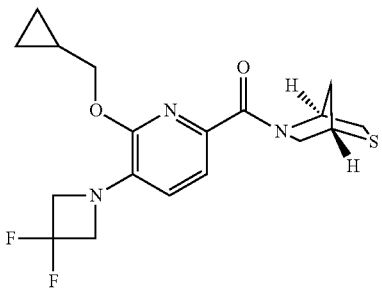 [SMILES: O=C(c1ccc(N2CC(F)(F)C2)c(OCC2CC2)n1)N1C[C@@H]2C[C@H]1CS2]

In analogy to the procedure described in Example 47 b), 6-cyclopropylmethoxy-5-(3,3-difluoro-azetidin-1-yl)-pyridine-2-carboxylic acid (Example 1 b)) was reacted with (1S,4S)-2-thia-5-azabicyclo[2.2.1]heptane hydrochloride (125136-43-8) in the presence of TBTU and DIEA to obtain the title compound as colorless oil; MS (EI): m/e=382.5 [MH⁺].

Example 63

((1S,4S)-5-Benzyl-2,5-diaza-bicyclo[2.2.1]hept-2-yl)-[6-cyclopropylmethoxy-5-(3,3-difluoro-azetidin-1-yl)-pyridin-2-yl]-methanone

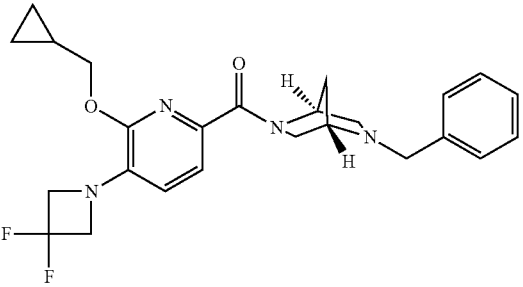 [SMILES: O=C(c1ccc(N2CC(F)(F)C2)c(OCC2CC2)n1)N1C[C@@H]2C[C@H]1CN2Cc1ccccc1]

In analogy to the procedure described in Example 47 b), 6-cyclopropylmethoxy-5-(3,3-difluoro-azetidin-1-yl)-pyridine-2-carboxylic acid (Example 1 b)) was reacted with (1S,4S)-2-benzyl-2,5-diazabicyclo[2.2.1]heptane dihydrobromide (116258-17-4) in the presence of TBTU and DIEA to obtain the title compound as colorless oil; MS (EI): m/e=455.7 [MH⁺].

Example 64

[6-Cyclopropylmethoxy-5-(3,3-difluoro-azetidin-1-yl)-pyridin-2-yl]-(2-methyl-3-phenyl-piperidin-1-yl)-methanone

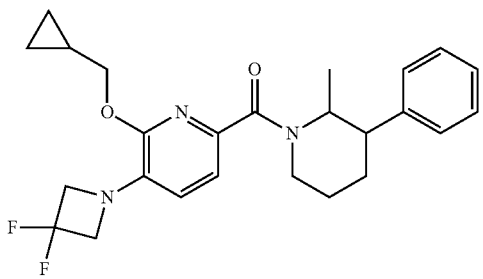 [SMILES: CC1C(c2ccccc2)CCCN1C(=O)c1ccc(N2CC(F)(F)C2)c(OCC2CC2)n1]

In analogy to the procedure described in Example 47 b), 6-cyclopropylmethoxy-5-(3,3-difluoro-azetidin-1-yl)-pyridine-2-carboxylic acid (Example 1 b)) was reacted with 2-methyl-3-phenylpiperidine (70769-67-4) in the presence of TBTU and DIEA to obtain the title compound as colorless oil; MS (EI): m/e=442.5 [MH$^+$].

Example 65

[6-Cyclopropylmethoxy-5-(3,3-difluoro-azetidin-1-yl)-pyridin-2-yl]-(1S,4S)-2-oxa-5-aza-bicyclo[2.2.1]hept-5-yl-methanone

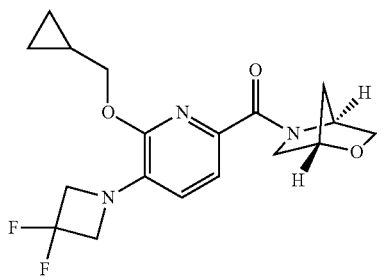 [SMILES: O=C(c1ccc(N2CC(F)(F)C2)c(OCC2CC2)n1)N1C[C@@H]2C[C@H]1CO2]

In analogy to the procedure described in Example 47 b), 6-cyclopropylmethoxy-5-(3,3-difluoro-azetidin-1-yl)-pyridine-2-carboxylic acid (Example 1 b)) was reacted with (1S,4S)-2-oxa-5-azabicyclo[2.2.1]heptane hydrochloride (31560-06-2) in the presence of TBTU and DIEA to obtain the title compound as colorless oil; MS (EI): m/e=366.5 [MH$^+$].

Example 66

[6-Cyclopropylmethoxy-5-(3,3-difluoro-azetidin-1-yl)-pyridin-2-yl]-(4-hydroxy-2,2-dimethyl-piperidin-1-yl)-methanone

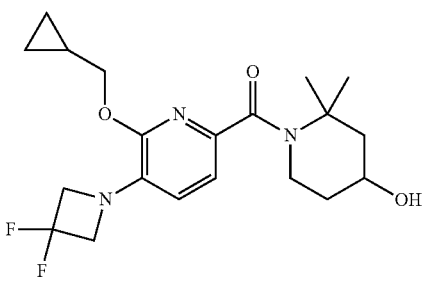 [SMILES: CC1(C)CC(O)CCN1C(=O)c1ccc(N2CC(F)(F)C2)c(OCC2CC2)n1]

In analogy to the procedure described in Example 47 b), 6-cyclopropylmethoxy-5-(3,3-difluoro-azetidin-1-yl)-pyridine-2-carboxylic acid (Example 1 b)) was reacted with 2,2-dimethylpiperidin-4-ol (937681-12-4) in the presence of TBTU and DIEA to obtain the title compound as colorless oil; MS (EI): m/e=396.6 [MH$^+$].

Example 67

1-[6-Cyclopropylmethoxy-5-(3,3-difluoro-azetidin-1-yl)-pyridine-2-carbonyl]-2-phenyl-piperidine-3-carboxylic acid ethyl ester

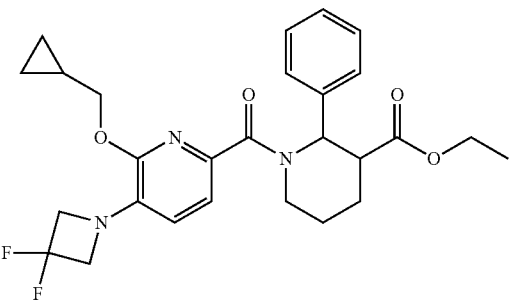 [SMILES: CCOC(=O)C1CCCN(C(=O)c2ccc(N3CC(F)(F)C3)c(OCC3CC3)n2)C1c1ccccc1]

In analogy to the procedure described in Example 47 b), 6-cyclopropylmethoxy-5-(3,3-difluoro-azetidin-1-yl)-pyridine-2-carboxylic acid (Example 1 b)) was reacted with ethyl 2-phenylpiperidine-3-carboxylate (54529-38-3) in the presence of TBTU and DIEA to obtain the title compound as colorless oil; MS (EI): m/e=500.2 [MH$^+$].

Example 68

(S)-1-(5-Cyclopropyl-6-cyclopropylmethoxy-pyridine-2-carbonyl)-4,4-difluoro-pyrrolidine-2-carboxylic acid amide

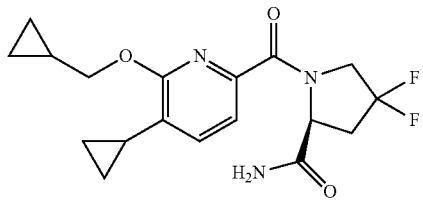 [SMILES: NC(=O)[C@@H]1CC(F)(F)CN1C(=O)c1ccc(C2CC2)c(OCC2CC2)n1]

The title compound was synthesized in analogy to Example 47 b, using 5-cyclopropyl-6-cyclopropylmethoxy-pyridine-2-carboxylic acid (Example 3 c, 50 mg, 214 µmol) and (2S)-4,4-difluoro-2-pyrrolidinecarboxamide hydrochloride (CAN 426844-51-1; 44 mg, 236 µmol) as starting materials and isolated (63 mg, 80%) as off-white solid; LC-MS (UV peak area, ESI) 100%, 366.1629 [MH$^+$].

Example 69

(2S,4S)-1-(5-Cyclopropyl-6-cyclopropylmethoxy-pyridine-2-carbonyl)-4-fluoro-pyrrolidine-2-carboxylic acid amide

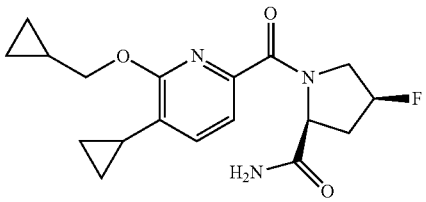 [SMILES: NC(=O)[C@@H]1C[C@H](F)CN1C(=O)c1ccc(C2CC2)c(OCC2CC2)n1]

The title compound was synthesized in analogy to Example 47 b, using 5-cyclopropyl-6-cyclopropylmethoxy-pyridine-2-carboxylic acid (Example 3 c, 50 mg, 214 µmol) and (2S,4S)-4-fluoro-2-pyrrolidinecarboxamide hydrochloride (1:1) (CAN 426844-23-7; 40 mg, 236 µmol) as starting materials and isolated (68 mg, 91%) as off-white solid; LC-MS (UV peak area, ESI) 100%, 348.1721 [MH$^+$].

Example 70

[6-Cyclopropylmethoxy-5-(3,3-difluoro-azetidin-1-yl)-pyridin-2-yl]-(hexahydrofuro[2,3-c]pyrrol-5-yl)-methanone

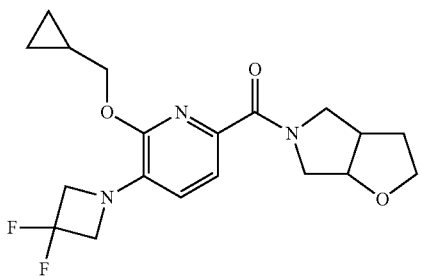 [SMILES: O=C(c1ccc(N2CC(F)(F)C2)c(OCC2CC2)n1)N1CC2CCOC2C1]

In analogy to the procedure described in Example 47 b), 6-cyclopropylmethoxy-5-(3,3-difluoro-azetidin-1-yl)-pyridine-2-carboxylic acid (Example 1 b)) was reacted with hexahydro-2H-furo[3,2-c]pyrrole (1214875-23-6) in the presence of TBTU and DIEA to obtain the title compound as colorless oil; MS (EI): m/e=380.5 [MH$^+$].

Example 71

[6-Cyclopropylmethoxy-5-(3,3-difluoro-azetidin-1-yl)-pyridin-2-yl]-(2,2-dioxo-2λ6-thia-6-aza-spiro[3.3]hept-6-yl)-methanone

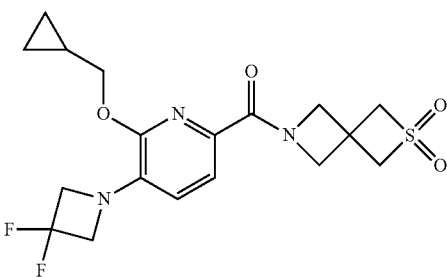 [SMILES: O=C(c1ccc(N2CC(F)(F)C2)c(OCC2CC2)n1)N1CC2(C1)CS(=O)(=O)C2]

In analogy to the procedure described in Example 47 b), 6-cyclopropylmethoxy-5-(3,3-difluoro-azetidin-1-yl)-pyridine-2-carboxylic acid (Example 1 b)) was reacted with 2-thia-6-azaspiro[3.3]heptane, 2,2-dioxide (1263182-09-7) in the presence of TBTU and DIEA to obtain the title compound as colorless oil; MS (EI): m/e=414.5 [MH$^+$].

Example 72

6-Cyclopropylmethoxy-5-(3,3-difluoro-azetidin-1-yl)-pyridine-2-carboxylic acid tert-butyl-(2-carbamoyl-ethyl)-amide

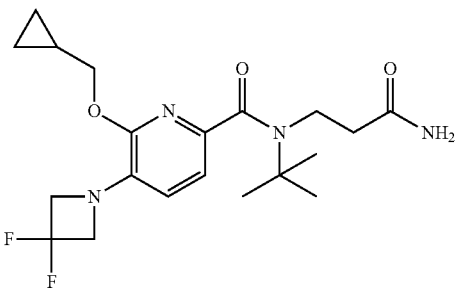 [SMILES: CC(C)(C)N(CCC(N)=O)C(=O)c1ccc(N2CC(F)(F)C2)c(OCC2CC2)n1]

In analogy to the procedure described in Example 47 b), 6-cyclopropylmethoxy-5-(3,3-difluoro-azetidin-1-yl)-pyridine-2-carboxylic acid (Example 1 b)) was reacted with 3-(tert-butylamino)propanamide (289656-97-9) in the presence of TBTU and DIEA to obtain the title compound as colorless oil; MS (EI): m/e=411.6 [MH$^+$].

Example 73

(S)-1-(5-Cyclopropyl-6-cyclopropylmethoxy-pyridine-2-carbonyl)-pyrrolidine-2-carboxylic acid amide

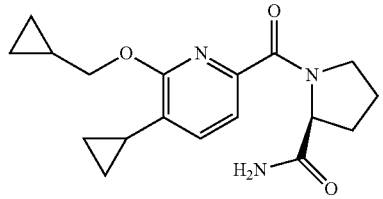 [SMILES: NC(=O)[C@@H]1CCCN1C(=O)c1ccc(C2CC2)c(OCC2CC2)n1]

The title compound was synthesized in analogy to Example 47 b, using 5-cyclopropyl-6-cyclopropylmethoxy-pyridine-2-carboxylic acid (Example 3 c, 40 mg, 171 µmol) and (2S)-2-pyrrolidinecarboxamide (CAN 7531-52-4; 21.5 mg, 189 µmol) as starting materials and isolated (49 mg, 87%) as white solid; LC-MS (UV peak area, ESI) 100%, 330.1818 [MH$^+$].

Example 74

1-[6-Cyclopropylmethoxy-5-(3,3-difluoro-azetidin-1-yl)-pyridine-2-carbonyl]-1,8-diaza-spiro[4.5]decane-8-carboxylic acid tert-butyl ester

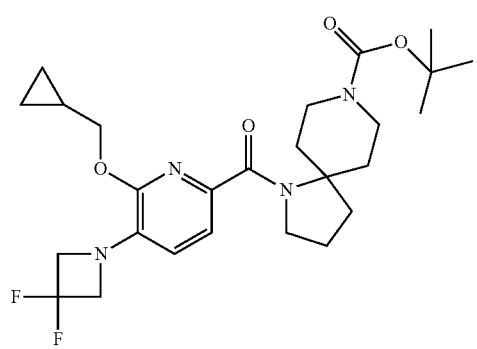 [SMILES: CC(C)(C)OC(=O)N1CCC2(CCCN2C(=O)c2ccc(N3CC(F)(F)C3)c(OCC3CC3)n2)CC1]

In analogy to the procedure described in Example 47 b), 6-cyclopropylmethoxy-5-(3,3-difluoro-azetidin-1-yl)-pyridine-2-carboxylic acid (Example 1 b)) was reacted with tert-butyl 1,8-diazaspiro[4.5]decane-8-carboxylate hydrochloride (851325-42-3) in the presence of TBTU and DIEA to obtain the title compound as yellow oil; MS (EI): m/e=507.6 [MH⁺].

Example 75

(S)-1-{5-Cyclopropyl-6-[(R,S)-1-(tetrahydro-furan-2-yl)methoxy]-pyridine-2-arbonyl}-4,4-difluoro-pyrrolidine-2-carboxylic acid amide

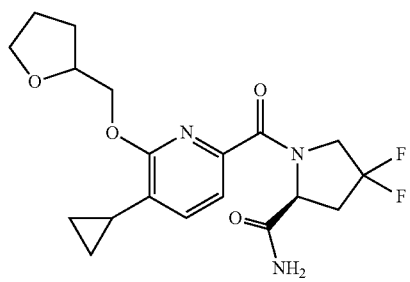 [SMILES: NC(=O)[C@@H]1CC(F)(F)CN1C(=O)c1ccc(C2CC2)c(OCC2CCCO2)n1]

In analogy to the procedure described in Example 47 b), 5-cyclopropyl-6-(tetrahydro-furan-2-ylmethoxy)-pyridine-2-carboxylic acid (Example 4 b)) was reacted with (S)-4,4-difluoropyrrolidine-2-carboxamide hydrochloride (CAN 426844-51-1) in the presence of TBTU and DIEA to obtain the title compound as white solid; MS (EI): m/e=396.5 [MH⁺].

Example 76

(S)-1-[5-Cyclopropyl-6-(4-fluoro-benzyl)-pyridine-2-carbonyl]-4,4-difluoro-pyrrolidine-2-carboxylic acid amide

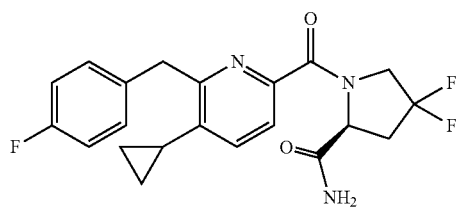 [SMILES: NC(=O)[C@@H]1CC(F)(F)CN1C(=O)c1ccc(C2CC2)c(Cc2ccc(F)cc2)n1]

In analogy to the procedure described in Example 47 b), 5-cyclopropyl-6-(4-fluoro-benzyl)-pyridine-2-carboxylic acid (Example 5 g)) was reacted with (S)-4,4-difluoropyrrolidine-2-carboxamide hydrochloride (CAN 426844-51-1) in the presence of TBTU and DIEA to obtain the title compound as colorless oil; MS (EI): m/e=404.5 [MH⁺].

Example 77

(+)-1-[6-Cyclopropylmethoxy-5-(3,3-difluoro-azetidin-1-yl)-pyridine-2-carbonyl]-4,4-dimethyl-pyrrolidine-2-carboxylic acid amide

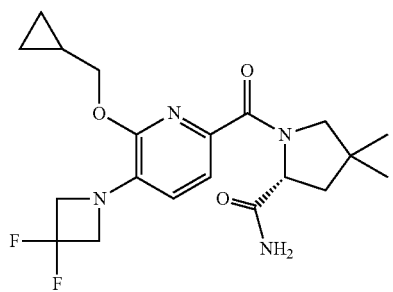 [SMILES: CC1(C)C[C@H](C(N)=O)N(C(=O)c2ccc(N3CC(F)(F)C3)c(OCC3CC3)n2)C1]

In analogy to the procedure described in Example 47 b), 6-cyclopropylmethoxy-5-(3,3-difluoro-azetidin-1-yl)-pyridine-2-carboxylic acid (Example 1 b)) was reacted with 4,4-dimethylpyrrolidine-2-carboxamide hydrochloride (Example 90 d) in the presence of TBTU and DIEA. The mixture of enantiomers was separated by chiral HPLC (Reprosil Chiral NR). The (+) enantiomer was isolated as yellow solid; MS (EI): m/e=409.6 [MH⁺]; $\alpha_D^{20}$ (DMSO)=+19.3°.

Example 78

(−)-1-[6-Cyclopropylmethoxy-5-(3,3-difluoro-azetidin-1-yl)-pyridine-2-carbonyl]-4,4-dimethyl-pyrrolidine-2-carboxylic acid amide

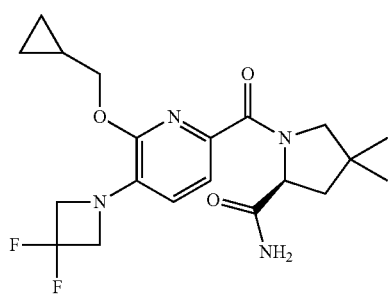 [SMILES: CC1(C)C[C@@H](C(N)=O)N(C(=O)c2ccc(N3CC(F)(F)C3)c(OCC3CC3)n2)C1]

In analogy to the procedure described in Example 47 b), 6-cyclopropylmethoxy-5-(3,3-difluoro-azetidin-1-yl)-pyridine-2-carboxylic acid (Example 1 b)) was reacted with 4,4-dimethylpyrrolidine-2-carboxamide hydrochloride (Example 90 d) in the presence of TBTU and DIEA. The mixture of enantiomers was separated by chiral HPLC (Reprosil Chiral NR). The (−) enantiomer was isolated as yellow solid; MS (EI): m/e=409.6 [MH⁺]; $\alpha_D^{20}$ (DMSO)=−29.3°.

Example 79

(2S,4S)-1-[6-Cyclopropylmethoxy-5-(3,3-difluoro-azetidin-1-yl)-pyridine-2-carbonyl]-4-hydroxy-pyrrolidine-2-carboxylic acid amide

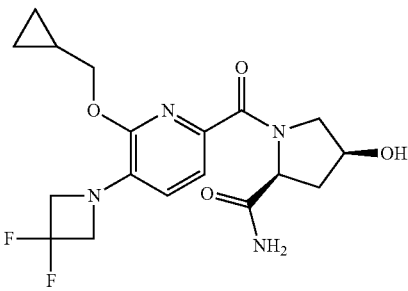 [SMILES: NC(=O)[C@@H]1C[C@H](O)CN1C(=O)c1ccc(N2CC(F)(F)C2)c(OCC2CC2)n1]

In analogy to the procedure described in Example 47 b), 6-cyclopropylmethoxy-5-(3,3-difluoro-azetidin-1-yl)-pyridine-2-carboxylic acid (Example 1 b)) was reacted with (2S,4S)-4-hydroxypyrrolidine-2-carboxamide hydrochloride (851233-67-5) in the presence of TBTU and DIEA to obtain the title compound as colorless oil; MS (EI): m/e=397.5 [MH$^+$].

Example 80

(2S,4S)-1-[6-Cyclopropylmethoxy-5-(3,3-difluoro-azetidin-1-yl)-pyridine-2-carbonyl]-4-fluoro-pyrrolidine-2-carboxylic acid amide

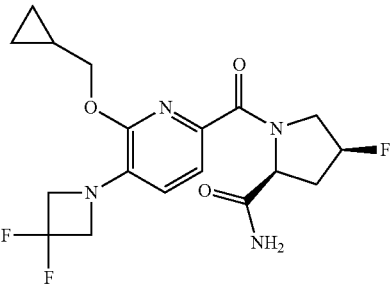 [SMILES: NC(=O)[C@@H]1C[C@H](F)CN1C(=O)c1ccc(N2CC(F)(F)C2)c(OCC2CC2)n1]

In analogy to the procedure described in Example 47 b), 6-cyclopropylmethoxy-5-(3,3-difluoro-azetidin-1-yl)-pyridine-2-carboxylic acid (Example 1 b)) was reacted with (2S,4S)-4-fluoropyrrolidine-2-carboxamide hydrochloride (426844-23-7) in the presence of TBTU and DIEA to obtain the title compound as white solid; MS (EI): m/e=399.4 [MH$^+$].

Example 81

6-Cyclopropylmethoxy-5-(3,3-difluoro-azetidin-1-yl)-pyridine-2-carboxylic acid cyclopropyl-(5-methyl-[1,3,4]oxadiazol-2-ylmethyl)-amide a) Cyclopropyl-(5-methyl-[1,3,4]oxadiazol-2-ylmethyl)-amine

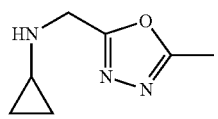

A mixture of cyclopropanamine (765-30-0, 194 mg, 236 µL, 3.39 mmol) and 2-(chloromethyl)-5-methyl-1,3,4-oxadiazole (3914-42-9, 90 mg, 679 µmol) was stirred for 16 h at ambient temperature. The mixture was concentrated under reduced pressure and the residue taken up in ice-water/saturated aqueous Na$_2$CO$_3$ solution 1/1 (20 mL) and EtOAc (30 mL). The layers were separated and the aqueous layer was extracted one more time with EtOAc (30 mL). The combined extracts were washed with ice-water/brine 1/1 (15 mL), dried over Na$_2$SO$_4$ and brought to dryness to give the title compound (36 mg, 35%) as yellow oil which was sufficiently pure to be used in the next reaction step; MS (EI): m/e=154.2 [MH$^+$].

b) 6-Cyclopropylmethoxy-5-(3,3-difluoro-azetidin-1-yl)-pyridine-2-carboxylic acid cyclopropyl-(5-methyl-[1,3,4]oxadiazol-2-ylmethyl)-amide

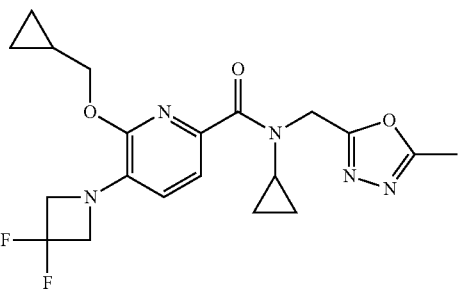 [SMILES: Cc1nnc(CN(C(=O)c2ccc(N3CC(F)(F)C3)c(OCC3CC3)n2)C2CC2)o1]

In analogy to the procedure described in Example 47 b), 6-cyclopropylmethoxy-5-(3,3-difluoro-azetidin-1-yl)-pyridine-2-carboxylic acid (Example 1 b)) was reacted with cyclopropyl-(5-methyl-[1,3,4]oxadiazol-2-ylmethyl)-amine in the presence of TBTU and DIEA to obtain the title compound as colorless oil; MS (EI): m/e=420.6 [MH$^+$].

Example 82

[6-Cyclopropylmethoxy-5-(3,3-difluoro-azetidin-1-yl)-pyridin-2-yl]-(3-hydroxy-1-oxa-7-aza-spiro[4.4]non-7-yl)-methanone a) 1-Oxa-7-azaspiro[4.4]nonan-3-ol hydrochloride

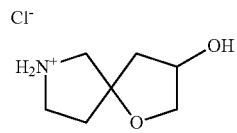

A mixture of tert-butyl 3-hydroxy-1-oxa-7-azaspiro[4.4]nonane-7-carboxylate (CAN 1331825-50-3, 33 mg, 136 µmol) and a 4 M solution of HCl in dioxane (339 µL, 1.36 mmol) in dioxane (0.3 mL) was stirred at ambient temperature for 3 h to give the title compound (14 mg, 58%) as light brown oil which was sufficiently pure to be used in the next step; MS (EI): m/e=144.2 [(M-Cl)H$^+$].

b) [6-Cyclopropylmethoxy-5-(3,3-difluoro-azetidin-1-yl)-pyridin-2-yl]-(3-hydroxy-1-oxa-7-aza-spiro[4.4]non-7-yl)-methanone

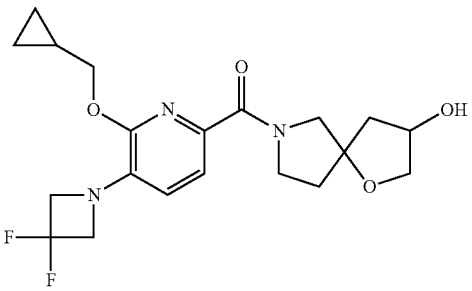 [SMILES: O=C(c1ccc(N2CC(F)(F)C2)c(OCC2CC2)n1)N1CCC2(CC(O)CO2)C1]

In analogy to the procedure described in Example 47 b), 6-cyclopropylmethoxy-5-(3,3-difluoro-azetidin-1-yl)-pyridine-2-carboxylic acid (Example 1 b)) was reacted with 1-oxa-7-azaspiro[4.4]nonan-3-ol hydrochloride in the presence of TBTU and DIEA to obtain the title compound as yellow oil; MS (EI): m/e=410.5 [MH$^+$].

Example 83

[6-Cyclopropylmethoxy-5-(3,3-difluoro-azetidin-1-yl)-pyridin-2-yl]-(7-hydroxy-5-oxa-2-aza-spiro[3.4]oct-2-yl)-methanone a) 7-Hydroxy-5-oxa-2-azonia-spiro[3.4]octane hydrochloride

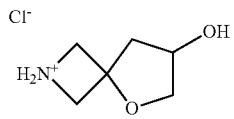

In analogy to the procedure described in Example 82 a), tert-butyl 7-hydroxy-5-oxa-2-azaspiro[3.4]octane-2-carboxylate (which can be prepared in analogy to tert-butyl 3-hydroxy-1-oxa-7-azaspiro[4.4]nonane-7-carboxylate (CAN 1331825-50-3) starting from 3-oxoazetidine-1-carboxylic acid tert-butyl ester (CAN 398489-26-4) as described in A. I. Moskalenko et al., Russian Journal of Organic Chemistry, 47(7), 1091-1096; 2011) was treated with a 4 M solution of HCl in dioxane to give the title compound as colorless solid which was sufficiently pure to be used in the next step; MS (EI): m/e=130.2 [(M-Cl)H$^+$].

b) [6-Cyclopropylmethoxy-5-(3,3-difluoro-azetidin-1-yl)-pyridin-2-yl]-(7-hydroxy-5-oxa-2-aza-spiro[3.4]oct-2-yl)-methanone

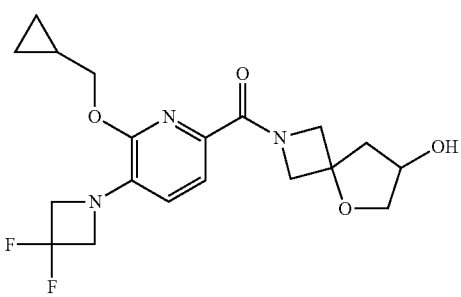 [SMILES: O=C(c1ccc(N2CC(F)(F)C2)c(OCC2CC2)n1)N1CC2(CC(O)CO2)C1]

In analogy to the procedure described in Example 47 b), 6-cyclopropylmethoxy-5-(3,3-difluoro-azetidin-1-yl)-pyridine-2-carboxylic acid (Example 1 b)) was reacted with 5-oxa-2-azaspiro[3.4]octan-7-ol hydrochloride in the presence of TBTU and DIEA to obtain the title compound as yellow oil; MS (EI): m/e=396.5 [MH$^+$].

Example 84

[5-Cyclopropyl-6-(2,2,3,3,3-pentafluoro-propoxy)-pyridin-2-yl]-(2,2-dimethyl-pyrrolidin-1-yl)-methanone a) 5-Bromo-6-(2,2,3,3,3-pentafluoro-propoxy)-pyridine-2-carboxylic acid

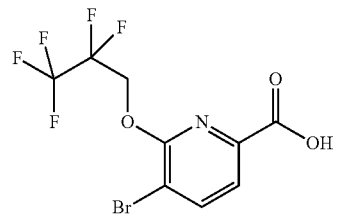 [SMILES: O=C(O)c1ccc(Br)c(OCC(F)(F)C(F)(F)F)n1]

To a solution of 6-chloro-5-bromo-pyridine-2-carboxylic acid (CAN 959958-25-9, 1.7 g, 7.19 mmol) in DMF (90 mL) and THF (30 mL) was added potassium tert-butoxide (2.02 g, 18.0 mmol) and 2,2,3,3,3-pentafluoropropan-1-ol (5.73 mL, 57.5 mmol). The mixture was stirred at 140° C. for 4 days, cooled and poured into ice-water (100 mL). 2 M Hydrochloric acid (15 mL) was added to adjust the pH to 2-3 and the mixture was extracted with TBME, organic layers were washed twice with water, pooled, dried with Na$_2$SO$_4$, filtered and concentrated in vacuo. The crude material was purified by flash chromatography (silica gel, ethyl acetate/n-heptane gradient) to give the title compound (548 mg, 22%) as light-brown solid; LC-MS (UV peak area, ESI) 100%, 347.9306 [M-H$^-$].

b) 5-Cyclopropyl-6-(2,2,3,3,3-pentafluoro-propoxy)-pyridine-2-carboxylic acid

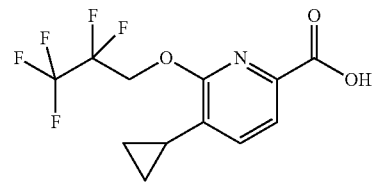 [SMILES: O=C(O)c1ccc(C2CC2)c(OCC(F)(F)C(F)(F)F)n1]

A mixture of 5-bromo-6-(2,2,3,3,3-pentafluoro-propoxy)-pyridine-2-carboxylic acid (501 mg, 1.43 mmol), cyclopropylboronic acid (CAN 411235-57-9, 184 mg, 2.15 mmol), palladium diacetate (CAN 3375-31-3, 16.1 mg, 71.6 μmol), tricyclohexylphosphine (CAN 2622-14-2, 8.03 mg, 28.6 μmol) and potassium phosphate (1.06 g, 5.01 mmol) in toluene/water (20/1 v/v, 10.5 mL) was stirred at 100° C. for 22 hours. After cooling the mixture was poured into ice-water (80 mL). 2 M Hydrochloric acid (25 mL) was added and the mixture was extracted with TBME, organic layers were washed twice with water, pooled, dried with Na$_2$SO$_4$, filtered and concentrated in vacuo. The crude material was purified by flash chromatography (silica gel, ethyl acetate/n-heptane gradient) to give the title compound (340 mg, 76%) as off-white solid; LC-MS (UV peak area, ESI) 96.6%, 310.0513 [M-H$^-$].

c) [5-Cyclopropyl-6-(2,2,3,3,3-pentafluoro-propoxy)-pyridin-2-yl]-(2,2-dimethyl-pyrrolidin-1-yl)-methanone

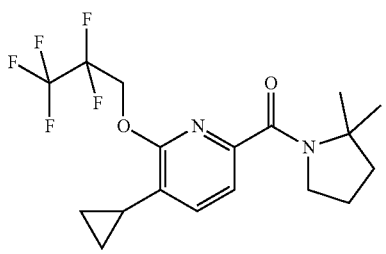 [SMILES: CC1(C)CCCN1C(=O)c1ccc(C2CC2)c(OCC(F)(F)C(F)(F)F)n1]

The title compound was synthesized in analogy to Example 47 b, using 5-cyclopropyl-6-(2,2,3,3,3-pentafluoro-propoxy)-pyridine-2-carboxylic acid (40 mg, 129 μmol) and 2,2-dimethylpyrrolidine (CAN 35018-15-6; 18 μL, 141 μmol) as starting materials and isolated (41 mg, 81%) as light-brown oil; LC-MS (UV peak area, ESI) 100%, 393.1611 [MH$^+$].

Example 85

[6-Cyclopropylmethoxy-5-(3,3-difluoro-azetidin-1-yl)-pyridin-2-yl]-(1S,5R)-8-oxa-3-aza-bicyclo[3.2.1]oct-3-yl-methanone

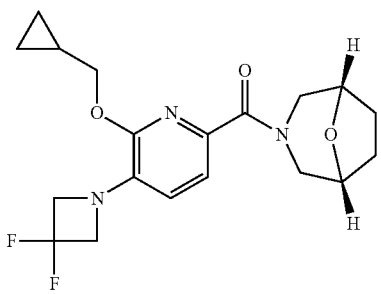 [SMILES: O=C(c1ccc(N2CC(F)(F)C2)c(OCC2CC2)n1)N1C[C@H]2CC[C@@H](C1)O2]

In analogy to the procedure described in Example 47 b), 6-cyclopropylmethoxy-5-(3,3-difluoro-azetidin-1-yl)-pyridine-2-carboxylic acid (Example 1 b)) was reacted with (1R,5S)-8-oxa-3-azabicyclo[3.2.1]octane hydrochloride (54745-74-3) in the presence of TBTU and DIEA to obtain the title compound as colorless oil; MS (EI): m/e=380.5 [MH$^+$].

Example 86

[6-Cyclopropylmethoxy-5-(3,3-difluoro-azetidin-1-yl)-pyridin-2-yl]-(1R,5S)-3-oxa-8-aza-bicyclo[3.2.1]oct-8-yl-methanone

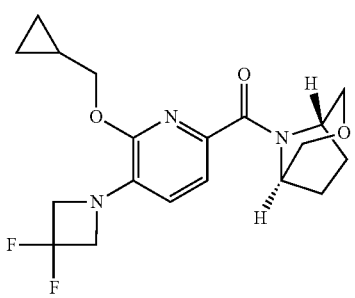 [SMILES: O=C(c1ccc(N2CC(F)(F)C2)c(OCC2CC2)n1)N1[C@@H]2CC[C@H]1COC2]

In analogy to the procedure described in Example 47 b), 6-cyclopropylmethoxy-5-(3,3-difluoro-azetidin-1-yl)-pyridine-2-carboxylic acid (Example 1 b)) was reacted with (1R,5S)-3-oxa-8-azabicyclo[3.2.1]octane hydrochloride (904316-92-3) in the presence of TBTU and DIEA to obtain the title compound as colorless oil; MS (EI): m/e=380.6 [MH$^+$].

Example 87

(R)-1-[5-Cyclopropyl-6-(2,2,3,3,3-pentafluoro-propoxy)-pyridine-2-carbonyl]-4,4-difluoro-pyrrolidine-2-carboxylic acid amide

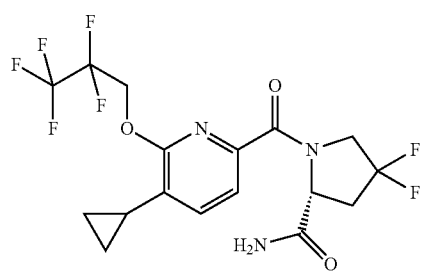 [SMILES: NC(=O)[C@H]1CC(F)(F)CN1C(=O)c1ccc(C2CC2)c(OCC(F)(F)C(F)(F)F)n1]

The title compound was synthesized in analogy to Example 47 b, using 5-cyclopropyl-6-(2,2,3,3,3-pentafluoro-propoxy)-pyridine-2-carboxylic acid (30 mg, 96 μmol) and (2R)-4,4-difluoropyrrolidine-2-carboxamide hydrochloride (CAN 1315053-41-8; 19.8 mg, 106 μmol) as starting materials and isolated (38 mg, 89%) as white solid; LC-MS (UV peak area, ESI) 97%, 444.1155 [MH$^+$].

Example 88

1-(5-Cyclopropyl-6-cyclopropylmethoxy-pyridine-2-carbonyl)-piperidine-2-carboxylic acid amide

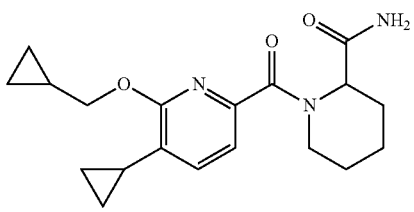 [SMILES: NC(=O)C1CCCCN1C(=O)c1ccc(C2CC2)c(OCC2CC2)n1]

The title compound was synthesized in analogy to Example 47 b, using 5-cyclopropyl-6-cyclopropylmethoxy-pyridine-2-carboxylic acid (Example 3 c, 100 mg, 429 μmol) and 2-piperidinecarboxamide (CAN 19889-77-1, 60.4 mg, 472 μmol) as starting materials and isolated (135 mg, 92%) as white solid; LC-MS (UV peak area, ESI) 100%, 344.1972 [MH$^+$].

Example 89

4-(5-Cyclopropyl-6-cyclopropylmethoxy-pyridine-2-carbonyl)-thiomorpholine-3-carboxylic acid amide

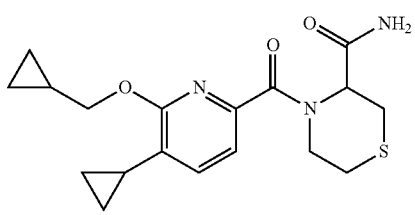 [SMILES: NC(=O)C1CSCCN1C(=O)c1ccc(C2CC2)c(OCC2CC2)n1]

The title compound was synthesized in analogy to Example 47 b, using 5-cyclopropyl-6-cyclopropylmethoxy-pyridine-2-carboxylic acid (Example 3 c, 100 mg, 429 µmol) and 3-thiomorpholinecarboxamide (CAN 103742-31-0, 68.9 mg, 472 µmol) as starting materials and isolated (119 mg, 77%) as white solid; LC-MS (UV peak area, ESI) 100%, 362.1540 [MH$^+$].

Example 90

1-(5-Cyclopropyl-6-cyclopropylmethoxy-pyridine-2-carbonyl)-4,4-dimethyl-pyrrolidine-2-carboxylic acid amide a) 4,4-Dimethyl-pyrrolidine-1,2-dicarboxylic acid 1-tert-butylester

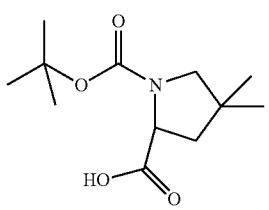 [SMILES: CC1(C)CC(C(=O)O)N(C(=O)OC(C)(C)C)C1]

To a solution of 4,4-dimethyl-proline (1.7 g, 11.8 mmol) in dry dioxane (29 mL) and water (24 mL) was added 1 N sodium hydroxide solution (9 mL) followed by slow addition of di-tert-butyldicarbonate (1.80 g, 8.2 mmol) dissolved in dioxane (5 mL) at ambient temperature. Additional 1 N sodium hydroxide solution (3 mL) was added and the mixture was stirred overnight. Additional di-tert-butyldicarbonate (1.80 g, 8.2 mmol) dissolved in dioxane (5 mL) was added and stirring continued for 3 hours. The mixture was concentrated, 1 N sodium bisulfite solution (22 mL) was added and the suspension was extracted with ethyl acetate. Organic phases were washed with water and brine, combined, dried over MgSO$_4$, filtered and concentrated. The solid was crystallized from diethylether by addition of heptane and dried in vacuo to give the title compound (2.54 g, 89%) as white crystalline solid; MS (ESI) 242.0 [M−H$^−$].

b) 4,4-Dimethyl-pyrrolidine-1,2-dicarboxylic acid 1-tert-butyl ester 2-(2,5-dioxo-pyrrolidin-1-yl) ester

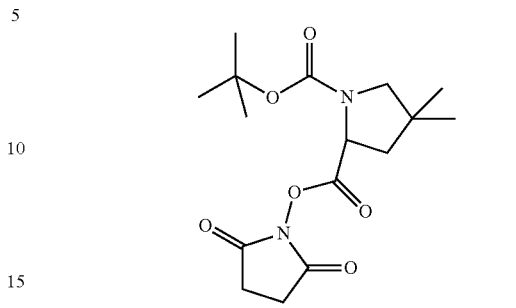

A solution of 4,4-dimethyl-pyrrolidine-1,2-dicarboxylic acid 1-tert-butylester (2.0 g, 8.22 mmol) in THF (20 mL) was cooled to 0° C. To the cold solution was added N-hydroxysuccinimide (1.2 g, 10.4 mmol) and diisopropylcarbodiimide (1.32 g, 10.4 mmol). Cooling was removed and the mixture stirred for 3 hours at room temperature. The urea was filtered off, washed with diethylether and the filtrates were concentrated. The residue was partitioned between ethyl acetate and cold water; organic phases were washed with cold brine, combined, dried with MgSO$_4$, filtered and concentrated in vacuo. The residue was purified by flash chromatography (silica, heptane/ethyl acetate 9:1) to give the title compound (1.95 g, 70%) as colorless oil; MS (ESI) 341.1 [MH$^+$].

b) 2-Carbamoyl-4,4-dimethyl-pyrrolidine-1-carboxylic acid tert-butyl ester

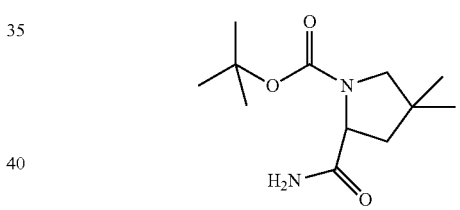

A solution of 4,4-dimethyl-pyrrolidine-1,2-dicarboxylic acid 1-tert-butyl ester 2-(2,5-dioxo-pyrrolidin-1-yl) ester (1.9 g, 5.58 mmol) in DCM (20 mL) was cooled to 0° C. Gaseous ammonia was bubbled for 15 minutes through the cold solution, and stirring was continued for 1 hour in the cold. The succinimide was filtered off, washed with DCM and the filtrates were partitioned between ethyl acetate and cold brine; organic phases were combined, dried with Na$_2$SO$_4$, filtered and concentrated in vacuo. The residue was purified by flash chromatography (silica, ethyl acetate) to give the title compound (1.33 g, 98%) as colorless foam; MS (ESI) 243.1 [MH$^+$].

d) 4,4-Dimethyl-pyrrolidine-2-carboxylic acid amide hydrochloride

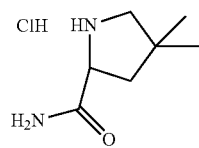

A solution of 2-carbamoyl-4,4-dimethyl-pyrrolidine-1-carboxylic acid tert-butyl ester (1.2 g, 4.95 mmol) in dioxane (5 mL) was cooled to 10° C. Hydrogen chloride dissolved in dioxane (10 mL, 6.4 N) was added and the mixture was stirred for 1.5 hours. Diethylether (50 mL) was added to completely precipitate the product, which was filtered and dried to give the title compound (0.84 g, 95%) as colorless solid; MS (ESI) 143.0 [MH$^+$].

e) 1-(5-Cyclopropyl-6-cyclopropylmethoxy-pyridine-2-carbonyl)-4,4-dimethyl-pyrrolidine-2-carboxylic acid amide

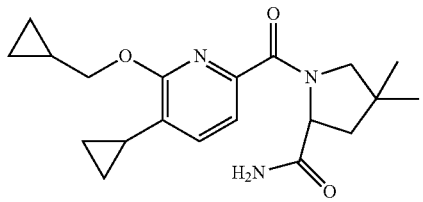 [SMILES: CC1(C)CC(C(N)=O)N(C(=O)c2ccc(C3CC3)c(OCC3CC3)n2)C1]

The title compound was synthesized in analogy to Example 47 b, using 5-cyclopropyl-6-cyclopropylmethoxy-pyridine-2-carboxylic acid (Example 3 c, 100 mg, 429 μmol) and 4,4-dimethyl-pyrrolidine-2-carboxylic acid amide hydrochloride (84.3 mg, 472 μmol) as starting materials and isolated (145 mg, 95%) as white foam; LC-MS (UV peak area, ESI) 100%, 358.2124 [MH$^+$].

Example 91

(+)-1-(5-Cyclopropyl-6-cyclopropylmethoxy-pyridine-2-carbonyl)-piperidine-2-carboxylic acid amide

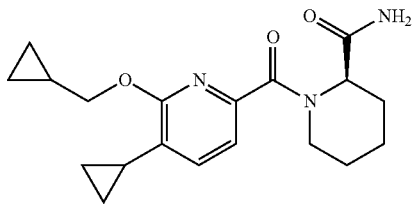 [SMILES: NC(=O)[C@H]1CCCCN1C(=O)c1ccc(C2CC2)c(OCC2CC2)n1]

The enantiomers of 1-(5-cyclopropyl-6-cyclopropylmethoxy-pyridine-2-carbonyl)-piperidine-2-carboxylic acid amide (Example 88) were separated by chiral HPLC (Reprosil Chiral NR, 25% ethanol in n-heptane). The (+) enantiomer (47 mg, 40%) was isolated as white solid; LC-MS (UV peak area/ESI) 100%, 344.1976 [MH$^+$]; (+) enantiomer, ~100% ee; $\alpha_D^{20}$ (MeOH)=+24.8°.

Example 92

(−)-1-(5-Cyclopropyl-6-cyclopropylmethoxy-pyridine-2-carbonyl)-piperidine-2-carboxylic acid amide

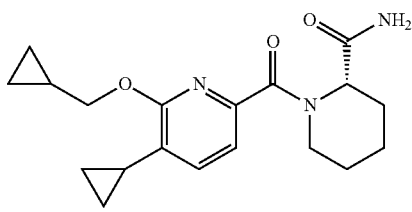 [SMILES: NC(=O)[C@@H]1CCCCN1C(=O)c1ccc(C2CC2)c(OCC2CC2)n1]

The enantiomers of 1-(5-cyclopropyl-6-cyclopropylmethoxy-pyridine-2-carbonyl)-piperidine-2-carboxylic acid amide (Example 88) were separated by chiral HPLC (Reprosil Chiral NR, 25% ethanol in n-heptane). The (−) enantiomer (47 mg, 40%) was isolated as white solid; LC-MS (UV peak area/ESI) 100%, 344.1966 [MH$^+$]; (−) enantiomer, ~100% ee; $\alpha_D^{20}$ (MeOH)=−26.5°.

Example 93

(−)-4-(5-Cyclopropyl-6-cyclopropylmethoxy-pyridine-2-carbonyl)-thiomorpholine-3-carboxylic acid amide

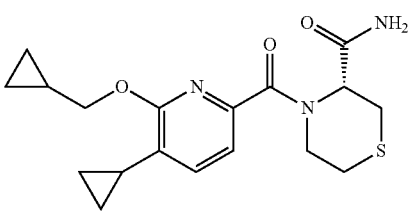 [SMILES: NC(=O)[C@@H]1CSCCN1C(=O)c1ccc(C2CC2)c(OCC2CC2)n1]

The enantiomers of 4-(5-cyclopropyl-6-cyclopropylmethoxy-pyridine-2-carbonyl)-thiomorpholine-3-carboxylic acid amide (Example 89) were separated by chiral HPLC (Reprosil Chiral NR, 30% ethanol in n-heptane). The (−) enantiomer (49 mg, 47%) was isolated as white solid; LC-MS (UV peak area/ESI) 100%, 362.1541 [MH$^+$]; (−) enantiomer, ~100% ee.

Example 94

(+)-1-(5-Cyclopropyl-6-cyclopropylmethoxy-pyridine-2-carbonyl)-4,4-dimethyl-pyrrolidine-2-carboxylic acid amide

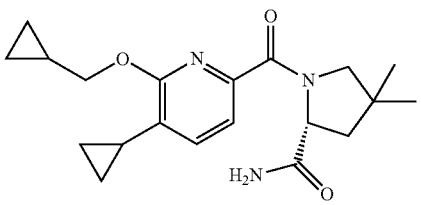 [SMILES: CC1(C)C[C@H](C(N)=O)N(C(=O)c2ccc(C3CC3)c(OCC3CC3)n2)C1]

The enantiomers of 1-(5-cyclopropyl-6-cyclopropylmethoxy-pyridine-2-carbonyl)-4,4-dimethyl-pyrrolidine-2-carboxylic acid amide (Example 90 e) were separated by chiral HPLC (Reprosil Chiral NR, 20% ethanol in n-heptane). The (+) enantiomer (65 mg, 49%) was isolated as white foam; LC-MS (UV peak area/ESI) 100%, 358.2125 [MH$^+$]; (+) enantiomer, ~79% ee; $\alpha_D^{20}$ (MeOH)=+56.9°.

Example 95

(−)-1-(5-Cyclopropyl-6-cyclopropylmethoxy-pyridine-2-carbonyl)-4,4-dimethyl-pyrrolidine-2-carboxylic acid amide

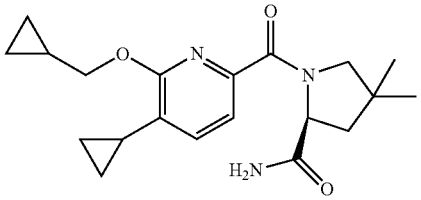 [SMILES: CC1(C)C[C@@H](C(N)=O)N(C(=O)c2ccc(C3CC3)c(OCC3CC3)n2)C1]

The enantiomers of 1-(5-cyclopropyl-6-cyclopropyl-methoxy-pyridine-2-carbonyl)-4,4-dimethyl-pyrrolidine-2-carboxylic acid amide (Example 90 e) were separated by chiral HPLC (Reprosil Chiral NR, 20% ethanol in n-heptane). The (−) enantiomer (50 mg, 38%) was isolated as white foam; LC-MS (UV peak area/ESI) 100%, 358.2133 [MH$^+$]; (−) enantiomer, ~99.5% ee; $\alpha_D^{20}$ (MeOH)=−89.0°.

Example 96

3-(5-Cyclopropyl-6-cyclopropylmethoxy-pyridine-2-carbonyl)-thiazolidine-4-carboxylic acid amide

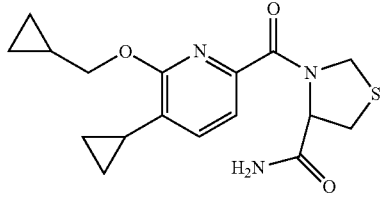

The title compound was synthesized in analogy to Example 47 b, using 5-cyclopropyl-6-cyclopropylmethoxy-pyridine-2-carboxylic acid (Example 3 c, 100 mg, 429 µmol) and 4-thiazolidinecarboxamide (CAN 103749-87-7, 62.3 mg, 472 µmol) as starting materials and isolated (114 mg, 77%) as white solid; LC-MS (UV peak area, ESI) 100%, 348.1377 [MH$^+$].

Example 97

(−)-3-(5-Cyclopropyl-6-cyclopropylmethoxy-pyridine-2-carbonyl)-thiazolidine-4-carboxylic acid amide

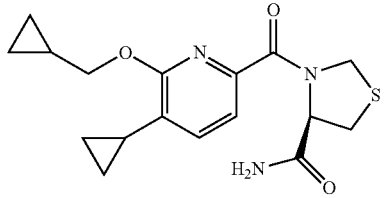 [SMILES: NC(=O)[C@@H]1CSCN1C(=O)c1ccc(C2CC2)c(OCC2CC2)n1]

The enantiomers of 3-(5-cyclopropyl-6-cyclopropylmethoxy-pyridine-2-carbonyl)-thiazolidine-4-carboxylic acid amide (Example 96) were separated by chiral HPLC (Reprosil Chiral NR, 40% ethanol in n-heptane). The (−) enantiomer (48 mg, 48%) was isolated as white solid; LC-MS (UV peak area/ESI) 97.9%, 348.1378 [MH$^+$]; (−) enantiomer, ~100% ee.

Example 98

1-[6-Cyclopropylmethoxy-5-(3,3-difluoro-azetidin-1-yl)-pyridine-2-carbonyl]-4,4-dimethyl-pyrrolidine-2-carboxylic acid amide

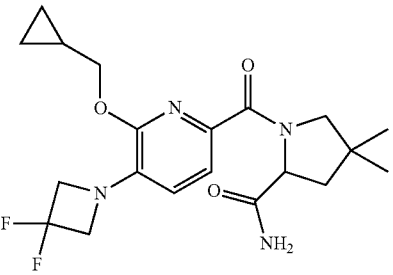 [SMILES: CC1(C)CC(C(N)=O)N(C(=O)c2ccc(N3CC(F)(F)C3)c(OCC3CC3)n2)C1]

In analogy to the procedure described in Example 47 b), 6-cyclopropylmethoxy-5-(3,3-difluoro-azetidin-1-yl)-pyridine-2-carboxylic acid (Example 1 b)) was reacted with 4,4-dimethyl-pyrrolidine-2-carboxylic acid amide hydrochloride (Example 90 d)) in the presence of TBTU and DIEA to obtain the title compound as colorless oil; MS (EI): m/e=380.6 [MH$^+$].

Example 99

[6-Cyclopropylmethoxy-5-(3,3-difluoro-azetidin-1-yl)-pyridin-2-yl]-(5-oxa-2-aza-spiro[3.4]oct-2-yl)-methanone

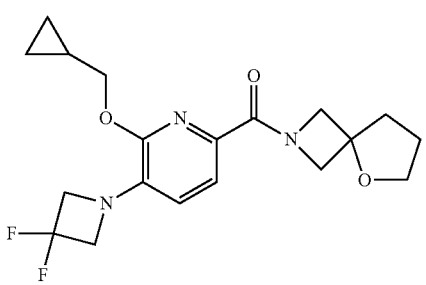 [SMILES: O=C(c1ccc(N2CC(F)(F)C2)c(OCC2CC2)n1)N1CC2(CCCO2)C1]

In analogy to the procedure described in Example 47 b), 6-cyclopropylmethoxy-5-(3,3-difluoro-azetidin-1-yl)-pyridine-2-carboxylic acid (Example 1 b)) was reacted with 5-oxa-2-azaspiro[3.4]octane hydrochloride (1359656-11-3) in the presence of TBTU and DIEA to obtain the title compound as colorless oil; MS (EI): m/e=380.5 [MH$^+$].

Example 100

[6-Cyclopropylmethoxy-5-(3,3-difluoro-azetidin-1-yl)-pyridin-2-yl]-(1-oxa-7-aza-spiro[4.4]non-7-yl)-methanone

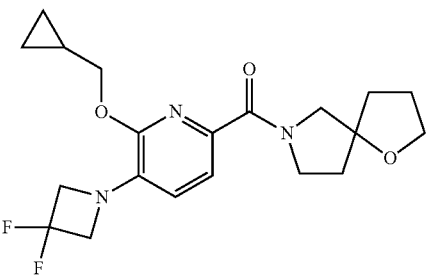 [SMILES: O=C(c1ccc(N2CC(F)(F)C2)c(OCC2CC2)n1)N1CCC2(CCCO2)C1]

In analogy to the procedure described in Example 47 b), 6-cyclopropylmethoxy-5-(3,3-difluoro-azetidin-1-yl)-pyridine-2-carboxylic acid (Example 1 b)) was reacted with 1-oxa-7-azaspiro[4.4]nonane (176-12-5) in the presence of TBTU and DIEA to obtain the title compound as colorless oil; MS (EI): m/e=394.5 [MH$^+$].

Example 101

(5-Aza-spiro[3.4]oct-5-yl)-[6-cyclopropylmethoxy-5-(3,3-difluoro-azetidin-1-yl)-pyridin-2-yl]-methanone

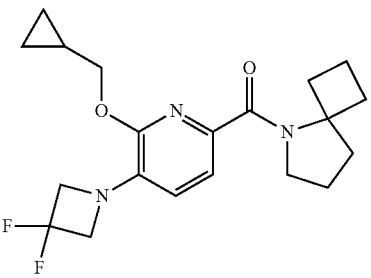 [SMILES: O=C(c1ccc(N2CC(F)(F)C2)c(OCC2CC2)n1)N1CCCC12CCC2]

In analogy to the procedure described in Example 47 b), 6-cyclopropylmethoxy-5-(3,3-difluoro-azetidin-1-yl)-pyridine-2-carboxylic acid (Example 1 b)) was reacted with 5-azaspiro[3.4]octane (52876-78-5) in the presence of TBTU and DIEA to obtain the title compound as colorless oil; MS (EI): m/e=378.5 [MH$^+$].

Example 102

[6-Cyclopropylmethoxy-5-(3,3-difluoro-azetidin-1-yl)-pyridin-2-yl]-(3,3-difluoro-azetidin-1-yl)-methanone

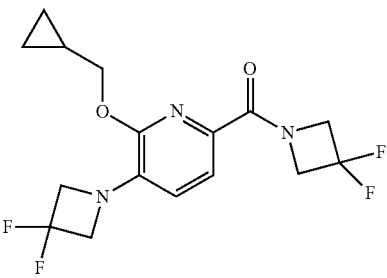 [SMILES: O=C(c1ccc(N2CC(F)(F)C2)c(OCC2CC2)n1)N1CC(F)(F)C1]

In analogy to the procedure described in Example 47 b), 6-cyclopropylmethoxy-5-(3,3-difluoro-azetidin-1-yl)-pyridine-2-carboxylic acid (Example 1 b)) was reacted with 3,3-difluoroazetidine hydrochloride (CAN 288315-03-7) in the presence of TBTU and DIEA to obtain the title compound as colorless solid; MS (EI): m/e=360.4 [MH$^+$].

Example 103

[6-Cyclopropylmethoxy-5-(3,3-difluoro-azetidin-1-yl)-pyridin-2-yl]-(1,1-difluoro-5-aza-spiro[2.4]hept-5-yl)-methanone

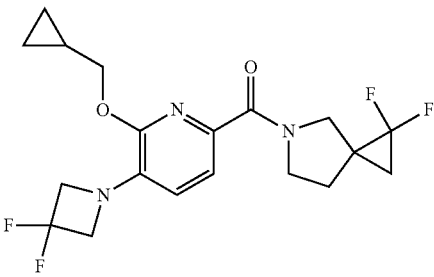 [SMILES: O=C(c1ccc(N2CC(F)(F)C2)c(OCC2CC2)n1)N1CCC2(C1)CC2(F)F]

In analogy to the procedure described in Example 47 b), 6-cyclopropylmethoxy-5-(3,3-difluoro-azetidin-1-yl)-pyridine-2-carboxylic acid (Example 1 b)) was reacted with 1,1-difluoro-5-azaspiro[2.4]heptane hydrochloride (1215071-12-7) in the presence of TBTU and DIEA to obtain the title compound as colorless solid; MS (EI): m/e=400.5 [MH$^+$].

Example 104

(5-Aza-spiro[2.4]hept-5-yl)-[6-cyclopropylmethoxy-5-(3,3-difluoro-azetidin-1-yl)-pyridin-2-yl]-methanone

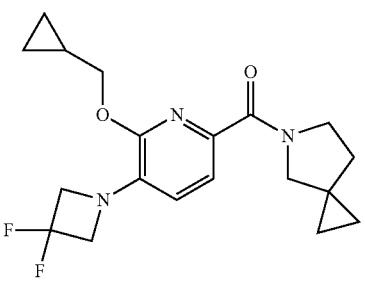 [SMILES: O=C(c1ccc(N2CC(F)(F)C2)c(OCC2CC2)n1)N1CCC2(CC2)C1]

In analogy to the procedure described in Example 47 b), 6-cyclopropylmethoxy-5-(3,3-difluoro-azetidin-1-yl)-pyridine-2-carboxylic acid (Example 1 b)) was reacted with 5-azaspiro[2.4]heptane hydrochloride (3659-21-0) in the presence of TBTU and DIEA to obtain the title compound as colorless oil; MS (EI): m/e=364.5 [MH$^+$].

Example 105

6-Cyclopropylmethoxy-5-(3,3-difluoro-azetidin-1-yl)-pyridine-2-carboxylic acid cyclopropylmethyl-methyl-amide

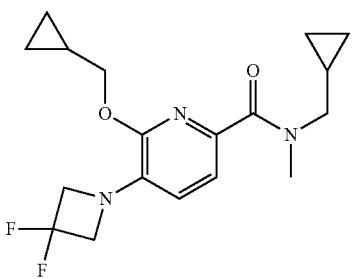 [SMILES: CN(CC1CC1)C(=O)c1ccc(N2CC(F)(F)C2)c(OCC2CC2)n1]

In analogy to the procedure described in Example 47 b), 6-cyclopropylmethoxy-5-(3,3-difluoro-azetidin-1-yl)-pyridine-2-carboxylic acid (Example 1 b)) was reacted with 1-cyclopropyl-N-methylmethanamine hydrochloride (77335-18-

Example 106

[6-Cyclopropylmethoxy-5-(3,3-difluoro-azetidin-1-yl)-pyridin-2-yl]-(4-cyclopropylmethyl-piperazin-1-yl)-methanone

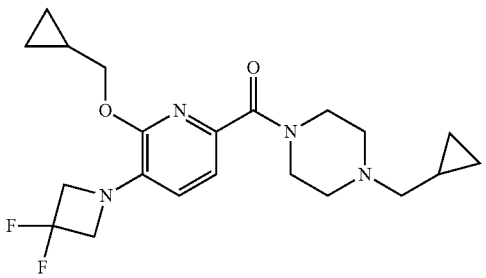 [SMILES: O=C(c1ccc(N2CC(F)(F)C2)c(OCC2CC2)n1)N1CCN(CC2CC2)CC1]

In analogy to the procedure described in Example 47 b), 6-cyclopropylmethoxy-5-(3,3-difluoro-azetidin-1-yl)-pyridine-2-carboxylic acid (Example 1 b)) was reacted with 1-(cyclopropylmethyl)piperazine (57184-25-5) in the presence of TBTU and DIEA to obtain the title compound as colorless oil; MS (EI): m/e=407.6 [MH⁺].

Example 107

3-[6-Cyclopropylmethoxy-5-(3,3-difluoro-azetidin-1-yl)-pyridine-2-carbonyl]-3-aza-bicyclo[3.1.0]hexane-6-carboxylic acid ethyl ester

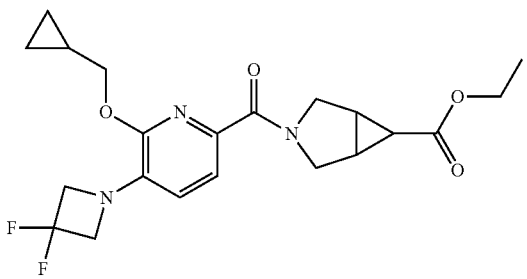 [SMILES: CCOC(=O)C1C2CN(C(=O)c3ccc(N4CC(F)(F)C4)c(OCC4CC4)n3)CC21]

In analogy to the procedure described in Example 47 b), 6-cyclopropylmethoxy-5-(3,3-difluoro-azetidin-1-yl)-pyridine-2-carboxylic acid (Example 1 b)) was reacted with ethyl 3-azabicyclo[3.1.0]hexane-6-carboxylate (179236-79-4) in the presence of TBTU and DIEA to obtain the title compound as colorless oil; MS (EI): m/e=422.5 [MH⁺].

3) in the presence of TBTU and DIEA to obtain the title compound as colorless oil; MS (EI): m/e=352.4 [MH⁺].

Example 108

1-[6-Cyclopropylmethoxy-5-(3,3-difluoro-azetidin-1-yl)-pyridine-2-carbonyl]-pyrrolidine-2-carboxylic acid methyl ester

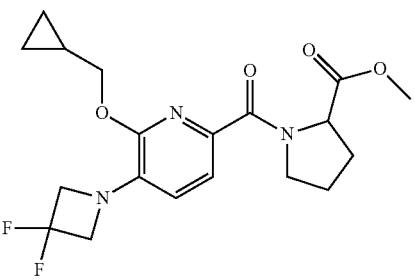 [SMILES: COC(=O)C1CCCN1C(=O)c1ccc(N2CC(F)(F)C2)c(OCC2CC2)n1]

In analogy to the procedure described in Example 47 b), 6-cyclopropylmethoxy-5-(3,3-difluoro-azetidin-1-yl)-pyridine-2-carboxylic acid (Example 1 b)) was reacted with methyl pyrrolidine-2-carboxylate hydrochloride (79397-50-5) in the presence of TBTU and DIEA to obtain the title compound as colorless oil; MS (EI): m/e=396.5 [MH⁺].

Example 109

4-[6-Cyclopropylmethoxy-5-(3,3-difluoro-azetidin-1-yl)-pyridine-2-carbonyl]-piperazine-1-carboxylic acid benzyl ester

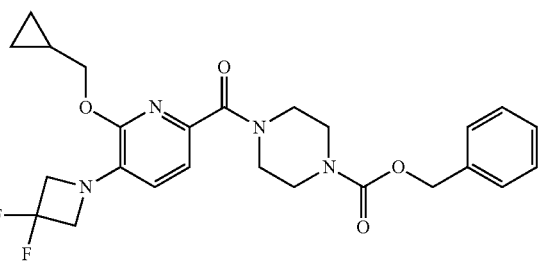

In analogy to the procedure described in Example 47 b), 6-cyclopropylmethoxy-5-(3,3-difluoro-azetidin-1-yl)-pyridine-2-carboxylic acid (Example 1 b)) was reacted with benzyl piperazine-1-carboxylate (31166-44-6) in the presence of TBTU and DIEA to obtain the title compound as light brown oil; MS (EI): m/e=487.5 [MH⁺].

Example 110

3-[6-Cyclopropylmethoxy-5-(3,3-difluoro-azetidin-1-yl)-pyridine-2-carbonyl]-3-aza-bicyclo[3.1.0]hexane-6-carboxylic acid

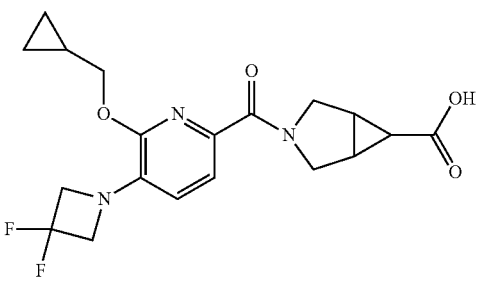 [SMILES: O=C(O)C1C2CN(C(=O)c3ccc(N4CC(F)(F)C4)c(OCC4CC4)n3)CC21]

In analogy to the procedure described in Example 24, 3-[6-cyclopropylmethoxy-5-(3,3-difluoro-azetidin-1-yl)-pyridine-2-carbonyl]-3-aza-bicyclo[3.1.0]hexane-6-carboxylic acid ethyl ester (Example 107) was saponified to give the title compound as colorless solid; MS (EI): m/e=394.5 [MH⁺].

Example 111

1-[5-Cyclopropyl-6-(4-fluoro-benzyl)-pyridine-2-carbonyl]-1,8-diaza-spiro[4.5]decane-8-carboxylic acid tert-butyl ester

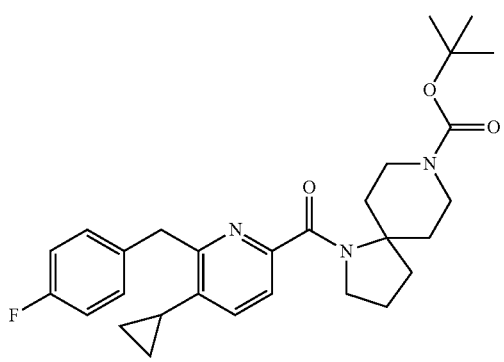 [SMILES: CC(C)(C)OC(=O)N1CCC2(CCCN2C(=O)c2ccc(C3CC3)c(Cc3ccc(F)cc3)n2)CC1]

In analogy to the procedure described in Example 47 b), 5-cyclopropyl-6-(4-fluoro-benzyl)-pyridine-2-carboxylic acid (Example 5 g)) was reacted with tert-butyl 1,8-diazaspiro[4.5]decane-8-carboxylate (937729-06-1) in the presence of TBTU and DIEA to obtain the title compound as colorless oil; MS (EI): m/e=494.6 [MH⁺].

Example 112

(−)-3-[6-Cyclopropylmethoxy-5-(3,3-difluoro-azetidin-1-yl)-pyridine-2-carbonyl]-thiazolidine-4-carboxylic acid amide

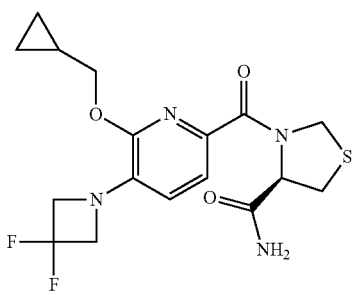 [SMILES: NC(=O)[C@@H]1CSCN1C(=O)c1ccc(N2CC(F)(F)C2)c(OCC2CC2)n1]

In analogy to the procedure described in Example 47 b), 6-cyclopropylmethoxy-5-(3,3-difluoro-azetidin-1-yl)-pyridine-2-carboxylic acid (Example 1 b)) was reacted with 4-thiazolidinecarboxamide (CAN 103749-87-7) in the presence of TBTU and DIEA. The mixture of enantiomers was separated by chiral HPLC (Reprosil Chiral NR). The (−) enantiomer was isolated as white solid; MS (EI): m/e=399.4 [MH⁺]; α$_D^{20}$ (DMSO)=−547.6°.

Example 113

[5-Cyclopropyl-6-(4-fluoro-benzyl)-pyridin-2-yl]-(1,8-diaza-spiro[4.5]dec-1-yl)-methanone

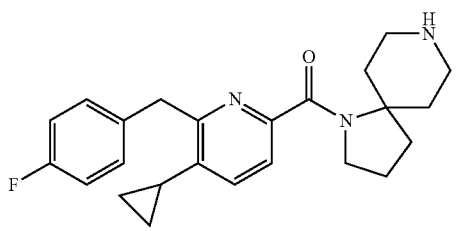 [SMILES: O=C(c1ccc(C2CC2)c(Cc2ccc(F)cc2)n1)N1CCCC12CCNCC2]

A solution of tert-butyl 1-(5-cyclopropyl-6-(4-fluorobenzyl)picolinoyl)-1,8-diazaspiro[4.5]decane-8-carboxylate (Example 111, 19 mg, 38.5 µmol) and 2,2,2-trifluoroacetic acid (43.9 mg, 29.5 µL, 385 µmol) in DCM (0.4 mL) was stirred for 12 h at ambient temperature. The reaction mixture was poured onto 20 mL saturated aqueous NaHCO₃ solution/ice and extracted with EtOAc (2×20 mL). The combined extracts were washed with ice-water/brine (20 mL), dried over Na₂SO₄ and brought to dryness to give the title compound (14 mg, 92%) as colorless oil; MS (EI): m/e=394.5 [MH⁺].

Example 114

1-[6-Cyclopropylmethoxy-5-(3,3-difluoro-azetidin-1-yl)-pyridine-2-carbonyl]-pyrrolidine-2-carboxylic acid amide a) 1-(6-(Cyclopropylmethoxy)-5-(3,3-difluoroazetidin-1-yl)picolinoyl)pyrrolidine-2-carboxylic acid

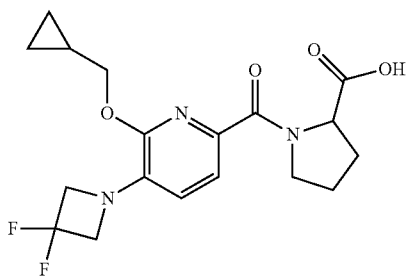 [SMILES: O=C(O)C1CCCN1C(=O)c1ccc(N2CC(F)(F)C2)c(OCC2CC2)n1]

In analogy to the procedure described in Example 24, 1-[6-cyclopropylmethoxy-5-(3,3-difluoro-azetidin-1-yl)-pyridine-2-carbonyl]-pyrrolidine-2-carboxylic acid methyl ester (Example 108) was saponified to give the title compound as colorless solid; MS (EI): m/e=382.5 [MH⁺].

b) 1-[6-Cyclopropylmethoxy-5-(3,3-difluoro-azetidin-1-yl)-pyridine-2-carbonyl]-pyrrolidine-2-carboxylic acid amide

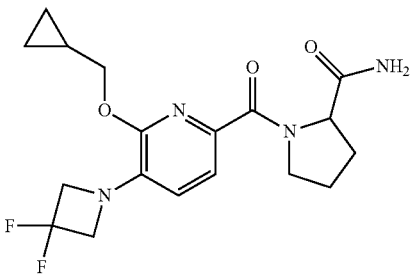 [SMILES: NC(=O)C1CCCN1C(=O)c1ccc(N2CC(F)(F)C2)c(OCC2CC2)n1]

To an ice-cold solution of 1-(6-(cyclopropylmethoxy)-5-(3,3-difluoroazetidin-1-yl)picolinoyl)pyrrolidine-2-carboxylic acid (8.6 mg, 22.6 μmol) in DMF (2 mL) was added carbonyldiimidazole (10.2 mg, 63.1 μmol). After 5 minutes the reaction mixture was warmed to ambient temperature and stirred for 2 h. NH₃ gas was bubbled through the solution for 10 minutes and stirring was continued for 12 h. The reaction mixture was poured onto ice-water (20 mL) and extracted with EtOAc (2×20 mL). The combined extracts were dried over Na₂SO₄ and concentrated in vacuo to give the title compound (9 mg, quant.) as colorless wax; MS (EI): m/e=381.5 [MH⁺].

Example 115

(−)-3-(5-Cyclopropyl-6-cyclopropylmethoxy-pyridine-2-carbonyl)-1,1-dioxo-1$\lambda^6$-thiazolidine-4-carboxylic acid amide

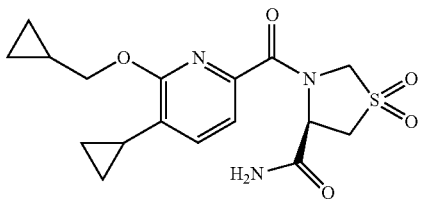 [SMILES: NC(=O)[C@@H]1CS(=O)(=O)CN1C(=O)c1ccc(C2CC2)c(OCC2CC2)n1]

To a suspension of (−)-3-(5-cyclopropyl-6-cyclopropylmethoxy-pyridine-2-carbonyl)-thiazolidine-4-carboxylic acid amide (Example 97, 60 mg, 173 μmol) in DCM (6 mL) was added m-CPBA (65.6 mg, 380 μmol) and the reaction mixture was stirred at room temperature for 3 hours. 1 N sodium hydroxide solution (3 mL) was added and the mixture was dried by filtration over ChemElut® and concentrated in vacuo. The residue was purified by flash chromatography (silica, DCM/methanol 0-5%) to give the title compound (21 mg, 32%) as white solid; LC-MS (UV peak area/ESI) 100%, 380.1286 [MH⁺].

Example 116

(1S,4R)-3-(5-Cyclopropyl-6-cyclopropylmethoxy-pyridine-2-carbonyl)-1-oxo-1$\lambda^4$-thiazolidine-4-carboxylic acid amide or (1R,4S)-3-(5-cyclopropyl-6-cyclopropylmethoxy-pyridine-2-carbonyl)-1-oxo-1$\lambda^4$-thiazolidine-4-carboxylic acid amide

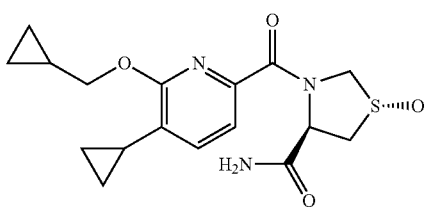

To a suspension of (−)-3-(5-cyclopropyl-6-cyclopropylmethoxy-pyridine-2-carbonyl)-thiazolidine-4-carboxylic acid amide (Example 97, 60 mg, 173 μmol) in DCM (6 mL) was added m-CPBA (65.6 mg, 380 μmol) and the reaction mixture was stirred at room temperature for 3 hours. 1 N sodium hydroxide solution (3 mL) was added and the mixture was dried by filtration over ChemElut® and concentrated in vacuo. The residue was purified by flash chromatography (silica, DCM/methanol 0-5%) to give the title compound (30 mg, 48%) as white solid; LC-MS (UV peak area/ESI) 95.8%, 364.1335 [MH⁺].

Example 117

(+)-3-(5-Cyclopropyl-6-cyclopropylmethoxy-pyridine-2-carbonyl)-1,1-dioxo-1$\lambda^6$-thiazolidine-4-carboxylic acid amide a) (+)-3-(5-Cyclopropyl-6-cyclopropylmethoxy-pyridine-2-carbonyl)-thiazolidine-4-carboxylic acid amide

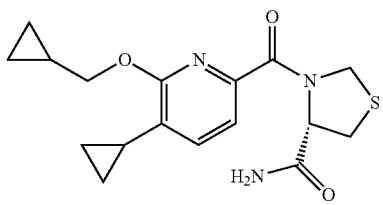 [SMILES: NC(=O)[C@H]1CSCN1C(=O)c1ccc(C2CC2)c(OCC2CC2)n1]

The enantiomers of 3-(5-cyclopropyl-6-cyclopropylmethoxy-pyridine-2-carbonyl)-thiazolidine-4-carboxylic acid amide (Example 96) were separated by chiral HPLC (Reprosil Chiral NR, 40% ethanol in n-heptane). The (+) enantiomer (34 mg, 34%) was isolated as white solid; LC-MS (UV peak area/ESI) 100%, 348.1380 [MH⁺]; (+) enantiomer, ~100% ee.

b) (+)-3-(5-Cyclopropyl-6-cyclopropylmethoxy-pyridine-2-carbonyl)-1,1-dioxo-1λ⁶-thiazolidine-4-carboxylic acid amide

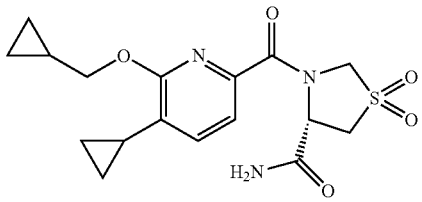 [SMILES: NC(=O)[C@H]1CS(=O)(=O)CN1C(=O)c1ccc(C2CC2)c(OCC2CC2)n1]

To a suspension of (+)-3-(5-cyclopropyl-6-cyclopropyl-methoxy-pyridine-2-carbonyl)-thiazolidine-4-carboxylic acid amide (60 mg, 173 µmol) in DCM (6 mL) was added m-CPBA (65.6 mg, 380 µmol) and the reaction mixture was stirred at room temperature for over night. 1 N sodium hydroxide solution (3 mL) was added and the mixture was dried by filtration over ChemElut® and concentrated in vacuo. The residue was purified by flash chromatography (silica, DCM/methanol 0-5%) to give the title compound (31 mg, 47%) as white solid; LC-MS (UV peak area/ESI) 99.0%, 380.1279 [MH⁺].

Example 118

[6-Cyclopropylmethoxy-5-(3,3-difluoro-azetidin-1-yl)-pyridin-2-yl]-(3,3,4,4-tetrafluoro-pyrrolidin-1-yl)-methanone

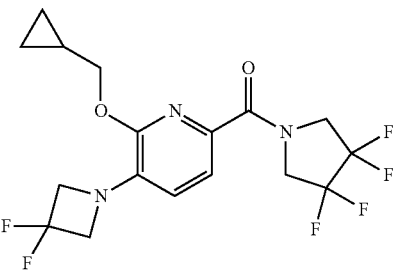 [SMILES: O=C(c1ccc(N2CC(F)(F)C2)c(OCC2CC2)n1)N1CC(F)(F)C(F)(F)C1]

In analogy to the procedure described in Example 47 b), 6-cyclopropylmethoxy-5-(3,3-difluoro-azetidin-1-yl)-pyridine-2-carboxylic acid (Example 1 b)) was reacted with 3,3,4,4-tetrafluoropyrrolidine hydrochloride (1810-13-5) in the presence of TBTU and DIEA to obtain the title compound as colorless oil; MS (EI): m/e=410.5 [MH⁺].

Example 119

[6-Cyclopropylmethoxy-5-(3,3-difluoro-azetidin-1-yl)-pyridin-2-yl]-(2,6-dimethyl-morpholin-4-yl)-methanone

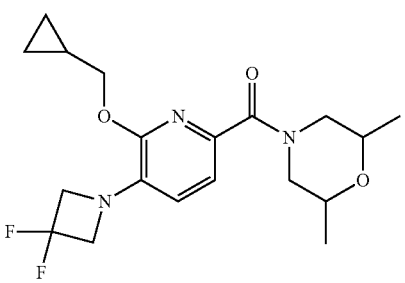 [SMILES: CC1CN(C(=O)c2ccc(N3CC(F)(F)C3)c(OCC3CC3)n2)CC(C)O1]

In analogy to the procedure described in Example 47 b), 6-cyclopropylmethoxy-5-(3,3-difluoro-azetidin-1-yl)-pyridine-2-carboxylic acid (Example 1 b)) was reacted with 2,6-dimethylmorpholine (141-91-3) in the presence of TBTU and DIEA to obtain the title compound as colorless oil; MS (EI): m/e=382.5 [MH⁺].

Example 120

(R)-3-[6-Cyclopropylmethoxy-5-(3,3-difluoro-azetidin-1-yl)-pyridine-2-carbonyl]-5,5-dimethyl-thiazolidine-4-carboxylic acid amide a) (R)-5,5-Dimethylthiazolidine-4-carboxamide hydrochloride

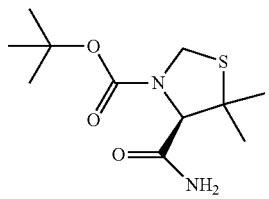 [SMILES: CC(C)(C)OC(=O)N1CSC(C)(C)[C@H]1C(N)=O]

In analogy to the procedure described in Example 114 b), (R)-3-(tert-butoxycarbonyl)-5,5-dimethylthiazolidine-4-carboxylic acid (CAN 117918-23-7) was converted to the title compound in the form of a colorless solid; MS (EI): m/e=260 [M⁺].

b) (R)-5,5-Dimethylthiazolidine-4-carboxamide hydrochloride

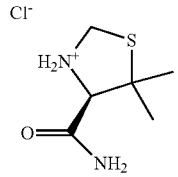

In analogy to the procedure described in Example 82 a), (R)-tert-butyl 4-carbamoyl-5,5-dimethylthiazolidine-3-carboxylate was treated with a 4 M solution of HCl in dioxane to give the title compound as yellow solid which was sufficiently pure to be used in the next step; MS (EI): m/e=161.2 [(M-Cl)H⁺].

c) (R)-3-[6-Cyclopropylmethoxy-5-(3,3-difluoro-azetidin-1-yl)-pyridine-2-carbonyl]-5,5-dimethyl-thiazolidine-4-carboxylic acid amide

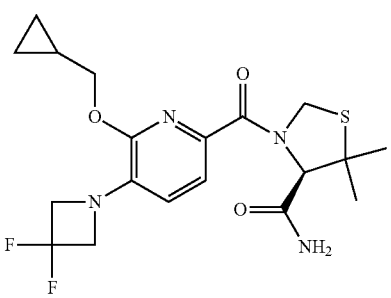 [SMILES: CC1(C)SCN(C(=O)c2ccc(N3CC(F)(F)C3)c(OCC3CC3)n2)[C@@H]1C(N)=O]

In analogy to the procedure described in Example 47 b), 6-cyclopropylmethoxy-5-(3,3-difluoro-azetidin-1-yl)-pyridine-2-carboxylic acid (Example 1 b)) was reacted with (R)-5,5-dimethylthiazolidine-4-carboxamide hydrochloride in the presence of TBTU and DIEA to obtain the title compound as light yellow solid; MS (EI): m/e=427.4 [MH+].

Example 121

(S)-1-[6-Cyclopropylmethoxy-5-(3,3-difluoro-azetidin-1-yl)-pyridine-2-carbonyl]-5,5-dimethyl-pyrrolidine-2-carboxylic acid amide a) (S)-5,5-Dimethylpyrrolidine-2-carboxamide hydrochloride

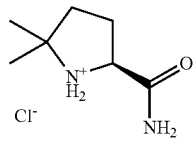

In analogy to the procedure described in Example 82 a), (S)-tert-butyl 5-carbamoyl-2,2-dimethylpyrrolidine-1-carboxylate (CAN 1292838-05-1) was treated with a 4 M solution of HCl in dioxane to give the title compound as colorless solid which was sufficiently pure to be used in the next step; MS (EI): m/e=143.2 [(M-Cl)H+].

b) (S)-1-[6-Cyclopropylmethoxy-5-(3,3-difluoro-azetidin-1-yl)-pyridine-2-carbonyl]-5,5-dimethyl-pyrrolidine-2-carboxylic acid amide

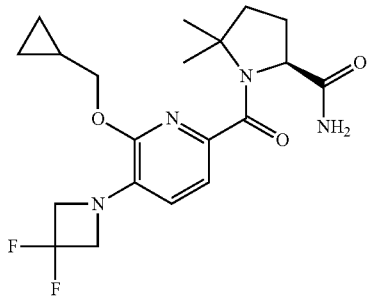 [SMILES: CC1(C)CC[C@@H](C(N)=O)N1C(=O)c1ccc(N2CC(F)(F)C2)c(OCC2CC2)n1]

In analogy to the procedure described in Example 47 b), 6-cyclopropylmethoxy-5-(3,3-difluoro-azetidin-1-yl)-pyridine-2-carboxylic acid (Example 1 b)) was reacted with (S)-5,5-dimethylpyrrolidine-2-carboxamide hydrochloride in the presence of TBTU and DIEA to obtain the title compound as colorless foam; MS (EI): m/e=409.5 [MH+].

Example 122

3-[6-Cyclopropylmethoxy-5-(3,3-difluoro-azetidin-1-yl)-pyridine-2-carbonyl]-thiazolidine-4-carboxylic acid amide

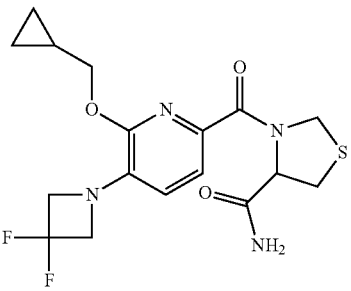

In analogy to the procedure described in Example 47 b), 6-cyclopropylmethoxy-5-(3,3-difluoro-azetidin-1-yl)-pyridine-2-carboxylic acid (Example 1 b)) was reacted with and 4-thiazolidinecarboxamide (CAN 103749-87-7) in the presence of TBTU and DIEA to obtain the title compound as white solid; MS (EI): m/e=399.5 [MH+].

Example 123

(2S,4R)-1-[5-Cyclopropyl-6-(cyclopropylmethoxy)pyridine-2-carbonyl]-4-fluoropyrrolidine-2-carboxamide

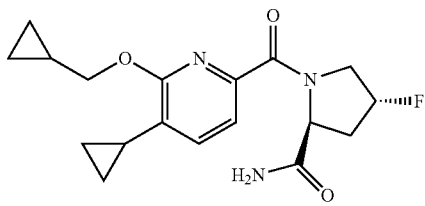 [SMILES: NC(=O)[C@@H]1C[C@@H](F)CN1C(=O)c1ccc(C2CC2)c(OCC2CC2)n1]

In analogy to the procedure described in Example 47 b), 5-cyclopropyl-6-cyclopropylmethoxy-pyridine-2-carboxylic acid (Example 3 c, 50 mg, 214 µmol) was reacted with (2S,4R)-4-fluoropyrrolidine-2-carboxamide hydrochloride (CAN 796884-06-5, 39.8 mg, 236 µmol) to obtain the title compound (54 mg, 73%) as white solid; LC-MS (UV peak area, ESI) 100%, 348.1727 [MH+].

Example 124

3-[6-(Cyclopropylmethoxy)-5-(3,3-difluoroazetidin-1-yl)pyridine-2-carbonyl]-1-oxo-1,3-thiazolidine-4-carboxamide

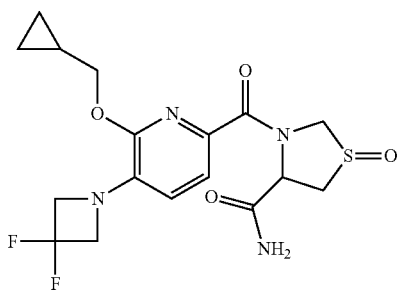 [SMILES: NC(=O)C1CS(=O)CN1C(=O)c1ccc(N2CC(F)(F)C2)c(OCC2CC2)n1]

3-Chloroperbencoic acid (172 mg, 994 µmol) was added to a solution of 3-[6-cyclopropylmethoxy-5-(3,3-difluoro-azetidin-1-yl)-pyridine-2-carbonyl]-thiazolidine-4-carboxylic acid amide (Example 122, 180 mg, 452 µmol) in dichloromethane (1.8 mL). The reaction mixture was stirred for 12 h at ambient temperature, poured onto sodiumthiosulfate/ice water (1×15 mL) and extracted with EtOAc (2×20 mL). The combined extracts were washed with ice/brine (1×25 mL), dried over $Na_2SO_4$ and filtered. The solvent was removed under reduced pressure and the residue purified by prep. HPLC (methanol/formic acid 95/5) to give the title compound (9 mg, 5%) as light yellow solid; MS (EI): m/e=415.4 [MH$^+$].

Example 125

3-[6-(Cyclopropylmethoxy)-5-(3,3-difluoroazetidin-1-yl)pyridine-2-carbonyl]-1,1-dioxo-1,3-thiazolidine-4-carboxamide

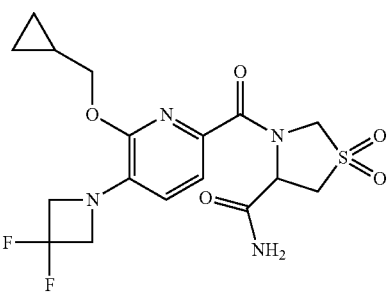 [SMILES: NC(=O)C1CS(=O)(=O)CN1C(=O)c1ccc(N2CC(F)(F)C2)c(OCC2CC2)n1]

3-Chloroperbencoic acid (172 mg, 994 µmol) was added to a solution of 3-[6-cyclopropylmethoxy-5-(3,3-difluoro-azetidin-1-yl)-pyridine-2-carbonyl]-thiazolidine-4-carboxylic acid amide (Example 122, 180 mg, 452 µmol) in dichloromethane (1.8 mL). The reaction mixture was stirred for 12 h at ambient temperature, poured onto sodiumthiosulfate/ice water (1×15 mL) and extracted with EtOAc (2×20 mL). The combined extracts were washed with ice/brine (1×25 mL), dried over $Na_2SO_4$ and filtered. The solvent was removed under reduced pressure and the residue purified by prep. HPLC (methanol/formic acid 95/5) to give the title compound (9 mg, 5%) as light yellow solid; MS (EI): m/e=431.4 [MH$^+$].

Example 126

(2S,4R)-1-[6-(Cyclopropylmethoxy)-5-(3,3-difluoro-azetidin-1-yl)pyridine-2-carbonyl]-4-fluoropyrrolidine-2-carboxamide

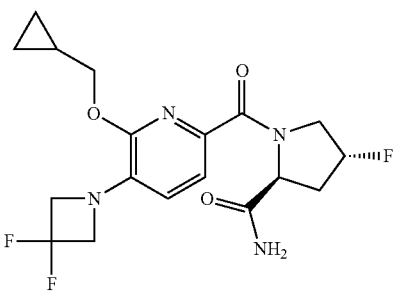 [SMILES: NC(=O)[C@@H]1C[C@@H](F)CN1C(=O)c1ccc(N2CC(F)(F)C2)c(OCC2CC2)n1]

In analogy to the procedure described in Example 47 b), 6-cyclopropylmethoxy-5-(3,3-difluoro-azetidin-1-yl)-pyridine-2-carboxylic acid (Example 1 b, 25 mg, 87.9 µmol) was reacted with (2S,4R)-4-fluoropyrrolidine-2-carboxamide hydrochloride (CAN 796884-06-5, 17.8 mg, 106 µmol) to obtain the title compound (17 mg, 49%) as white solid; MS (EI): m/e=399.4 [MH$^+$].

Example 127

(−)-3-[6-(Cyclopropylmethoxy)-5-(3,3-difluoroazetidin-1-yl)pyridine-2-carbonyl]-1,1-dioxo-1,3-thiazolidine-4-carboxamide

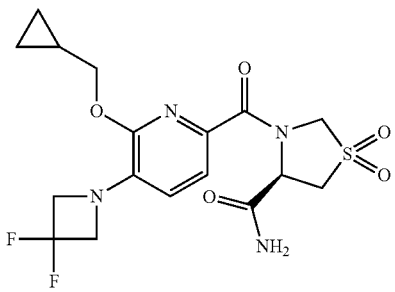 [SMILES: NC(=O)[C@@H]1CS(=O)(=O)CN1C(=O)c1ccc(N2CC(F)(F)C2)c(OCC2CC2)n1]

a) O3-tert-Butyl O4-methyl 1,1-dioxo-1,3-thiazolidine-3,4-dicarboxylate

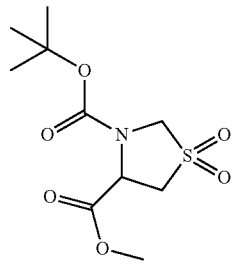 [SMILES: COC(=O)C1CS(=O)(=O)CN1C(=O)OC(C)(C)C]

3-Chloroperbenzoic acid (698 mg, 4.04 mmol) was added to an ice cold solution of O3-tert-butyl O4-methyl thiazolidine-3,4-dicarboxylate (CAN 63664-10-8, 0.5 g, 2.02 mmol) in dichloromethane (4 mL). The suspension was stirred for 2 h at ambient temperature. Additional 3-chloroperbenzoic acid (349 mg, 2.02 mmol) was added and stirring was continued for 12 h at ambient temperature. The reaction mixture was poured onto ice water/saturated $NaHCO_3$-solution (50 mL) and the layers were separate. The aqueous layer was extracted with dichloromethane (2×50 mL). The combined organic layers were washed with ice water/brine (30 mL), dried over $Na_2SO_4$ and concentrated in vacuo to give a yellow oil which was purified by column chromatography (20 g silicagel, heptane/AcOEt 0-20% in 120 min) to obtain the title compound (362 mg, 64%) as colorless liquid, MS (ESI) m/e=180.1 [MH-Boc⁺].

b) 3-tert-Butoxycarbonyl-1,1-dioxo-1,3-thiazolidine-4-carboxylic acid

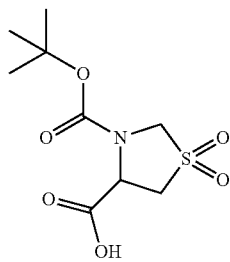 [SMILES: CC(C)(C)OC(=O)N1CS(=O)(=O)CC1C(=O)O]

A solution of O3-tert-butyl O4-methyl 1,1-dioxo-1,3-thiazolidine-3,4-dicarboxylate (Example 127 a, 0.35 g, 1.25 mmol) and lithium hydroxide hydrate (63.1 mg, 1.5 mmol) in THF (3.5 mL) and water (1.05 mL) was stirred for 20 h at ambient temperature. The reaction mixture was poured onto ice/0.1N HCl (25 mL) and extracted with EtOAc (2×25 mL). The combined extracts were washed with ice/brine (1×25 mL), dried over Na₂SO₄ and filtered. The solvent was removed under reduced pressure to give the title compound (306 mg, 92%) as colorless foam, MS (ESI) m/e=264.05 [M−H⁻].

c) tert-Butyl 4-carbamoyl-1,1-dioxo-1,3-thiazolidine-3-carboxylate

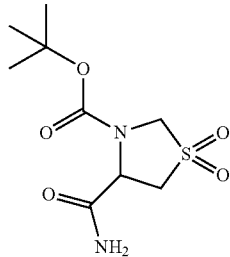 [SMILES: CC(C)(C)OC(=O)N1CS(=O)(=O)CC1C(N)=O]

Carbonyldiimidazole (520 mg, 3.21 mmol) was added to an ice cold solution of 3-tert-butoxycarbonyl-1,1-dioxo-1,3-thiazolidine-4-carboxylic acid (Example 127 b, 304 mg, 1.15 mmol) in DMF (1 mL). After 5 min. the mixture was warmed to ambient temperature and stirred for 2 h. Gaseous NH₃ was bubbled for 10 min through the solution while the temperature was kept below 20° C. Stirring was continued for 12 h at ambient temperature. The reaction mixture was poured into 30 mL ice/water/1N HCl and extracted with EtOAc (2×30 mL). The combined extracts were washed with ice/brine (20 mL), dried over Na₂SO₄ and concentrated in vacuo to give the title compound (197 mg, 65%) as white solid, MS (ESI) m/e=263.1 [M−H⁻].

d) 1,1-Dioxo-1,3-thiazolidine-4-carboxamide hydrochloride

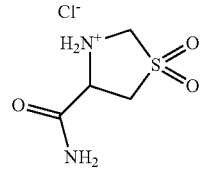

An ice cold 4 M solution of HCl in dioxane (4.73 mL, 18.9 mmol) was added to a solution of tert-butyl 4-carbamoyl-1,1-dioxo-1,3-thiazolidine-3-carboxylate (Example 127 c, 500 mg, 1.89 mmol) in dichloromethane (10.2 mL). The mixture was stirred for 4 d at ambient temperature. Removal of the solvent in vacuo yielded the title compound (388 mg, quant.) as white solid which was used in the next step without further purification, MS (ESI) m/e=198.99 [M−H⁻].

e) (−)-3-[6-(Cyclopropylmethoxy)-5-(3,3-difluoro-azetidin-1-yl)pyridine-2-carbonyl]-1,1-dioxo-1,3-thiazolidine-4-carboxamide A solution of 6-cyclopropylmethoxy-5-(3,3-difluoro-azetidin-1-yl)-pyridine-2-carboxylic acid (Example 1 b, 200 mg, 704 μmol), 1,1-dioxo-1,3-thiazolidine-4-carboxamide hydrochloride (Example 127 d, 169 mg, 844 μmol), 2-bromo-1-ethylpyridinium tetrafluoroborate (212 mg, 774 μmol) and DIEA (273 mg, 361 μL, 2.11 mmol) in THF (20 mL) was stirred for 24 h at ambient temperature. The solvent was removed under reduced pressure, ice/sat. aqueous NaHCO₃ (75 mL) and EtOAc (75 mL) were added and the layers were separated. The aqueous layer was extracted with EtOAc (75 mL). The combined extracts were washed with ice/0.1N HCl (75 mL) and ice/brine (75 mL), dried over Na₂SO₄ and filtered. The solvent was removed under reduced pressure to give a yellow solid which was recrystallized from EtOAc (3 mL). The crude product was purified by chiral HPLC (Reprosil Chiral NR, EtOH/heptane 40%/60%) to give the title compound (63 mg, 21%) as colorless oil, MS (EI): m/e=431.3 [MH⁺].

Example 128

3-[6-(Cyclopropylmethoxy)-5-(3-methoxyazetidin-1-yl)pyridine-2-carbonyl]-1,1-dioxo-1,3-thiazolidine-4-carboxamide

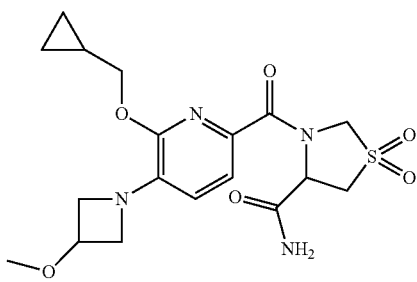 [SMILES: COC1CN(c2ccc(C(=O)N3CS(=O)(=O)CC3C(N)=O)nc2OCC2CC2)C1]

a) 6-(Cyclopropylmethoxy)-5-(3-methoxyazetidin-1-yl)pyridine-2-carboxylic acid

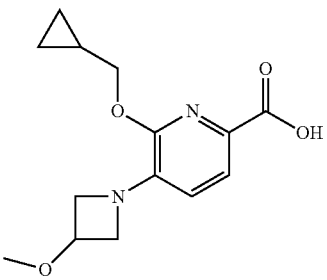 [SMILES: COC1CN(c2ccc(C(=O)O)nc2OCC2CC2)C1]

Under a nitrogen atmosphere, 3-methoxyazetidine (38 mg, 0.44 mmol), BINAP (23 mg, 0.037 mmol), $Pd_2(dba)_3$ (17 mg, 0.02 mmol) and $Cs_2CO_3$ (240 mg, 0.735 mmol) were added to a solution of 5-bromo-6-(cyclopropylmethoxy)pyridine-2-carboxylic acid (CAN 1415898-37-1, 100 mg, 0.37 mmol) in toluene (4 mL). The reaction mixture was stirred overnight at 110° C. and then concentrated under reduced pressure. The residue was dissolved in water and extracted with ethyl acetate (30 mL). The aqueous layer was adjusted to pH 2 by addition of 1N HCl. The resulting precipitate was collected by filtration and dried in vacuo. Chromatographical purification over silica gel using petroleum ether/ethyl acetate=1/2 provided the title compound (35 mg, 34%) as a yellow solid, LC-MS: 265.2 [MH$^+$].

b) 3-[6-(Cyclopropylmethoxy)-5-(3-methoxyazetidin-1-yl)pyridine-2-carbonyl]-1,1-dioxo-1,3-thiazolidine-4-carboxamide In analogy to the procedure described in Example 127 e), 6-(cyclopropylmethoxy)-5-(3-methoxyazetidin-1-yl)pyridine-2-carboxylic acid (Example 128 a, 30 mg, 108 μmol) was reacted with 1,1-dioxo-1,3-thiazolidine-4-carboxamide hydrochloride (Example 127 d, 26.0 mg, 129 μmol) to give the title compound (15 mg, 33%) as off-white solid, MS (EI): m/e=425.5 [MH$^+$].

Example 129

(2S)-1-[6-(Cyclopropylmethoxy)-5-(1-hydroxycyclobutyl)pyridine-2-carbonyl]-4,4-difluoropyrrolidine-2-carboxamide

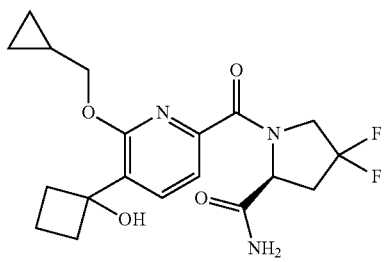

In analogy to the procedure described in Example 127 e), 6-(cyclopropylmethoxy)-5-(1-hydroxycyclobutyl)pyridine-2-carboxylic acid (CAN 1415899-53-4, 15 mg, 57 μmol) was reacted with (S)-4,4-difluoropyrrolidine-2-carboxamide hydrochloride (CAN 426844-51-1, 10.6 mg, 57 μmol) to give the title compound (6 mg, 21%) as light yellow oil, LC-MS (UV peak area, ESI) 100%, 396.1740 [MH$^+$].

Example 130

(2S)-1-[6-(Cyclopropylmethoxy)-5-(1-fluorocyclobutyl)pyridine-2-carbonyl]-4,4-difluoropyrrolidine-2-carboxamide

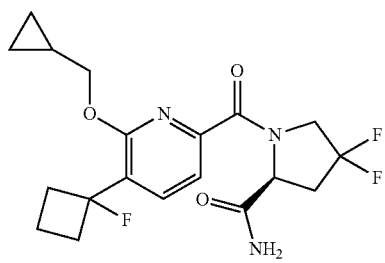 [SMILES: NC(=O)[C@@H]1CC(F)(F)CN1C(=O)c1ccc(C2(F)CCC2)c(OCC2CC2)n1]

a) 1-(2-Chloro-6-methylpyridin-3-yl)cyclobutanol

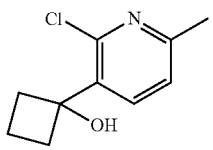

A suspension of molecular sieves (4 Å) and 3-bromo-2-chloro-6-methylpyridine (CAN 185017-72-5, 5 g, 24.2 mmol) in THF (50 mL) was cooled to −15° C. 1.3 M isopropyl magnesium chloride lithium chloride complex solution in THF (19.6 mL, 25.4 mmol) was added within 30 min. Stirring was continued for 1 h at −15° C. Cyclobutanone (1.87 g, 2.00 mL, 26.6 mmol) was slowly added. Stirring was continued for 2 h at −15° C. and for further 2 h at 0° C. Water (2.5 mL) was added, the mixture was concentrated in vacuo, and poured onto sat. aqueous $NH_4Cl$ solution. The mixture was extracted with EtOAc (2×100 mL). The combined extracts were washed with ice water (50 mL), dried over $Na_2SO_4$ and concentrated in vacuo. The residue was purified by flash chromatography (silica gel, 140 g, heptane/EtOAc 0-40% in 120 min.) to give the title compound (3.33 g, 70%) as white solid, MS (ESI): m/e=198.1 [MH$^+$].

b) 2-Chloro-3-(1-fluorocyclobutyl)-6-methylpyridine

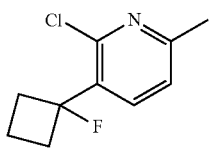

Diethylaminosulfur trifluoride (1.22 g, 1.00 mL, 7.57 mmol) was added to an ice cold solution of 1-(2-chloro-6-methylpyridin-3-yl)cyclobutanol (Example 130 a, 1 g, 5.06 mmol) in dichloromethane (10 mL) keeping the temperature below 5° C. The reaction mixture was stirred for 30 min. at 0° C., poured onto ice water/sat. aqueous Na₂CO₃ solution (35 mL) and extracted with dichloromethane (2×50 mL). The organic layers were combined, washed with ice water/brine (30 mL), dried over Na₂SO₄ and concentrated in vacuo. The residue was purified by flash chromatography (silica gel, 50 g, heptane/EtOAc 0-10% in 75 min) to give the title compound (939 mg, 93%) as colorless oil, MS (ESI): m/e=200.3 [MH⁺].

c) 2-Chloro-3-(1-fluorocyclobutyl)-6-methylpyridine 1-oxide

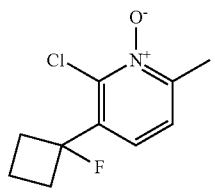

3-Chlorobenzoperoxoic acid (173 mg, 1.00 mmol) was added in 2 portions to a solution of 2-chloro-3-(1-fluorocyclobutyl)-6-methylpyridine (Example 130 b, 100 mg, 501 μmol) in dichloromethane (2 mL). The reaction mixture was stirred at ambient temperature for 72 h, poured onto a 10% aqueous Na₂S₂O₃ solution (30 mL) and extracted with dichloromethane (2×40 mL). The combined organic layers were washed with ice water/brine (30 mL), dried over Na₂SO₄ and concentrated in vacuo. The residue was dissolved in dichloromethane, washed with sat. NaHCO₃ solution (30 mL) and ice water (30 mL), dried over Na₂SO₄ and concentrated in vacuo to give the title compound (81 mg, 74%) as yellow oil, MS (ESI): m/e=216.3 [MH⁺].

d) (6-Chloro-5-(1-fluorocyclobutyl)pyridin-2-yl)methanol

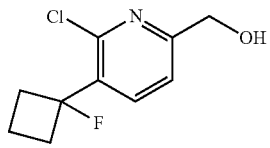 [SMILES: OCc1ccc(C2(F)CCC2)c(Cl)n1]

Trifluoroacetic anhydride (1.27 g, 840 μL, 6.04 mmol) was added under ice cooling to a solution of 2-chloro-3-(1-fluorocyclobutyl)-6-methylpyridine 1-oxide (Example 130 c, 869 mg, 4.03 mmol) in dichloromethane (10.9 mL). The mixture was stirred at ambient temperature for 72 h. Upon ice bath cooling 5 N NaOH solution (1 mL) and afterwards ice water (20 mL) were added. The mixture was extracted with dichloromethane (2×40 mL). The combined organic layers were washed with icewater/brine (20 mL), dried over Na₂SO₄ and concentrated in vacuo. The residue was purified by flash chromatography (silica gel, 50 g, heptane/EtOAc 0-40% in 120 min.) to give the title compound (279 mg, 32%) as light yellow oil, MS (ESI): m/e=216.3 [MH⁺].

e) 6-Chloro-5-(1-fluorocyclobutyl)pyridine-2-carboxylic acid

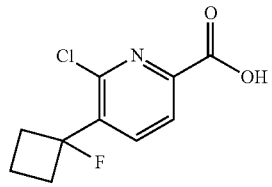 [SMILES: O=C(O)c1ccc(C2(F)CCC2)c(Cl)n1]

Aqueous phosphate buffer (pH=6.7, 0.7 mL) and TEMPO (2.54 mg, 16.2 μmol) were added to a solution of (6-chloro-5-(1-fluorocyclobutyl)pyridin-2-yl)methanol (Example 130 d, 50 mg, 232 μmol) in acetonitrile (1 mL) under an argon atmosphere. The reaction mixture was warmed to 35° C. A solution of sodium chlorite (52.4 mg, 464 μmol) in 150 μL water and a solution of sodium hypochlorite (2.66 mg, 2.19 μL, 4.64 μmol) in 100 μL water were added simultaneously over a period of 30 min. Stirring was continued at 35° C. for 20 h. Water (40 mL) and 2 N NaOH solution (8 mL) were added. The mixture was poured into an ice cold Na₂SO₃ solution (1.62 Na₂SO₃ g in 30 mL water) and stirred for 30 min. at ambient temperature. Under ice cooling the mixture was acidified with 25 mL 2 N HCl solution and extracted with a mixture of 100 mL EtOAc and 20 mL THF. The organic layer was dried over Na₂SO₄, filtered and the solvent concentrated in vacuo to give the title compound (66 mg, 90%) as yellow oil, MS(ESI): m/e=230.4 [MH⁺].

f) 6-(Cyclopropylmethoxy)-5-(1-fluorocyclobutyl)pyridine-2-carboxylic acid

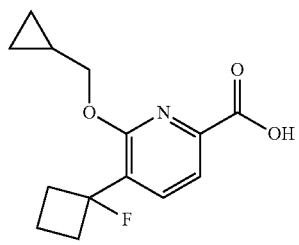 [SMILES: O=C(O)c1ccc(C2(F)CCC2)c(OCC2CC2)n1]

Powdered potassium hydroxide (240 mg, 4.28 mmol) was added to a solution of 6-chloro-5-(1-fluorocyclobutyl)pyridine-2-carboxylic acid (Example 130 e, 393 mg, 1.71 mmol) in DMSO (7.86 mL). The mixture was stirred at ambient temperature for 15 minutes. Cyclopropylmethanol (136 mg, 153 μL, 1.88 mmol) was added and stirring was continued for 5 h at 60° C. Additional cyclopropylmethanol (68 mg, 76 μL, 94 mmol) was added, the mixture was stirred for 14 h at ambient temperature, poured onto ice/brine (100 mL) and extracted with TBME (2×100 mL). The aqueous layer was acidified with 1 N HCl and extracted with EtOAc (2×150 mL). The combined organic layers were washed with ice/brine (50 mL), dried over Na₂SO₄ and filtered. The solvent was removed under reduced pressure and the residue was purified by flash-chromatography (20 g SiO₂, dichloromethane/MeOH 0-3% in 75 min) to give the title compound (65 mg, 31%) as colorless oil, MS (ESI) m/e=264.5 [M–H⁻].

g) (2S)-1-[6-(Cyclopropylmethoxy)-5-(1-fluorocyclobutyl)pyridine-2-carbonyl]-4,4-difluoropyrrolidine-2-carboxamide In analogy to the procedure described in Example 127 e), 6-(cyclopropylmethoxy)-5-(1-fluorocyclobutyl)pyridine-2-carboxylic acid (Example 130 f, 20 mg, 49.8 μmol) was reacted with (S)-4,4-difluoropyrrolidine-2-carboxamide hydrochloride (CAN 426844-51-1, 11.1 mg, 59.7 μmol) to give the title compound (18 mg, 91%) as off-white solid, MS (EI): m/e=398.4 [MH⁺].

Example 131

3-[6-(Cyclopropylmethoxy)-5-(1-hydroxycyclobutyl)pyridine-2-carbonyl]-1,1-dioxo-1,3-thiazolidine-4-carboxamide

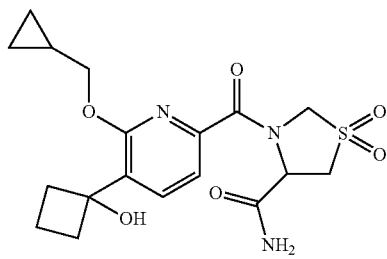

In analogy to the procedure described in Example 127 e), 6-(cyclopropylmethoxy)-5-(1-hydroxycyclobutyl)pyridine-2-carboxylic acid (CAN 1415899-53-4, 50 mg, 190 μmol) was reacted with 1,1-dioxo-1,3-thiazolidine-4-carboxamide hydrochloride (Example 127 d, 45.7 mg, 228 μmol) to give the title compound (7 mg, 8%) as colorless oil, MS (EI): m/e=410.5 [MH⁺].

Example 132

(2S)-1-[6-(Cyclopropylmethoxy)-5-(3,3-difluoroazetidin-1-yl)pyridine-2-carbonyl]-4-hydroxy-4-methylpyrrolidine-2-carboxamide

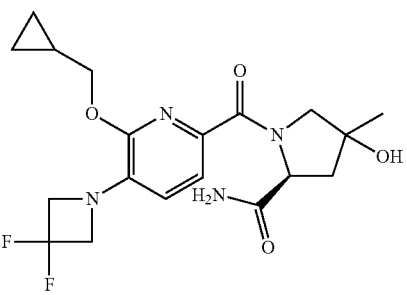 [SMILES: CC1(O)C[C@@H](C(N)=O)N(C(=O)c2ccc(N3CC(F)(F)C3)c(OCC3CC3)n2)C1]

a) (2S)-tert-Butyl 2-carbamoyl-4-hydroxy-4-methylpyrrolidine-1-carboxylate

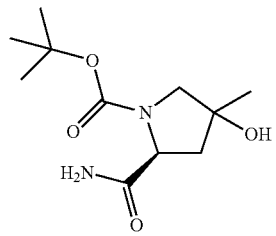 [SMILES: CC1(O)C[C@@H](C(N)=O)N(C(=O)OC(C)(C)C)C1]

A solution of (2S)-1-tert-butyl 2-methyl 4-hydroxy-4-methylpyrrolidine-1,2-dicarboxylate (CAN 1430105-48-8, 50 mg, 193 μmol) in a 7 M solution of NH₃ in methanol (551 μL, 3.86 mmol) was stirred at ambient temperature for 72 h. The solvent was removed in vacuo to obtain the title compound (48 mg, quant.) as colorless oil, MS (ESI) m/e=145.2 [MH-Boc⁺].

b) (2S)-4-Hydroxy-4-methylpyrrolidine-2-carboxamide hydrochloride

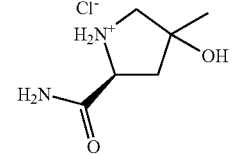

A solution of (2S)-tert-butyl 2-carbamoyl-4-hydroxy-4-methylpyrrolidine-1-carboxylate (Example 132 a, 46 mg, 188 μmol) in a solution of 4 M HCl in dioxane (942 μL, 3.8 mmol) was stirred at ambient temperature for 5 h. The solvent was removed in vacuo to give the title compound (36 mg, quant.) as light brown solid, MS (ESI) m/e=145.2 [MH⁺].

c) (2S)-1-[6-(Cyclopropylmethoxy)-5-(3,3-difluoro-azetidin-1-yl)pyridine-2-carbonyl]-4-hydroxy-4-methylpyrrolidine-2-carboxamide In analogy to the procedure described in Example 47 b), 6-cyclopropylmethoxy-5-(3,3-difluoro-azetidin-1-yl)-pyridine-2-carboxylic acid (Example 1 b, 20 mg, 70.4 μmol) was reacted with (2S)-4-hydroxy-4-methylpyrrolidine-2-carboxamide hydrochloride (Example 132 b, 15.3 mg, 84.4 μmol) to obtain the title compound (22 mg, 76%) as off-white solid; MS (EI): m/e=411.5 [MH⁺].

Example 133

3-[6-(Cyclopropylmethoxy)-5-(1-fluorocyclobutyl)pyridine-2-carbonyl]-1,1-dioxo-1,3-thiazolidine-4-carboxamide

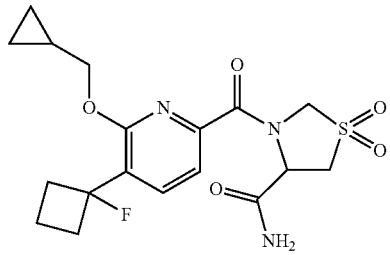 [SMILES: NC(=O)C1CS(=O)(=O)CN1C(=O)c1ccc(C2(F)CCC2)c(OCC2CC2)n1]

In analogy to the procedure described in Example 127 e), 6-(cyclopropylmethoxy)-5-(1-fluorocyclobutyl)pyridine-2-carboxylic acid (Example 130 f) was reacted with 1,1-dioxo-1,3-thiazolidine-4-carboxamide hydrochloride (Example 127 d) to give the title compound as yellow oil, MS (EI): m/e=412.13 [MH⁺].

Example 134

(2S)-1-[6-(Cyclopropylmethoxy)-5-(3-fluorooxetan-3-yl)pyridine-2-carbonyl]-4,4-difluoropyrrolidine-2-carboxamide

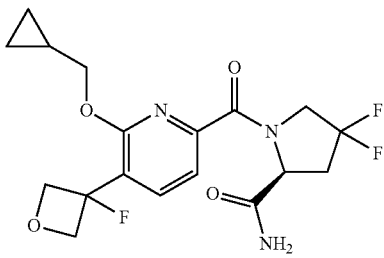 [SMILES: NC(=O)[C@@H]1CC(F)(F)CN1C(=O)c1ccc(C2(F)COC2)c(OCC2CC2)n1]

a) 3-(2-Chloro-6-methylpyridin-3-yl)oxetan-3-ol

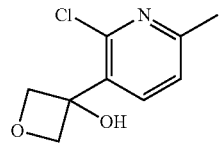

In analogy to the procedure described in Example 130 a), 3-bromo-2-chloro-6-methylpyridine (CAN 185017-72-5, 5 g, 24.2 mmol) was reacted with oxetan-3-one (CAN 6704-31-0, 1.75 g, 1.42 mL, 24.2 mmol) to give the title compound (3.42 g, 71%) as off-white solid, MS (ESI): m/e=200.5 [MH⁺].

b) 2-Chloro-3-(3-fluorooxetan-3-yl)-6-methylpyridine

In analogy to the procedure described in Example 130 b), 3-(2-chloro-6-methylpyridin-3-yl)oxetan-3-ol (Example 134 a, 1.5 g, 7.51 mmol) was reacted with diethylaminosulfur trifluoride to obtain the title compound (850 mg, 56%) as colorless liquid, MS (ESI): m/e=202.1 [MH⁺].

c) 2-Chloro-3-(3-fluorooxetan-3-yl)-6-methylpyridine 1-oxide

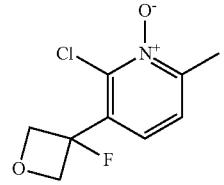

In analogy to the procedure described in Example 130 c), 2-chloro-3-(3-fluorooxetan-3-yl)-6-methylpyridine (Example 134 b, 850 mg, 4.22 mmol) was oxidized to give the title compound (875 mg, 95%) as light brown solid, MS (ESI): m/e=218.4 [MH⁺].

d) (6-Chloro-5-(3-fluorooxetan-3-yl)pyridin-2-yl)methanol

In analogy to the procedure described in Example 130 d), 2-chloro-3-(3-fluorooxetan-3-yl)-6-methylpyridine 1-oxide (Example 134 c, 870 mg, 4 mmol) was rearranged to give the title compound (154 mg, 18%) as colorless liquid, MS (ESI): m/e=218.4 [MH⁺].

e) 6-Chloro-5-(3-fluorooxetan-3-yl)pyridine-2-carboxylic acid

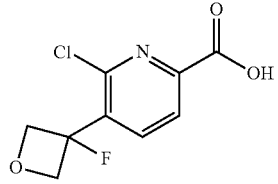 [SMILES: O=C(O)c1ccc(C2(F)COC2)c(Cl)n1]

In analogy to the procedure described in Example 130 e), (6-chloro-5-(3-fluorooxetan-3-yl)pyridin-2-yl)methanol (Example 134 d, 154 mg, 708 μmol) was oxidized to obtain the title compound (66 mg, 40%) as off-white solid, MS(ESI): m/e=232.1 [MH⁺].

f) 6-(Cyclopropylmethoxy)-5-(3-fluorooxetan-3-yl)pyridine-2-carboxylic acid

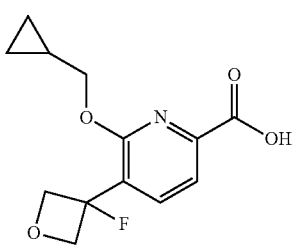 [SMILES: O=C(O)c1ccc(C2(F)COC2)c(OCC2CC2)n1]

6-Chloro-5-(3-fluorooxetan-3-yl)pyridine-2-carboxylic acid (Example 134 e, 44 mg, 190 μmol) and cyclopropylmethanol (CAN 2516-33-8, 17.8 mg, 20.0 μL, 247 μmol) were dissolved in DMF (1.32 mL). A solution of sodium 2-methylpropan-2-olate (42.0 mg, 437 μmol) in THF (800 μL) was added and the mixture was heated to 50° C. for 3 h and for additional 3 h to 70° C. After cooling to ambient temperature, the reaction mixture was poured onto ice/0.1 N HCl (25 mL) and extracted with EtOAc (2×25 mL). The combined extracts were washed with ice/brine (20 mL), dried over $Na_2SO_4$, filtered and evaporated to dryness. The residue was purified by thin layer chromatography (2 mm $SiO_2$, dichloromethane/MeOH 19:1, elution with EtOAc) to give the title compound (11 mg, 22 mg) as colorless oil, MS (ESI) m/e=268.2 [MH$^+$].

g) (2S)-1-[6-(Cyclopropylmethoxy)-5-(3-fluorooxetan-3-yl)pyridine-2-carbonyl]-4,4-difluoropyrrolidine-2-carboxamide In analogy to the procedure described in Example 127 e), 6-(cyclopropylmethoxy)-5-(3-fluorooxetan-3-yl)pyridine-2-carboxylic acid (Example 134 f, 25 mg, 93.5 μmol) was reacted with (S)-4,4-difluoropyrrolidine-2-carboxamide hydrochloride (CAN 426844-51-1, 20.9 mg, 112 μmol) to give the title compound (20 mg, 54%) as colorless oil, MS (EI): m/e=400.2 [MH$^+$].

Example 135

5-[6-(Cyclopropylmethoxy)-5-(3,3-difluoroazetidin-1-yl)pyridine-2-carbonyl]-5-azaspiro[2.4]heptane-6-carboxamide

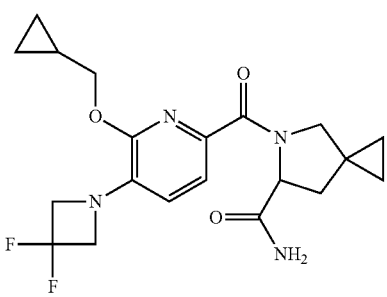 [SMILES: NC(=O)C1CC2(CC2)CN1C(=O)c1ccc(N2CC(F)(F)C2)c(OCC2CC2)n1]

a) tert-Butyl 6-carbamoyl-5-azaspiro[2.4]heptane-5-carboxylate

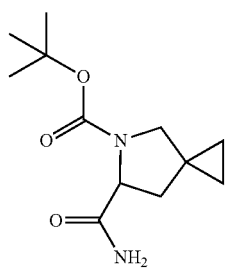 [SMILES: CC(C)(C)OC(=O)N1CC2(CC2)CC1C(N)=O]

In analogy to the procedure described in Example 127 c), 5-(tert-butoxycarbonyl)-5-azaspiro[2.4]heptane-6-carboxylic acid (CAN 1454843-77-6, 112 mg, 464 μmol) was condensed with ammonia to give the title compound (87 mg, 78%) as colorless liquid, MS (EI): m/e=240.0 [M$^+$].

b) 5-Azaspiro[2.4]heptane-6-carboxamide hydrochloride

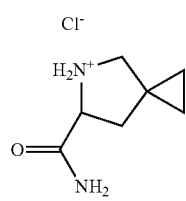

In analogy to the procedure described in Example 132 b), tert-butyl 6-carbamoyl-5-azaspiro[2.4]heptane-5-carboxylate (Example 135 a, 65 mg, 270 μmol) was deprotected to give the title compound (55 mg, quant.) as light yellow solid, LC-MS (UV peak area/ESI) 100%, 141.1023 [MH$^+$].

c) 5-[6-(Cyclopropylmethoxy)-5-(3,3-difluoroazetidin-1-yl)pyridine-2-carbonyl]-5-azaspiro[2.4]heptane-6-carboxamide In analogy to the procedure described in Example 127 e), 6-cyclopropylmethoxy-5-(3,3-difluoro-azetidin-1-yl)-pyridine-2-carboxylic acid (Example 1 b, 18.6 mg, 106 μmol) was reacted with 5-azaspiro[2.4]heptane-6-carboxamide hydrochloride (Example 135 b, 18.6 mg, 106 μmol) to obtain the title compound (16 mg, 56%) as colorless liquid, MS (EI): m/e=407.3 [MH$^+$].

Example 136

[6-(Cyclopropylmethoxy)-5-(3,3-difluoroazetidin-1-yl)pyridin-2-yl]-[3-(2,2,2-trifluoro-1-hydroxyethyl)pyrrolidin-1-yl]methanone

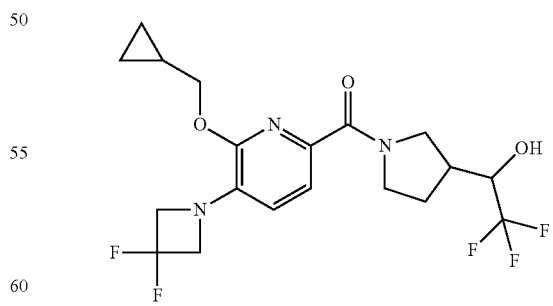

In analogy to the procedure described in Example 127 e), 6-cyclopropylmethoxy-5-(3,3-difluoro-azetidin-1-yl)-pyridine-2-carboxylic acid (Example 1 b, 20 mg, 70.4 μmol) was reacted with 2,2,2-trifluoro-1-(pyrrolidin-3-yl)ethanol hydrochloride (CAN of corresponding free base: 943906-23-

Example 137

[6-(Cyclopropylmethoxy)-5-(3,3-difluoroazetidin-1-yl)pyridin-2-yl]-[3-(hydroxymethyl)-3-(trifluoromethyl)pyrrolidin-1-yl]methanone

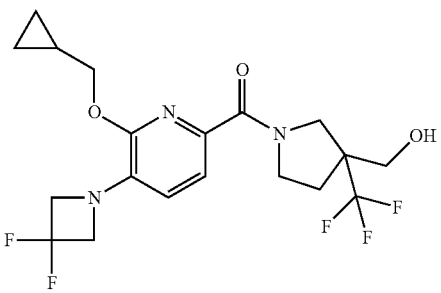 [SMILES: O=C(c1ccc(N2CC(F)(F)C2)c(OCC2CC2)n1)N1CCC(CO)(C(F)(F)F)C1]

In analogy to the procedure described in Example 127 e), 6-cyclopropylmethoxy-5-(3,3-difluoro-azetidin-1-yl)-pyridine-2-carboxylic acid (Example 1 b, 20 mg, 70.4 µmol) was reacted with (3-(trifluoromethyl)pyrrolidin-3-yl)methanol hydrochloride (CAN 1260812-78-9, 17.4 mg, 84.4 µmol) to obtain the title compound (11 mg, 36%) as colorless liquid, MS (EI): m/e=436.4 [MH⁺].

Example 138

[6-(Cyclopropylmethoxy)-5-(3,3-difluoroazetidin-1-yl)pyridin-2-yl]-[3-hydroxy-3-(trifluoromethyl)pyrrolidin-1-yl]methanone

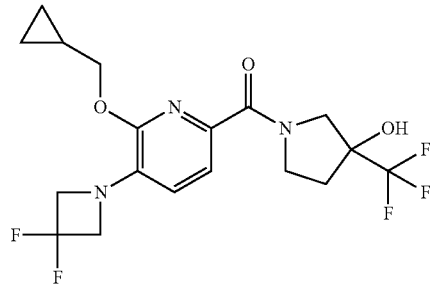 [SMILES: O=C(c1ccc(N2CC(F)(F)C2)c(OCC2CC2)n1)N1CCC(O)(C(F)(F)F)C1]

In analogy to the procedure described in Example 127 e), 6-cyclopropylmethoxy-5-(3,3-difluoro-azetidin-1-yl)-pyridine-2-carboxylic acid (Example 1 b, 40 mg, 141 µmol) was reacted with 3-(trifluoromethyl)pyrrolidin-3-ol hydrochloride (CAN 1334147-81-7, 32.4 mg, 169 µmol) to obtain the title compound (28 mg, 47%) as off-white solid, MS (EI): m/e=422.3 [MH⁺].

Example 139

[6-(Cyclopropylmethoxy)-5-(3,3-difluoroazetidin-1-yl)pyridin-2-yl]-[3-hydroxy-3-(trifluoromethyl)azetidin-1-yl]methanone

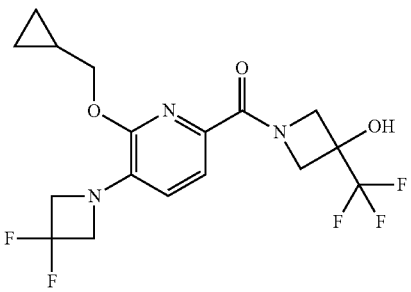 [SMILES: O=C(c1ccc(N2CC(F)(F)C2)c(OCC2CC2)n1)N1CC(O)(C(F)(F)F)C1]

In analogy to the procedure described in Example 127 e), 6-cyclopropylmethoxy-5-(3,3-difluoro-azetidin-1-yl)-pyridine-2-carboxylic acid (Example 1 b, 40 mg, 141 µmol) was reacted with 3-(trifluoromethyl)azetidin-3-ol hydrochloride (CAN 848192-96-1, 30.0 mg, 169 µmol) to obtain the title compound (32 mg, 56%) as off-white solid, MS (EI): m/e=408.3 [MH⁺].

Example 140

(+)-(2S)-1-[6-(Cyclopropylmethoxy)-5-(3,3-difluoroazetidin-1-yl)pyridine-2-carbonyl]-4-hydroxy-4-methylpyrrolidine-2-carboxamide

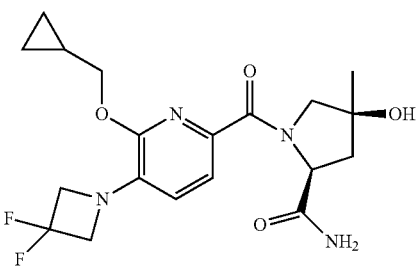 [SMILES: C[C@]1(O)C[C@@H](C(N)=O)N(C(=O)c2ccc(N3CC(F)(F)C3)c(OCC3CC3)n2)C1]

In analogy to the procedure described in Example 127 e), 6-cyclopropylmethoxy-5-(3,3-difluoro-azetidin-1-yl)-pyridine-2-carboxylic acid (Example 1 b, 50 mg, 176 µmol) was reacted with (2S)-4-hydroxy-4-methylpyrrolidine-2-carboxamide hydrochloride (Example 132 b, 39.7 mg, 176 µmol) and purified by chiral HPLC to obtain the title compound (8 mg, 10%) as white solid, LC-MS (UV peak area, ESI) 93%, 411.1854 [MH⁺].

Example 141

[5-Cyclopropyl-6-(cyclopropylmethoxy)pyridin-2-yl]-[3-(2,2,2-trifluoro-1-hydroxyethyl)pyrrolidin-1-yl]methanone

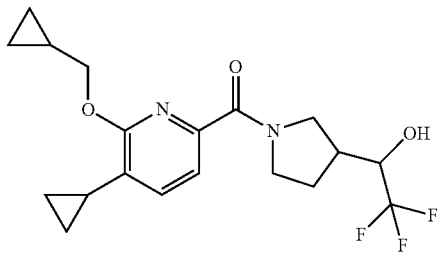 [SMILES: O=C(c1ccc(C2CC2)c(OCC2CC2)n1)N1CCC(C(O)C(F)(F)F)C1]

In analogy to the procedure described in Example 127 e), 5-cyclopropyl-6-cyclopropylmethoxy-pyridine-2-carboxylic acid (Example 3 c, 20 mg, 85.7 µmol) was reacted with 2,2,2-trifluoro-1-(pyrrolidin-3-yl)ethanol hydrochloride (CAN of corresponding free base: 943906-23-8, 21.2 mg, 103 µmol) to obtain the title compound (16 mg, 49%) as colorless liquid, MS (EI): m/e=385.3 [MH+].

Example 142

[5-Cyclopropyl-6-(cyclopropylmethoxy)pyridin-2-yl]-[3-(hydroxymethyl)-3-(trifluoromethyl)pyrrolidin-1-yl]methanone

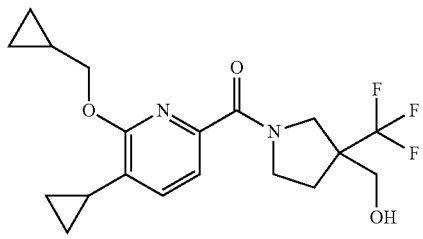 [SMILES: O=C(c1ccc(C2CC2)c(OCC2CC2)n1)N1CCC(CO)(C(F)(F)F)C1]

In analogy to the procedure described in Example 127 e), 5-cyclopropyl-6-cyclopropylmethoxy-pyridine-2-carboxylic acid (Example 3 c, 20 mg, 85.7 µmol) was reacted with (3-(trifluoromethyl)pyrrolidin-3-yl)methanol hydrochloride (CAN 1260812-78-9, 21.2 mg, 103 µmol) to obtain the title compound (12 mg, 36%) as colorless liquid, MS (EI): m/e=385.3 [MH+].

Example 143

[5-Cyclopropyl-6-(cyclopropylmethoxy)pyridin-2-yl]-[3-hydroxy-3-(trifluoromethyl)pyrrolidin-1-yl]methanone

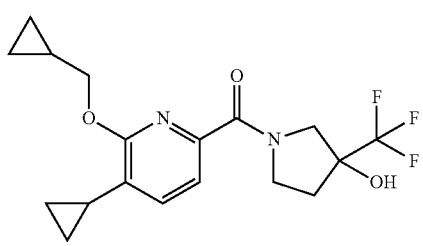 [SMILES: O=C(c1ccc(C2CC2)c(OCC2CC2)n1)N1CCC(O)(C(F)(F)F)C1]

In analogy to the procedure described in Example 127 e), 5-cyclopropyl-6-cyclopropylmethoxy-pyridine-2-carboxylic acid (Example 3 c, 20 mg, 85.7 µmol) was reacted with 3-(trifluoromethyl)pyrrolidin-3-ol hydrochloride (CAN 1334147-81-7, 19.7 mg, 103 µmol) to obtain the title compound (15 mg, 47%) as colorless liquid, MS (EI): m/e=371.3 [MH+].

Example 144

[5-Cyclopropyl-6-(cyclopropylmethoxy)pyridin-2-yl]-[3-hydroxy-3-(trifluoromethyl)azetidin-1-yl]methanone

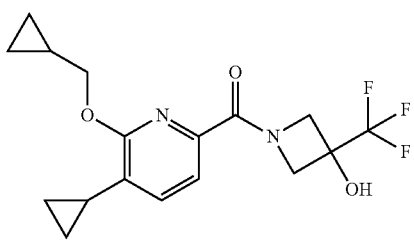 [SMILES: O=C(c1ccc(C2CC2)c(OCC2CC2)n1)N1CC(O)(C(F)(F)F)C1]

In analogy to the procedure described in Example 127 e), 5-cyclopropyl-6-cyclopropylmethoxy-pyridine-2-carboxylic acid (Example 3 c, 20 mg, 85.7 µmol) was reacted with 3-(trifluoromethyl)azetidin-3-ol hydrochloride (CAN 848192-96-1, 18.3 mg, 103 µmol) to obtain the title compound (7 mg, 23%) as colorless oil, MS (EI): m/e=357.3 [MH+].

Example 145

(6S)-5-[6-(Cyclopropylmethoxy)-5-(3,3-difluoroazetidin-1-yl)pyridine-2-carbonyl]-5-azaspiro[2.4]heptane-6-carboxamide

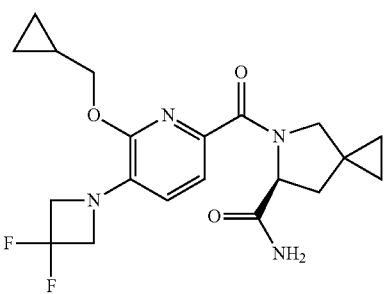 [SMILES: NC(=O)[C@@H]1CC2(CC2)CN1C(=O)c1ccc(N2CC(F)(F)C2)c(OCC2CC2)n1]

In analogy to the procedure described in Example 127 e), 6-cyclopropylmethoxy-5-(3,3-difluoro-azetidin-1-yl)-pyridine-2-carboxylic acid (Example 1 b, 50 mg, 176 µmol) was reacted with 5-azaspiro[2.4]heptane-6-carboxamide hydrochloride (Example 135 b, 37.3 mg, 211 µmol) and purified by

Example 146

[(3aR,6aS)-1,3,3a,4,6,6a-Hexahydrofuro[3,4-c]pyrrol-5-yl]-[6-(cyclopropylmethoxy)-5-(3,3-difluoro-azetidin-1-yl)pyridin-2-yl]methanone

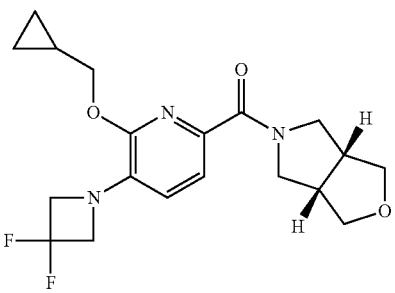 [SMILES: O=C(c1ccc(N2CC(F)(F)C2)c(OCC2CC2)n1)N1C[C@H]2COC[C@H]2C1]

In analogy to the procedure described in Example 127 e), 6-cyclopropylmethoxy-5-(3,3-difluoro-azetidin-1-yl)-pyridine-2-carboxylic acid (Example 1 b, 30 mg, 106 µmol) was reacted with (3aR,6aS)-hexahydro-1H-furo[3,4-c]pyrrole hydrochloride (CAN 57710-36-8, 15.8 mg, 106 µmol) to obtain the title compound (22 mg, 55%) as white solid, MS (EI): m/e=380.3 [MH$^+$].

Example 147

(2S)-1-[5-(3,3-Difluoroazetidin-1-yl)-6-(2-fluoroethoxyl)pyridine-2-carbonyl]-4,4-difluoro-pyrrolidine-2-carboxamide

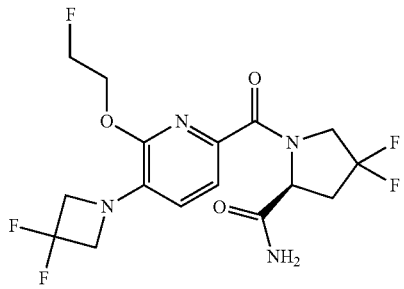 [SMILES: NC(=O)[C@@H]1CC(F)(F)CN1C(=O)c1ccc(N2CC(F)(F)C2)c(OCCF)n1]

a) Methyl 5-bromo-6-(2-fluoroethoxyl)pyridine-2-carboxylate

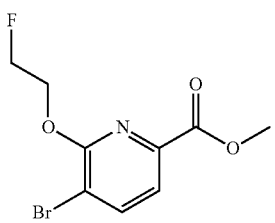

Lithium 2-methylpropan-2-olate (4.17 mL, 9.18 mmol) was added within 30 minutes at ambient temperature to a solution of methyl 5-bromo-6-chloro-pyridine-2-carboxylate (CAN 1214353-79-3, 1 g, 3.99 mmol) and 2-fluoroethanol (CAN 371-62-0, 332 mg, 300 µL, 5.19 mmol) in DMF (6.67 mL). The reaction mixture was heated to 70° C. and stirred for 6 h. After cooling to ambient temperature, water (5 mL) and 2N HCl (5 mL) were added. The mixture was poured onto ice/brine (50 mL) and extracted with EtOAc (2×50 mL). The combined extracts were washed with ice/brine (50 mL), dried over Na$_2$SO$_4$, filtered and evaporated to dryness. The crude product was purified by flash-chromatography (50 g SiO$_2$, heptane/0-30% EtOAc in 120 min.) to give the title compound (132 mg, 12%) as light brown solid, MS (ESI) m/e=278.0 [MH$^+$].

b) Methyl 5-(3,3-difluoroazetidin-1-yl)-6-(2-fluoroethoxyl)pyridine-2-carboxylate

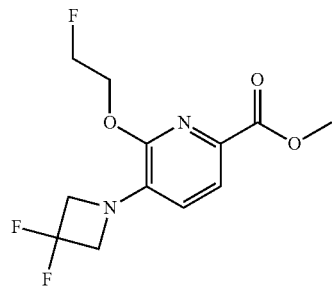 [SMILES: COC(=O)c1ccc(N2CC(F)(F)C2)c(OCCF)n1]

In analogy to the procedure described in Example 1 a), methyl 5-bromo-6-(2-fluoroethoxyl)pyridine-2-carboxylate (Example 147 a, 130 mg, 467 µmol) was reacted with 3,3-difluoroazetidine hydrochloride (CAN 288315-03-7, 66.6 mg, 514 µmol) in the presence of palladium (II) acetate, 2,2'-bis(diphenylphosphino)-1,1'-binaphthyl and cesium carbonate to give the title compound (73 mg, 54%) as light yellow solid, MS (ESI) m/e=291.1 [MH$^+$].

c) 5-(3,3-Difluoroazetidin-1-yl)-6-(2-fluoroethoxyl)pyridine-2-carboxylic acid

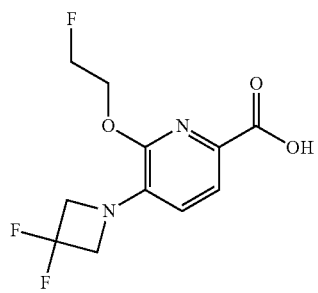 [SMILES: O=C(O)c1ccc(N2CC(F)(F)C2)c(OCCF)n1]

A solution of methyl 5-(3,3-difluoroazetidin-1-yl)-6-(2-fluoroethoxyl)pyridine-2-carboxylate (Example 147 b, 73 mg, 252 µmol) and lithium hydroxide hydrate (12.7 mg, 302 µmol) in tetrahydrofuran (500 µL) and water (50.0 µL) was stirred for 12 h at ambient temperature. The reaction mixture was poured onto ice/0.1 N HCl (25 mL) and extracted with EtOAc (2×25 mL). The combined extracts were washed with ice/brine (25 mL), dried over Na$_2$SO$_4$, filtered and evaporated d) (2S)-1-[5-(3,3-Difluoroazetidin-1-yl)-6-(2-fluoro-ethoxy)pyridine-2-carbonyl]-4,4-difluoro-pyrrolidine-2-carboxamide In analogy to the procedure described in Example 127 e), 5-(3,3-difluoroazetidin-1-yl)-6-(2-fluoroethoxyl)pyridine-2-carboxylic acid (Example 147 c, 25 mg, 90.5 μmol) was reacted with (S)-4,4-difluoropyrrolidine-2-carboxamide hydrochloride (CAN 426844-51-1, 20.3 mg, 109 μmol) to obtain the title compound (16 mg, 43%) as off-white solid, MS (ESI): m/e=409.1304 [MH$^+$].

Example 148

[6-(Cyclopropylmethoxy)-5-(3,3-difluoroazetidin-1-yl)-2-pyridyl]-[3-fluoro-3-(hydroxymethyl)azetidin-1-yl]methanone

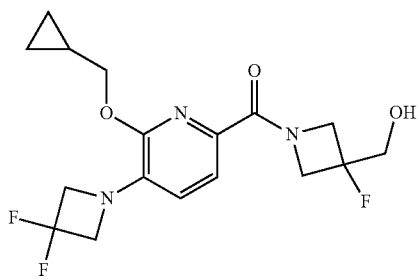 [SMILES: O=C(c1ccc(N2CC(F)(F)C2)c(OCC2CC2)n1)N1CC(F)(CO)C1]

In analogy to the procedure described in Example 127 e), 6-cyclopropylmethoxy-5-(3,3-difluoro-azetidin-1-yl)-pyridine-2-carboxylic acid (Example 1 b, 20 mg, 70.4 μmol) was reacted with (3-fluoroazetidin-3-yl)methanol (CAN 1268520-93-9, 8.87 mg, 84.4 μmol) to obtain the title compound (11 mg, 42%) as colorless liquid, MS (ESI): m/e=372.2 [MH$^+$].

Example 149

[6-(Cyclopropylmethoxy)-5-(3,3-difluoroazetidin-1-yl)-2-pyridyl]-(3-fluoro-3-methyl-azetidin-1-yl)methanone

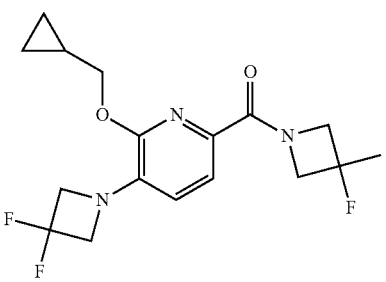 [SMILES: CC1(F)CN(C(=O)c2ccc(N3CC(F)(F)C3)c(OCC3CC3)n2)C1]

In analogy to the procedure described in Example 127 e), 6-cyclopropylmethoxy-5-(3,3-difluoro-azetidin-1-yl)-pyridine-2-carboxylic acid (Example 1 b, 20 mg, 70.4 μmol) was reacted with 3-fluoro-3-methylazetidine hydrochloride (CAN 1427379-42-7, 10.6 mg, 84.4 μmol) to obtain the title compound (6 mg, 24%) as off-white solid, MS (ESI): m/e=356.2 [MH$^+$].

Example 150

(3-Cyclopropyl-3-fluoroazetidin-1-yl)-[6-(cyclopropylmethoxy)-5-(3,3-difluoroazetidin-1-yl)pyridin-2-yl]methanone

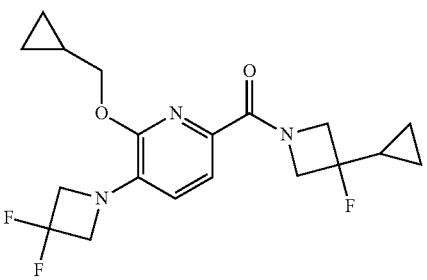 [SMILES: O=C(c1ccc(N2CC(F)(F)C2)c(OCC2CC2)n1)N1CC(F)(C2CC2)C1]

In analogy to the procedure described in Example 127 e), 6-cyclopropylmethoxy-5-(3,3-difluoro-azetidin-1-yl)-pyridine-2-carboxylic acid (Example 1 b, 20 mg, 70.4 μmol) was reacted with 3-cyclopropyl-3-fluoroazetidine hydrochloride (CAN 936548-77-5, 12.8 mg, 84.4 μmol) to obtain the title compound (8 mg, 30%) as colorless liquid, MS (ESI): m/e=382.3 [MH$^+$].

Example 151

(−)-5-[6-(Cyclopropylmethoxy)-5-(3,3-difluoroazetidin-1-yl)pyridine-2-carbonyl]-5-azaspiro[2.4]heptane-4-carboxamide

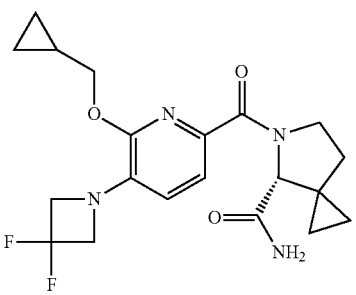 [SMILES: NC(=O)[C@@H]1N(C(=O)c2ccc(N3CC(F)(F)C3)c(OCC3CC3)n2)CCC12CC2]

a) tert-Butyl 4-formyl-5-azaspiro[2.4]heptane-5-carboxylate and tert-butyl 4-ethyl-2-formyl-4-methyl-pyrrolidine-1-carboxylate

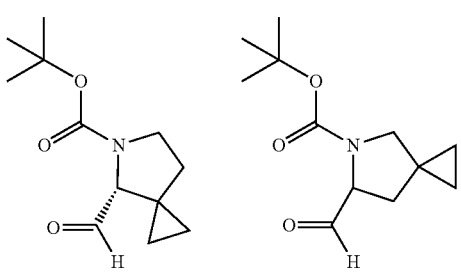 [SMILES: CC(C)(C)OC(=O)N1CCC2(CC2)[C@@H]1C=O ; CC(C)(C)OC(=O)N1CC2(CC2)CC1C=O]

A solution of s-butyllithium in cyclohexane (1.13 mL, 1.58 mmol) was added at −30° C. within 5 min. to a solution of tert-butyl 5-azaspiro[2.4]heptane-5-carboxylate (CAN 1026796-26-8, 240 mg, 1.22 mmol) in THF (9.6 mL). After stirring for 5 min. DMF (177 mg, 188 μL, 2.43 mmol) was added and stirring at −30° C. was continued for 10 min. The mixture was allowed to warm to ambient temperature and stirring was continued for 15 min. The reaction mixture was poured onto ice/saturated NH₄Cl-solution (25 mL) and extracted with EtOAc (2×25 mL). The combined extracts were washed with ice/brine (25 mL), dried over Na₂SO₄, filtered and evaporated to dryness. The crude product was purified by prep. TLC (2 mm SiO₂.heptan/EtOAc 4:1, elution with EtOAc) to give the title compounds (145 mg, 53%) as colorless liquid, MS (ESI) m/e=126.1 [MH-Boc⁺].

b) 5-tert-Butoxycarbonyl-5-azaspiro[2.4]heptane-4-carboxylic acid and 1-tert-butoxycarbonyl-4-ethyl-4-methyl-pyrrolidine-2-carboxylic acid

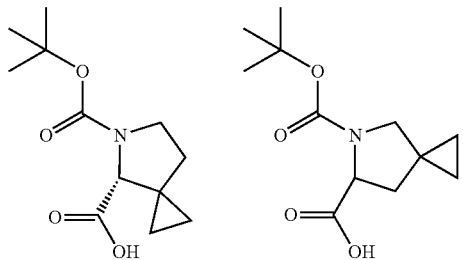 [SMILES: CC(C)(C)OC(=O)N1CCC2(CC2)[C@@H]1C(=O)O ; CC(C)(C)OC(=O)N1CC2(CC2)CC1C(=O)O]

A mixture of tert-butyl 4-formyl-5-azaspiro[2.4]heptane-5-carboxylate and tert-butyl 4-ethyl-2-formyl-4-methyl-pyrrolidine-1-carboxylate (Example 151 a, 142 mg, 630 μmol) was dissolved in t-BuOH (3.69 mL) and 2-methyl-2-butene (1.99 mL). A solution of sodium chlorite (114 mg, 1.26 mmol) and sodium dihydrogen phosphate dihydrate (151 mg, 1.26 mmol) in water (568 μL) was added. The mixture was stirred at ambient temperature for 90 minutes and concentrated in vacuo. The residue was dissolved in water (10 mL). The pH was adjusted to 3-4 by dropwise addition of 2 N HCl. The mixture was extracted with EtOAc (2×25 mL) and the combined extracts were washed with ice/brine (25 mL), dried over Na₂SO₄ and evaporated to dryness. The crude product was poured onto ice/brine/1 M NaOH (20 mL) and extracted with tBuOMe (2×25 mL). The aqueous layer was acidified with icewater/1M HCl (20 mL) and extracted with EtOAc (2×25 mL). The combined extracts were washed with ice/brine (25 mL) dried over Na₂SO₄, filtered and evaporated to dryness to obtain the title compounds (155 mg, quant.) as colorless oil.

c) tert-Butyl 4-carbamoyl-5-azaspiro[2.4]heptane-5-carboxylate and tert-butyl 2-carbamoyl-4-ethyl-4-methyl-pyrrolidine-1-carboxylate

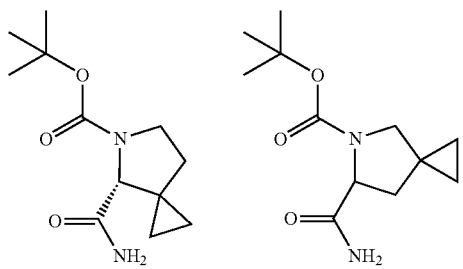 [SMILES: CC(C)(C)OC(=O)N1CCC2(CC2)[C@@H]1C(N)=O ; CC(C)(C)OC(=O)N1CC2(CC2)CC1C(N)=O]

In analogy to the procedure described in Example 127 c), a mixture of 5-tert-butoxycarbonyl-5-azaspiro[2.4]heptane-4-carboxylic acid and 1-tert-butoxycarbonyl-4-ethyl-4-methyl-pyrrolidine-2-carboxylic acid (Example 151 b, 152 mg, 630 μmol) was condensed with ammonia to give the title compounds (118 mg, 78%) as off-white amorphous, MS (EI): m/e=141.1 [MH-Boc⁺].

d) 5-Azaspiro[2.4]heptane-4-carboxamide hydrochloride and 5-azaspiro[2.4]heptane-6-carboxamide hydrochloride

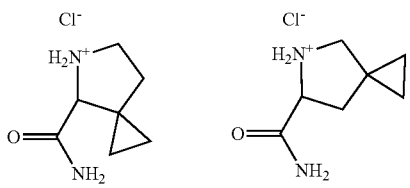 [SMILES: [Cl-] ; [Cl-] ; NC(=O)C1[NH2+]CCC12CC2 ; NC(=O)C1CC2(CC2)C[NH2+]1]

A mixture of tert-butyl 4-carbamoyl-5-azaspiro[2.4]heptane-5-carboxylate and tert-butyl 2-carbamoyl-4-ethyl-4-methyl-pyrrolidine-1-carboxylate (Example 151 c, 115 mg, 479 μmol) was dissolved in a 4 M solution of HCl in dioxane (2.39 mL, 9.55 mmol) and stirred for 4 h at ambient temperature. Removal of the solvent in vacuo gave the title compounds (115 mg, quant.) as light yellow oil.

e) (−)-5-[6-(Cyclopropylmethoxy)-5-(3,3-difluoro-azetidin-1-yl)pyridine-2-carbonyl]-5-azaspiro[2.4]heptane-4-carboxamide In analogy to the procedure described in Example 127 e), 6-cyclopropylmethoxy-5-(3,3-difluoro-azetidin-1-yl)-pyridine-2-carboxylic acid (Example 1 b, 80 mg, 281 μmol) was reacted with a mixture of 5-azaspiro[2.4]heptane-4-carboxamide hydrochloride and 5-azaspiro[2.4]heptane-6-carboxamide hydrochloride (Example 151 d, 59.7 mg, 338 μmol) to obtain the title compound after preparative chiral HPLC (10 mg, 9%) as off-white solid, MS (ESI): m/e=407.3 [MH⁺].

Example 152

(+)-5-[6-(Cyclopropylmethoxy)-5-(3,3-difluoroazetidin-1-yl)pyridine-2-carbonyl]-5-azaspiro[2.4]heptane-4-carboxamide

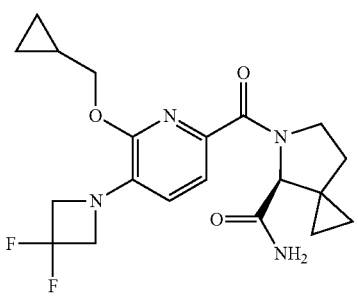 [SMILES: NC(=O)[C@H]1N(C(=O)c2ccc(N3CC(F)(F)C3)c(OCC3CC3)n2)CCC12CC2]

In analogy to the procedure described in Example 127 e), 6-cyclopropylmethoxy-5-(3,3-difluoro-azetidin-1-yl)-pyridine-2-carboxylic acid (Example 1 b, 80 mg, 281 μmol) was reacted with a mixture of 5-azaspiro[2.4]heptane-4-carboxamide hydrochloride and 5-azaspiro[2.4]heptane-6-carboxamide hydrochloride (Example 151 d, 59.7 mg, 338 μmol) to obtain the title compound after preparative chiral HPLC (22 mg, 19%) as off-white solid, MS (ESI): m/e=407.3 [MH+].

Example 153

Pharmacological Tests

The following tests were carried out in order to determine the activity of the compounds of formula (I).
Radioligand Binding Assay The affinity of the compounds of the invention for cannabinoid CB1 receptors was determined using recommended amounts of membrane preparations (PerkinElmer) of human embryonic kidney (HEK) cells expressing the human CNR1 or CNR2 receptors in conjunction with 1.5 or 2.6 nM [3H]-CP-55,940 (Perkin Elmer) as radioligand, respectively. Binding was performed in binding buffer (50 mM Tris, 5 mM MgCl2, 2.5 mM EDTA, and 0.5% (wt/vol) fatty acid free BSA, pH 7.4 for CB1 receptor and 50 mM Tris, 5 mM $MgCl_2$, 2.5 mM EGTA, and 0.1% (wt/vol) fatty acid free BSA, pH 7.4 for CB2 receptor) in a total volume of 0.2 ml for 1 h at 30° C. shaking. The reaction was terminated by rapid filtration through microfiltration plates coated with 0.5% polyethylenimine (UniFilter GF/B filter plate; Packard). Bound radioactivity was analyzed for Ki using nonlinear regression analysis (Activity Base, ID Business Solution, Limited), with the Kd values for [3H]CP55,940 determined from saturation experiments. The compounds of formula (I) show an excellent affinity for the CB2 receptor with affinities below 10 μM, more particularly of 1 nM to 3 μM and most particularly of 1 nM to 100 nM.
cAMP Assay CHO cells expressing human CB1 or CB2 receptors are seeded 17-24 hours prior to the experiment 50.000 cells per well in a black 96 well plate with flat clear bottom (Corning Costar #3904) in DMEM (Invitrogen No. 31331), 1×HT supplement, with 10% fetal calf serum and incubated at 5% $CO_2$ and 37° C. in a humidified incubator. The growth medium was exchanged with Krebs Ringer Bicarbonate buffer with 1 mM IBMX and incubated at 30° C. for 30 min. Compounds were added to a final assay volume of 100 μl and incubated for 30 min at 30° C. Using the cAMP-Nano-TRF detection kit the assay (Roche Diagnostics) was stopped by the addition of 50 μl lysis reagent (Tris, NaCl, 1.5% Triton X100, 2.5% NP40, 10% $NaN_3$) and 50 μl detection solutions (20 μM mAb Alexa700-cAMP 1:1, and 48 μM Ruthenium-2-AHA-cAMP) and shaken for 2 h at room temperature. The time-resolved energy transfer is measured by a TRF reader (Evotec Technologies GmbH), equipped with a ND:YAG laser as excitation source. The plate is measured twice with the excitation at 355 nm and at the emission with a delay of 100 ns and a gate of 100 ns, total exposure time 10 s at 730 (bandwidth 30 nm) or 645 nm (bandwidth 75 nm), respectively. The FRET signal is calculated as follows: FRET=T730-Alexa730-P(T645-B645) with P=Ru730-B730/Ru645-B645, where T730 is the test well measured at 730 nM, T645 is the test well measured at 645 nm, B730 and B645 are the buffer controls at 730 nm and 645 nm, respectively. cAMP content is determined from the function of a standard curve spanning from 10 μM to 0.13 nM cAMP.

$EC_{50}$ values were determined using Activity Base analysis (ID Business Solution, Limited). The $EC_{50}$ values for a wide range of cannabinoid agonists generated from this assay were in agreement with the values published in the scientific literature.

The compounds of the invention are CB2 agonists with $EC_{50}$ below 0.5 μM and selectivity versus CB1 in the corresponding assay of at least 10 fold. Particular compound of the invention are CB2 agonists with $EC_{50}$ below 0.05 μM and selectivity versus CB1 in the corresponding assay of at least 100 fold.

For example, the following compounds showed the following human $EC_{50}$ values in the functional cAMP assay described above:

| Example | human CB2 EC50 [μM] | human CB1 EC50 [μM] |
|---|---|---|
| 1 | 0.0046 | >10 |
| 2 | 0.2969 | >10 |
| 3 | 0.0072 | >10 |
| 4 | 0.0085 | >10 |
| 5 | 0.0008 | 0.2681 |
| 6 | 0.1056 | >10 |
| 7 | 0.0006 | 0.2923 |
| 8 | 0.0126 | >10 |
| 9 | 0.0038 | >10 |
| 10 | 0.6615 | >10 |
| 11 | 0.3643 | >10 |
| 12 | 0.1335 | >10 |
| 13 | 0.1188 | >10 |
| 14 | 0.0073 | >10 |
| 15 | 0.2488 | >10 |
| 16 | 0.008 | >10 |
| 17 | 0.0052 | >10 |
| 18 | 0.0006 | >10 |
| 19 | 0.8556 | >10 |
| 20 | 0.0053 | >10 |
| 21 | 0.0028 | >10 |
| 22 | 0.025 | >10 |
| 23 | 0.0058 | >10 |
| 24 | 0.3397 | >10 |
| 25 | 0.037 | >10 |
| 26 | 0.3055 | >10 |
| 27 | 0.7736 | >10 |
| 28 | 0.4143 | >10 |
| 29 | 0.4138 | >10 |
| 30 | 0.0345 | >10 |
| 31 | 0.0821 | >10 |
| 32 | 0.2559 | >10 |
| 33 | 0.0554 | >10 |
| 34 | 0.0911 | >10 |
| 35 | 0.1834 | >10 |
| 36 | 0.2257 | >10 |
| 37 | 0.3644 | >10 |
| 38 | 0.2124 | >10 |
| 39 | 0.1422 | >10 |
| 40 | 0.0818 | >10 |
| 41 | 0.9659 | >10 |
| 42 | 0.009 | >10 |
| 43 | 0.0349 | >10 |
| 44 | 0.0031 | 0.408 |
| 45 | 0.0068 | >10 |
| 46 | 0.3596 | >10 |
| 47 | 0.1131 | >10 |
| 48 | 0.108 | >10 |
| 49 | 0.1386 | >10 |
| 50 | 0.2374 | >10 |
| 51 | 0.7888 | >10 |
| 52 | 0.6454 | >10 |
| 53 | 0.0037 | >10 |
| 54 | 0.4621 | >10 |
| 55 | 0.0554 | >10 |
| 56 | 0.0369 | >10 |
| 57 | 0.0018 | >10 |
| 58 | 0.5937 | >10 |
| 59 | 0.0142 | >10 |
| 60 | 0.003075 | >10 |
| 61 | 0.3912 | >10 |

| Example | human CB2 EC50 [μM] | human CB1 EC50 [μM] |
|---|---|---|
| 62 | 0.0091 | >10 |
| 63 | 0.198 | >10 |
| 64 | 0.0405 | >10 |
| 65 | 0.1001 | >10 |
| 66 | 0.0056 | >10 |
| 67 | 0.3676 | >10 |
| 68 | 0.0027 | >10 |
| 69 | 1.0416 | >10 |
| 70 | 0.1037 | >10 |
| 71 | 0.4435 | >10 |
| 72 | 0.664 | >10 |
| 73 | 0.6365 | >10 |
| 74 | 0.0115 | >10 |
| 75 | 0.0162 | >10 |
| 76 | 0.0002 | 0.1673 |
| 77 | 0.1942 | >10 |
| 78 | 0.0012 | >10 |
| 79 | 0.5188 | >10 |
| 80 | 0.3415 | >10 |
| 81 | 0.6525 | >10 |
| 82 | 0.3556 | >10 |
| 83 | 0.7595 | >10 |
| 84 | 0.0189 | >10 |
| 85 | 0.0854 | >10 |
| 86 | 0.0727 | >10 |
| 87 | 0.768 | >10 |
| 88 | 0.1802 | >10 |
| 89 | 0.3184 | >10 |
| 90 | 0.0148 | >10 |
| 91 | 0.8929 | >10 |
| 92 | 0.1008 | >10 |
| 93 | 0.3269 | >10 |
| 94 | 0.0802 | >10 |
| 95 | 0.0104 | >10 |
| 96 | 0.1034 | >10 |
| 97 | 0.0723 | >10 |
| 98 | 0.0066 | >10 |
| 99 | 0.3052 | >10 |
| 100 | 0.0208 | >10 |
| 101 | 0.0049 | >10 |
| 102 | 0.1806 | >10 |
| 103 | 0.0048 | >10 |
| 104 | 0.0074 | >10 |
| 105 | 0.218 | >10 |
| 106 | 0.1229 | >10 |
| 107 | 0.7574 | >10 |
| 108 | 0.1556 | >10 |
| 109 | 0.3604 | >10 |
| 110 | 0.3855 | >10 |
| 111 | 0.008 | 2.7772 |
| 112 | 0.0198 | >10 |
| 113 | 0.212 | >10 |
| 114 | 0.4732 | >10 |
| 115 | 0.0072 | >10 |
| 116 | 0.6715 | >10 |
| 117 | 0.4851 | >10 |
| 118 | 0.0132 | >10 |
| 119 | 0.5991 | >10 |
| 120 | 0.042 | >10 |
| 121 | 0.112 | >10 |
| 122 | 0.05 | >10 |
| 123 | 0.0584 | >10 |
| 124 | 0.0526 | >10 |
| 125 | 0.0095 | >10 |
| 126 | 0.04 | >10 |
| 127 | 0.0034 | >10 |
| 128 | 0.0302 | >10 |
| 129 | 0.0758 | >10 |
| 130 | 0.0023 | >10 |
| 131 | 0.0625 | >10 |
| 132 | 0.0301 | >10 |
| 133 | 0.0102 | >10 |
| 134 | 0.0522 | >10 |
| 135 | 0.0156 | >10 |
| 136 | 0.0329 | >10 |
| 137 | 0.0538 | >10 |
| 138 | 0.0835 | >10 |
| 139 | 0.042 | >10 |
| 140 | 0.0406 | >10 |
| 141 | 0.2619 | >10 |
| 142 | 0.0263 | >10 |
| 143 | 0.0878 | >10 |
| 144 | 0.073 | >10 |
| 145 | 0.3562 | >10 |
| 146 | 0.1673 | >10 |
| 147 | 1.167 | >10 |
| 148 | 0.451 | >10 |
| 149 | 0.079 | >10 |
| 150 | 0.008 | >10 |
| 151 | 0.818 | >10 |
| 152 | 0.338 | >10 |

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is then mixed with sodium starch glycolate and magnesium stearate and compressed to yield kernels of 120 or 350 mg respectively. The kernels are lacquered with an aq. solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

The invention claimed is:

1. A compound of formula (I)

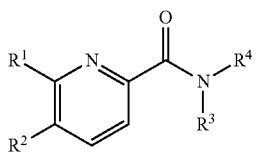

wherein
- $R^1$ is cycloalkylalkoxy, halophenyl, tetrahydrofuranylalkoxy, halophenylalkyl, haloalkyloxy, alkylsulfonyl, tetrahydropyranylalkoxy or halogen;
- $R^2$ is alkyl, pyrrolidinyl, cycloalkyl, haloazetidinyl, haloalkyl, cycloalkylalkoxy, haloalkyloxy, halocycloalkyl, hydroxycycloalkyl or halooxetanyl;
- one of $R^3$ and $R^4$ is alkyl, cycloalkyl, haloalkyl or hydroxyalkyl and the other one is alkyl, alkyloxyalkyl, (haloazetidinyl)(cycloalkyloxy)pyridinylcarbonyloxyalkyl, haloalkylcycloalkyl, hydroxyalkyl, phenylalkyl, alkoxycarbonylalkyl, carboxyalkyl, alkylaminocarbonylalkyl, (alkyloxadiazolyl)(cycloalkylalkyl)alkyl, (alkyloxadiazolyl)(cycloalkyl)alkyl, pyridazinylalkyl, aminocarbonylalkyl, alkyloxadiazolylalkyl, alkyltetrazolylalkyl, formyl, phenyl, dialkylpyrazolyl, alkylcarbonylpiperidinyl or cycloalkylalkyl;
- or $R^3$ and $R^4$ together with the nitrogen atom to which they are attached form heterocyclyl or substituted heterocyclyl;
- wherein heterocyclyl is 6-oxa-1-aza-spiro[3.3]heptyl, oxazolidinyl, morpholinyl, pyrrolidinyl, piperazinyl, 2-oxa-5-aza-spiro[3.4]octyl, piperidinyl, 6-aza-bicyclo[3.2.1.]octyl, imidazolidinyl, 4-aza-spiro[2.4]heptyl, 2-aza-bicyclo[2.2.1]heptyl, 2-thia-5-aza-bicyclo[2.2.1]heptyl, 2,5-diazabicyclo[2.2.1]heptyl, 2-oxa-5-aza-bicyclo[2.2.1]heptyl, hexahydro-furo[2,3-c]pyrrolyl, 2-thia-6-aza-spiro[3.3]heptyl, 1,8-diaza-spiro[4.5]decyl, 1-oxa-7-aza-spiro[4.4]nonyl, 5-oxa-2-aza-spiro[3.4]octyl, 8-oxa-3-aza-bicyclo[3.2.1]octyl, 3-oxa-8-aza-bicyclo[3.2.1]octyl, thiomorpholinyl, thiazolidinyl, 5-aza-spiro[3.4]octyl, azetidinyl, 5-aza-spiro[2.4]heptyl, 3-aza-bicyclo[3.1.0]hexyl or 5-aza-spiro[2.4]heptyl, 1,3,3a,4,6,6a-hexahydrofuro[3,4-c]pyrrolyl; and
- wherein substituted heterocyclyl is heterocyclyl substituted with one to four substituents independently selected from alkyl, oxo, hydroxyl, carboxyl, alkylcarbonylamino, alkyloxyalkyl, hydroxyalkyl, aminocarbonyl, halogen, phenylalkyl, phenyl, alkoxycarbonyl, cycloalkylalkyl, phenylalkoxycarbonyl, cycloalkyl, halohydroxyalkyl and haloalkyl;
- provided that $R^3$ and $R^4$ together with the nitrogen atom to which they are attached don't form unsubstituted piperidinyl, unsubstituted thiomorpholinyl or hydroxyalkylpyrrolidinyl;

or a pharmaceutically acceptable salt or ester thereof.

2. A compound according to claim 1, wherein $R^1$ is cycloalkylalkoxy, tetrahydrofuranylalkoxy, alkylsulfonyl or halophenylalkyl.

3. A compound according to claim 1, wherein $R^1$ is cyclopropylmethoxy, tetrahydrofuranylmethoxy, isobutylsulfonyl or fluorophenylmethyl.

4. A compound according to claim 1, wherein $R^2$ is haloazetidinyl, cycloalkyl or halocycloalkyl.

5. A compound according to claim 1, wherein $R^2$ is difluoroazetidinyl, cyclopropyl or fluorocyclobutyl.

6. A compound according to claim 1, wherein one of $R^3$ and $R^4$ is alkyl and the other one is alkyl or haloalkylcycloalkyl.

7. A compound according to claim 1, wherein one of $R^3$ and $R^4$ is methyl and the other one is tert.-butyl or trifluoromethylcyclopropyl.

8. A compound according to claim 1, wherein $R^3$ and $R^4$ together with the nitrogen atom to which they are attached form heterocyclyl or substituted heterocyclyl, wherein heterocyclyl is oxazolidinyl, morpholinyl, pyrrolidinyl, 6-aza-bicyclo[3.2.1.]octyl, 4-aza-spiro[2.4]heptyl, 2-thia-5-aza-bicyclo[2.2.1]heptyl, 5-aza-spiro[3.4]octyl, 5-aza-spiro[2.4]heptyl, 1,8-diaza-spiro[4.5]decyl, thiazolidinyl or 5-aza-spiro[2.4]heptyl, and wherein substituted heterocyclyl is heterocyclyl substituted with one to three substituents independently selected from alkyl, hydroxyalkyl, halogen, aminocarbonyl, alkoxycarbonyl, oxo or hydroxyl.

9. A compound according to claim 1, wherein $R^3$ and $R^4$ together with the nitrogen atom to which they are attached form heterocyclyl or substituted heterocyclyl, wherein heterocyclyl is oxazolidinyl, morpholinyl, pyrrolidinyl, 6-aza-bicyclo[3.2.1.]octyl, 4-aza-spiro[2.4]heptyl, 2-thia-5-aza-bicyclo[2.2.1]heptyl, 5-aza-spiro[3.4]octyl, 5-aza-spiro[2.4]heptyl, 1,8-diaza-spiro[4.5]decyl, thiazolidinyl or 5-aza-spiro[2.4]heptyl, and wherein substituted heterocyclyl is heterocyclyl substituted with one to three substituents independently selected from methyl, hydroxymethyl, fluoro, aminocarbonyl, tert.-butoxycarbonyl, oxo or hydroxyl.

10. A compound according to claim 1, wherein $R^3$ and $R^4$ together with the nitrogen atom to which they are attached form dimethyloxazolidinyl, dimethylmorpholinyl, dimethylpyrrolidinyl, trimethyl-6-aza-bicyclo[3.2.1.]octyl, (hydroxymethyl)(difluoro)pyrrolidinyl, 4-aza-spiro[2.4]heptyl, (aminocarbonyl)(difluoro)pyrrolidinyl, 2-thia-5-aza-bicyclo[2.2.1]heptyl, (aminocarbonyl)(dimethyl)pyrrolidinyl, 5-aza-spiro[3.4]octyl, difluoro-5-aza-spiro[2.4]heptyl, 5-aza-spiro[2.4]heptyl, tert.-butoxycarbonyl-1,8-diaza-spiro[4.5]decyl, aminocarbonyl-1,1-dioxo-1λ6-thiazolidinyl, aminocarbonyl-1,1-dioxo-1,3-thiazolidinyl, (aminocarbonyl)(methyl)(hydroxyl)pyrrolidinyl or (aminocarbonyl)-5-aza-spiro[2.4]heptyl.

11. A compound according to claim 1 selected from
- 6-Cyclopropylmethoxy-5-(3,3-difluoro-azetidin-1-yl)-pyridine-2-carboxylic acid tert-butyl-methyl-amide;
- 6-Cyclopropylmethoxy-5-(3,3-difluoro-azetidin-1-yl)-pyridine-2-carboxylic acid dimethylamide;
- 5-Cyclopropyl-6-cyclopropylmethoxy-pyridine-2-carboxylic acid tert-butyl-methyl-amide;
- 5-Cyclopropyl-6-(tetrahydro-furan-2-ylmethoxy)-pyridine-2-carboxylic acid tert-butyl-methyl-amide;

5-Cyclopropyl-6-(4-fluoro-benzyl)-pyridine-2-carboxylic acid tert-butyl-methyl-amide;
5-Cyclopropyl-6-(2-methyl-propane-1-sulfonyl)-pyridine-2-carboxylic acid tert-butyl-methyl-amide;
6-Cyclopropylmethoxy-5-(3,3-difluoro-azetidin-1-yl)-pyridine-2-carboxylic acid tert-butyl-ethyl-amide;
6-Cyclopropylmethoxy-5-(3,3-difluoro-azetidin-1-yl)-pyridine-2-carboxylic acid diisopropylamide;
6-Cyclopropylmethoxy-5-(3,3-difluoro-azetidin-1-yl)-pyridine-2-carboxylic acid (2-methoxy-1,1-dimethyl-ethyl)-methyl-amide;
[6-Cyclopropylmethoxy-5-(3,3-difluoro-azetidin-1-yl)-pyridin-2-yl]-(6-oxa-1-aza-spiro[3.3]hept-1-yl)-methanone;
[6-Cyclopropylmethoxy-5-(3,3-difluoro-azetidin-1-yl)-pyridin-2-yl]-(2-oxa-6-aza-spiro[3.3]hept-6-yl)-methanone;
6-Cyclopropylmethoxy-5-(3,3-difluoro-azetidin-1-yl)-pyridine-2-carboxylic acid 2-{[6-cyclopropylmethoxy-5-(3,3-difluoro-azetidin-1-yl)-pyridine-2-carbonyl]-methyl-amino}-2-methyl-propyl ester;
5-Cyclopropyl-6-(2,2,2-trifluoro-1-methyl-ethoxy)-pyridine-2-carboxylic acid tert-butyl-methyl-amide;
[6-Cyclopropylmethoxy-5-(3,3-difluoro-azetidin-1-yl)-pyridin-2-yl]-(4,4-dimethyl-oxazolidin-3-yl)-methanone;
6-(Tetrahydro-furan-2-ylmethoxy)-5-trifluoromethyl-pyridine-2-carboxylic acid tert-butyl-methyl-amide;
6-Cyclopropylmethoxy-5-(3,3-difluoro-azetidin-1-yl)-pyridine-2-carboxylic acid methyl-(1-trifluoromethyl-cyclopropyl)-amide;
[6-Cyclopropylmethoxy-5-(3,3-difluoro-azetidin-1-yl)-pyridin-2-yl]-(3,3-dimethyl-morpholin-4-yl)-methanone;
[6-Cyclopropylmethoxy-5-(3,3-difluoro-azetidin-1-yl)-pyridin-2-yl]-(2,2-dimethyl-pyrrolidin-1-yl)-methanone;
6-Cyclopropylmethoxy-5-(3,3-difluoro-azetidin-1-yl)-pyridine-2-carboxylic acid (2-hydroxy-1,1-dimethyl-ethyl)-(2-methoxy-ethyl)-amide;
6-Cyclopropylmethoxy-5-(3,3-difluoro-azetidin-1-yl)-pyridine-2-carboxylic acid tert-butyl-(2-methoxy-ethyl)-amide;
6-Cyclopropylmethoxy-5-(3,3-difluoro-azetidin-1-yl)-pyridine-2-carboxylic acid ethyl-(1-trifluoromethyl-cyclopropyl)-amide;
6-Cyclopropylmethoxy-5-(3,3-difluoro-azetidin-1-yl)-pyridine-2-carboxylic acid benzyl-(1-trifluoromethyl-cyclopropyl)-amide;
{tert-Butyl-[6-cyclopropylmethoxy-5-(3,3-difluoro-azetidin-1-yl)-pyridine-2-carbonyl]-amino}-acetic acid ethyl ester;
{tert-Butyl-[6-cyclopropylmethoxy-5-(3,3-difluoro-azetidin-1-yl)-pyridine-2-carbonyl]-amino}-acetic acid;
6-Cyclopropylmethoxy-5-(3,3-difluoro-azetidin-1-yl)-pyridine-2-carboxylic acid benzyl-tert-butyl-amide;
6-Cyclopropylmethoxy-5-(3,3-difluoro-azetidin-1-yl)-pyridine-2-carboxylic acid tert-butyl-methylcarbamoylmethyl-amide;
6-Cyclopropylmethoxy-5-(3,3-difluoro-azetidin-1-yl)-pyridine-2-carboxylic acid tert-butyl-dimethylcarbamoylmethyl-amide;
4-[6-Cyclopropylmethoxy-5-(3,3-difluoro-azetidin-1-yl)-pyridine-2-carbonyl]-3,3-dimethyl-piperazin-2-one;
4-[6-Cyclopropylmethoxy-5-(3,3-difluoro-azetidin-1-yl)-pyridine-2-carbonyl]-3,3-diethyl-piperazin-2-one;
[5-Cyclopropyl-6-(2-methyl-propane-1-sulfonyl)-pyridin-2-yl]-(2,2-dimethyl-pyrrolidin-1-yl)-methanone;
[5-Cyclopropyl-6-(2-methyl-propane-1-sulfonyl)-pyridin-2-yl]-(4,4-dimethyl-oxazolidin-3-yl)-methanone;
6-Cyclopropylmethoxy-5-(3,3-difluoro-azetidin-1-yl)-pyridine-2-carboxylic acid [(S)-2-cyclopropyl-1-(5-methyl-[1,2,4]oxadiazol-3-yl)-ethyl]-methyl-amide;
5-Cyclopropyl-6-(tetrahydro-pyran-4-ylmethoxy)-pyridine-2-carboxylic acid [cyclopropyl-(5-methyl-[1,2,4]oxadiazol-3-yl)-methyl]-methyl-amide;
(+)-6-Cyclopropylmethoxy-5-(3,3-difluoro-azetidin-1-yl)-pyridine-2-carboxylic acid methyl-(3-methyl-1-pyridazin-3-yl-butyl)-amide;
6-Cyclopropylmethoxy-5-(3,3-difluoro-azetidin-1-yl)-pyridine-2-carboxylic acid tert-butyl-carbamoylmethyl-amide;
6-Cyclopropylmethoxy-5-(3,3-difluoro-azetidin-1-yl)-pyridine-2-carboxylic acid tert-butyl-(5-methyl-[1,3,4]oxadiazol-2-ylmethyl)-amide;
[6-Cyclopropylmethoxy-5-(3,3-difluoro-azetidin-1-yl)-pyridin-2-yl]-(3-hydroxy-3-methyl-pyrrolidin-1-yl)-methanone;
[6-Cyclopropylmethoxy-5-(3,3-difluoro-azetidin-1-yl)-pyridin-2-yl]-(2-oxa-5-aza-spiro[3.4]oct-5-yl)-methanone;
6-Cyclopropylmethoxy-5-(3,3-difluoro-azetidin-1-yl)-pyridine-2-carboxylic acid ethyl-(2-methoxy-ethyl)-amide;
6-Cyclopropylmethoxy-5-(3,3-difluoro-azetidin-1-yl)-pyridine-2-carboxylic acid tert-butyl-(1-methyl-1H-tetrazol-5-ylmethyl)-amide;
N-{1-[6-Cyclopropylmethoxy-5-(3,3-difluoro-azetidin-1-yl)-pyridine-2-carbonyl]-pyrrolidin-3-yl}-acetamide;
[5-Cyclopropyl-6-(4-fluoro-benzyl)-pyridin-2-yl]-(4,4-dimethyl-piperidin-1-yl)-methanone;
[5-Cyclopropyl-6-(tetrahydro-furan-2-ylmethoxy)-pyridin-2-yl]-(4,4-dimethyl-piperidin-1-yl)-methanone;
[5-Cyclopropyl-6-(4-fluoro-benzyl)-pyridin-2-yl]-(4,4-dimethyl-oxazolidin-3-yl)-methanone;
[6-Cyclopropylmethoxy-5-(3,3-difluoro-azetidin-1-yl)-pyridin-2-yl]-((1S,5R)-1,3,3-trimethyl-6-aza-bicyclo[3.2.1]oct-6-yl)-methanone;
[6-Cyclopropylmethoxy-5-(3,3-difluoro-azetidin-1-yl)-pyridin-2-yl]-((R)-2-methoxymethyl-pyrrolidin-1-yl)-methanone;
(6-Chloro-5-cyclopropylmethoxy-pyridin-2-yl)-(2,2-dimethyl-pyrrolidin-1-yl)-methanone;
(6-Cyclopropylmethoxy-5-trifluoromethoxy-pyridin-2-yl)-(4,4-dimethyl-oxazolidin-3-yl)-methanone;
(6-Chloro-5-cyclopropylmethoxy-pyridin-2-yl)-(4,4-dimethyl-oxazolidin-3-yl)-methanone;
6-Cyclopropylmethoxy-5-(3,3-difluoro-azetidin-1-yl)-pyridine-2-carboxylic acid (1-acetyl-piperidin-4-yl)-cyclopropyl-amide;
6-(Cyclopropylmethoxy)-5-(3,3-difluoroazetidin-1-yl)-N-formyl-N-methylpyridine-2-carboxamide;
6-Cyclopropylmethoxy-5-(3,3-difluoro-azetidin-1-yl)-pyridine-2-carboxylic acid methyl-phenyl-amide;
[6-Cyclopropylmethoxy-5-(3,3-difluoro-azetidin-1-yl)-pyridin-2-yl]-((S)-4,4-difluoro-2-hydroxymethyl-pyrrolidin-1-yl)-methanone;
6-Cyclopropylmethoxy-5-(3,3-difluoro-azetidin-1-yl)-pyridine-2-carboxylic acid (1,4-dimethyl-1H-pyrazol-3-yl)-methyl-amide;
[6-Cyclopropylmethoxy-5-(3,3-difluoro-azetidin-1-yl)-pyridin-2-yl]-(2,2-dimethyl-morpholin-4-yl)-methanone;

(R)-2-tert-Butyl-1-[6-cyclopropylmethoxy-5-(3,3-difluoro-azetidin-1-yl)-pyridine-2-carbonyl]-3-methyl-imidazolidin-4-one;
(4-Aza-spiro[2.4]hept-4-yl)-[6-cyclopropylmethoxy-5-(3,3-difluoro-azetidin-1-yl)-pyridin-2-yl]-methanone;
3-{1-[6-Cyclopropylmethoxy-5-(3,3-difluoro-azetidin-1-yl)-pyridine-2-carbonyl]-piperidin-4-yl}-5,5-dimethyl-pyrrolidin-2-one;
(1S,4R)-2-Aza-bicyclo[2.2.1]hept-2-yl-[6-cyclopropylmethoxy-5-(3,3-difluoro-azetidin-1-yl)-pyridin-2-yl]-methanone;
(S)-1-[6-Cyclopropylmethoxy-5-(3,3-difluoro-azetidin-1-yl)-pyridine-2-carbonyl]-4,4-difluoro-pyrrolidine-2-carboxylic acid amide;
[6-Cyclopropylmethoxy-5-(3,3-difluoro-azetidin-1-yl)-pyridin-2-yl]-(4-hydroxy-4-methyl-piperidin-1-yl)-methanone;
[6-Cyclopropylmethoxy-5-(3,3-difluoro-azetidin-1-yl)-pyridin-2-yl]-(1S,4S)-2-thia-5-aza-bicyclo[2.2.1]hept-5-yl-methanone;
((1S,4S)-5-Benzyl-2,5-diaza-bicyclo[2.2.1]hept-2-yl)-[6-cyclopropylmethoxy-5-(3,3-difluoro-azetidin-1-yl)-pyridin-2-yl]-methanone;
[6-Cyclopropylmethoxy-5-(3,3-difluoro-azetidin-1-yl)-pyridin-2-yl]-(2-methyl-3-phenyl-piperidin-1-yl)-methanone;
[6-Cyclopropylmethoxy-5-(3,3-difluoro-azetidin-1-yl)-pyridin-2-yl]-(1S,4S)-2-oxa-5-aza-bicyclo[2.2.1]hept-5-yl-methanone;
[6-Cyclopropylmethoxy-5-(3,3-difluoro-azetidin-1-yl)-pyridin-2-yl]-(4-hydroxy-2,2-dimethyl-piperidin-1-yl)-methanone;
1-[6-Cyclopropylmethoxy-5-(3,3-difluoro-azetidin-1-yl)-pyridine-2-carbonyl]-2-phenylpiperidine-3-carboxylic acid ethyl ester;
(S)-1-(5-Cyclopropyl-6-cyclopropylmethoxy-pyridine-2-carbonyl)-4,4-difluoro-pyrrolidine-2-carboxylic acid amide;
(2S,4S)-1-(5-Cyclopropyl-6-cyclopropylmethoxy-pyridine-2-carbonyl)-4-fluoro-pyrrolidine-2-carboxylic acid amide;
[6-Cyclopropylmethoxy-5-(3,3-difluoro-azetidin-1-yl)-pyridin-2-yl]-(hexahydro-furo[2,3-c]pyrrol-5-yl)-methanone;
[6-Cyclopropylmethoxy-5-(3,3-difluoro-azetidin-1-yl)-pyridin-2-yl]-(2,2-dioxo-2λ6-thia-6-aza-spiro[3.3]hept-6-yl)-methanone;
6-Cyclopropylmethoxy-5-(3,3-difluoro-azetidin-1-yl)-pyridine-2-carboxylic acid tert-butyl-(2-carbamoyl-ethyl)-amide;
(S)-1-(5-Cyclopropyl-6-cyclopropylmethoxy-pyridine-2-carbonyl)-pyrrolidine-2-carboxylic acid amide;
1-[6-Cyclopropylmethoxy-5-(3,3-difluoro-azetidin-1-yl)-pyridine-2-carbonyl]-1,8-diaza-spiro[4.5]decane-8-carboxylic acid tert-butyl ester;
(S)-1-{5-Cyclopropyl-6-[(R,S)-1-(tetrahydro-furan-2-yl)methoxy]-pyridine-2-carbonyl}-4,4-difluoro-pyrrolidine-2-carboxylic acid amide;
(S)-1-[5-Cyclopropyl-6-(4-fluoro-benzyl)-pyridine-2-carbonyl]-4,4-difluoro-pyrrolidine-2-carboxylic acid amide;
(+)-1-[6-Cyclopropylmethoxy-5-(3,3-difluoro-azetidin-1-yl)-pyridine-2-carbonyl]-4,4-dimethyl-pyrrolidine-2-carboxylic acid amide;
(−)-1-[6-Cyclopropylmethoxy-5-(3,3-difluoro-azetidin-1-yl)-pyridine-2-carbonyl]-4,4-dimethyl-pyrrolidine-2-carboxylic acid amide;
(2S,4S)-1-[6-Cyclopropylmethoxy-5-(3,3-difluoro-azetidin-1-yl)-pyridine-2-carbonyl]-4-hydroxy-pyrrolidine-2-carboxylic acid amide;
(2S,4S)-1-[6-Cyclopropylmethoxy-5-(3,3-difluoro-azetidin-1-yl)-pyridine-2-carbonyl]-4-fluoro-pyrrolidine-2-carboxylic acid amide;
6-Cyclopropylmethoxy-5-(3,3-difluoro-azetidin-1-yl)-pyridine-2-carboxylic acid cyclopropyl-(5-methyl-[1,3,4]oxadiazol-2-ylmethyl)-amide;
[6-Cyclopropylmethoxy-5-(3,3-difluoro-azetidin-1-yl)-pyridin-2-yl]-(3-hydroxy-1-oxa-7-aza-spiro[4.4]non-7-yl)-methanone;
[6-Cyclopropylmethoxy-5-(3,3-difluoro-azetidin-1-yl)-pyridin-2-yl]-(7-hydroxy-5-oxa-2-aza-spiro[3.4]oct-2-yl)-methanone;
[5-Cyclopropyl-6-(2,2,3,3,3-pentafluoro-propoxy)-pyridin-2-yl]-(2,2-dimethyl-pyrrolidin-1-yl)-methanone;
[6-Cyclopropylmethoxy-5-(3,3-difluoro-azetidin-1-yl)-pyridin-2-yl]-(1S,5R)-8-oxa-3-aza-bicyclo[3.2.1]oct-3-yl-methanone;
[6-Cyclopropylmethoxy-5-(3,3-difluoro-azetidin-1-yl)-pyridin-2-yl]-(1R,5S)-3-oxa-8-aza-bicyclo[3.2.1]oct-8-yl-methanone;
(R)-1-[5-Cyclopropyl-6-(2,2,3,3,3-pentafluoro-propoxy)-pyridine-2-carbonyl]-4,4-difluoro-pyrrolidine-2-carboxylic acid amide;
1-(5-Cyclopropyl-6-cyclopropylmethoxy-pyridine-2-carbonyl)-piperidine-2-carboxylic acid amide;
4-(5-Cyclopropyl-6-cyclopropylmethoxy-pyridine-2-carbonyl)-thiomorpholine-3-carboxylic acid amide;
1-(5-Cyclopropyl-6-cyclopropylmethoxy-pyridine-2-carbonyl)-4,4-dimethyl-pyrrolidine-2-carboxylic acid amide;
(+)-1-(5-Cyclopropyl-6-cyclopropylmethoxy-pyridine-2-carbonyl)-piperidine-2-carboxylic acid amide;
(−)-1-(5-Cyclopropyl-6-cyclopropylmethoxy-pyridine-2-carbonyl)-piperidine-2-carboxylic acid amide;
(−)-4-(5-Cyclopropyl-6-cyclopropylmethoxy-pyridine-2-carbonyl)-thiomorpholine-3-carboxylic acid amide;
(+)-1-(5-Cyclopropyl-6-cyclopropylmethoxy-pyridine-2-carbonyl)-4,4-dimethyl-pyrrolidine-2-carboxylic acid amide;
(−)-1-(5-Cyclopropyl-6-cyclopropylmethoxy-pyridine-2-carbonyl)-4,4-dimethyl-pyrrolidine-2-carboxylic acid amide;
3-(5-Cyclopropyl-6-cyclopropylmethoxy-pyridine-2-carbonyl)-thiazolidine-4-carboxylic acid amide;
(−)-3-(5-Cyclopropyl-6-cyclopropylmethoxy-pyridine-2-carbonyl)-thiazolidine-4-carboxylic acid amide;
1-[6-Cyclopropylmethoxy-5-(3,3-difluoro-azetidin-1-yl)-pyridine-2-carbonyl]-4,4-dimethyl-pyrrolidine-2-carboxylic acid amide;
[6-Cyclopropylmethoxy-5-(3,3-difluoro-azetidin-1-yl)-pyridin-2-yl]-(5-oxa-2-aza-spiro[3.4]oct-2-yl)-methanone;
[6-Cyclopropylmethoxy-5-(3,3-difluoro-azetidin-1-yl)-pyridin-2-yl]-(1-oxa-7-aza-spiro[4.4]non-7-yl)-methanone;
(5-Aza-spiro[3.4]oct-5-yl)-[6-cyclopropylmethoxy-5-(3,3-difluoro-azetidin-1-yl)-pyridin-2-yl]-methanone;
[6-Cyclopropylmethoxy-5-(3,3-difluoro-azetidin-1-yl)-pyridin-2-yl]-(3,3-difluoro-azetidin-1-yl)-methanone;
[6-Cyclopropylmethoxy-5-(3,3-difluoro-azetidin-1-yl)-pyridin-2-yl]-(1,1-difluoro-5-aza-spiro[2.4]hept-5-yl)-methanone;
(5-Aza-spiro[2.4]hept-5-yl)-[6-cyclopropylmethoxy-5-(3,3-difluoro-azetidin-1-yl)-pyridin-2-yl]-methanone;

6-Cyclopropylmethoxy-5-(3,3-difluoro-azetidin-1-yl)-pyridine-2-carboxylic acid cyclopropylmethyl-methyl-amide;

[6-Cyclopropylmethoxy-5-(3,3-difluoro-azetidin-1-yl)-pyridin-2-yl]-(4-cyclopropylmethyl-piperazin-1-yl)-methanone;

3-[6-Cyclopropylmethoxy-5-(3,3-difluoro-azetidin-1-yl)-pyridine-2-carbonyl]-3-aza-bicyclo[3.1.0]hexane-6-carboxylic acid ethyl ester;

1-[6-Cyclopropylmethoxy-5-(3,3-difluoro-azetidin-1-yl)-pyridine-2-carbonyl]-pyrrolidine-2-carboxylic acid methyl ester;

4-[6-Cyclopropylmethoxy-5-(3,3-difluoro-azetidin-1-yl)-pyridine-2-carbonyl]-piperazine-1-carboxylic acid benzyl ester;

3-[6-Cyclopropylmethoxy-5-(3,3-difluoro-azetidin-1-yl)-pyridine-2-carbonyl]-3-aza-bicyclo[3.1.0]hexane-6-carboxylic acid;

1-[5-Cyclopropyl-6-(4-fluoro-benzyl)-pyridine-2-carbonyl]-1,8-diaza-spiro[4.5]decane-8-carboxylic acid tert-butyl ester;

(−)-3-[6-Cyclopropylmethoxy-5-(3,3-difluoro-azetidin-1-yl)-pyridine-2-carbonyl]-thiazolidine-4-carboxylic acid amide;

[5-Cyclopropyl-6-(4-fluoro-benzyl)-pyridin-2-yl]-(1,8-diaza-spiro[4.5]dec-1-yl)-methanone;

1-[6-Cyclopropylmethoxy-5-(3,3-difluoro-azetidin-1-yl)-pyridine-2-carbonyl]-pyrrolidine-2-carboxylic acid amide;

(−)-3-(5-Cyclopropyl-6-cyclopropylmethoxy-pyridine-2-carbonyl)-1,1-dioxo-1λ6-thiazolidine-4-carboxylic acid amide;

(1S,4R)-3-(5-Cyclopropyl-6-cyclopropylmethoxy-pyridine-2-carbonyl)-1-oxo-1λ4-thiazolidine-4-carboxylic acid amide;

(1R,4S)-3-(5-Cyclopropyl-6-cyclopropylmethoxy-pyridine-2-carbonyl)-1-oxo-1λ4-thiazolidine-4-carboxylic acid amide;

(+)-3-(5-Cyclopropyl-6-cyclopropylmethoxy-pyridine-2-carbonyl)-1,1-dioxo-1λ6-thiazolidine-4-carboxylic acid amide;

[6-Cyclopropylmethoxy-5-(3,3-difluoro-azetidin-1-yl)-pyridin-2-yl]-(3,3,4,4-tetrafluoro-pyrrolidin-1-yl)-methanone;

[6-Cyclopropylmethoxy-5-(3,3-difluoro-azetidin-1-yl)-pyridin-2-yl]-(2,6-dimethyl-morpholin-4-yl)-methanone;

(R)-3-[6-Cyclopropylmethoxy-5-(3,3-difluoro-azetidin-1-yl)-pyridine-2-carbonyl]-5,5-dimethyl-thiazolidine-4-carboxylic acid amide;

(S)-1-[6-Cyclopropylmethoxy-5-(3,3-difluoro-azetidin-1-yl)-pyridine-2-carbonyl]-5,5-dimethyl-pyrrolidine-2-carboxylic acid amide;

3-[6-Cyclopropylmethoxy-5-(3,3-difluoro-azetidin-1-yl)-pyridine-2-carbonyl]-thiazolidine-4-carboxylic acid amide;

(2S,4R)-1-[5-Cyclopropyl-6-(cyclopropylmethoxy)pyridine-2-carbonyl]-4-fluoropyrrolidine-2-carboxamide;

3-[6-(Cyclopropylmethoxy)-5-(3,3-difluoroazetidin-1-yl)pyridine-2-carbonyl]-1-oxo-1,3-thiazolidine-4-carboxamide;

3-[6-(Cyclopropylmethoxy)-5-(3,3-difluoroazetidin-1-yl)pyridine-2-carbonyl]-1,1-dioxo-1,3-thiazolidine-4-carboxamide;

(2S,4R)-1-[6-(Cyclopropylmethoxy)-5-(3,3-difluoroazetidin-1-yl)pyridine-2-carbonyl]-4-fluoropyrrolidine-2-carboxamide;

(−)-3-[6-(Cyclopropylmethoxy)-5-(3,3-difluoroazetidin-1-yl)pyridine-2-carbonyl]-1,1-dioxo-1,3-thiazolidine-4-carboxamide;

3-[6-(Cyclopropylmethoxy)-5-(3-methoxyazetidin-1-yl)pyridine-2-carbonyl]-1,1-dioxo-1,3-thiazolidine-4-carboxamide;

(2S)-1-[6-(Cyclopropylmethoxy)-5-(1-hydroxycyclobutyl)pyridine-2-carbonyl]-4,4-difluoropyrrolidine-2-carboxamide;

(2S)-1-[6-(Cyclopropylmethoxy)-5-(1-fluorocyclobutyl)pyridine-2-carbonyl]-4,4-difluoropyrrolidine-2-carboxamide;

3-[6-(Cyclopropylmethoxy)-5-(1-hydroxycyclobutyl)pyridine-2-carbonyl]-1,1-dioxo-1,3-thiazolidine-4-carboxamide;

(2S)-1-[6-(Cyclopropylmethoxy)-5-(3,3-difluoroazetidin-1-yl)pyridine-2-carbonyl]-4-hydroxy-4-methylpyrrolidine-2-carboxamide;

3-[6-(Cyclopropylmethoxy)-5-(1-fluorocyclobutyl)pyridine-2-carbonyl]-1,1-dioxo-1,3-thiazolidine-4-carboxamide;

(2S)-1-[6-(Cyclopropylmethoxy)-5-(3-fluorooxetan-3-yl)pyridine-2-carbonyl]-4,4-difluoropyrrolidine-2-carboxamide;

5-[6-(Cyclopropylmethoxy)-5-(3,3-difluoroazetidin-1-yl)pyridine-2-carbonyl]-5-azaspiro[2.4]heptane-6-carboxamide;

[6-(Cyclopropylmethoxy)-5-(3,3-difluoroazetidin-1-yl)pyridin-2-yl]-[3-(2,2,2-trifluoro-1-hydroxyethyl)pyrrolidin-1-yl]methanone;

[6-(Cyclopropylmethoxy)-5-(3,3-difluoroazetidin-1-yl)pyridin-2-yl]-[3-(hydroxymethyl)-3-(trifluoromethyl)pyrrolidin-1-yl]methanone;

[6-(Cyclopropylmethoxy)-5-(3,3-difluoroazetidin-1-yl)pyridin-2-yl]-[3-hydroxy-3-(trifluoromethyl)pyrrolidin-1-yl]methanone;

[6-(Cyclopropylmethoxy)-5-(3,3-difluoroazetidin-1-yl)pyridin-2-yl]-[3-hydroxy-3-(trifluoromethyl)azetidin-1-yl]methanone;

(+)-(2S)-1-[6-(Cyclopropylmethoxy)-5-(3,3-difluoroazetidin-1-yl)pyridine-2-carbonyl]-4-hydroxy-4-methylpyrrolidine-2-carboxamide;

[5-Cyclopropyl-6-(cyclopropylmethoxy)pyridin-2-yl]-[3-(2,2,2-trifluoro-1-hydroxyethyl)pyrrolidin-1-yl]methanone;

[5-Cyclopropyl-6-(cyclopropylmethoxy)pyridin-2-yl]-[3-(hydroxymethyl)-3-(trifluoromethyl)pyrrolidin-1-yl]methanone;

[5-Cyclopropyl-6-(cyclopropylmethoxy)pyridin-2-yl]-[3-hydroxy-3-(trifluoromethyl)pyrrolidin-1-yl]methanone;

[5-Cyclopropyl-6-(cyclopropylmethoxy)pyridin-2-yl]-[3-hydroxy-3-(trifluoromethyl)azetidin-1-yl]methanone;

(6S)-5-[6-(Cyclopropylmethoxy)-5-(3,3-difluoroazetidin-1-yl)pyridine-2-carbonyl]-5-azaspiro[2.4]heptane-6-carboxamide;

[(3aR,6aS)-1,3,3a,4,6,6a-Hexahydrofuro[3,4-c]pyrrol-5-yl]-[6-(cyclopropylmethoxy)-5-(3,3-difluoroazetidin-1-yl)pyridin-2-yl]methanone;

(2S)-1-[5-(3,3-Difluoroazetidin-1-yl)-6-(2-fluoroethoxy)pyridine-2-carbonyl]-4,4-difluoro-pyrrolidine-2-carboxamide;

[6-(Cyclopropylmethoxy)-5-(3,3-difluoroazetidin-1-yl)-2-pyridyl]-[3-fluoro-3-(hydroxymethyl)azetidin-1-yl]methanone;

[6-(Cyclopropylmethoxy)-5-(3,3-difluoroazetidin-1-yl)-2-pyridyl]-(3-fluoro-3-methyl-azetidin-1-yl)methanone;

(3-Cyclopropyl-3-fluoroazetidin-1-yl)-[6-(cyclopropylmethoxy)-5-(3,3-difluoroazetidin-1-yl)pyridin-2-yl]methanone;

(−)-5-[6-(Cyclopropylmethoxy)-5-(3,3-difluoroazetidin-1-yl)pyridine-2-carbonyl]-5-azaspiro[2.4]heptane-4-carboxamide; and (+)-5-[6-(Cyclopropylmethoxy)-5-(3,3-difluoroazetidin-1-yl)pyridine-2-carbonyl]-5-azaspiro[2.4]heptane-4-carboxamide.

12. A compound according to claim 1 selected from

6-Cyclopropylmethoxy-5-(3,3-difluoro-azetidin-1-yl)-pyridine-2-carboxylic acid tert-butyl-methyl-amide;

5-Cyclopropyl-6-(tetrahydro-furan-2-ylmethoxy)-pyridine-2-carboxylic acid tert-butyl-methyl-amide;

[6-Cyclopropylmethoxy-5-(3,3-difluoro-azetidin-1-yl)-pyridin-2-yl]-(4,4-dimethyl-oxazolidin-3-yl)-methanone;

6-Cyclopropylmethoxy-5-(3,3-difluoro-azetidin-1-yl)-pyridine-2-carboxylic acid methyl-(1-trifluoromethyl-cyclopropyl)-amide;

[6-Cyclopropylmethoxy-5-(3,3-difluoro-azetidin-1-yl)-pyridin-2-yl]-(3,3-dimethyl-morpholin-4-yl)-methanone;

[5-Cyclopropyl-6-(2-methyl-propane-1-sulfonyl)-pyridin-2-yl]-(2,2-dimethyl-pyrrolidin-1-yl)-methanone;

[5-Cyclopropyl-6-(4-fluoro-benzyl)-pyridin-2-yl]-(4,4-dimethyl-oxazolidin-3-yl)-methanone;

[6-Cyclopropylmethoxy-5-(3,3-difluoro-azetidin-1-yl)-pyridin-2-yl]-((1S,5R)-1,3,3-trimethyl-6-aza-bicyclo[3.2.1]oct-6-yl)-methanone;

[6-Cyclopropylmethoxy-5-(3,3-difluoro-azetidin-1-yl)-pyridin-2-yl]-((S)-4,4-difluoro-2-hydroxymethyl-pyrrolidin-1-yl)-methanone;

(4-Aza-spiro[2.4]hept-4-yl)-[6-cyclopropylmethoxy-5-(3,3-difluoro-azetidin-1-yl)-pyridin-2-yl]-methanone;

[6-Cyclopropylmethoxy-5-(3,3-difluoro-azetidin-1-yl)-pyridin-2-yl]-(1S,4S)-2-thia-5-aza-bicyclo[2.2.1]hept-5-yl-methanone;

(S)-1-(5-Cyclopropyl-6-cyclopropylmethoxy-pyridine-2-carbonyl)-4,4-difluoro-pyrrolidine-2-carboxylic acid amide;

(−)-1-[6-Cyclopropylmethoxy-5-(3,3-difluoro-azetidin-1-yl)-pyridine-2-carbonyl]-4,4-dimethyl-pyrrolidine-2-carboxylic acid amide;

(5-Aza-spiro[3.4]oct-5-yl)-[6-cyclopropylmethoxy-5-(3,3-difluoro-azetidin-1-yl)-pyridin-2-yl]-methanone;

[6-Cyclopropylmethoxy-5-(3,3-difluoro-azetidin-1-yl)-pyridin-2-yl]-(1,1-difluoro-5-aza-spiro[2.4]hept-5-yl)-methanone;

(5-Aza-spiro[2.4]hept-5-yl)-[6-cyclopropylmethoxy-5-(3,3-difluoro-azetidin-1-yl)-pyridin-2-yl]-methanone;

1-[5-Cyclopropyl-6-(4-fluoro-benzyl)-pyridine-2-carbonyl]-1,8-diaza-spiro[4.5]decane-8-carboxylic acid tert-butyl ester;

(−)-3-(5-Cyclopropyl-6-cyclopropylmethoxy-pyridine-2-carbonyl)-1,1-dioxo-1λ6-thiazolidine-4-carboxylic acid amide;

3-[6-(Cyclopropylmethoxy)-5-(3,3-difluoroazetidin-1-yl)pyridine-2-carbonyl]-1,1-dioxo-1,3-thiazolidine-4-carboxamide;

(−)-3-[6-(Cyclopropylmethoxy)-5-(3,3-difluoroazetidin-1-yl)pyridine-2-carbonyl]-1,1-dioxo-1,3-thiazolidine-4-carboxamide;

(2S)-1-[6-(Cyclopropylmethoxy)-5-(1-hydroxycyclobutyl)pyridine-2-carbonyl]-4,4-difluoropyrrolidine-2-carboxamide;

(2S)-1-[6-(Cyclopropylmethoxy)-5-(1-fluorocyclobutyl)pyridine-2-carbonyl]-4,4-difluoropyrrolidine-2-carboxamide;

(2S)-1-[6-(Cyclopropylmethoxy)-5-(3,3-difluoroazetidin-1-yl)pyridine-2-carbonyl]-4-hydroxy-4-methylpyrrolidine-2-carboxamide;

3-[6-(Cyclopropylmethoxy)-5-(1-fluorocyclobutyl)pyridine-2-carbonyl]-1,1-dioxo-1,3-thiazolidine-4-carboxamide; and 5-[6-(Cyclopropylmethoxy)-5-(3,3-difluoroazetidin-1-yl)pyridine-2-carbonyl]-5-azaspiro[2.4]heptane-6-carboxamide.

13. A process for the preparation of a compound of claim 1 comprising one of the following steps:

(a) the reaction of a compound of formula (A)

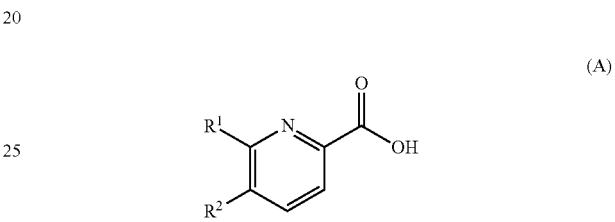

in the presence of NHR$^3$R$^4$, an amide bond forming coupling agent and a base; or (b) the reaction of a compound of formula (B)

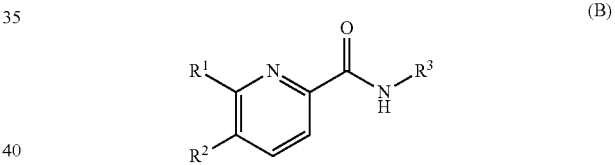

with a compound of formula R$^4$—X;

wherein R$^1$ to R$^4$ are as defined in claim 1 and X is a leaving group.

14. A compound manufactured according to a process of claim 13.

15. A pharmaceutical composition comprising a compound of claim 1 and a therapeutically inert carrier.

16. A method for the treatment of pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, amyotrophic lateral sclerosis, stroke, transient ischemic attack or uveitis, which method comprises administering an effective amount of a compound of claim 1 to a patient in need thereof.

* * * * *